US008796293B2

(12) United States Patent
Davies et al.

(10) Patent No.: US 8,796,293 B2
(45) Date of Patent: Aug. 5, 2014

(54) PURINE AND DEAZAPURINE DERIVATIVES AS PHARMACEUTICAL COMPOUNDS

(75) Inventors: Thomas Glanmor Davies, Cambridge (GB); Michelle Dawn Garrett, Surrey (GB); Robert George Boyle, Cambridge (GB); Ian Collins, Redhill (GB)

(73) Assignees: Astex Therapeutics Limited, Cambridge (GB); The Institute of Cancer Research: Royal Cancer Hospital, London (GB); Cancer Research Technology Limited, London (GB)

( * ) Notice: Subject to any disclaimer, the term of this patent is extended or adjusted under 35 U.S.C. 154(b) by 691 days.

(21) Appl. No.: 12/298,462

(22) PCT Filed: Apr. 25, 2007

(86) PCT No.: PCT/GB2007/001518
§ 371 (c)(1),
(2), (4) Date: Oct. 24, 2008

(87) PCT Pub. No.: WO2007/125321
PCT Pub. Date: Nov. 8, 2007

(65) Prior Publication Data
US 2010/0022564 A1 Jan. 28, 2010

(30) Foreign Application Priority Data

Apr. 25, 2006 (GB) .................................. 0608176.4
Apr. 25, 2006 (GB) .................................. 0608179.8

(51) Int. Cl.
*A61K 31/519* (2006.01)
*A61K 31/44* (2006.01)
*C07D 471/04* (2006.01)
*C07D 473/34* (2006.01)

(52) U.S. Cl.
CPC ............ *C07D 471/04* (2013.01); *C07D 473/34* (2013.01)
USPC .......................... 514/265.1; 514/341; 514/343

(58) Field of Classification Search
CPC ............................. C07D 471/04; C07D 473/34
USPC ........................................ 514/265.1, 341, 343
See application file for complete search history.

(56) References Cited

U.S. PATENT DOCUMENTS 6,162,804 A 12/2000 Bilodeau et al.
6,432,947 B1 8/2002 Arnaiz et al.

(Continued)

FOREIGN PATENT DOCUMENTS

EP 1444982 A1 8/2004
GB 1047935 A 11/1966

(Continued)

OTHER PUBLICATIONS

Calabresi P and Chabner BA, "Section IX Chemotherapy of Neoplastic Diseases—Introduction," Goodman & Gilman's the Pharmacological Basis of Therapeutics 10th ed., 2001, Hardman JG, Limbird LE, and Gilman AG, Eds, McGraw-Hill, New York 2001, 1381-1388 (pp. 1381, 1383-1385, and 1388 provided).*
Dowling RJ, Topisirovic I, Fonseca BD, and Sonenberg N, "Dissecting the role of mTOR: lessons from mTOR inhibitors.," Biochimica et Biophysica Acta, Mar. 2010, 1804(3), 433-439.*
Emory University, CancerQuest.org, http://www.cancerquest.org/index.cfm?/page=381, accessed Jul. 2, 2010.*
Gibbons JJ, Abraham RT, and Yu K, "Mammalian target of rapamycin: discovery of rapamycin reveals a signaling pathway important for normal and cancer cell growth," Seminars in Oncology, Dec. 2009, 8(23), 3831-3837.*

(Continued)

*Primary Examiner* — Paul Zarek
(74) *Attorney, Agent, or Firm* — Heslin Rothenberg Farley & Mesiti P.C.

(57) ABSTRACT

The invention provides a compound of the formula (I) or salts, solvates, tautomers or N-oxides thereof, wherein T is N or $CR^5$; $J^1$-$J^2$ is N=C($R^6$), ($R^7$)C=N, ($R^8$)N—C(O), ($R^8$)$_2$C—C(O), N=N or ($R^7$)C=C($R^6$); E is a monocyclic carbocyclic or heterocyclic group of 5 or 6 ring members, the heterocyclic group containing up to 3 heteroatoms selected from O, N and S; $Q^1$ is a bond or a saturated $C_{1-3}$ hydrocarbon linker group, one of the carbon atoms in the linker group being optionally be replaced by an oxygen or nitrogen atom, or an adjacent pair of carbon atoms may be replaced by $CONR^q$ or $NR^qCO$ where $R^q$ is hydrogen or methyl, or $R^q$ is a $C_{1-4}$alkylene chain linked to $R^1$ or a carbon atom of $Q^1$ to form a cyclic moiety; and wherein the carbon atoms of the linker group $Q^1$ may optionally bear one or more substituents selected from fluorine and hydroxy; $Q^2$ is a bond or a saturated hydrocarbon linker group containing from 1 to 3 carbon atoms, wherein one of the carbon atoms in the linker group may optionally be replaced by an oxygen or nitrogen atom; and wherein the carbon atoms of the linker group may optionally bear one or more substituents selected from fluorine and hydroxy, provided that the hydroxy group when present is not located at a carbon atom α with respect to the G group; and provided that when E is aryl or heteroaryl, then $Q^2$ is other than a bond; G is hydrogen, $NR^2R^3$, OH or SH provided that when E is aryl or heteroaryl and $Q^2$ is a bond, then G is hydrogen; $R^1$ is hydrogen or an aryl or heteroaryl group, with the proviso that when $R^1$ is hydrogen and G is $NR^2R^3$, then $Q^2$ is a bond; and $R^2$, $R^3R^4$, $R^6$ and $R^8$ are as defined in the claims, wherein the compound is for use in: (a) the treatment or prophylaxis of a disease or condition in which the modulation (e.g. inhibition) of ROCK kinase or protein kinase P70S6K is indicated; and/or (b) the treatment of a subject or patient population in which the modulation (e.g. inhibition) of ROCK kinase or protein kinase P70S6K is indicated.

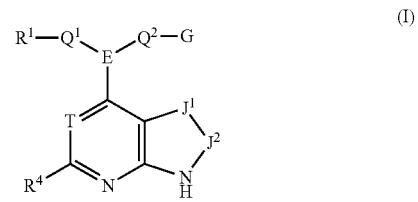

(I)

17 Claims, No Drawings

(56) References Cited

U.S. PATENT DOCUMENTS

| | | | |
|---|---|---|---|
| 8,546,407 | B2 | 10/2013 | Berdini et al. |
| 2002/0094974 | A1 | 7/2002 | Castelhano et al. |
| 2003/0045536 | A1 | 3/2003 | Castelhano et al. |
| 2003/0073708 | A1 | 4/2003 | Castelhano et al. |
| 2003/0139427 | A1 | 7/2003 | Castelhano et al. |
| 2004/0082598 | A1 | 4/2004 | Castelhano et al. |
| 2004/0082599 | A1 | 4/2004 | Castelhano et al. |
| 2006/0111362 | A1 | 5/2006 | Kira et al. |
| 2006/0148844 | A1 | 7/2006 | Nakade et al. |
| 2007/0135402 | A1 | 6/2007 | Habashita et al. |
| 2008/0070936 | A1 | 3/2008 | Castelhano et al. |

FOREIGN PATENT DOCUMENTS

| | | | |
|---|---|---|---|
| WO | 9500516 | | 1/1995 |
| WO | 9738665 | | 10/1997 |
| WO | 9907703 | | 2/1999 |
| WO | 9962908 | | 12/1999 |
| WO | 9965908 | | 12/1999 |
| WO | 9965909 | | 12/1999 |
| WO | 0075145 | A1 | 12/2000 |
| WO | 0107050 | A1 | 2/2001 |
| WO | 0146196 | A1 | 6/2001 |
| WO | 0218348 | A2 | 3/2002 |
| WO | 02057267 | A1 | 7/2002 |
| WO | 03057696 | A1 | 7/2003 |
| WO | 03088908 | A2 | 10/2003 |
| WO | 2004014850 | A2 | 2/2004 |
| WO | 2004037823 | A1 | 5/2004 |
| WO | 2004043380 | A2 | 5/2004 |
| WO | 2004074287 | A1 | 9/2004 |
| WO | 2004080463 | A1 | 9/2004 |
| WO | 2004094426 | A1 | 11/2004 |
| WO | 2005003128 | A1 | 1/2005 |
| WO | 2005020921 | A2 | 3/2005 |
| WO | 2005026149 | A1 | 3/2005 |
| WO | 2005044181 | A2 | 5/2005 |
| WO | 2005051304 | A2 | 6/2005 |
| WO | 2005117909 | A2 | 12/2005 |
| WO | WO 2005/117909 | * 12/2005 | ......... A61K 31/7076 |
| WO | 2006046023 | A1 | 5/2006 |
| WO | 2006046024 | A1 | 5/2006 |
| WO | 2006071819 | A1 | 7/2006 |
| WO | 2006075094 | A2 | 7/2006 |
| WO | 2006075095 | A2 | 7/2006 |
| WO | 2006091450 | A1 | 8/2006 |
| WO | 2006135639 | A1 | 12/2006 |
| WO | 2007007919 | A2 | 1/2007 |
| WO | 2007025090 | A2 | 3/2007 |
| WO | 2007084667 | A2 | 7/2007 |
| WO | 2007125310 | A2 | 11/2007 |
| WO | 2007125315 | A2 | 11/2007 |
| WO | 2007125320 | A1 | 11/2007 |
| WO | 2007125321 | A2 | 11/2007 |
| WO | 2007125325 | A1 | 11/2007 |
| WO | 2008075109 | A1 | 6/2008 |
| WO | 2008075110 | A1 | 6/2008 |
| WO | 2009047563 | A1 | 4/2009 |

OTHER PUBLICATIONS

National Institute on Aging, NIH, "AgePage," http://www.nia.nih.gov/HealthInformation/Publications/cancer.htm, accessed Jul. 2, 2010.*

Olson MF, "Applications for Rock kinase inhibition," Current Opinion in Cell Biology, Apr. 2008, 20(2), 242-248.*

Pollard JR and Mortimore M, "Discovery and development of aurora kinase inhibitors as anticancer agents," Journal of Medicinal Chemistry, May 2009, 52(9), 2629-2651.*

Vippagunta SR, Brittain HG, and Grant D J, "Crystalline solids," Advanced Drug Delivery Reviews, May 2001,48(1), 3-26.*

Kinzler K and Vogelstein B, "The Genetic Basis of Human Cancer 2nd ed." Vogelstein B and Kinzler K Eds, McGraw-Hill, 2002 (p. 3 provided).*

Barnett et al : "The Akt/PKB Family of 1-15 Protein Kinases : A Review of Small Molecule Inhibitors and Progress Towards Target Validation" Current Topics in Medicinal Chemistry, Bentham Science Publishers, Hilversum, NL, vol. 5, No. 2, Jan. 1, 2005, pp. 109-125, XP009074071, ISSN : 1568-0266.

Quintela J M et al "Pyrazolopyrimidines: synthesis, effect on histamine release from rat peritoneal mast cells and cytotoxic activity" European Journal of Medicinal Chemistry, Elsevier, Paris vol. 36, No. 4, May 2001, pp. 321-322 (ISSN 0223-5234).

"Substances with antineoplastic activity II. 6-carboxyalkylthiopurines", M. Semonsky et al, Collection of Czechoslovakian Chemical Communications, (1960), 25, 1091-1099.

"Potential Purine Antagonists. XIV. Synthesis of some 4-(substitutedamino)pyrazolo-[3,4-d]pyrimidines", C. W. Noell & R. K. Robins, J. Org. Chem., (1958), 23, 1547-1550.

"Weitere Untersuchungen an $N^6$-Derivaten des Adenins" ("Further studies on N6-derivatives of adenine"), H. Lettre & H. Ballweg, Naturwissenschaften, (1958), 45, 364.

"Structure-activity relationships among purines related to 6-mercaptopurine" Cancer Research, (1958), 18, 445-456.

"Synthesis of potent anticancer agents" K Panagopolous et al Arzneimittel-Forschung, (1965), 15(3), 204-207.

Chemical Abstract No. 106:196130 & JP 62010085A2 (Yoshitomi).

International Search Report and Written Opinion of the International Searching Authority, issued in connection with International Application No. PCT/GB2007/001518.

Luke, Richard; "Discovery of AZD5363—An orally bioavailable, potent inhibitor of AKT kinases;" PowerPoint talk slides; May 21, 2012; Oncology Innovative Medicines, AstraZeneca, Alderley Park, UK.

Luke et al. "Discovery of AZD5363, an orally bioavailable, potent, ATP-competitive inhibitor of AKT kinases;" American Association for Cancer Research poster; Apr. 2011; Oncology iMed, AstraZeneca, Alderley Park, Macclesfield, UK.

Davies et al. "CCT129254 (AT11854) is a well tolerated, orally bioavailable inhibitor of AKT/PKB with pharmacodynamic and antitumor activity in a range of preclinical models;" American Association for Cancer Research poster; Nov. 2009; Astra Zeneca, Alderley Park, Macclesfield, UK; Astex Therapeutics, Cambridge, UK; Cancer Research UK Centre for Cancer Therapeutics at The Institute for Cancer Research, Sutton, UK.

U.S. Appl. No. 14/017,814, Berdini et al., filed Sep. 4, 2013.

* cited by examiner

PURINE AND DEAZAPURINE DERIVATIVES AS PHARMACEUTICAL COMPOUNDS

CROSS REFERENCE TO RELATED APPLICATIONS

This application is a national phase filing under 35 U.S.C. §371 of PCT International Application PCT/GB2007/001518, filed Apr. 25, 2007, and published under PCT Article 21(2) in English as WO 2007/125321 A2 on Nov. 8, 2007. PCT/GB2007/001518 claimed priority from British application Nos. 0608176.4 filed on Apr. 25, 2006 and 0608179.8 filed on Apr. 25, 2006. The entire contents of each of the prior applications are incorporated herein by reference.

TECHNICAL FIELD

This invention relates to the use of purine, purinone and deazapurine and deazapurinone compounds in: (a) the treatment or prophylaxis of a disease or condition in which the modulation (e.g. inhibition) of ROCK kinase is indicated; and/or (b) the treatment of a subject or patient population in which the modulation (e.g. inhibition) of ROCK kinase is indicated; and/or (c) the treatment or prophylaxis of a disease or condition in which the modulation (e.g. inhibition) of protein kinase p70S6K is indicated; and/or (d) the treatment of a subject or patient population in which the modulation (e.g. inhibition) of protein kinase p70S6K is indicated. The invention also relates to said compounds for said uses and to various pharmaceutical compositions containing the purine, purinone and deazapurine and deazapurinone compounds.

BACKGROUND OF THE INVENTION

Protein Kinases

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J.*, 9:576-596 (1995); Knighton, et al., *Science*, 253:407-414 (1991); Hiles, et al., *Cell*, 70:419-429 (1992); Kunz, et al., *Cell*, 73:585-596 (1993); Garcia-Bustos, et al., *EMBO J.*, 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Apoptosis or programmed cell death is an important physiological process which removes cells no longer required by an organism. The process is important in early embryonic growth and development allowing the non-necrotic controlled breakdown, removal and recovery of cellular components. The removal of cells by apoptosis is also important in the maintenance of chromosomal and genomic integrity of growing cell populations. There are several known checkpoints in the cell growth cycle at which DNA damage and genomic integrity are carefully monitored. The response to the detection of anomalies at such checkpoints is to arrest the growth of such cells and initiate repair processes. If the damage or anomalies cannot be repaired then apoptosis is initiated by the damaged cell in order to prevent the propagation of faults and errors. Cancerous cells consistently contain numerous mutations, errors or rearrangements in their chromosomal DNA. It is widely believed that this occurs in part because the majority of tumours have a defect in one or more of the processes responsible for initiation of the apoptotic process. Normal control mechanisms cannot kill the cancerous cells and the chromosomal or DNA coding errors continue to be propagated. As a consequence restoring these pro-apoptotic signals or suppressing unregulated survival signals is an attractive means of treating cancer.

The signal transduction pathway containing the enzymes phosphatidylinositol 3-kinase (PI3K), PDK1 and PKB amongst others, has long been known to mediate increased resistance to apoptosis or survival responses in many cells. There is a substantial amount of data to indicate that this pathway is an important survival pathway used by many growth factors to suppress apoptosis. The enzymes of the PI3K family are activated by a range of growth and survival factors e.g. EGF, PDGF and through the generation of polyphosphatidylinositols, initiates the activation of the downstream signalling events including the activity of the kinases PDK1 and protein kinase B (PKB) also known as akt. This is also true in host tissues, e.g. vascular endothelial cells as well as neoplasias.

Protein Kinase p70S6K

The 70 kDa ribosomal protein kinase p70S6K (also known as SK6, p70/p85 S6 kinase, p70/p85 ribosomal S6 kinase and pp 70s6k) is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. This response may be under the control of mTOR since rapamycin acts to inhibit p70S6K activity and blocks protein synthesis, specifically as a result of a down-regulation of translation of these mRNA's encoding ribosomal proteins. p70S6K is also regulated by PI3K and its downstream target AKT. Wortmannin and rapamycin cause a decrease in p70S6K phosphorylation at sites dependent of the PI3K pathway. Mutant p70S6K is inhibited by wortmannin but not by rapamycin suggesting that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidime tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indication that p70S6K function is essential for the progression from G1 to S phase in the cell cycle. Furthermore inhibition of cell cycle proliferation at the G1 to S phase of the cell cycle by rapamycin has been identified as a consequence of inhibition of the production of the hyperphosphorylated, activated form of p70S6K.

The tumor suppressor LKB1 activates AMPK which phosphorylates the TSC1/2 complex in the mTOR/p70S6K pathway, therefore feeds into p70S6K through a PKB independent pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations.

A role for p70S6K in tumor cell proliferation and protection of cells from apoptosis is supported based on its participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11—Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M Barlund, O Monni, J Kononen, R Cornelison, J Torhorst, G Sauter, O-P Kallioniemi and Kallioniemi A, *Cancer Res.*, 2000, 60:5340-5346). It has been shown that 17q23 amplifications in breast cancer involve the PAT1, RAD51C, PS6K, and SIGMA1B genes (Cancer Res. (2000): 60, pp. 5371-5375).

The p70S6K gene has been identified as a target of amplification and overexpression in this region, and statistically significant association between amplification and poor prognosis has been observed.

Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported.

p70S6K has been implicated in metabolic diseases and disorders. It was reported that the absence of p70S6 protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

ROCK Kinases

The ROCK kinase family comprises two known members: ROCK1 and ROCK2:
ROCK1. Synonyms: Rho-associated protein kinase 1; p160 ROCK; P160 ROK; p160 ROCK-1, Rho-associated, coiled-coil containing protein kinase 1; Rho kinase 1; ROK beta.
ROCK2. Synonyms: Rho-associated protein kinase 2; p164 ROCK; p164 ROK; p164 ROCK-2; Rho-associated, coiled-coil containing protein kinase 2, Rho kinase 2; ROK alpha.

The process of metastasis involves a restructuring of the cytoskeleton as well as cell-cell and cell-matrix adhesions allowing cells to break away from the tumor mass, invade local tissue, and ultimately spread throughout the body. These effects on cell morphology and adhesion are regulated by members of the Rho GTPase family.

Activated RhoA is capable of interacting with several effecter proteins including the ROCK kinases ROCK1 and ROCK2. ROCK1 and ROCK2 can be activated by the RhoA-GTP complex via physical association. Activated ROCKs phosphorylate a number of substrates and play important roles in pivotal cellular functions. The substrates for ROCKs include myosin binding subunit of myosin light chain phosphatase (MBS, also named MYPT1), adducin, moesin, myosin light chain (MLC), LIM kinase, and the transcription factor FHL. The phosphorylation of theses substrates modulate the biological activity of the proteins and provide a means to alter a cell's response to external stimuli.

Elevated expression of RhoA and RhoC, as well as the Rho effector proteins ROCK1 and ROCK2, are commonly observed in human cancers, including in the progression of testicular germ cell tumours, small breast carcinomas with metastatic ability, invasion and metastasis of bladder cancer, tumor progression in ovarian carcinoma.

Progression of tumors to invasive and metastatic forms requires that tumor cells undergo dramatic morphologic changes, a process regulated by Rho GTPases. Actomyosin contractility is a mechanism by which cells exert locomotory force against their environment. Signalling downstream of the small GTPase Rho increases contractility through ROCK-mediated regulation of myosin-II light chain (MLC2) phosphorylation.

The ROCK kinases are thought to participate in the induction of focal adhesions and stress fibers and to mediate calcium sensitization of smooth muscle contraction by enhancing phosphorylation of the regulatory light chain of myosin.

In vivo studies have also shown that ROCK inhibition reduced the invasiveness of several tumor cell lines. ROCK inhibitors, such as Y-27632 or WF-536, have been used in some studies to demonstrate these properties.

Inhibitors of ROCKs have been suggested for use in the treatments of a variety of diseases. These include cardiovascular diseases such as hypertension, chronic and congestive heart failure, cardiac hypertrophy, restenosis, chronic renal failure and atherosclerosis. Also, because of its muscle relaxing properties, inhibitors may also be suitable for asthma, male erectile dysfunction, female sexual dysfunction and over-active bladder I syndrome.

ROCK inhibitors have been shown to possess anti-inflammatory properties. Thus they can be used as treatment for neuroinflammatory diseases such as stroke, multiple sclerosis, Alzheimer's disease, Parkinson's disease, amyotrophic lateral sclerosis and inflammatory pain, as well as other inflammatory diseases such as rheumatoid arthritis, irritable bowel syndrome, and inflammatory bowel disease. Based on their neurite outgrowth inducing effects, ROCK inhibitors could be useful drugs for neuronal regeneration, inducing new axonal growth and axonal rewiring across lesions within the CNS. ROCK inhibitors are therefore likely to be useful for regenerative treatment of CNS disorders such as spinal cord injury, acute neuronal injury (stroke, traumatic brain injury), Parkinsons disease, Alzheimers disease and other neurodegenerative disorders. Since ROCK inhibitors reduce cell proliferation and cell migration, they could be useful in treating cancer and tumor metastasis. Finally, there is evidence to suggest that ROCK inhibitors suppress cytoskeletal rearrangement upon virus invasion, thus they also have potential therapeutic value in anti-viral and anti-bacterial applications. ROCK inhibitors are also useful for the treatment of insulin resistance and diabetes.

ROCK Inhibitor Y-27632

Adhesion of tumour cells to host cell layers and subsequent transcellular migration are pivotal steps in cancer invasion and metastasis. The small GTPase Rho controls cell adhesion and motility through reorganization of the actin cytoskeleton and regulation of actomyosin contractility. Cultured rat MM1 hepatoma cells migrate in a serum-dependent, Rho-mediated manner, through a mesothelial cell monolayer in vitro. Among several proteins isolated as putative target molecules of Rho, the ROCK kinases are thought to participate in the induction of focal adhesions and stress fibres in cultured cells, and to mediate calcium sensitization of smooth muscle contraction by enhancing phosphorylation of the regulatory light chain of myosin. Transfection of MM1 cells with cDNA encoding a dominant active mutant of ROCK conferred invasive activity independently of serum and Rho. In contrast, expression of a dominant negative, kinase-defective ROCK mutant substantially attenuated the invasive phenotype.

A specific ROCK inhibitor (Y-27632) blocked both Rho-mediated activation of actomyosin and invasive activity of these cells. Furthermore, continuous delivery of this inhibitor using osmotic pumps considerably reduced the dissemination of MM1 cells implanted into the peritoneal cavity of syngeneic rats. These results indicate that ROCK plays an essential part in tumor cell invasion, and demonstrate its potential as a therapeutic target for the prevention of cancer invasion and metastasis.

VEGF induced the activation of RhoA and recruited RhoA to the cell membrane of human ECs. This increase in RhoA activity is necessary for the VEGF-induced reorganization of the F-actin cytoskeleton, as demonstrated by adenoviral transfection of dominant-negative RhoA. Rho kinase mediated this effect of RhoA, as was demonstrated by the use of Y-27632, a specific inhibitor of Rho kinase. Inhibition of Rho kinase prevented the VEGF-enhanced EC migration in response to mechanical wounding but had no effect on basal EC migration. Furthermore, in an in vitro model for angiogenesis, inhibition of either RhoA or Rho kinase attenuated the VEGF-mediated ingrowth of ECs in a 3-dimensional fibrin matrix. CONCLUSIONS: VEGF-induced cytoskeletal changes in ECs require RhoA and Rho kinase, and activation of RhoA/Rho kinase signaling is involved in the VEGF-induced in vitro EC migration and angiogenesis.

Y-27632 can relax smooth muscle and increase vascular blood flow. Y-27632 is a small molecule that can enter cells and is not toxic in rats after oral administration of 30 mg/kg for 10 days. Effective doses for the use of this compound are approximately 30 uM. It reduces blood pressure in hypertensive rats, but does not affect blood pressure in normal rats. This has led to the identification of Rho signalling antagonists in treatment of hypertension (Somlyo, 1997 Nature 389:908; Uehata et al., 1997 Nature 389:990).

The use of a specific inhibitor of ROCK, Y-27632 (Uehata, et al., Nature, 389, 990 994, 1997, Davies, et al., Biochemical Journal., 351, 95-105, 2000, and Ishizaki, et al., Molecular Pharmacology., 57, 976-983, 2000), has demonstrated a role for this enzyme in Ca2+ independent regulation of contraction in a number of tissues, including vascular (Uehata, et al., Nature., 389, 990-994, 1997), airway (Ilikuka et al., European Journal of 30 Pharmacology., 406, 273-279, 2000) and genital (Chitaley et al., Nature Medicine., 7(1), 119-122, 2001) smooth muscles. In addition, Jezior et al. British Journal of Pharmacology., 134, 78-87, 2001 have shown that Y-27632 attenuates bethanechol-evoked contractions in isolated rabbit urinary 35 bladder smooth muscle.

The Rho kinase inhibitor Y-27632 has been tested for the following disease applications:

Hypertension (Uehata et al., 1997 IBID; Chitaley et al., 2001a IBID; Chrissobolis and 15 Sobey, 2001 C. Circ. Res 88:774)

Asthma (Iizuka et al., 2000 Eur. J. Pharmacol 406:273; Nakahara et al. Eur. J. Pharmacol 389:103, 2000)

Pulmonary vasoconstriction (Takamura et al., 2001 Hepatology 33:577)

Vascular disease (Miyata et al., 2000 Thromb Vasc Biol 20:2351; Robertson et al., 2000 Br. J. Pharmacol 131:5)

Penile erectile dysfunction (Chitaley et al., 2001b Nature Medicine 7:119; Mills et al., 2001 J. Appl. Physiol. 91: 1269; Rees et al., Br. J. Pharmacol 133:455 2001)

Glaucoma (Honjo et al., 2001 Methods Enzymol 42:137; Rao et al., 2001 Invest. Opthalmol. Urs. Sci. 42:1029)

Cell transformation (Sahai et al., 1999 Curr. Biol. 9:136-5)

Prostate cancer metastasis (Somlyo et al., 2000 BBRC 269:652)

Hepatocellular carcinoma and metastasis (Imamura et al., 2000; Takamura et al., 2001)

Liver fibrosis (Tada et al., 2001 J. Hepatol 34:529; Wang et al., 2001 Am. J. Respir. Cell Mol. Biol. 25:628)

Kidney fbrosis (Ohlci et al., J. Heart Lung Transplant 20:956 2001)

Cardioprotection and allograft survival (Ohici et al., 2001 IBID)

Cerebral vasospasm (Sato et al., 2000 Circ. Res 87: 195).

ROCK Kinase and Cardiovascular Disease

There is growing evidence that ROCKs, the immediate downstream targets of the small guanosine triphosphate-binding protein Rho, may contribute to cardiovascular disease. ROCKs play a central role in diverse cellular functions such as smooth muscle contraction, stress fiber formation and cell migration and proliferation. Overactivity of ROCKs is observed in cerebral ischemia, coronary vasospasm, hypertension, vascular inflammation, arteriosclerosis and atherosclerosis. ROCKs, therefore, may be an important and still relatively unexplored therapeutic target in cardiovascular disease. Recent experimental and clinical studies using ROCK inhibitors such as Y-27632 and fasudil have revealed a critical role of ROCKs in embryonic development, inflammation and oncogenesis. This review will focus on the potential role of ROCKs in cellular functions and discuss the prospects of ROCK inhibitors as emerging therapy for cardiovascular diseases.

Abnormal smooth-muscle contractility may be a major cause of disease states such as hypertension, and a smooth-muscle relaxant that modulates this process would be useful therapeutically. Smooth-muscle contraction is regulated by the cytosolic Ca2+ concentration and by the Ca2+ sensitivity of myofilaments: the former activates myosin light-chain kinase and the latter is achieved partly by inhibition of myosin phosphatase.

Rho signaling pathways in vascular smooth muscle cells are highly activated in hypertension, a condition associated with a variety of vascular diseases, including restenosis injury and atherosclerosis.

Hypertension is a cardiovascular disorder characterized by increased peripheral vascular resistance and/or vascular structural remodeling. Recently, rapidly growing evidence from hypertensive animal models suggests that small GTPase Rho and its downstream effector, Rho-kinase, play an important role in the pathogenesis of hypertension. Activation of the Rho/Rho-kinase pathway is essential for smooth muscle contractility in hypertension. A greater RhoA expression and an enhanced RhoA activity have been observed in aortas of hypertensive rats, such as genetic spontaneously hypertensive rats and N(omega)-nitro-L-arginine methyl ester-induced hypertension.

ROCK Kinase and Neurological Diseases

Abnormal activation of the Rho/ROCK pathway has been observed in various disorders of the central nervous system. Injury to the adult vertebrate brain and spinal cord activates ROCKs, thereby inhibiting neurite growth and sprouting. Inhibition of ROCKs results in accelerated regeneration and enhanced functional recovery after spinal-cord injury in mammals, and inhibition of the Rho/ROCK pathway has also proved to be efficacious in animal models of stroke, inflammatory and demyelinating diseases, Alzheimer's disease and neuropathic pain. ROCK inhibitors therefore have potential for preventing neurodegeneration and stimulating neuroregeneration in various neurological disorders.

The development of a neuron requires a series of steps that begins with migration from its birth place and initiation of process outgrowth, and ultimately leads to differentiation and the formation of connections that allow it to communicate with appropriate targets. Over the past several years, it has become clear that the Rho family of GTPases and related molecules play an important role in various aspects of neuronal development, including neurite outgrowth and differentiation, axon pathfinding, and dendritic spine formation and maintenance.

One common denominator for both neurite outgrowth inhibition and neurite repulsion is actin rearrangements within the growth cone. Central to the regulation of the actin cytoskeleton in both neuronal and non-neuronal cells is the Rho family of small GTPases. Rho family members cycle between an inactive GDP-bound form and an active GTP-bound form. Several lines of evidence suggest that manipulating the activity state of Rho GTPases may modulate growth cone collapse and neurite outgrowth inhibition.

More recently, behaviorally, inactivation of Rho pathway can induce rapid recovery of locomotion and progressive recuperation of forelimb-hindlimb coordination. These findings provide evidence that the Rho signaling pathway is a potential target for therapeutic interventions after spinal cord injury.

WO 93/13072 (Italfarmaco) discloses a class of bis-sulphonamido diamines as protein kinase inhibitors.

WO 99/65909 (Pfizer) discloses a class of pyrrole[2,3-d] pyrimidine compounds having protein tyrosine kinase activity and which are of potential use as immunosuppressant agents.

WO 2004/074287 (Astra Zeneca) discloses piperazinyl-pyridyl amides for use in treating autoimmune diseases such as arthritis. The piperazine group in the compounds can be linked to a purine group.

WO02/18348 (F. Hoffman La Roche) discloses a class of amino-quinazoline derivatives as alpha-1 adrenergic antagonists. A method for preparing the amino-quinazoline compounds involves the use of a gem-disubstituted cyclic amine such as piperidine in which one of the gem substituents is an aminomethyl group.

WO03/088908 (Bristol Myers Squibb) discloses N-heteroaryl-4,4-disubstituted piperidines as potassium channel inhibitors.

WO01/07050 (Schering) discloses substituted piperidines as nociceptin receptor ORL-1 agonists for use in treating cough.

US 2003/0139427 (OSI) discloses pyrrolidine- and piperidine-substituted purines and purine analogues having adenosine receptor binding activity.

WO 2004/043380 (Harvard College et al.) discloses technetium and rhenium labelled imaging agents containing disubstituted piperidine metal ion-chelating ligands.

WO 97/38665 (Merck) discloses gem-disubstituted piperidine derivatives having farnesyl transferase inhibitory activity.

EP 1568699 (Eisai) discloses 1,3-dihydroimidazole fused ring compounds having DPPIV-inhibiting activity. The compounds are described as having a range of potential uses including the treatment of cancer.

US 2003/0073708 and US 2003/045536 (both in the name of Castelhano et al, WO 02/057267 (OSI Pharmaceuticals) and WO 99/62518 (Cadus Pharmaceutical Corporation) each disclose a class of 4-aminodeazapurines in which the 4-amino group can form part of a cyclic amine such as azetidine, pyrrolidine and piperidine. The compounds are described as having adenosine receptor antagonist activity.

U.S. Pat. No. 6,162,804 (Merck) discloses a class of benzimidazole and aza-benzimidazole compounds that have tyrosine kinase inhibitor activity.

SUMMARY OF THE INVENTION

The present invention is based, at least in part, on the discovery of a variety of novel medical applications for compounds having the formula (I) as defined herein.

In particular, the present inventors have now discovered that compounds of the formula (I) find application in: (a) the treatment or prophylaxis of a disease or condition in which the modulation (e.g. inhibition) of ROCK kinase or protein kinase P70S6K is indicated; and/or (b) the treatment of a subject or patient population in which the modulation (e.g. inhibition) of ROCK kinase or protein kinase P70S6K is indicated.

Accordingly, in one aspect, the invention provides a compound of the formula (I):

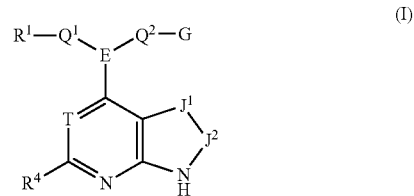

or salts, solvates, tautomers or N-oxides thereof, wherein
T is N or a group $CR^5$;
$J^1$-$J^2$ represents a group selected from $N=C(R^6)$, $(R^7)C=N$, $(R^8)N-C(O)$, $(R^8)_2C-C(O)$, $N=N$ and $(R^7)C=C(R^6)$;
E is a monocyclic carbocyclic or heterocyclic group of 5 or 6 ring members wherein the heterocyclic group contains up to 3 heteroatoms selected from O, N and S;

$Q^1$ is a bond or a saturated hydrocarbon linker group containing from 1 to 3 carbon atoms, wherein one of the carbon atoms in the linker group may optionally be replaced by an oxygen or nitrogen atom, or an adjacent pair of carbon atoms may be replaced by $CONR^q$ or $NR^qCO$ where $R^q$ is hydrogen, $C_{1-4}$ alkyl or cyclopropyl, or $R^q$ is a $C_{1-4}$ alkylene chain that links to $R^1$ or to another carbon atom of $Q^1$ to form a cyclic moiety; and wherein the carbon atoms of the linker group $Q^1$ may optionally bear one or more substituents selected from fluorine and hydroxy;

$Q^2$ is a bond or a saturated hydrocarbon linker group containing from 1 to 3 carbon atoms, wherein one of the carbon atoms in the linker group may optionally be replaced by an oxygen or nitrogen atom; and wherein the carbon atoms of the linker group may optionally bear one or more substituents selected from fluorine and hydroxy, provided that the hydroxy group when present is not located at a carbon atom a with respect to the G group;

G is selected from hydrogen, $NR^2R^3$, OH and SH with the proviso that when E is aryl or heteroaryl and $Q^2$ is a bond, then G is hydrogen;

$R^1$ is hydrogen or an aryl or heteroaryl group, with the proviso that when $R^1$ is hydrogen and G is $NR^2R^3$, then $Q^2$ is a bond;

$R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, hydroxy, cyano, amino, methylamino, dimethylamino, methoxy and a monocyclic or bicyclic aryl or heteroaryl group;

or $R^2$ and $R^3$ together with the nitrogen atom to which they are attached form a cyclic group selected from an imidazole group and a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the group $Q^2$ form a saturated monocyclic heterocyclic group having 4-7 ring members and optionally containing a second heteroatom ring member selected from O and N;

or $NR^2R^3$ when present and a carbon atom of linker group $Q^2$ to which it is attached together form a cyano group; and $R^4$, $R^6$ and $R^8$ are each independently selected from hydrogen, halogen, $C_{1-5}$ saturated hydrocarbyl, cyano, $CONH_2$, $CONHR^9$, $CF_3$, $NH_2$, $NHCOR^9$ and $NHCONHR^9$;

$R^5$ and $R^7$ are each independently selected from hydrogen, halogen, $C_{1-5}$ saturated hydrocarbyl, cyano and $CF_3$;

$R^9$ is phenyl or benzyl each optionally substituted by one or substituents selected from halogen, hydroxy, trifluoromethyl, cyano, nitro, carboxy, amino, mono- or di-$C_{1-4}$ hydrocarbylamino; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$;

wherein the compound is for use in: (a) the treatment or prophylaxis of a disease or condition in which the modulation (e.g. inhibition) of ROCK kinase or protein kinase P70S6K is indicated; and/or (b) the treatment of a subject or patient population in which the modulation (e.g. inhibition) of ROCK kinase or protein kinase P70S6K is indicated.

In a further aspect, the invention provides a compound of the formula (Ia):

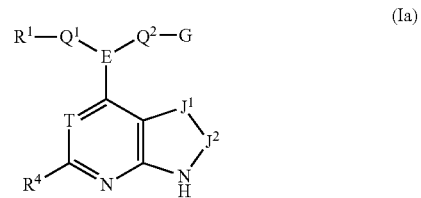

(Ia)

or salts, solvates, tautomers or N-oxides thereof, wherein

T is N or a group $CR^5$;

$J^1$-$J^2$ represents a group selected from N=$C(R^6)$, $(R^7)C$=N, $(R^8)$N—$C(O)$, $(R^8)_2C$—$C(O)$, N=N and $(R^7)C$=$C(R^6)$;

E is a monocyclic carbocyclic or heterocyclic group of 5 or 6 ring members wherein the heterocyclic group contains up to 3 heteroatoms selected from O, N and S;

$Q^1$ and $Q^2$ are the same or different and are each a bond or a saturated hydrocarbon linker group containing from 1 to 3 carbon atoms, wherein one of the carbon atoms in the linker group may optionally be replaced by an oxygen or nitrogen atom; and wherein the carbon atoms of the or each linker group $Q^1$ and $Q^2$ may optionally bear one or more substituents selected from fluorine and hydroxy, provided that the hydroxy group when present is not located at a carbon atom a with respect to the G group;

G is selected from hydrogen, $NR^2R^3$, OH and SH with the proviso that when E is aryl or heteroaryl and $Q^2$ is a bond, then G is hydrogen;

$R^1$ is hydrogen or an aryl or heteroaryl group, with the proviso that when $R^1$ is hydrogen and G is $NR^2R^3$, then $Q^2$ is a bond;

$R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, hydroxy, amino, methylamino, dimethylamino, methoxy and a monocyclic or bicyclic aryl or heteroaryl group;

or $R^2$ and $R^3$ together with the nitrogen atom to which they are attached form a cyclic group selected from an imidazole group and a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the group $Q^2$ form a saturated monocyclic heterocyclic group having 4-7 ring members and optionally containing a second heteroatom ring member selected from O and N;

or $NR^2R^3$ when present and a carbon atom of linker group $Q^2$ to which it is attached together form a cyano group; and $R^4$, $R^6$ and $R^8$ are each independently selected from hydrogen, halogen, $C_{1-5}$ saturated hydrocarbyl, cyano, $CONH_2$, $CONHR^9$, $CF_3$, $NH_2$, $NHCOR^9$ and $NHCONHR^9$;

R[5] and R[7] are each independently selected from hydrogen, halogen, $C_{1-5}$ saturated hydrocarbyl, cyano and $CF_3$;

R[9] is phenyl or benzyl each optionally substituted by one or substituents selected from halogen, hydroxy, trifluoromethyl, cyano, nitro, carboxy, amino, mono- or di-$C_{1-4}$ hydrocarbylamino; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^1$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$;

wherein the compound is for use in: (a) the treatment or prophylaxis of a disease or condition in which the modulation (e.g. inhibition) of ROCK kinase or protein kinase P70S6K is indicated; and/or (b) the treatment of a subject or patient population in which the modulation (e.g. inhibition) of ROCK kinase or protein kinase P70S6K is indicated.

In another aspect, the invention provides a compound of the formula (Ib):

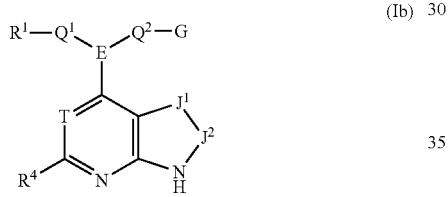

(Ib)

or salts, solvates, tautomers or N-oxides thereof, wherein
T is N or a group $CR^5$;
$J^1$-$J^2$ represents a group selected from N=C(R[6]), (R[7])C=N, (R[8])N—C(O), (R[8])$_2$C—C(O), N=N and (R[7])C=C(R[6]);
E is a monocyclic carbocyclic or heterocyclic group of 5 or 6 ring members wherein the heterocyclic group contains up to 3 heteroatoms selected from O, N and S;
$Q^1$ and $Q^2$ are the same or different and are each a bond or a saturated hydrocarbon linker group containing from 1 to 3 carbon atoms, wherein one of the carbon atoms in the linker group may optionally be replaced by an oxygen or nitrogen atom; and wherein the carbon atoms of the or each linker group $Q^1$ and $Q^2$ may optionally bear one or more substituents selected from fluorine and hydroxy, provided that the hydroxy group when present is not located at a carbon atom a with respect to the G group;
G is selected from hydrogen, $NR^2R^3$, OH and SH with the proviso that when E is aryl or heteroaryl and $Q^2$ is a bond, then G is hydrogen;
R[1] is hydrogen or an aryl or heteroaryl group, with the proviso that when R[1] is hydrogen and G is $NR^2R^3$, then $Q^2$ is a bond;
R[2] and R[3] are independently selected from hydrogen; $C_{1-4}$ hydrocarbyl and $C_{1-4}$ acyl wherein the hydrocarbyl and acyl groups are optionally substituted by a monocyclic or bicyclic aryl or heteroaryl group;

or R[2] and R[3] together with the nitrogen atom to which they are attached form a saturated monocyclic heterocyclic group having 4-7 ring members and optionally containing a second heteroatom ring member selected from O and N;

or one of R[2] and R[3] together with the nitrogen atom to which they are attached and one or more atoms from the group $Q^2$ form a saturated monocyclic heterocyclic group having 4-7 ring members and optionally containing a second heteroatom ring member selected from O and N;

or $NR^2R^3$ when present and a carbon atom of linker group $Q^2$ to which it is attached together form a cyano group; and R[4], R[6] and R[8] are each independently selected from hydrogen, halogen, $C_{1-5}$ saturated hydrocarbyl, cyano, $CONH_2$, $CONHR^9$, $CF_3$, $NH_2$, $NHCOR^9$ or $NHCONHR^9$;

R[5] and R[7] are each independently selected from hydrogen, halogen, $C_{1-5}$ saturated hydrocarbyl, cyano and $CF_3$;

R[9] is phenyl or benzyl each optionally substituted by one or substituents selected from halogen, hydroxy, trifluoromethyl, cyano, nitro, carboxy, amino, mono- or di-$C_{1-4}$ hydrocarbylamino; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$;

wherein the compound is for use in: (a) the treatment or prophylaxis of a disease or condition in which the modulation (e.g. inhibition) of ROCK kinase or protein kinase P70S6K is indicated; and/or (b) the treatment of a subject or patient population in which the modulation (e.g. inhibition) of ROCK kinase or protein kinase P70S6K is indicated.

In another aspect, the invention provides a compound of the formula (Ic):

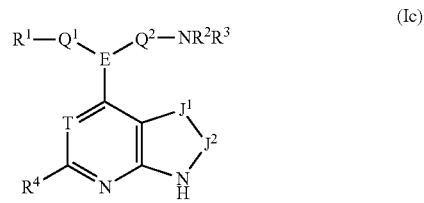

(Ic)

or salts, solvates, tautomers or N-oxides thereof, wherein
T is N or a group $CR^5$;
$J^1$-$J^2$ represents a group selected from N=C(R[6]), (R[7])C=N, (R[8])N—C(O), (R[8])$_2$C—C(O), N=N and (R[7])C=C(R[6]);

E is a monocyclic carbocyclic or heterocyclic group of 5 or 6 ring members wherein the heterocyclic group contains up to 3 heteroatoms selected from O, N and S;

$Q^1$ is a bond or a saturated hydrocarbon linker group containing from 1 to 3 carbon atoms, wherein one of the carbon atoms in the linker group may optionally be replaced by an oxygen or nitrogen atom, or an adjacent pair of carbon atoms may be replaced by $CONR^q$ or $NR^qCO$ where $R^q$ is hydrogen, $C_{1-4}$ alkyl or cyclopropyl, or $R^q$ is a $C_{1-4}$ alkylene chain that links to $R^1$ or to another carbon atom of $Q^1$ to form a cyclic moiety; and wherein the carbon atoms of the linker group $Q^1$ may optionally bear one or more substituents selected from fluorine and hydroxy;

$Q^2$ is a bond or a saturated hydrocarbon linker group containing from 1 to 3 carbon atoms, wherein one of the carbon atoms in the linker group may optionally be replaced by an oxygen or nitrogen atom; and wherein the carbon atoms of the linker group may optionally bear one or more substituents selected from fluorine and hydroxy, provided that the hydroxy group when present is not located at a carbon atom a with respect to the G group; and provided that when E is aryl or heteroaryl, then $Q^2$ is other than a bond;

$R^1$ is an aryl or heteroaryl group;

$R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, cyano, hydroxy, amino, methylamino, dimethylamino, methoxy and a monocyclic or bicyclic aryl or heteroaryl group;

or $R^2$ and $R^3$ together with the nitrogen atom to which they are attached form a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the group $Q^2$ form a saturated monocyclic heterocyclic group having 4-7 ring members and optionally containing a second heteroatom ring member selected from O and N;

or $NR^2R^3$ and a carbon atom of linker group $Q^2$ to which it is attached together form a cyano group; and $R^4$, $R^6$ and $R^8$ are each independently selected from hydrogen, halogen, $C_{1-5}$ saturated hydrocarbyl, cyano, $CONH_2$, $CONHR^9$, $CF_3$, $NH_2$, $NHCOR^9$ or $NHCONHR^9$;

$R^5$ and $R^7$ are each independently selected from hydrogen, halogen, $C_{1-5}$ saturated hydrocarbyl, cyano and $CF_3$;

$R^9$ is phenyl or benzyl each optionally substituted by one or substituents selected from halogen, hydroxy, trifluoromethyl, cyano, nitro, carboxy, amino, mono- or di-$C_{1-4}$ hydrocarbylamino; a group $R^a$-$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$;

wherein the compound is for use in: (a) the treatment or prophylaxis of a disease or condition in which the modulation (e.g. inhibition) of ROCK kinase or protein kinase P70S6K is indicated; and/or (b) the treatment of a subject or patient population in which the modulation (e.g. inhibition) of ROCK kinase or protein kinase P70S6K is indicated.

In another aspect, the invention provides a compound of the formula (Id):

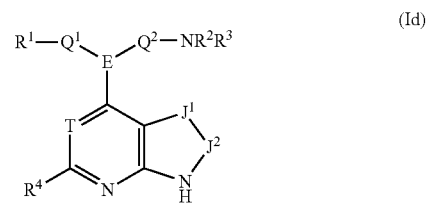

(Id)

or salts, solvates, tautomers or N-oxides thereof, wherein

T is N or a group $CR^5$;

$J^1$-$J^2$ represents a group selected from $N=C(R^6)$, $(R^7)C=N$, $(R^8)N-C(O)$, $(R^8)_2C-C(O)$, $N=N$ and $(R^7)C=C(R^6)$;

E is a monocyclic carbocyclic or heterocyclic group of 5 or 6 ring members wherein the heterocyclic group contains up to 3 heteroatoms selected from O, N and S;

$Q^1$ and $Q^2$ are the same or different and are each a bond or a saturated hydrocarbon linker group containing from 1 to 3 carbon atoms, wherein one of the carbon atoms in the linker group may optionally be replaced by an oxygen or nitrogen atom; and wherein the carbon atoms of the or each linker group $Q^1$ and $Q^2$ may optionally bear one or more substituents selected from fluorine and hydroxy, provided that the hydroxy group when present is not located at a carbon atom a with respect to the G group; and provided that when E is aryl or heteroaryl, then $Q^2$ is other than a bond;

$R^1$ is an aryl or heteroaryl group;

$R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, hydroxy, amino, methylamino, dimethylamino, methoxy and a monocyclic or bicyclic aryl or heteroaryl group;

or $R^2$ and $R^3$ together with the nitrogen atom to which they are attached form a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the group $Q^2$ form a saturated monocyclic heterocyclic group having 4-7 ring members and optionally containing a second heteroatom ring member selected from O and N;

or $NR^2R^3$ and a carbon atom of linker group $Q^2$ to which it is attached together form a cyano group; and $R^4$, $R^6$ and $R^8$ are each independently selected from hydrogen, halogen, $C_{1-5}$ saturated hydrocarbyl, cyano, $CONH_2$, $CONHR^9$, $CF_3$, $NH_2$, $NHCOR^9$ or $NHCONHR^9$;

$R^5$ and $R^7$ are each independently selected from hydrogen, halogen, $C_{1-5}$ saturated hydrocarbyl, cyano and $CF_3$;

$R^9$ is phenyl or benzyl each optionally substituted by one or substituents selected from halogen, hydroxy, trifluoromethyl, cyano, nitro, carboxy, amino, mono- or di-$C_{1-4}$ hydrocarbylamino; a group $R^a$—$R^b$ wherein $R^a$ is a bond, O, CO, $X^1C(X^2)$, $C(X^2)X^1$, $X^1C(X^2)X^1$, S, SO, $SO_2$, $NR_1$, $SO_2NR^c$ or $NR^cSO_2$; and $R^b$ is selected from hydrogen, heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and $X^1$ is O, S or $NR^c$ and $X^2$ is =O, =S or =$NR^c$;

wherein the compound is for use in: (a) the treatment or prophylaxis of a disease or condition in which the modulation (e.g. inhibition) of ROCK kinase or protein kinase P70S6K is indicated; and/or (b) the treatment of a subject or patient population in which the modulation (e.g. inhibition) of ROCK kinase or protein kinase P70S6K is indicated.

The invention also provides:

A compound per se of the formula (I) as defined herein, wherein the compound is for use in: (a) the treatment or prophylaxis of a disease or condition in which the modulation (e.g. inhibition) of ROCK kinase or protein kinase P70S6K is indicated; and/or (b) the treatment of a subject or patient population in which the modulation (e.g. inhibition) of ROCK kinase or protein kinase P70S6K is indicated.

A compound of the formula (I) as defined herein wherein the compound is for use in: (a) the treatment or prophylaxis of a disease or condition in which the modulation (e.g. inhibition) of ROCK kinase or protein kinase P70S6K is indicated; and/or (b) the treatment of a subject or patient population in which the modulation (e.g. inhibition) of ROCK kinase or protein kinase P70S6K is indicated.

The use of a compound of the formula (I) as defined herein for the manufacture of a medicament for use in: (a) the treatment or prophylaxis of a disease or condition in which the modulation (e.g. inhibition) of ROCK kinase or protein kinase P70S6K is indicated; and/or (b) the treatment of a subject or patient population in which the modulation (e.g. inhibition) of ROCK kinase or protein kinase P70S6K is indicated.

A method for the prophylaxis or treatment of a disease state or condition mediated by ROCK kinase or protein kinase P70S6K, which method comprises administering to a subject in need thereof a compound of the formula (I) as defined herein.

A method for treating a disease or condition comprising or arising from abnormal cell growth or abnormally arrested cell death in a mammal, the method comprising administering to the mammal a compound of the formula (I) as defined herein in an amount effective to inhibit ROCK kinase or protein kinase P70S6K activity.

A method of inhibiting ROCK kinase or protein kinase P70S6K, which method comprises contacting the kinase with a kinase-inhibiting compound of the formula (I) as defined herein.

A method of modulating a cellular process (for example cell division) by inhibiting the activity of a ROCK kinase or protein kinase P70S6K using a compound of the formula (I) as defined herein.

A compound of the formula (I) as defined herein for use in the prophylaxis or treatment of a disease state or condition mediated by ROCK kinase or protein kinase P70S6K.

The use of a compound of the formula (I) as defined herein for the manufacture of a medicament for the prophylaxis or treatment of a disease state or condition mediated by ROCK kinase or protein kinase P70S6K.

The use of a compound of the formula (I) as defined herein for the manufacture of a medicament for the prophylaxis or treatment of a disease state or condition arising from abnormal cell growth or abnormally arrested cell death mediated by ROCK kinase or protein kinase P70S6K.

A method for alleviating or reducing the incidence of a disease or condition comprising or arising from abnormal cell growth or abnormally arrested cell death in a mammal mediated by ROCK kinase or protein kinase P70S6K, which method comprises administering to the mammal a compound of the formula (I) as defined herein in an amount effective in inhibiting abnormal cell growth.

The use of a compound of the formula (I) as defined herein for the manufacture of a medicament for the prophylaxis or treatment of any one of the disease states or conditions disclosed herein.

A method for the treatment or prophylaxis of any one of the disease states or conditions disclosed herein, which method comprises administering to a patient (e.g. a patient in need thereof) a compound (e.g. a therapeutically effective amount) of the formula (I) as defined herein.

A method for alleviating or reducing the incidence of a disease state or condition disclosed herein, which method comprises administering to a patient (e.g. a patient in need thereof) a compound (e.g. a therapeutically effective amount) of the formula (I) as defined herein.

A method for the diagnosis and treatment of a disease state or condition mediated by ROCK kinase or protein kinase P70S6K, which method comprises (i) screening a patient to determine whether a disease or condition from which the patient is or may be suffering is one which would be susceptible to treatment with a compound having activity against ROCK kinase or protein kinase P70S6K; and (ii) where it is indicated that the disease or condition from which the patient is thus susceptible, thereafter administering to the patient a compound of the formula (I) as defined herein.

The use of a compound of the formula (I) as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against ROCK kinase or protein kinase P70S6K.

The invention also provides the further combinations, uses, methods, compounds and processes as set out in the claims below.

General Preferences and Definitions

Any one or more of the following optional provisos may apply in any combination to any one of the formulae (I), (Ia), (Ib), (Ic), (Id), (II), (IIa), (III), (IV), (V), (VI), (VII) and any sub-groups and embodiments as defined herein.

(i) When $J^1J^2$ is $(R^7)C=C(R^6)$ and $R^1$ is an aryl or heteroaryl group, the aryl or heteroaryl group bears one or more substituents (i.e. a moiety other than hydrogen) as defined herein.

(ii) When $Q^1$ is a bond, and E is a piperazine group, $R^1$ is other than a substituted pyridyl group linked to a nitrogen atom of the piperazine group wherein the substituted pyridyl group is substituted by an amide moiety.

(iii) When $Q^1$ contains a nitrogen atom and the moiety $Q^2$-G contains a heterocyclic group, $R^1$ is other than a substituted aminoquinoxaline group.

As used herein, the terms "ROCK kinase(s)" and "ROCK(s)" are synonomous generic terms embracing all members of the ROCK kinase family, so including both ROCK1 and ROCK2 as species within the genus. References inter alia to ROCK kinase inhibitors, ROCK kinase modulation and ROCK kinase activity are to be interpreted accordingly.

The term "Rho protein" is a term of art used to define a large family of GTP-binding proteins that are involved in regulation of actin organization, including RhoA and RhoC.

As used herein, the term "Rho signalling pathway" defines any cellular signaling pathway in which one or more members of the Rho proteins are involved. Particularly relevant to the invention are Rho signaling pathways in which a ROCK kinase (e.g. ROCK1 and/or ROCK2) is a proximate effector (e.g. a binding partner) for one or more Rho protein(s), and such Rho signaling pathways are preferred in embodiments of the invention defined inter alia by reference to a Rho signaling pathway.

As used herein, the term "modulation", as applied to the ROCK kinase or protein kinase p70S6K as described herein, is intended to define a change in the level of biological activity of the kinases. Thus, modulation encompasses physiological changes which effect an increase or decrease in kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity, or at the level of enzyme (e.g. ROCK or p70S6K) activity (for example by allosteric mechanisms, competitive inhibition, active-site inactivation, perturbation of feedback inhibitory pathways etc.). Thus, modulation may imply elevated/suppressed expression or over- or under-expression of the kinase, including gene amplification (i.e. multiple gene copies) and/or increased or decreased expression by a transcriptional effect, as well as hyper- (or hypo-)activity and (de)activation of the kinase (including (de)activation) by mutation(s). The terms "modulated" and "modulate" are to be interpreted accordingly.

As used herein, the term "mediated", as used in conjunction with the kinases (i.e. the ROCKs and protein kinase p70S6K) as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the role played by the kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase overexpression) need not necessarily be the proximal cause of the disease, state or condition: rather, it is contemplated that ROCK- or protein kinase p70S6K-mediated diseases, states or conditions include those having multifactorial aetiologies and complex progressions in which the kinase is only partially involved. In cases where the term is applied to treatment, prophylaxis or intervention (e.g. in the "ROCK-mediated treatments", "ROCK-mediated prophylaxis", "protein kinase p70S6K-mediated treatments" and "p70S6K-mediated prophylaxis" of the invention), the role played by the kinase may be direct or indirect and may be necessary and/or sufficient for the operation of the treatment, prophylaxis or outcome of the intervention. Many ROCK-mediated physiological processes, diseases, states, conditions, therapies, treatments or interventions of the invention involve the Rho signaling pathway (as herein defined) and may therefore, by extension, be dubbed "Rho-mediated" physiological processes, diseases, states, conditions, therapies, treatments or interventions.

The term "indicated" is a term of art used herein in relation to a disease, condition, subject or patient population to convey the clinical desirability or necessity of a particular intervention in relation to that disease, condition, subject or patient population. Thus, references herein to a disease, condition, subject or patient population "in which the modulation (e.g. inhibition) of ROCK kinase is indicated" is intended to define those diseases etc. in which modulation of ROCK kinase is either clinically desirable or necessary. This might be the case, for example, where modulation of ROCK kinase would be palliative, preventative or (at least partially) curative.

The term "intervention" is a term of art used herein to define any agency which effects a physiological change at any level. Thus, the intervention may comprises the induction or repression of any physiological process, event, biochemical pathway or cellular/biochemical event. The interventions of the invention typically effect (or contribute to) the therapy, treatment or prophylaxis of a disease or condition.

The following general preferences and definitions shall apply to each of the moieties T, E, G, $Q^1$, $Q^2$ $J^1$, $J^2$, T and $R^1$ to $R^9$ and any sub-definition, sub-group or embodiment thereof, unless the context indicates otherwise.

Any references to Formula (I) herein shall be taken also to refer to formulae (Ia), (Ib), (Ic), (Id), (II), (IIa), (III), (IV), (V), (VI), (VII) and any other sub-group of compounds within formula (I)), or embodiment thereof, unless the context requires otherwise.

In this specification, references to "the bicyclic group", when used in regard to the point of attachment of the group E shall, unless the context indicates otherwise, be taken to refer to the group:

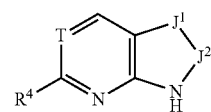

References to "carbocyclic" and "heterocyclic" groups as used herein shall, unless the context indicates otherwise, include both aromatic and non-aromatic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members.

The carbocyclic or heterocyclic groups can be aryl or heteroaryl groups having from 5 to 12 ring members, more usually from 5 to 10 ring members. The term "aryl" as used herein refers to a carbocyclic group having aromatic character and the term "heteroaryl" is used herein to denote a heterocyclic group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring. The aryl or heteroaryl groups can be monocyclic or bicyclic groups and can be unsubstituted or substituted with one or more substituents, for example one or more groups $R^{10}$ as defined herein.

The term non-aromatic group embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings. Each ring may contain up to about four heteroatoms typically selected from nitrogen, sulphur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a a 5- or 6-membered ring containing 1, 2 or 3 ring heteroatoms;
e) a pyrazole ring fused to a a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered ring containing 1, 2 or 3 ring heteroatoms; and
o) a cyclopentyl ring fused to a 5- or 6-membered ring containing 1, 2 or 3 ring heteroatoms.

Particular examples of bicyclic heteroaryl groups containing a six membered ring fused to a five membered ring include but are not limited to benzfuran, benzthiophene, benzimidazole, benzoxazole, benzisoxazole, benzthiazole, benzisothiazole, isobenzofuran, indole, isoindole, indolizine, indoline, isoindoline, purine (e.g., adenine, guanine), indazole, benzodioxole and pyrazolopyridine groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, indoline and indane groups.

Examples of carbocyclic aryl groups include phenyl, naphthyl, indenyl, and tetrahydronaphthyl groups.

Examples of non-aromatic heterocyclic groups include unsubstituted or substituted (by one or more groups $R^{10}$) heterocyclic groups having from 3 to 12 ring members, typically 4 to 12 ring members, and more usually from 5 to 10 ring members. Such groups can be monocyclic or bicyclic, for example, and typically have from 1 to 5 heteroatom ring members (more usually 1, 2, 3 or 4 heteroatom ring members) typically selected from nitrogen, oxygen and sulphur.

When sulphur is present, it may, where the nature of the adjacent atoms and groups permits, exist as —S—, —S(O)— or —S(O)$_2$—.

The heteroclyic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic urea moieties (e.g. as in imidazolidin-2-one), cyclic thiourea moieties, cyclic thioamides, cyclic thioesters, cyclic ester moieties (e.g. as in butyrolactone), cyclic sulphones (e.g. as in sulpholane and sulpholene), cyclic sulphoxides, cyclic sulphonamides and combinations thereof (e.g. morpholine and thiomorpholine and its S-oxide and S,S-dioxide).

Examples of monocyclic non-aromatic heterocyclic groups include 5-, 6- and 7-membered monocyclic heterocyclic groups. Particular examples include morpholine, thiomorpholine and its S-oxide and S,S-dioxide (particularly thiomorpholine), piperidine (e.g. 1-piperidinyl, 2-piperidinyl 3-piperidinyl and 4-piperidinyl), N-alkyl piperidines such as N-methyl piperidine, piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine, N-ethyl piperazine and N-isopropylpiperazine. In general, preferred non-aromatic heterocyclic groups include piperidine, pyrrolidine, azetidine, morpholine, piperazine and N-alkyl piperazines.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Preferred non-aromatic carbocyclic groups are monocyclic rings and most preferably saturated monocyclic rings.

Typical examples are three, four, five and six membered saturated carbocyclic rings, e.g. optionally substituted cyclopentyl and cyclohexyl rings.

One sub-set of non-aromatic carbocyclic groups includes unsubstituted or substituted (by one or more groups $R^{10}$) monocyclic groups and particularly saturated monocyclic groups, e.g. cycloalkyl groups. Examples of such cycloalkyl groups include cyclopropyl, cyclobutyl, cyclopentyl, cyclohexyl and cycloheptyl; more typically cyclopropyl, cyclobutyl, cyclopentyl and cyclohexyl, particularly cyclohexyl.

Further examples of non-aromatic cyclic groups include bridged ring systems such as bicycloalkanes and azabicycloalkanes although such bridged ring systems are generally less preferred. By "bridged ring systems" is meant ring systems in which two rings share more than two atoms, see for example Advanced Organic Chemistry, by Jerry March, 4$^{th}$ Edition, Wiley Interscience, pages 131-133, 1992. Examples of bridged ring systems include bicyclo[2.2.1]heptane, azabicyclo[2.2.1]heptane, bicyclo[2.2.2]octane, aza-bicyclo[2.2.2]octane, bicyclo[3.2.1]octane and aza-bicyclo[3.2.1] octane.

Where reference is made herein to carbocyclic and heterocyclic groups, the carbocyclic or heterocyclic ring can, unless the context indicates otherwise, be unsubstituted or substituted by one or more substituent groups $R^{10}$ selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$-$R^b$ wherein $R^a$ is a bond, O, CO, $X^1C(X^2)$, $C(X^2)$ $X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$;

$R^c$ is selected from hydrogen and $C_{1-4}$ hydrocarbyl; and
$X^1$ is O, S or $NR^c$ and $X^2$ is =O, =S or =$NR^c$.

Where the substituent group $R^{10}$ comprises or includes a carbocyclic or heterocyclic group, the said carbocyclic or heterocyclic group may be unsubstituted or may itself be substituted with one or more further substituent groups $R^{10}$. In one sub-group of compounds of the formula (I) as defined herein, such further substituent groups $R^{10}$ may include carbocyclic or heterocyclic groups, which are typically not themselves further substituted. In another sub-group of compounds of the formula (I) as defined herein, the said further substituents do not include carbocyclic or heterocyclic groups but are otherwise selected from the groups listed above in the definition of $R^{10}$.

The substituents $R^{10}$ may be selected such that they contain no more than 20 non-hydrogen atoms, for example, no more than 15 non-hydrogen atoms, e.g. no more than 12, or 10, or 9, or 8, or 7, or 6, or 5 non-hydrogen atoms.

One sub-group of substituents $R^{10}$ is represented by $R^{10a}$ which consists of substituents selected from halogen, hydroxy, trifluoromethyl, cyano, nitro, carboxy, amino, mono- or di-$C_{1-4}$ hydrocarbylamino, carbocyclic and heterocyclic groups having from 3 to 7 ring members; a group $R^a$-$R^b$ wherein $R^a$ is a bond, O, CO, OC(O), $NR^cC(O)$, $OC(NR^c)$, C(O)O, C(O)$NR^c$, OC(O)O, $NR^cC(O)O$, $OC(O)NR^1$, $NR^cC(O)NR^c$, S, SO, $SO_2$, $NR^c$, $SO_2NR^c$ or $NR^cSO_2$; and $R^b$ is selected from hydrogen, carbocyclic and heterocyclic groups having from 3 to 7 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 7 ring members and wherein one or more carbon atoms of the $C_{1-8}$ hydrocarbyl group may optionally be replaced by O, S, SO, $SO_2$, $NR^c$, OC(O), $NR^cC(O)$, $OC(NR^c)$, C(O)O, C(O)$NR^c$, OC(O)O, $NR^cC(O)O$, $OC(O)NR^c$ or $NR^cC(O)NR^c$;

$R^c$ is selected from hydrogen and $C_{1-4}$ hydrocarbyl.

Another sub-group of substituents $R^{10}$ is represented by $R^{10b}$ which consists of substituents selected from halogen, hydroxy, trifluoromethyl, cyano, amino, mono- or di-$C_{1-4}$ alkylamino, cyclopropylamino, carbocyclic and heterocyclic groups having from 3 to 7 ring members; a group $R^a$-$R^b$ wherein $R^a$ is a bond, O, CO, OC(O), $NR^cC(O)$, $OC(NR^c)$, C(O)O, C(O)$NR^c$, S, SO, $SO_2$, $NR^c$, $SO_2NR^c$ or $NR^cSO_2$; and $R^b$ is selected from hydrogen, carbocyclic and heterocyclic groups having from 3 to 7 ring members, and a $C_{1-8}$ hydrocarbyl group optionally substituted by one or more substituents selected from hydroxy, oxo, halogen, cyano, amino, mono- or di-$C_{1-4}$ alkylamino, carbocyclic and heterocyclic groups having from 3 to 7 ring members and wherein one or more carbon atoms of the $C_{1-8}$ hydrocarbyl group may optionally be replaced by O, S, SO, $SO_2$ or $NR^c$; provided that $R^a$ is not a bond when $R^b$ is hydrogen; and $R^c$ is selected from hydrogen and $C_{1-4}$ alkyl.

A further sub-group of substituents $R^{10}$ is represented by $R^{10c}$ which consists of substituents selected from:
halogen,
hydroxy,
trifluoromethyl,
cyano,
amino, mono- or di-$C_{1-4}$ alkylamino,
cyclopropylamino,
monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy; a group $R^a$-$R^b$;

$R^a$ is a bond, O, CO, OC(O), $NR^cC(O)$, $OC(NR^c)$, C(O)O, C(O)$NR^c$, S, SO, $SO_2$, $NR^c$, $SO_2NR^c$ or $NR^cSO_2$;

$R^b$ is selected from hydrogen, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy;

and $R^b$ is further selected from a $C_{1-8}$ hydrocarbyl group optionally substituted by one or more substituents selected from hydroxy, oxo, halogen, cyano, amino, mono- or di-$C_{1-4}$ alkylamino, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy, and wherein one or two carbon atoms of the $C_{1-8}$ hydrocarbyl group may optionally be replaced by O, S or $NR^c$; provided that $R^a$ is not a bond when $R^b$ is hydrogen; and $R^c$ is selected from hydrogen and $C_{1-4}$ alkyl.

Where the carbocyclic and heterocyclic groups have a pair of substituents on adjacent ring atoms, the two substituents may be linked so as to form a cyclic group. For example, an adjacent pair of substituents on adjacent carbon atoms of a ring may be linked via one or more heteroatoms and optionally substituted alkylene groups to form a fused oxa-, dioxa-, aza-, diaza- or oxa-aza-cycloalkyl group. Examples of such linked substituent groups include:

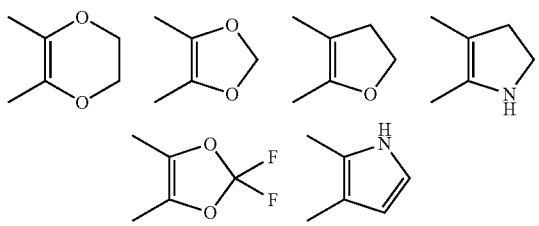

Examples of halogen substituents include fluorine, chlorine, bromine and iodine. Fluorine and chlorine are particularly preferred.

In the definition of the compounds of the formula (I) above and as used hereinafter, the term "hydrocarbyl" is a generic term encompassing aliphatic, alicyclic and aromatic groups having an all-carbon backbone and consisting of carbon and hydrogen atoms, except where otherwise stated.

In certain cases, as defined herein, one or more of the carbon atoms making up the carbon backbone may be replaced by a specified atom or group of atoms. Examples of hydrocarbyl groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, can be substituted by one or more substituents as defined herein. The examples and preferences expressed below apply to each of the hydrocarbyl substituent groups or hydrocarbyl-containing substituent groups referred to in the various definitions of substituents for compounds of the formula (I) and sub-groups thereof as defined herein unless the context indicates otherwise.

Generally by way of example, the hydrocarbyl groups can have up to eight carbon atoms, unless the context requires otherwise. Within the sub-set of hydrocarbyl groups having 1 to 8 carbon atoms, particular examples are $C_{1-6}$ hydrocarbyl groups, such as $C_{1-4}$ hydrocarbyl groups (e.g. $C_{1-3}$ hydrocarbyl groups or $C_{1-2}$ hydrocarbyl groups), specific examples being any individual value or combination of values selected from $C_1$, $C_2$, $C_3$, $C_4$, $C_5$, $C_6$, $C_7$ and $C_8$ hydrocarbyl groups.

The term "saturated hydrocarbyl", whether used alone or together with a suffix such as "oxy" (e.g. as in "hydrocarbyloxy"), refers to a non-aromatic hydrocarbon group containing no multiple bonds such as C=C and C≡C.

Particular hydrocarbyl groups are saturated hydrocarbyl groups such as alkyl and cycloalkyl groups as defined herein.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups having 1 to 8 carbon atoms, particular examples are $C_{1-6}$ alkyl groups, such as $C_{1-4}$ alkyl groups (e.g. $C_{1-3}$ alkyl groups or $C_{1-2}$ alkyl groups).

Examples of cycloalkyl groups are those derived from cyclopropane, cyclobutane, cyclopentane, cyclohexane and cycloheptane. Within the sub-set of cycloalkyl groups the cycloalkyl group will have from 3 to 8 carbon atoms, particular examples being $C_{3-6}$ cycloalkyl groups.

Examples of alkenyl groups include, but are not limited to, ethenyl(vinyl), 1-propenyl, 2-propenyl(allyl), isopropenyl, butenyl, buta-1,4-dienyl, pentenyl, and hexenyl. Within the sub-set of alkenyl groups the alkenyl group will have 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 8 carbon atoms, and particular examples are $C_{3-5}$ cycloalkenyl groups.

Examples of alkynyl groups include, but are not limited to, ethynyl and 2-propynyl (propargyl) groups. Within the sub-set of alkynyl groups having 2 to 8 carbon atoms, particular examples are $C_{2-6}$ alkynyl groups, such as $C_{2-4}$ alkynyl groups.

Examples of carbocyclic aryl groups include substituted and unsubstituted phenyl, naphthyl, indane and indene groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

When present, and where stated, a hydrocarbyl group can be optionally substituted by one or more substituents selected from hydroxy, oxo, alkoxy, carboxy, halogen, cyano, nitro, amino, mono- or di-$C_{1-4}$ hydrocarbylamino, and monocyclic or bicyclic carbocyclic and heterocyclic groups having from 3 to 12 (typically 3 to 10 and more usually 5 to 10) ring members. Preferred substituents include halogen such as fluorine. Thus, for example, the substituted hydrocarbyl group can be a partially fluorinated or perfluorinated group such as difluoromethyl or trifluoromethyl. In one embodiment preferred substituents include monocyclic carbocyclic and heterocyclic groups having 3-7 ring members.

Where stated, one or more carbon atoms of a hydrocarbyl group may optionally be replaced by O, S, SO, $SO_2$, $NR^c$, $X^1C(X^2)$, $C(X^2)X^1$ or $X^1C(X^2)X^1$ (or a sub-group thereof) wherein $X^1$ and $X^2$ are as hereinbefore defined, provided that at least one carbon atom of the hydrocarbyl group remains. For example, 1, 2, 3 or 4 carbon atoms of the hydrocarbyl group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbyl group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$). Further examples include ureas, carbonates and carbamates (C—C—C replaced by $X^1C(X^2)X^1$).

Where an amino group has two hydrocarbyl substituents, they may, together with the nitrogen atom to which they are attached, and optionally with another heteroatom such as nitrogen, sulphur, or oxygen, link to form a ring structure of 4 to 7 ring members.

The term "aza-cycloalkyl" as used herein refers to a cycloalkyl group in which one of the carbon ring members has been replaced by a nitrogen atom. Thus examples of aza-cycloalkyl groups include piperidine and pyrrolidine. The term "oxa-cycloalkyl" as used herein refers to a cycloalkyl group in which one of the carbon ring members has been replaced by an oxygen atom. Thus examples of oxa-cycloalkyl groups include tetrahydrofuran and tetrahydropyran. In an analogous manner, the terms "diaza-cycloalkyl", "dioxa-cycloalkyl" and "aza-oxa-cycloalkyl" refer respectively to cycloalkyl groups in which two carbon ring members have been replaced by two nitrogen atoms, or by two oxygen atoms, or by one nitrogen atom and one oxygen atom.

The definition "$R^a$-$R^b$" as used herein, either with regard to substituents present on a carbocyclic or heterocyclic moiety, or with regard to other substituents present at other locations on the compounds of the formula (I) as defined herein, includes inter alia compounds wherein $R^a$ is selected from a bond, O, CO, OC(O), SC(O), $NR^cC(O)$, OC(S), SC(S), $NR^cC(S)$, OC($NR^c$), SC($NR^c$), $NR^cC(NR^c)$, C(O)O, C(O)S, C(O)$NR^c$, C(S)O, C(S)S, C(S)$NR^c$, C($NR^c$)O, C($NR^c$)S, C($NR^c$)$NR^c$, OC(O)O, SC(O)O, $NR^cC(O)O$, OC(S)O, SC(S)O, $NR^cC(S)O$, OC($NR^c$)O, SC($NR^c$)O, $NR^cC(NR^c)O$, OC(O)S, SC(O)S, $NR^cC(O)S$, OC(S)S, SC(S)S, $NR^cC(S)S$, OC($NR^c$)S, SC($NR^c$)S, $NR^cC(NR^c)S$, OC(O)$NR^c$, SC(O)$NR^c$, $NR^cC(O)NR^c$, OC(S)$NR^c$, SC(S)$NR^c$, $NR^cC(S)NR^c$, OC($NR^c$)$NR^c$, SC($NR^c$)$NR^c$, $NR^cC(NR^cNR^c)$, S, SO, $SO_2$, $NR^c$, $SO_2NR^c$ and $NR^cSO_2$ wherein $R^c$ is as hereinbefore defined.

The moiety $R^b$ can be hydrogen or it can be a group selected from carbocyclic and heterocyclic groups having from 3 to 12 ring members (typically 3 to 10 and more usually from 5 to 10), and a $C_{1-8}$ hydrocarbyl group optionally substituted as hereinbefore defined. Examples of hydrocarbyl, carbocyclic and heterocyclic groups are as set out above.

When $R^a$ is O and $R^b$ is a $C_{1-8}$ hydrocarbyl group, $R^a$ and $R^b$ together form a hydrocarbyloxy group. Preferred hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy).

The hydrocarbyloxy groups can be substituted by various substituents as defined herein. For example, the alkoxy groups can be substituted by halogen (e.g. as in difluoromethoxy and trifluoromethoxy), hydroxy (e.g. as in hydroxyethoxy), $C_{1-2}$ alkoxy (e.g. as in methoxyethoxy), hydroxy-$C_{1-2}$ alkyl (as in hydroxyethoxyethoxy) or a cyclic group (e.g. a cycloalkyl group or non-aromatic heterocyclic group as hereinbefore defined). Examples of alkoxy groups bearing a non-aromatic heterocyclic group as a substituent are those in which the heterocyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkoxy group is a $C_{1-4}$ alkoxy group, more typically a $C_{1-3}$ alkoxy group such as methoxy, ethoxy or n-propoxy.

Alkoxy groups may be substituted by, for example, a monocyclic group such as pyrrolidine, piperidine, morpholine and piperazine and N-substituted derivatives thereof such as N-benzyl, N—$C_{1-4}$ acyl and N—$C_{1-4}$ alkoxycarbonyl. Particular examples include pyrrolidinoethoxy, piperidinoethoxy and piperazinoethoxy.

When $R^a$ is a bond and $R^b$ is a $C_{1-8}$ hydrocarbyl group, examples of hydrocarbyl groups $R^a$-$R^b$ are as hereinbefore defined. The hydrocarbyl groups may be saturated groups such as cycloalkyl and alkyl and particular examples of such groups include methyl, ethyl and cyclopropyl. The hydrocarbyl (e.g. alkyl) groups can be substituted by various groups and atoms as defined herein. Examples of substituted alkyl groups include alkyl groups substituted by one or more halogen atoms such as fluorine and chlorine (particular examples including bromoethyl, chloroethyl, difluoromethyl, 2,2,2-trifluoroethyl and perfluoroalkyl groups such as trifluoromethyl), or hydroxy (e.g. hydroxymethyl and hydroxyethyl), $C_{1-8}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. $C_{1-2}$ alkoxy such as methoxy—as in methoxyethyl), and cyclic groups such as cycloalkyl groups, aryl groups, heteroaryl groups and non-aromatic heterocyclic groups as hereinbefore defined).

Particular examples of alkyl groups substituted by a cyclic group are those wherein the cyclic group is a saturated cyclic amine such as morpholine, piperidine, pyrrolidine, piperazine, $C_{1-4}$-alkyl-piperazines, $C_{3-7}$-cycloalkyl-piperazines, tetrahydropyran or tetrahydrofuran and the alkyl group is a $C_{1-4}$ alkyl group, more typically a $C_{1-3}$ alkyl group such as methyl, ethyl or n-propyl. Specific examples of alkyl groups substituted by a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted by aryl groups and heteroaryl groups include benzyl, phenethyl and pyridylmethyl groups.

When $R^a$ is $SO_2NR^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is $SO_2NR^c$ include aminosulphonyl, $C_{1-4}$ alkylaminosulphonyl and di-$C_{1-14}$ alkylaminosulphonyl groups, and sulphonamides formed from a cyclic amino group such as piperidine, morpholine, pyrrolidine, or an optionally N-substituted piperazine such as N-methyl piperazine.

Examples of groups $R^a$-$R^b$ where $R^a$ is $SO_2$ include alkylsulphonyl, heteroarylsulphonyl and arylsulphonyl groups, particularly monocyclic aryl and heteroaryl sulphonyl groups. Particular examples include methylsulphonyl, phenylsulphonyl and toluenesulphonyl.

When $R^a$ is $NR^c$, $R^b$ can be, for example, hydrogen or an optionally substituted $C_{1-8}$ hydrocarbyl group, or a carbocyclic or heterocyclic group. Examples of $R^a$-$R^b$ where $R^a$ is $NR^c$ include amino, $C_{1-4}$ alkylamino (e.g. methylamino, ethylamino, propylamino, isopropylamino, tert-butylamino), di-$C_{1-4}$ alkylamino (e.g. dimethylamino and diethylamino) and cycloalkylamino (e.g. cyclopropylamino, cyclopentylamino and cyclohexylamino).

Specific Embodiments of and Preferences for E, T, G, $Q^1$, $Q^2$, $J^1$, $J^2$ and $R^1$ to $R^{10}$

T

In formula (I) as defined herein, T can be nitrogen or a group $CR^5$ and $J^1$-$J^2$ can represent a group selected from $N=C(R^6)$, $(R^7)C=N$, $(R^8)N-C(O)$, $(R^8)_2C-C(O)$ and $(R^7)C=C(R^6)$. Thus the bicyclic group can take the form of, for example:

- a purine (T is N, $J^1$-$J^2$ is $N=C(R^6)$);
- a 3H-imidazo[4,5-b]pyridine (T is $CR^5$, $J^1$-$J^2$ is $N=C(R^6)$);
- a 7H-pyrrolo[2,3-d]pyrimidine (T is N, $J^1$-$J^2$ is $(R^7)C=C(R^6)$);
- a 1H-pyrrolo[2,3-b]pyridine (T is $CR^5$, $J^1$-$J^2$ is $(R^7)C=C(R^6)$);
- a 5,7-dihydro-pyrrolo[2,3-d]pyrimidin-6-one (T is N, $J^1$-$J^2$ is $(R^8)_2C-C(O)$);
- a 3H-[1,2,3]triazolo[4,5-d]pyrimidine (T is N, $J^1$-$J^2$ is $N=N$);
- a 3H-[1,2,3]triazolo[4,5-b]pyridine (T is $CR^5$, $J^1$-$J^2$ is $N=N$);
- a 7,9-dihydro-purin-8-one (T is N, $J^1$-$J^2$ is $(R^8)N-C(O)$);
- a 1H-pyrazolo[3,4-d]pyrimidine (T is N, $J^1$-$J^2$ is $(R^7)C=N$); or
- a pyrazolo[3,4-b]pyridine (T is $CR^5$, $J^1$-$J^2$ is $(R^7)C=N$).

$R^4$ $R^4$ is selected from hydrogen; halogen; $C_{1-6}$ hydrocarbyl optionally substituted by halogen, hydroxy or $C_{1-2}$ alkoxy; cyano; $CONH_2$; $CONHR^9$; $CF_3$; $NH_2$; $NHCOR^9$ and $NHCONHR^9$. More typically, $R^4$ is selected from hydrogen, chlorine, fluorine and methyl, and preferably $R^4$ is hydrogen.

$R^5$ $R^5$ is selected from hydrogen; halogen; $C_{1-6}$ hydrocarbyl optionally substituted by halogen, hydroxy or $C_{1-2}$ alkoxy; cyano; $CONH_2$; $CONHR^9$; $CF_3$; $NH_2$; $NHCOR^9$ and $NHCONHR^9$. More typically, $R^5$ is selected from hydrogen, halogen, $C_{1-5}$ saturated hydrocarbyl, cyano and $CF_3$. Preferably, $R^5$ is selected from hydrogen, chlorine, fluorine and methyl, and more preferably $R^5$ is hydrogen.

$R^6$ $R^6$ is selected from hydrogen; halogen; $C_{1-6}$ hydrocarbyl optionally substituted by halogen, hydroxy or $C_{1-2}$ alkoxy; cyano; $CONH_2$; $CONHR^9$; $CF_3$; $NH_2$; $NHCOR^9$ and $NHCONHR^9$. More typically $R^6$ is selected from hydrogen, chlorine, fluorine and methyl, and preferably $R^6$ is hydrogen.

$R^7$ $R^7$ is selected from hydrogen; halogen; $C_{1-6}$ hydrocarbyl optionally substituted by halogen, hydroxy or $C_{1-2}$ alkoxy; cyano; $CONH_2$; $CONHR^9$; $CF_3$; $NH_2$; $NHCOR^9$ and $NHCONHR^9$. More typically $R^7$ is selected from hydrogen, halogen, $C_{1-5}$ saturated hydrocarbyl, cyano and $CF_3$. Preferably, $R^7$ is selected from hydrogen, chlorine, fluorine and methyl, and more preferably $R^7$ is hydrogen.

$R^8$ $R^8$ is selected from hydrogen, halogen, $C_{1-5}$ saturated hydrocarbyl (e.g. alkyl), cyano, $CONH_2$, $CONHR^9$, $CF_3$, $NH_2$, $NHCOR^9$ and $NHCONHR^9$. In one embodiment, when attached to a nitrogen atom, $R^8$ is selected from hydrogen and $C_{1-5}$ saturated hydrocarbyl (e.g. alkyl) and more typically is selected from hydrogen, methyl and ethyl; and preferably is hydrogen. In another embodiment, when attached to a carbon atom, $R^8$ is selected from hydrogen, chlorine, fluorine, methyl, and ethyl; and preferably is hydrogen.

$R^9$ $R^9$ is phenyl or benzyl each optionally substituted as defined herein. Particular groups $R^9$ are phenyl and benzyl groups that are unsubstituted or are substituted with a solubilising group such as an alkyl or alkoxy group bearing an amino, substituted amino, carboxylic acid or sulphonic acid group. Particular examples of solubilising groups include amino-$C_{1-4}$-alkyl, mono-$C_{1-2}$-alkylamino-$C_{1-4}$-alkyl, di-$C_{1-2}$-alkylamino-$C_{1-4}$-alkyl, amino-$C_{1-4}$-alkoxy, mono-$C_{1-2}$-alkylamino-$C_{1-4}$-alkoxy, di-$C_{1-2}$-alkylamino-$C_{1-4}$-alkoxy, piperidinyl-$C_{1-4}$-alkyl, piperazinyl-$C_{1-4}$-alkyl, morpholinyl-$C_{1-4}$-alkyl, piperidinyl-$C_{1-4}$-alkoxy, piperazinyl-$C_{1-4}$-alkoxy and morpholinyl-$C_{1-14}$-alkoxy.

$Q^1$ and $Q^2$ $Q^1$ is a bond or a saturated hydrocarbon linker group containing from 1 to 3 carbon atoms, wherein one of the carbon atoms in the linker group may optionally be replaced by an oxygen or nitrogen atom, or an adjacent pair of carbon atoms may be replaced by $CONR^q$ or $NR^qCO$ where $R^q$ is hydrogen, $C_{1-4}$ alkyl or cyclopropyl, or $R^q$ is a $C_{1-4}$ alkylene chain that links to $R^1$ or to another carbon atom of $Q^1$ to form a cyclic moiety; and wherein the carbon atoms of the linker group $Q^1$ may optionally bear one or more substituents selected from fluorine and hydroxy.

$Q^2$ is a bond or a saturated hydrocarbon linker group containing from 1 to 3 carbon atoms, wherein one of the carbon atoms in the linker group may optionally be replaced by an oxygen or nitrogen atom; and wherein the carbon atoms of the linker group may optionally bear one or more substituents selected from fluorine and hydroxy, provided that the hydroxy group when present is not located at a carbon atom a with respect to the G group.

In one embodiment, $Q^1$ and $Q^2$ are the same or different and are each a bond or a saturated hydrocarbon linker group containing from 1 to 3 carbon atoms, wherein one of the carbon atoms in the linker group may optionally be replaced by an oxygen or nitrogen atom; and wherein the carbon atoms of the or each linker group $Q^1$ and $Q^2$ may optionally bear one or more substituents selected from fluorine and hydroxy, provided that the hydroxy group when present is not located at a carbon atom a with respect to the $G^2$ group.

In one group of compounds for use according to the invention, at least one of $Q^1$ and $Q^2$ represents a bond. Within this group of compounds, one sub-group consists of compounds in which both of $Q^1$ and $Q^2$ represent a bond. In another sub-group, one of $Q^1$ and $Q^2$ represents a bond, and the other represents a saturated hydrocarbon linker group containing from 1 to 3 carbon atoms, wherein one of the carbon atoms in the linker group may optionally be replaced by an oxygen or nitrogen atom.

When $Q^1$ and/or $Q^2$ are saturated hydrocarbon groups, the hydrocarbon groups are typically alkylene groups such as $(CH_2)_n$ where n is 1, 2 or 3, one particular example being $CH_2$. One of the carbon atoms in the alkylene group $Q^1$ may optionally be replaced by, for example, an oxygen atom, and an example of such a group is $CH_2-O-CH_2$.

The carbon atoms of the linker groups $Q^1$ and $Q^2$ may optionally bear one or more substituents selected from oxo, fluorine and hydroxy, provided that the hydroxy group is not located at a carbon atom a with respect to the $NR^2R^3$ group when present, and provided also that the oxo group is located at a carbon atom a with respect to the $NR^2R^3$ group when present. Typically, the hydroxy group, if present, is located at a position β with respect to G when G is other than hydrogen. In general, no more than one hydroxy group will be present. Where fluorine atoms are present, they may be present in a difluoromethylene or trifluoromethyl group, for example.

In one sub-group of compounds, $Q^1$ is a saturated hydrocarbon linker group containing from 1 to 3 carbon atoms, wherein an adjacent pair of carbon atoms is replaced by $CONR^q$ or $NR^qCO$ where $R^q$ is hydrogen, $C_{1-4}$ alkyl or cyclopropyl, or $R^q$ is a $C_{1-4}$ alkylene chain that links to $R^1$ or to another carbon atom of $Q^1$ to form a cyclic moiety. In one preferred embodiment, $R^q$ is hydrogen. In another embodiment, $R^q$ is $C_{1-4}$ alkyl or cyclopropyl, preferably methyl. In a further embodiment, $R^q$ is a $C_{1-4}$ alkylene chain that links to $R^1$ or to another carbon atom of $Q^1$ to form a cyclic moiety.

Examples of linker groups $Q^1$ containing $CONR^q$ or $NR^qCO$ are the groups $CH_2NHCO$ and $CH_2N(Me)CO$ where the carbonyl group is attached to E.

Examples of linker groups $Q^1$ containing $CONR^q$ or $NR^qCO$, where $R^q$ is a $C_{1-4}$ alkylene chain that links to another carbon atom of $Q^1$ to form a cyclic moiety, are groups represented by the formula:

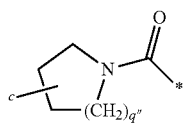

where * represents the point of attachment to the moiety E, q" is 0, 1 or 2, and the point of attachment to $R^1$ is indicated by the letter "c".

Examples of linker groups $Q^1$ containing $CONR^q$ or $NR^qCO$, where $R^q$ is a $C_{1-4}$ alkylene chain that links to $R^1$ to form a cyclic moiety, are groups represented by the formula:

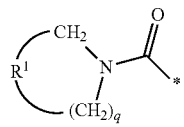

where q is as defined herein and $R^1$ is an aryl or heteroaryl group. Particular examples of moieties $R^1$-$Q^1$ of this type include 1,2,3,4-tetrahydroisoquinolin-2-ylcarbonyl.

It will be appreciated that that when an oxo group is present at the carbon atom adjacent an $NR^2R^3$ group, the compound of the formula (I) will be an amide.

In one embodiment of the invention, no fluorine atoms are present in the linker groups $Q^1$, and/or $Q^2$.

In another embodiment of the invention, no hydroxy groups are present in the linker groups $Q^1$ and/or $Q^2$.

In a further embodiment, no oxo group is present in the linker groups $Q^1$ and/or $Q^2$.

In one group of compounds of the formula (I) neither hydroxy groups nor fluorine atoms are present in the linker groups $Q^1$ and/or $Q^2$, e.g. the linker groups $Q^1$ and/or $Q^2$ are unsubstituted.

In another group of compounds for use according to the invention, the linker group $Q^2$ can have a branched configuration at the carbon atom attached to the $NR^2R^3$ group, when present. For example, the carbon atom attached to the $NR^2R^3$ group can be attached to a pair of gem-dimethyl groups.

$Q^1$ and $Q^2$ may be attached to the same atom of group E, or to different atoms. In one embodiment, $Q^1$ and $Q^2$ are attached to the same atom (i.e. a carbon atom) of group E.

G

The moiety G is selected from hydrogen, $NR^2R^3$, OH and SH with the proviso that when E is aryl or heteroaryl and $Q^2$ is a bond, then G is hydrogen. Thus, in the compounds of formula (I) as defined herein, an amino group $NR^2R^3$ or an SH or OH group are not directly linked to E when E is an aryl or heteroaryl group.

In one embodiment, G is hydrogen.

Preferably at least one of $R^1$ and G is other than hydrogen.

In another embodiment, G is selected from $NR^2R^3$, OH and SH. Within this embodiment, one particular sub-group of compounds is the group in which G is $NR^2R^3$.

Within the sub-group of compounds in which G is $NR^2R^3$, $R^2$ and $R^3$ can be independently selected from hydrogen; $C_{1-4}$ hydrocarbyl and $C_{1-4}$ acyl wherein the hydrocarbyl and acyl groups are optionally substituted by one or more substituents selected from fluorine, hydroxy, cyano, amino, methylamino, dimethylamino, methoxy and a monocyclic or bicyclic aryl or heteroaryl group;

In one group of compounds, $R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, hydroxy, amino, methylamino, dimethylamino, methoxy and a monocyclic or bicyclic aryl or heteroaryl group.

Within this group of compounds are the compounds wherein $R^2$ and $R^3$ are independently selected from hydrogen; $C_{1-4}$ hydrocarbyl and $C_{1-4}$ acyl wherein the hydrocarbyl and acyl groups are each optionally substituted by a monocyclic or bicyclic aryl or heteroaryl group.

Also within this group of compounds is the sub-group of compounds for use according to the invention wherein $R^2$ and $R^3$ are independently selected from hydrogen, $C_{1-4}$ hydrocarbyl and $C_{1-4}$ acyl.

In each of the foregoing groups and sub-groups of compounds, the hydrocarbyl group forming part of $NR^2R^3$ typically is an alkyl group, more usually a $C_1$, $C_2$ or $C_3$ alkyl group, for example a methyl group.

In a particular sub-group of compounds, $R^2$ and $R^3$ are independently selected from hydrogen and methyl and hence $NR^2R^3$ can be an amino, methylamino or dimethylamino group.

In one embodiment, $NR^2R^3$ is an amino group. In another particular embodiment, $NR^2R^3$ is a methylamino group.

In another group of compounds, $R^2$ and $R^3$ together with the nitrogen atom to which they are attached form a saturated monocyclic heterocyclic group having 4-7 ring members and optionally containing a second heteroatom ring member selected from O and N.

In another group of compounds, $NR^2R^3$ and a carbon atom of linker group $Q^2$ to which it is attached from a cyano group.

In a further group of compounds, $NR^2R^3$ is as hereinbefore defined except that $NR^2R^3$ and a carbon atom of linker group $Q^2$ to which it is attached may not form a cyano group.

The saturated monocyclic ring can be an azacycloalkyl group such as an azetidine, pyrrolidine, piperidine or azepane ring, and such rings are typically unsubstituted. Alternatively, the saturated monocyclic ring can contain an additional heteroatom selected from O and N, and examples of such groups include morpholine and piperazine. Where an additional N atom is present in the ring, this can form part of an NH group or an N—$C_{1-4}$alkyl group such as an N-methyl, N-ethyl, N-propyl or N-isopropyl group.

In a further group of compounds, one of $R^2$ and $R^3$ together with the nitrogen atom to which they are attached and one or more atoms from the linker group $Q^2$ form a saturated monocyclic heterocyclic group having 4-7 ring members and optionally containing a second heteroatom ring member selected from O and N.

$R^1$

The group $R^1$ is hydrogen or a heteroaryl group, wherein the aryl or heteroaryl group may be selected from the list of such groups set out in the section headed General Preferences and Definitions.

In one sub-group of compounds, $R^1$ is hydrogen.

In another sub-group of compounds, $R^1$ is an aryl or heteroaryl group.

When $R^1$ is aryl or heteroaryl, it can be monocyclic or bicyclic and, in one particular embodiment, is monocyclic. Particular examples of monocyclic aryl and heteroaryl groups are six membered aryl and heteroaryl groups containing up to 2 nitrogen ring members, and five membered heteroaryl groups containing up to 3 heteroatom ring members selected from O, S and N.

Examples of such groups include phenyl, naphthyl, thienyl, furan, pyrimidine and pyridine, with phenyl being presently preferred.

The aryl or heteroaryl group $R^1$ can be unsubstituted or substituted by up to 5 substituents, and examples of substituents are those listed in any one of groups $R^{10}R^{10}$, $R^{10b}$ and $R^{10c}$ above.

In one embodiment, the aryl or heteroaryl group $R^1$ is unsubstituted.

In another embodiment, the aryl or heteroaryl group $R^1$ is substituted by one or more substituents selected from those listed in any one of groups $R^{10}$ $R^{10a}$, $R^{10b}$ and $R^{10c}$ above.

One particular group of substituents for the aryl or heteroaryl group $R^1$ consists of hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by one or more $C_{1-2}$ alkoxy, halogen, hydroxy or optionally substituted phenyl or pyridyl groups; $C_{1-4}$ acylamino; benzoylamino; pyrrolidinocarbonyl; piperidinocarbonyl; morpholinocarbonyl; piperazinocarbonyl; five and six membered heteroaryl groups containing one or two heteroatoms selected from N, O and S, the heteroaryl groups being optionally substituted by one or more $C_{1-4}$ alkyl substituents; optionally substituted phenyl; optionally substituted pyridyl; and optionally substituted phenoxy; wherein the optional substituent for the phenyl, pyridyl and phenoxy groups are 1, 2 or 3 substituents selected from $C_{1-2}$ acyloxy, fluorine, chlorine, bromine, trifluoromethyl, cyano, $C_{1-2}$ hydrocarbyloxy and $C_{1-2}$ hydrocarbyl each optionally substituted by methoxy or hydroxy.

Another particular group of substituents for the aryl (e.g. phenyl) or heteroaryl group $R^1$ consists of hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by $C_{1-2}$ alkoxy or hydroxy; $C_{1-4}$ acylamino; benzoylamino; pyrrolidinocarbonyl; piperidinocarbonyl; morpholinocarbonyl; piperazinocarbonyl; five and six membered heteroaryl groups containing one or two heteroatoms selected from N, O and S, the heteroaryl groups being optionally substituted by one or more $C_{1-4}$ alkyl substituents; phenyl; pyridyl; and phenoxy wherein the phenyl, pyridyl and phenoxy groups are each optionally substituted with 1, 2 or 3 substituents selected from $C_{1-2}$ acyloxy, fluorine, chlorine, bromine, trifluoromethyl, cyano, $C_{1-2}$ hydrocarbyloxy and $C_{1-2}$ hydrocarbyl each optionally substituted by methoxy or hydroxy.

Although up to 5 substituents may be present, more typically there are 0, 1, 2, 3 or 4 substituents, preferably 0, 1, 2 or 3, and more preferably 0, 1 or 2.

In one embodiment, $R^1$ is unsubstituted (e.g. is an unsubstituted phenyl group) or substituted (e.g. is a substituted phenyl group) by up to 5 substituents selected from hydroxy; $C_{1-4}$ acyloxy; fluorine; chlorine; bromine; trifluoromethyl; trifluoromethoxy; difluoromethoxy; benzyloxy; cyano; $C_{1-4}$ hydrocarbyloxy and $C_{1-4}$ hydrocarbyl each optionally substituted by $C_{1-2}$ alkoxy or hydroxy.

In another embodiment, the group $R^1$ is unsubstituted (e.g. is an unsubstituted phenyl group) or substituted (e.g. is a substituted phenyl group) substituted by up to 5 substituents selected from hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by $C_{1-2}$ alkoxy or hydroxy.

In another embodiment, the group $R^1$ can have one or two substituents selected from fluorine, chlorine, trifluoromethyl, trifluoromethoxy, difluoromethoxy, benzyloxy, methyl and methoxy.

In a further embodiment, the group $R^1$ can have one or two substituents selected from fluorine, chlorine, trifluoromethyl, trifluoromethoxy, difluoromethoxy, benzyloxy, tert-butyl, methyl and methoxy.

For example, $R^1$ can have one or two substituents selected from fluorine, chlorine, trifluoromethyl, methyl and methoxy.

When $R^1$ is a phenyl group, particular examples of substituent combinations include mono-chlorophenyl and dichlorophenyl. Further examples include benzyloxyphenyl, trifluoromethoxyphenyl, tert-butylphenyl, methoxyphenyl, fluoro-chlorophenyl, difluorophenyl, and trifluoromethylphenyl.

In one sub-group of compounds, the group $R^1$ is a phenyl group having a substituent at the para position selected from fluorine, chlorine, trifluoromethyl, trifluoromethoxy, difluoromethoxy, benzyloxy, methyl and methoxy.

In another sub-group of compounds, the group $R^1$ is a phenyl group having a tert-butyl substituent at the para position.

In another sub-group of compounds, the group $R^1$ is a phenyl group having a substituent at the ortho position selected from fluorine, chlorine, trifluoromethyl, trifluoromethoxy, difluoromethoxy, methyl and methoxy, and optionally a second substituent at the meta or para position selected from the group $R^1$ is a phenyl group having a substituent at the para position selected from fluorine, chlorine, trifluoromethyl, trifluoromethoxy, difluoromethoxy, methyl and methoxy.

When $R^1$ is a six membered aryl or heteroaryl group, a substituent may advantageously be present at the para position on the six-membered ring. Where a substituent is present at the para position, it is preferably larger in size than a fluorine atom.

Particular examples of the group $R^1$ are shown in Table 1 below, the point of attachment to $Q^1$ (or E when $Q^1$ is a bond) being indicated by means of an asterisk.

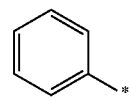 [SMILES: *c1ccccc1]

A1

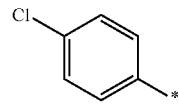 [SMILES: *c1ccc(Cl)cc1]

A2

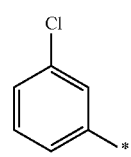

A3

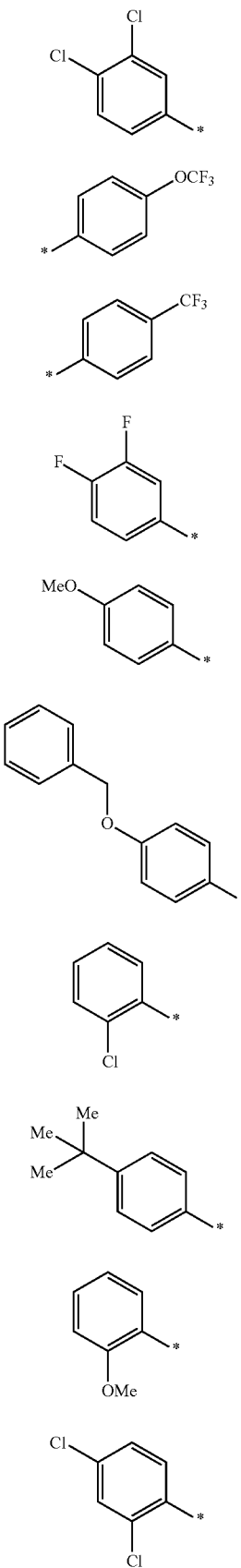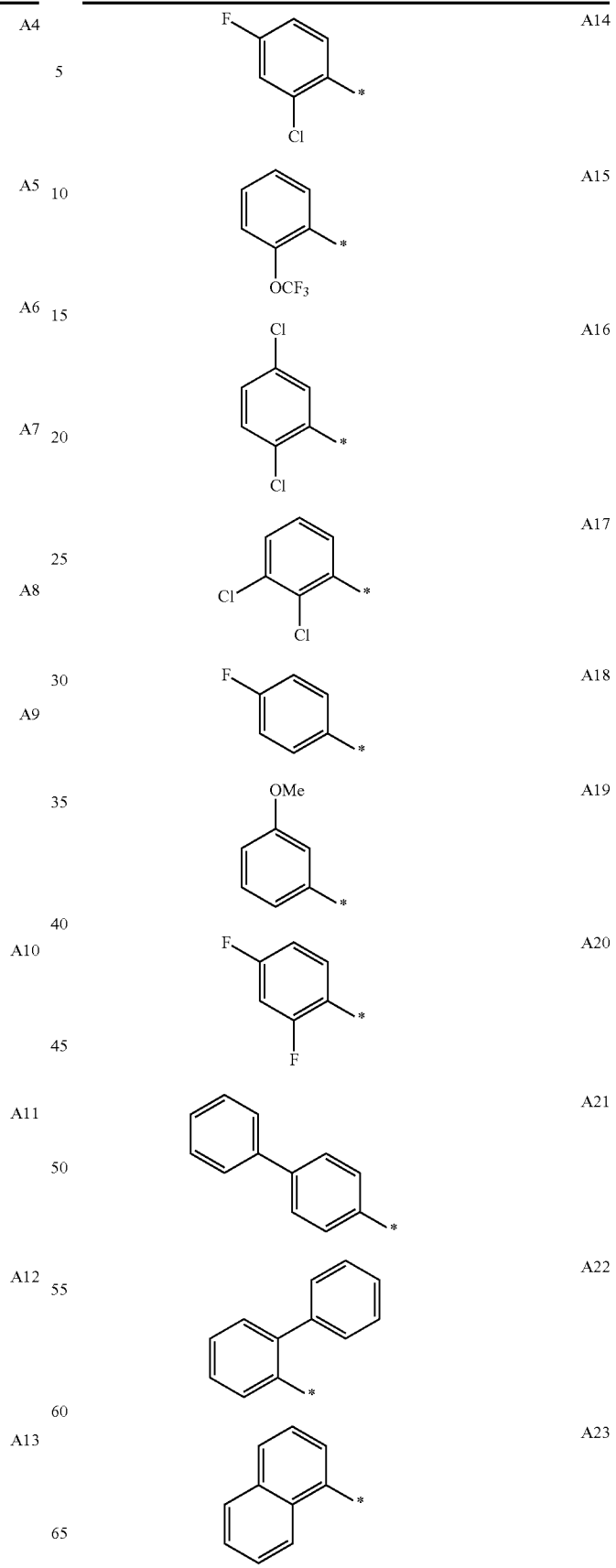

-continued

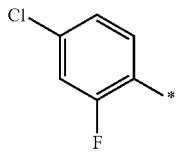 [SMILES: *c1ccc(Cl)cc1F] A24

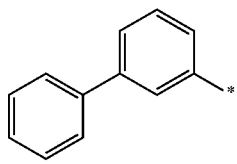 [SMILES: *c1cccc(-c2ccccc2)c1] A25

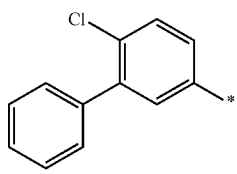 [SMILES: *c1ccc(Cl)c(-c2ccccc2)c1] A26

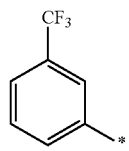 [SMILES: *c1cccc(C(F)(F)F)c1] A27

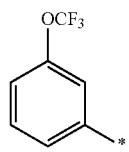 [SMILES: *c1cccc(OC(F)(F)F)c1] A28

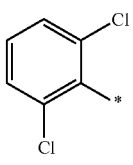 [SMILES: *c1c(Cl)cccc1Cl] A29

One set of preferred groups $R^1$ includes groups A2, A4 and A5 in Table 1.

Another set of preferred groups includes groups A2, A4, A5, A11, A11, A13, A14, A15, A16, A17, A18, A19 and A19.

E

In formula (I), E is a monocyclic carbocyclic or heterocyclic group of 5 or 6 ring members wherein the heterocyclic group contains up to 3 heteroatoms selected from O, N and S.

The carbocyclic or heterocyclic group E can be aromatic or non-aromatic.

In one embodiment, the carbocyclic or heterocyclic group E is non-aromatic.

In another embodiment, the carbocyclic or heterocyclic group E is aromatic.

When E is an aromatic group, i.e. an aryl or heteroaryl group, the group can be selected from the examples of such groups set out in the General Preferences and Definitions section above.

Particular aromatic cyclic groups E are aryl and heteroaryl groups containing a six membered aromatic or heteroaromatic ring such as a phenyl, pyridine, pyrazine, pyridazine or pyrimidine ring, more particularly a phenyl, pyridine, pyrazine or pyrimidine ring, and more preferably a pyridine or phenyl ring.

Examples of non-aromatic monocyclic are as set out in the General Preferences and Definitions section above.

Particular examples of groups include cycloalkanes such as cyclohexane and cyclopentane, and nitrogen-containing rings such as piperidine, pyrrolidine, piperidine, piperazine and piperazone.

One particular non-aromatic monocyclic group is a piperidine group and more particularly a piperidine group wherein the nitrogen atom of the piperidine ring is attached to the bicyclic group.

The moieties $Q^1$ and $Q^2$ can be attached to the same carbon atom in the group E or they can be attached to separate atoms. It will be appreciated that when the group E is aromatic, $Q^1$ and $Q^2$ cannot be attached to the same carbon atom in the group E but may be, for example, attached to adjacent carbon atoms.

In one embodiment, E is non-aromatic and $Q^1$ and $Q^2$ are attached to the same carbon atom in the group E.

In another embodiment, $Q^1$ and $Q^2$ are attached to different atoms in the group E.

It is preferred that the group $Q^2$ and the bicyclic group are attached to the group E in a meta or para relative orientation; i.e. $Q^2$ and the bicyclic group are not attached to adjacent ring members of the group E. Examples of groups such groups E include 1,4-phenylene, 1,3-phenylene, 2,5-pyridylene and 2,4-pyridylene, 1,4-piperidinyl, 1,4-piperindonyl, 1,4-piperazinyl, and 1,4-piperazonyl.

The groups E can be unsubstituted or can have up to 4 substituents $R^{11}$ which may be selected from the group $R^{10}$ as hereinbefore defined. More typically however, the substituents $R^{11}$ are selected from hydroxy; oxo (when E is non-aromatic); halogen (e.g. chlorine and bromine); trifluoromethyl; cyano; $C_{1-4}$ hydrocarbyloxy optionally substituted by $C_{1-2}$ alkoxy or hydroxy; and $C_{1-4}$ hydrocarbyl optionally substituted by $C_{1-2}$ alkoxy or hydroxy.

Typically, there are 0-3 substituents, more usually 0-2 substituents, for example 0 or 1 substituent. In one embodiment, the group E is unsubstituted.

In one particular group of compounds for use according to the invention, E is a group:

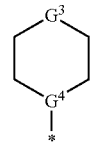

where $G^3$ is selected from C, CH, $CH_2$, N and NH; and $G^4$ is selected from N and CH.

Particular examples of the group E, together with their points of attachment to the groups $Q^1$ and $Q^2$ ($^a$) and the bicyclic group (*) are shown in Table 2 below.

TABLE 2

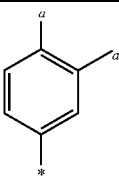 B1

TABLE 2-continued

| | |
|---|---|
| 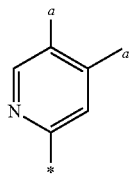 | B2 |
| 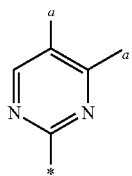 | B3 |
| 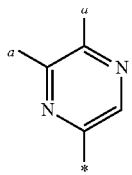 | B4 |
| 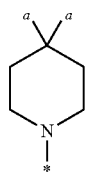 | B9 |
| 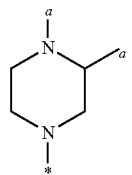 | B10 |
| 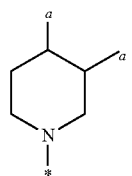 | B11 |
| 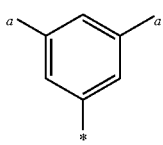 | B12 |

One preferred group E is group B9.

Particular and Preferred Sub-Groups of the Formula (I)

One sub-group of compounds of the formula (I) has the general formula (II):

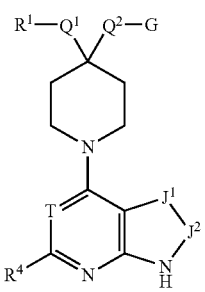

(II)

wherein $R^1$, $R^4$, $Q^1$, $Q^2$, T, $J^1$, $J^2$ and G are as defined herein in respect of formula (I) and sub-groups, examples and preferences thereof. Within Formula (II), particular compounds are those in which $Q^1$ is a bond or a $C_{1-2}$ alkylene group and $Q^2$ is a bond or a methylene group. Preferably $R^1$ is an aryl or heteroaryl group.

Within Formula (II), one sub-group of compounds has the general formula (IIa):

(IIa)

$$R^1—Q^1\quad Q^2—G$$

or a salt, solvate tautomer or N-oxide thereof;
wherein $R^1$ is an aryl or heteroaryl group;
G is selected from $NR^2R^3$, OH and SH;
and $R^4$, $Q^1$, $Q^2$, T, $J^1$ and $J^2$ are as defined herein.

In formulae (II) and (IIa), preferably G is $NR^2R^3$ and more preferably G is $NH_2$ or NHMe.

In formulae (II) and (IIa) and embodiments thereof, the group $R^1$ is preferably an optionally substituted aryl or heteroaryl group, and typically a monocyclic aryl or heteroaryl group of 5 or 6 ring members. Particular aryl and heteroaryl groups are phenyl, pyridyl, furanyl and thienyl groups, each optionally substituted. Optionally substituted phenyl groups are particularly preferred.

Alternatively, the group $R^1$ can be, for example, an optionally substituted naphthyl group, for example an optionally substituted 1-naphthyl group. One particular example of such a group is unsubstituted 1-naphthyl.

The aryl or heteroaryl group $R^1$ (e.g. a phenyl, pyridyl, furanyl or thienyl group) can be unsubstituted or substituted by up to 5 substituents, and examples of substituents are those listed above in groups $R^{10}$, $R^{10a}$, $R^{10b}$ and $R^{10c}$.

Particular sub-groups of compounds of the formulae (II) or (IIa) consist of compounds in which $R^1$ is unsubstituted phenyl or, more preferably, phenyl bearing 1 to 3 (and more preferably 1 or 2) substituents selected from hydroxy; $C_{1-4}$ acyloxy; fluorine; chlorine; bromine; trifluoromethyl; cyano; $C_{1-4}$ hydrocarbyloxy and $C_{1-4}$ hydrocarbyl groups wherein the $C_{1-4}$ hydrocarbyloxy and $C_{1-4}$ hydrocarbyl groups are each optionally substituted by one or more $C_{1-2}$ alkoxy, halogen, hydroxy or optionally substituted phenyl or pyridyl groups; $C_{1-4}$ acylamino; benzoylamino; pyrrolidinocarbonyl; piperidinocarbonyl; morpholinocarbonyl; piperazinocarbonyl; five and six membered heteroaryl groups containing one or two heteroatoms selected from N, O and S, the heteroaryl groups being optionally substituted by one or more $C_{1-4}$ alkyl substituents; optionally substituted phenyl; optionally substituted pyridyl; and optionally substituted phenoxy; wherein the optional substituent for the phenyl, pyridyl and phenoxy groups are 1, 2 or 3 substituents selected from $C_{1-2}$ acyloxy, fluorine, chlorine, bromine, trifluoromethyl, cyano, and $C_{1-2}$ hydrocarbyloxy and $C_{1-2}$ hydrocarbyl groups wherein the $C_{1-2}$ hydrocarbyloxy and $C_{1-2}$ hydrocarbyl groups are each optionally substituted by methoxy or hydroxy.

More particular sub-groups of compounds within formulae (II) and (IIa) consist of compounds wherein $R^1$ is unsubstituted phenyl or, more preferably, phenyl bearing 1 to 3 (and more preferably 1 or 2) substituents independently selected from hydroxy; $C_{1-4}$ acyloxy; fluorine; chlorine; bromine; trifluoromethyl; cyano; $C_{1-4}$ alkoxy or $C_{1-4}$ alkyl groups wherein the $C_{1-4}$ alkoxy and $C_{1-4}$ alkyl groups are each optionally substituted by one or more fluorine atoms or by $C_{1-2}$ alkoxy, hydroxy or optionally substituted phenyl; $C_{1-4}$ acylamino; benzoylamino; pyrrolidinocarbonyl; piperidinocarbonyl; morpholinocarbonyl; piperazinocarbonyl; optionally substituted phenyl; optionally substituted pyridyl; and optionally substituted phenoxy wherein the optionally substituted phenyl, pyridyl and phenoxy groups are each optionally substituted with 1, 2 or 3 substituents selected from $C_{1-2}$ acyloxy, fluorine, chlorine, bromine, trifluoromethyl, cyano, $C_{1-2}$ hydrocarbyloxy and $C_{1-2}$ hydrocarbyl each optionally substituted by methoxy or hydroxy.

Although up to 5 substituents may be present, more typically there are 0, 1, 2, 3 or 4 substituents, preferably 0, 1, 2 or 3, and more preferably 0, 1 or 2.

In one embodiment within each of formulae (II) and (IIa), $R^1$ is unsubstituted phenyl or a phenyl group substituted by 1 or 2 substituents independently selected from hydroxy; $C_{1-4}$ acyloxy; fluorine; chlorine; bromine; trifluoromethyl; trifluoromethoxy; difluoromethoxy; benzyloxy; cyano; $C_{1-4}$ hydrocarbyloxy and $C_{1-4}$ hydrocarbyl each optionally substituted by $C_{1-2}$ alkoxy or hydroxy.

More preferably, the group $R^1$ is a substituted phenyl group bearing 1 or 2 substituents independently selected from fluorine; chlorine; trifluoromethyl; trifluoromethoxy; difluoromethoxy; cyano; methoxy, ethoxy, i-propoxy, methyl, ethyl, propyl, isopropyl, tert-butyl and benzyloxy.

In one sub-group of compounds within each of formulae (II) and (IIa), the group $R^1$ is a phenyl group having a substituent at the para position selected from fluorine, chlorine, trifluoromethyl, trifluoromethoxy, difluoromethoxy, benzyloxy, methyl, tert-butyl and methoxy, and optionally a second substituent at the ortho- or meta-position selected from fluorine, chlorine or methyl. Within this sub-group, the phenyl group can be monosubstituted. Alternatively, the phenyl group can be disubstituted.

In a particular sub-group of compounds within each of formulae (II) and (IIa), the group $R^1$ is a monosubstituted phenyl group having a tert-butyl substituent at the para position.

In another particular sub-group of compounds within each of formulae (II) and (IIa), the group $R^1$ is a monosubstituted phenyl group having a chlorine substituent at the para position.

In a further sub-group of compounds within each of formulae (II) and (IIa), $R^1$ is a dichlorophenyl group, particular examples of which are 2,4-dichlorophenyl, 2,5-dichlorophenyl, 3,4-dichlorophenyl and 2,3-dichlorophenyl.

In each of formulae (II) and (IIa) and the above embodiments, sub-groups and examples thereof:
T is preferably N; and/or
$R^4$ is hydrogen; and/or
$J^1$-$J^2$ represents a group selected from N=CH, HN—C(O), (Me)NC(O), (Et)NC(O) and HC=CH; and/or
$Q^1$ is a bond or a $C_{1-2}$ alkylene group and $Q^2$ is a bond or a methylene group; and/or
G is $NR^2R^3$ and more preferably G is $NH_2$ or NHMe.

Another sub-group of compounds within Formula (II) has the general formula (III):

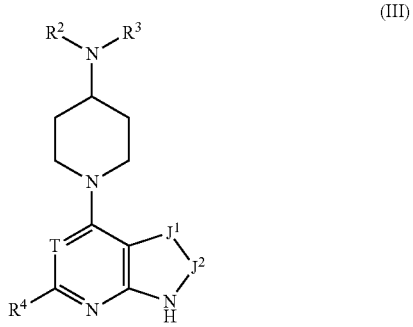

(III)

wherein $R^2$, $R^3$, $R^4$, T, $J^1$ and $J^2$ are as defined herein in respect of formula (I) and sub-groups, examples and preferences thereof.

Another sub-group of compounds within formula (II) has the general formula (IV):

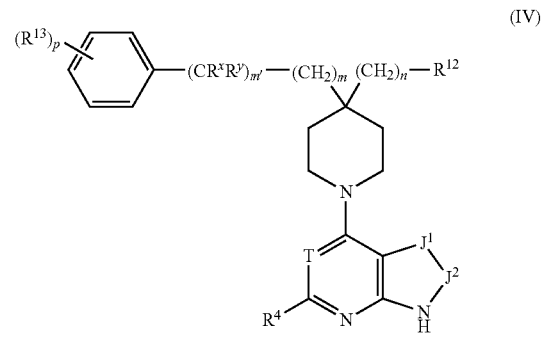

(IV)

wherein m is 0, 1 or 2; m' is 0 or 1 provided that the sum of m and m' is in the range 0 to 2; n is 0 or 1; p is 0, 1, 2 or 3; $R^x$ and $R^y$ are the same or different and each is selected from hydrogen, methyl and fluorine; $R^{12}$ is CN or $NR^2R^3$ and each $R^{13}$ is independently selected from $R^{10}$, $R^{10a}$, $R^{10b}$ and $R^{10c}$ wherein $J^1$, $J^2$, T, $R^2$, $R^3$, $R^4$, $R^{10}$, $R^{10a}$, $R^{10b}$ and $R^{10c}$ are as defined herein.

In formula (IV), m is preferably 0 or 1. When m' is 0, more preferably m is 1. When m' is 1, preferably m is 0.

In one group of compounds n is 0. In another group of compounds, n is 1.

Preferably p is 0, 1 or 2 and $R^{13}$ is selected from hydroxy; $C_{1-4}$ acyloxy; fluorine; chlorine; bromine; trifluoromethyl; trifluoromethoxy; difluoromethoxy; benzyloxy; cyano; $C_{1-4}$ hydrocarbyloxy and $C_{1-4}$ hydrocarbyl each optionally substituted by $C_{1-2}$ alkoxy or hydroxy.

More preferably, $R^{13}$ is selected from fluorine; chlorine; trifluoromethyl; trifluoromethoxy; difluoromethoxy; cyano; methoxy, ethoxy, i-propoxy, methyl, ethyl, propyl, isopropyl, tert-butyl and benzyloxy.

For example the phenyl group may have a substituent $R^{13}$ at the para position selected from fluorine, chlorine, trifluoromethyl, trifluoromethoxy, difluoromethoxy, benzyloxy, methyl, tert-butyl and methoxy, and optionally a second substituent at the ortho- or meta-position selected from fluorine, chlorine or methyl. Within this sub-group, the phenyl group can be monosubstituted. Alternatively, the phenyl group can be disubstituted.

In another sub-group of compounds, p is 1 and the substituent $R^{13}$ is a tert-butyl substituent at the para position.

In another sub-group of compounds, p is 1 and the substituent $R^{13}$ is a chlorine substituent at the para position.

In another sub-group of compounds, p is 2 and the phenyl group is a dichlorophenyl group, particular examples of which are 2,4-dichlorophenyl, 2,5-dichlorophenyl, 3,4-dichlorophenyl and 2,3-dichlorophenyl.

In one sub-group of compounds within formula (IV), $R^{12}$ is $NR^2R^3$ and more preferably $R^{12}$ is selected from $NH_2$, NHMe and $NMe_2$, with $NH_2$ being particularly preferred.

One particular sub-group of compounds within formula (IV) can be represented by the formula (V):

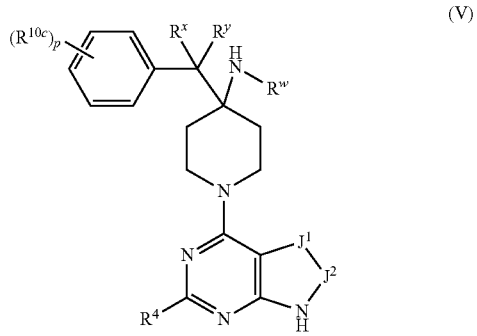

(V)

wherein $J^1, J^2, R^x, R^y, R^4$, p and $R^{10c}$ are as defined herein, and $R^w$ is hydrogen or methyl. In one embodiment, $R^w$ is hydrogen. In another embodiment, $R^w$ is methyl. Preferably, p is 0, 1 or 2 and each substituent $R^{10c}$ (when p is 1 or 2) is selected from the substituents listed above in respect of $R^{13}$ and its embodiments, sub-groups and examples.

In formulae (IV) and (V), $R^x$ and $R^y$ may both be hydrogen. Alternatively, $R^x$ and $R^y$ may both be methyl, or may both be fluorine, or one of $R^x$ and $R^y$ may be hydrogen and the other may be methyl or fluorine.

Another sub-group of compounds within formula (II) can be represented by formula (VI)

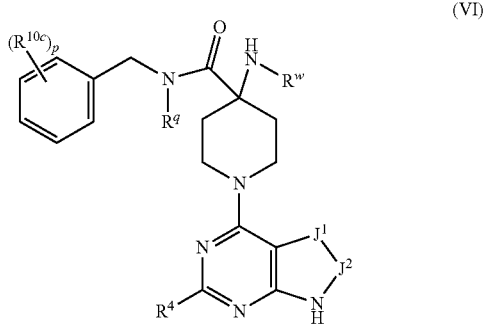

(VI)

wherein $R^q$ is hydrogen or methyl and $R^{10c}, R^4, R^w, J^1$ and $J^2$ are as defined herein.

Preferably, p is 0, 1 or 2 and each substituent $R^{10c}$ (when p is 1 or 2) is selected from the substituents listed above in respect of $R^{13}$ and its embodiments, sub-groups and examples.

In one group of compounds, $R^q$ is hydrogen. In another group of compounds, $R^q$ is methyl.

In one embodiment, $R^w$ is hydrogen. In another embodiment, $R^w$ is methyl.

Compounds of formulae (V) and (VI) show selectivity as inhibitors of PKB relative to PKA.

Particular compounds within formulae (V) and (VI) are those wherein $R^4$ is hydrogen.

In formulae (V) and (VI), the moiety $J^1J^2$ is preferably selected from N=CH, CH=CH, HN—C(O), (Me)NC(O) and (Et)NC(O), and more preferably from N=CH and CH=CH.

In one particularly preferred group of compounds within formulae (V) and (VI), the moiety $J^1$-$J^2$ is CH=CH.

In each of formulae (V) and (VI), one group of preferred substituents $R^{10c}$ consists of chlorine, fluorine, methyl, ethyl, isopropyl, methoxy, difluoromethoxy, trifluoromethoxy, trifluoromethyl, tert-butyl, cyano and benzyloxy.

In each of formulae (V) and (VI), a further group of preferred substituents $R^{10c}$ consists of chlorine, fluorine, methyl, methoxy, difluoromethoxy, trifluoromethoxy, trifluoromethyl, cyano and benzyloxy.

In formulae (V) and (VI), p is preferably 1 or 2.

In one embodiment, p is 1.

In another embodiment, p is 2.

When p is 1, the phenyl ring can be 2-substituted, or 3-substituted, or 4-substituted.

Particular examples of groups wherein p is 1 are the groups A2, A3, A5, A6, A8, A9, A10, A11, A12, A15, A18 and A19 in Table 1 above. More preferred groups are groups A2, A5, A10, A11, A15, A18 and A19 in Table 1.

When p is 2, the phenyl ring can be, for example, 2,3-disubstituted, 2,4-disubsubstituted, or 2,5-disubstituted.

Particular examples of groups wherein p is 2 are the groups A4, A7, A13, A14, A16, A17 and A20 in Table 1.

Another sub-group of compounds for use according to the invention can be represented by the formula (VII):

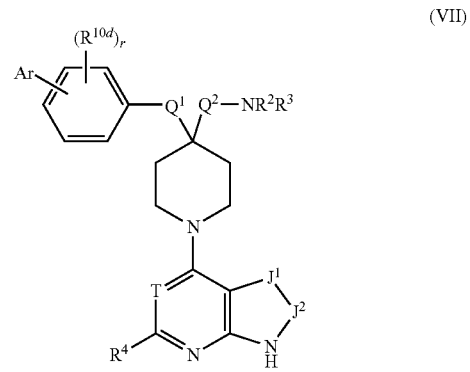

(VII)

wherein Ar is a 5- or 6-membered monocyclic aryl or heteroaryl group having up to 2 heteroatom ring members selected from O, N and S and being optionally substituted by one or two substituents selected from fluorine, chlorine, methyl and methoxy; $R^{10d}$ is a substituent selected from fluorine, chlorine, methyl, trifluoromethyl, trifluoromethoxy and methoxy; r is 0, 1 or 2 (more typically 0 or 1); and T, $Q^1$, $Q^2$, $NR^2R^3$, $R^4$, and $J^1$-$J^2$ are as defined herein.

In formula (VII), particular 5- or 6-membered monocyclic aryl or heteroaryl groups Ar can be selected from phenyl, pyridyl, furyl and thienyl, each optionally substituted as defined herein. One particular monocyclic aryl group is optionally substituted phenyl, with unsubstituted phenyl being a particular example.

Within formula (VII), preferred compounds are those compounds wherein $NR^2R^3$ is selected from $NH_2$, NHMe and $NMe_2$ (with $NH_2$ being particularly preferred); and/or $R^4$ is hydrogen or methyl (more preferably hydrogen); and/or T is CH or N; and/or $Q^1$ is selected from $CH_2$ and $CH_2NHCO$ (wherein the carbonyl group is attached to the piperidine ring); and/or $Q^2$ is selected from $CH_2$ and a bond (and more preferably is a bond); and/or $J^1$-$J^2$ is selected from CH=N and CH=CH.

For the avoidance of doubt, it is to be understood that each general and specific preference, embodiment and example of the groups $R^1$ may be combined with each general and specific preference, embodiment and example of the groups $R^2$ and/or $R^3$ and/or $R^4$ and/or $R^5$ and/or $R^6$ and/or $R^7$ and/or $R^8$ and $R^9$ and/or $R^{10}$ and/or $R^{11}$ and $J^1$-$J^2$ and/or T and/or $Q^1$ and/or $Q^2$ and that all such combinations are embraced by this application.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

Particular compounds for use according to the invention are as illustrated in the examples below and include:

methyl-[1-(9H-purin-6-yl)-piperidin-4-yl]-amine;
benzyl-[1-(9H-purin-6-yl)-piperidin-4-yl]-amine;
1-(9H-purin-6-yl)piperidin-4-ylamine;
6-(4-aminopiperidin-1-yl)-7,9-dihydropurin-8-one;
6-(4-benzyl-4-hydroxypiperidin-1-yl)-7,9-dihydropurin-8-one;
6-(piperazin-1-yl)-7,9-dihydropurin-8-one;
(3S)-6-(3-benzyloxymethylpiperazin-1-yl)-7,9-dihydropurin-8-one;
6-(4-phenethylaminopiperidin-1-yl)-7,9-dihydro-purin-8-one;
6-[4-(2-chlorobenzylamino)-piperidin-1-yl]-7,9-dihydropurin-8-one;
6-[4-(3-chlorobenzylamino)-piperidin-1-yl]-7,9-dihydropurin-8-one;
1-(1H-pyrazolo[3,4-d]pyrimidin-4-yl)-piperidin-4-ylamine;
1-(7H-pyrrolo[2,3-d]pyrimidin-4-yl)-piperidin-4-ylamine;
1-(1H-pyrrolo[2,3-b]pyridin-4-yl)-piperidin-4-ylamine;
C-[4-(4-chloro-phenyl)-1-(7H-pyrrolo[2,3-d]pyrimidin-4-yl)-piperidin-4-yl]-methylamine;
C-[4-(4-chloro-phenyl)-1-(9H-purin-6-yl)-piperidin-4-yl]-methylamine;
4-benzyl-1-(9H-purin-6-yl)piperidin-4-ylamine;
4-(4-chlorobenzyl)-1-(7H-pyrrolo[2,3-d]pyrimidin-4-yl)piperidin-4-ylamine;
4-(4-chlorobenzyl)-1-(9H-purin-6-yl)piperidin-4-yl amine;
C-[4-(4-chlorobenzyl)-1-(7H-pyrrolo[2,3-d]pyrimidin-4-yl) piperidin-4-yl]methylamine;
6-[4-aminomethyl-4-(4-chlorophenyl)piperidin-1-yl]-7,9-dihydropurin-8-one;
C-[4-(4-chlorophenyl)-1-(1H-pyrrolo[2,3-b]pyridin-4-yl)piperidin-4-yl]methylamine;
6-[4-aminomethyl-4-(4-chlorophenyl)piperidin-1-yl]-7-benzyl-7,9-dihydro-purin-8-one;
6-[4-aminomethyl-4-(4-chlorophenyl)piperidin-1-yl]-7-ethyl-7,9-dihydro-purin-8-one;
C-[4-(4-chlorobenzyl)-1-(9H-purin-6-yl)piperidin-4-yl]methylamine;
4-(4-chlorophenyl)-1-(7H-pyrrolo[2,3-d]pyrimidin-4-yl)piperidine-4-carbonitrile;
4-(4-chlorophenyl)-1-(7H-pyrrolo[2,3-d]pyrimidin-4-yl)piperidin-4-ylamine;
C-[4-(3-chlorophenyl)-1-(7H-pyrrolo[2,3-d]pyrimidin-4-yl)piperidin-4-yl]methylamine;
C-[4-(3-chlorophenyl)-1-(9H-purin-6-yl)piperidin-4-yl]methylamine;
C-[4-(3,4-dichlorophenyl)-1-(7H-pyrrolo[2,3-d]pyrimidin-4-yl)piperidin-4-yl]methylamine;
C-[4-(3,4-dichlorophenyl)-1-(9H-purin-6-yl)piperidin-4-yl]methylamine;
C-[1-(7H-pyrrolo[2,3-d]pyrimidin-4-yl)-4-trifluoromethoxyphenyl)piperidin-4-yl]methylamine;
C-[1-(9H-purin-6-yl)-4-(4-trifluoromethoxyphenyl)piperidin-4-yl]methylamine;
1-(5-phenyl-7H-pyrrolo[2,3-d]pyrimidin-4-yl)-piperidin-4-ylamine;
C-[1-(7H-pyrrolo[2,3-d]pyrimidin-4-yl)-4-(4-trifluoromethylphenyl)piperidin-4-yl]methylamine;
C-[1-(9H-purin-6-yl)-4-(4-trifluoromethylphenyl)piperidin-4-yl]methylamine;
C-[1-(7H-pyrrolo[2,3-d]pyrimidin-4-yl)-4-(3-trifluoromethylphenyl)piperidin-4-yl]methylamine;
C-[1-(9H-purin-6-yl)-4-(3-trifluoromethylphenyl)piperidin-4-yl]methylamine;
C-[4-(3,4-difluorophenyl)-1-(7H-pyrrolo[2,3-d]pyrimidin-4-yl)piperidin-4-yl]methylamine;
C-[4-(3,4-difluorophenyl)-1-(9H-purin-6-yl)piperidin-4-yl]methylamine;
C-[4-(4-methoxyphenyl)-1-(7H-pyrrolo[2,3-d]pyrimidin-4-yl)piperidin-4-yl]methylamine;
C-[4-(4-methoxyphenyl)-1-(9H-purin-6-yl)piperidin-4-yl]methylamine;
C-[4-(4-benzyloxyphenyl)-1-(7H-pyrrolo[2,3-d]pyrimidin-4-yl)piperidin-4-yl]methylamine;
C-[4-(4-benzyloxyphenyl)-1-(9H-purin-6-yl)piperidin-4-yl]methylamine;
[4-(4-chloro-phenyl)-1-(7H-pyrrolo[2,3-d]pyrimidin-4-yl)-piperidin-4-ylmethyl]-methyl-amine;
[4-(4-chlorophenyl)-1-(7H-pyrrolo[2,3-d]pyrimidin-4-yl)-piperidin-4-ylmethyl]-isopropylamine;
[4-(4-chlorobenzyl)-1-(7H-pyrrolo[2,3-d]pyrimidin-4-yl)-piperidin-4-yl]-dimethylamine;
C-[4-(3,4-dichlorobenzyl)-1-(7H-pyrrolo[2,3-d]pyrimidin-4-yl)piperidin-4-yl]methylamine;
C-[4-(3,4-dichlorobenzyl)-1-(9H-purin-6-yl)piperidin-4-yl]methylamine;
C-[1-(7H-pyrrolo[2,3-d]pyrimidin-4-yl)-4-(4-trifluoromethoxybenzyl)piperidin-4-yl]methylamine;
C-[1-(9H-purin-6-yl)-4-(4-trifluoromethoxybenzyl)piperidin-4-yl]methylamine;
4-(3,4-dichlorobenzyl)-1-(7H-pyrrolo[2,3-d]pyrimidin-4-yl)piperidin-4-ylamine;
4-(3,4-dichlorobenzyl)-1-(9H-purin-6-yl)piperidin-4-yl amine;
1-(7H-pyrrolo[2,3-d]pyrimidin-4-yl)-4-(4-trifluoromethoxybenzyl)piperidin-4-ylamine;
1-(9H-purin-6-yl)-4-(4-trifluoromethoxybenzyl)piperidin-4-ylamine;
1-(7H-pyrrolo[2,3-d]pyrimidin-4-yl)-4-(3-chlorobenzyl)piperidin-4-ylamine;

4-(4-chlorobenzyl)-1-(1H-pyrrolo[2,3-b]pyridin-4-yl)-piperidin-4-ylamine;
4-(2-chlorobenzyl)-1-(7H-pyrrolo[2,3-d]pyrimidin-4-yl)piperidin-4-ylamine;
4-(4-tert-Butylbenzyl)-1-(7H-pyrrolo[2,3-d]pyrimidin-4-yl) piperidin-4-ylamine;
4-(3-methoxybenzyl)-1-(7H-pyrrolo[2,3-d]pyrimidin-4-yl) piperidin-4-ylamine;
4-(3-trifluoromethoxybenzyl)-1-(7H-pyrrolo[2,3-d]pyrimidin-4-yl)piperidin-4-ylamine;
4-(2,4-dichlorobenzyl)-1-(7H-pyrrolo[2,3-d]pyrimidin-4-yl)piperidin-4-ylamine;
4-(2-chloro-4-fluorobenzyl)-1-(7H-pyrrolo[2,3-d]pyrimidin-4-yl)piperidin-4-ylamine;
4-(2,6-dichlorobenzyl)-1-(7H-pyrrolo[2,3-d]pyrimidin-4-yl)piperidin-4-ylamine;
[4-(4-chlorobenzyl)-1-(7H-pyrrolo[2,3-d]pyrimidin-4-yl)piperidin-4-yl]methylamine;
1-(7H-pyrrolo[2,3-d]pyrimidin-4-yl)-4-(2-trifluoromethoxybenzyl)piperidin-4-ylamine;
4-(2,5-dichlorobenzyl)-1-(7H-pyrrolo[2,3-d]pyrimidin-4-yl)piperidin-4-ylamine;
4-(2,3-dichlorobenzyl)-1-(7H-pyrrolo[2,3-d]pyrimidin-4-yl)piperidin-4-ylamine;
4-(4-tert-butylbenzyl)-1-(1H-pyrrolo[2,3-b]pyridin-4-yl)-piperidin-4-ylamine;
4-(2,4-dichlorobenzyl)-1-(1H-pyrrolo[2,3-b]pyridin-4-yl)-piperidin-4-ylamine;
C-[4-(4-chlorophenyl)-1-(1H-pyrrolo[2,3-b]pyridin-4-yl)-piperidin-4-yl]-methylamine;
4-amino-1-(7H-pyrrolo[2,3-d]pyrimidin-4-yl)-piperidine-4-carboxylic acid 4-chloro-benzylamide;
4-amino-1-(7H-pyrrolo[2,3-d]pyrimidin-4-yl)-piperidine-4-carboxylic acid 3-chloro-benzylamide;
4-amino-1-(7H-pyrrolo[2,3-d]pyrimidin-4-yl)-piperidine-4-carboxylic acid 4-trifluoromethyl-benzylamide;
4-amino-1-(7H-pyrrolo[2,3-d]pyrimidin-4-yl)-piperidine-4-carboxylic acid 4-fluoro-benzylamide;
4-amino-1-(7H-pyrrolo[2,3-d]pyrimidin-4-yl)-piperidine-4-carboxylic acid 2-chloro-benzylamide;
4-amino-1-(7H-pyrrolo[2,3-d]pyrimidin-4-yl)-piperidine-4-carboxylic acid 4-trifluoromethoxy-benzylamide;
4-amino-1-(7H-pyrrolo[2,3-d]pyrimidin-4-yl)-piperidine-4-carboxylic acid (4-chloro-benzyl)-methyl-amide;
4-amino-1-(7H-pyrrolo[2,3-d]pyrimidin-4-yl)-piperidine-4-carboxylic acid 4-tert-butyl-benzylamide;
4-amino-1-(7H-pyrrolo[2,3-d]pyrimidin-4-yl)-piperidine-4-carboxylic acid 2,4-dichloro-benzylamide;
4-amino-1-(7H-pyrrolo[2,3-d]pyrimidin-4-yl)-piperidine-4-carboxylic acid 3,4-dichloro-benzylamide; and
4-(4-chloro-benzyloxymethyl)-1-(7H-pyrrolo[2,3-d]pyrimidin-4-yl)-piperidin-4-ylamine;
[4-amino-1-(7H-pyrrolo[2,3-d]pyrimidin-4-yl)-piperidin-4-yl]-(3,4-dihydro-1H-isoquinolin-2-yl)-methanone;
[4-amino-1-(7H-pyrrolo[2,3-d]pyrimidin-4-yl)-piperidin-4-yl]-(2-phenyl-pyrrolidin-1-yl)-methanone;
4-(4-chlorobenzyl)-1-(1H-pyrazolo[3,4-b]pyridin-4-yl)-piperidin-4-ylamine;
4-(4-tert-butyl-benzyl)-1-(1H-pyrazolo[3,4-b]pyridin-4-yl)-piperidin-4-ylamine;
4-(4-tert-butyl-benzyl)-1-(1H-pyrrolo[2,3-b]pyridin-4-yl)-piperidin-4-ylamine;
N-[4-amino-1-(7H-pyrrolo[2,3-d]pyrimidin-4-yl)-piperidin-4-ylmethyl]-4-chloro-benzamide;
4-biphenyl-4-ylmethyl-1-(7H-pyrrolo[2,3-d]pyrimidin-4-yl)-piperidin-4-ylamine;
4-biphenyl-2-ylmethyl-1-(7H-pyrrolo[2,3-d]pyrimidin-4-yl)-piperidin-4-ylamine;
4-(2-methoxy-benzyl)-1-(7H-pyrrolo[2,3-d]pyrimidin-4-yl)-piperidin-4-ylamine;
4-naphthalen-1-ylmethyl-1-(7H-pyrrolo[2,3-d]pyrimidin-4-yl)-piperidin-4-ylamine;
4-amino-1-(7H-pyrrolo[2,3-d]pyrimidin-4-yl)-piperidine-4-carboxylic acid 4-chloro-2-fluoro-benzylamide;
4-amino-1-(7H-pyrrolo[2,3-d]pyrimidin-4-yl)-piperidine-4-carboxylic acid (biphenyl-3-ylmethyl)-amide;
4-biphenyl-3-ylmethyl-1-(7H-pyrrolo[2,3-d]pyrimidin-4-yl)-piperidin-4-ylamine; and
4-(6-chloro-biphenyl-3-ylmethyl)-1-(7H-pyrrolo[2,3-d]pyrimidin-4-yl)-piperidin-4-ylamine; and salts, solvates, tautomers and N-oxides thereof.

Salts, Solvates, Tautomers, Isomers, N-Oxides, Esters, Prodrugs and Isotopes

Unless otherwise specified, a reference to a particular compound also includes ionic, salt, solvate, and protected forms thereof, for example, as discussed below.

Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. As in the preceding sections of this application, all references to formula (I) should be taken to refer also to formulae (Ia), (Ib), (Ic), (Id), (II), (IIa), (III), (IV), (V), (VI), (VII) and sub-groups and embodiments thereof unless the context indicates otherwise.

Salt forms may be selected and prepared according to methods described in *Pharmaceutical Salts Properties, Selection, and Use*, P. Heinrich Stahl (Editor), Camille G. Wermuth (Editor), ISBN: 3-90639-026-8, Hardcover, 388 pages, August 2002.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I) as defined herein.

The salt forms of the compounds for use according to the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds, also find application in relation to the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I) as defined herein.

For example, when $J^1$-$J^2$ is N=$CR^6$, the tautomeric forms A and B are possible for the bicyclic group.

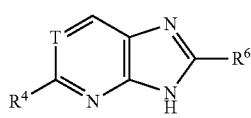

A

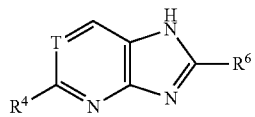

B

When $J^1$-$J^2$ is N=N, the tautomeric forms C and D are possible for the bicyclic group.

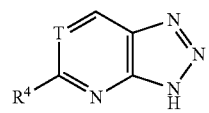

C

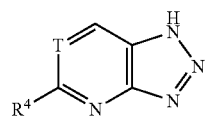

D

When $J^1$-$J^2$ is HN—CO, the tautomeric forms E, F and G are possible for the bicyclic group.

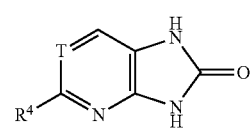

E

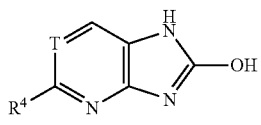

F

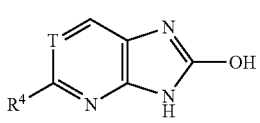

G

All such tautomers are embraced by formula (I) as defined herein.

Other examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

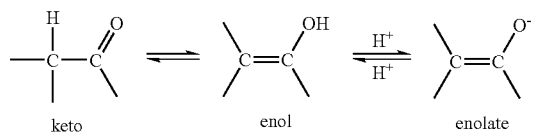

keto    enol    enolate

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and/isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds for use according to the invention include compounds with one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by Formula (I) as defined herein. In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds. By "prodrugs" is meant for example any compound that is converted in vivo into a biologically active compound of the formula (I) as defined herein.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl
(e.g., -Me, -Et, -nPr, -iPr, -nBu, -sBu, -iBu, -tBu);
$C_{1-7}$-aminoalkyl
(e.g., aminoethyl; 2-(N,N-diethylamino)ethyl; 2-(4-morpholino)ethyl); and
acyloxy-$C_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy)carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in Antibody-directed Enzyme Prodrug Therapy (ADEPT), Gene-directed Enzyme Prodrug Therapy (GDEPT), Polymer-directed Enzyme Prodrug Therapy (PDEPT), Ligand-directed Enzyme Prodrug Therapy (LIDEPT), etc.). For example, the prodrug may be a sugar derivative or other glycoside conjugate, or may be an amino acid ester derivative.

Methods for the Preparation of Compounds of the Formula (I)

In this section, references to compounds of the formula (I) include formulae (Ia), (Ib), (Ic), (Id), (II), (IIa), (III), (IV), (V), (VI), (VII) and each of the sub-groups and embodiments thereof as defined herein unless the context requires otherwise.

In a further aspect, the invention provides a process for the preparation of a compound of the formula (I) as defined herein.

Compounds of the formula (I) wherein E is an aryl or heteroaryl group can be prepared by reaction of a compound of the formula (X) with a compound of the formula (XI) where (X) and (XI) may be suitably protected and wherein T, $J^1$, $J^2$, $Q^1$, $Q^2$, G, E, and $R^1$ to $R^5$ are as hereinbefore defined, one of the groups X and Y is chlorine, bromine or iodine or a trifluoromethanesulphonate (triflate) group, and the other one of the groups X and Y is a boronate residue, for example a boronate ester or boronic acid residue.

$$R^1-Q^1\diagdown_{E}\diagup Q^2-G \quad\quad (X)$$
$$|$$
$$X$$

$$(XI)$$

The reaction can be carried out under typical Suzuki Coupling conditions in the presence of a palladium catalyst such as tetrakis(triphenylphosphine)palladium and a base (e.g. a carbonate such as potassium carbonate). The reaction may be carried out in a polar solvent, for example an aqueous solvent such as aqueous ethanol, or an ether such as dimethoxyethane, and the reaction mixture is typically subjected to heating, for example to a temperature of 80° C. or more, e.g. a temperature in excess of 100° C.

An illustrative synthetic route involving a Suzuki coupling step is shown in Scheme 1. In Scheme 1, the bromo compound (XII) in which E is an aryl or heteroaryl group, is converted to a boronic acid (XIII) by reaction with an alkyl lithium such as butyl lithium and a borate ester (iPrO)$_3$B. The reaction is typically carried out in a dry polar solvent such as tetrahydrofuran at a reduced temperature (for example −78° C.).

The resulting boronic acid (XIII) is then reacted with the N-protected chloro compound (XIV) in the presence of bis(triphenylphosphine)palladium under the conditions described above. The protecting group PG (which can be for example a tetrahydropyranyl (THP) group) is then removed by treatment with an acid such as hydrochloric acid to give the compound of the formula (I').

In Scheme 1, where G is other than hydrogen, it is typically protected with a suitable protecting group of which examples are set out below. One particular protecting group which may be used in the context of a Suzuki coupling for protecting an amino group is the tert-butoxycarbonyl group which can be introduced by reacting the amino group with di-tert-butylcarbonate in the presence of a base such as triethylamine. Removal of the protecting group is typically accomplished at the same time as removal of the protecting group PG on the bicyclic group.

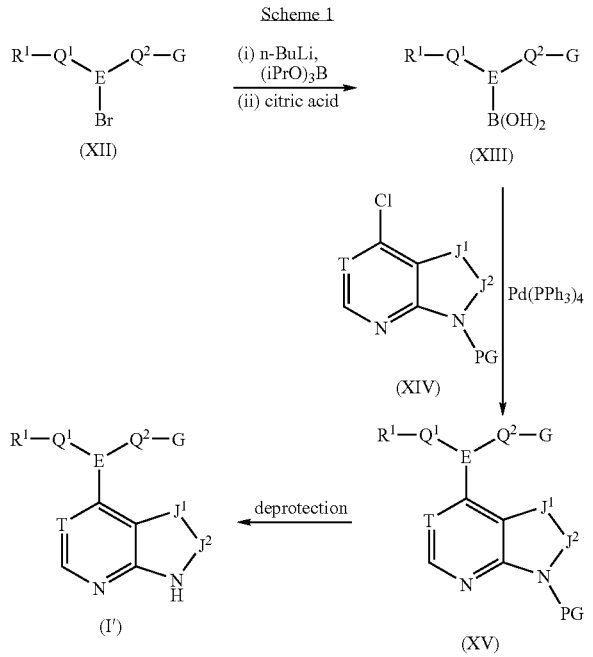

(I')

In the preparative procedure outlined above, the coupling of the aryl or heteroaryl group E to the bicyclic group is accomplished by reacting a halo-purine (or deaza analogue thereof) or halo-aryl or heteroaryl compound with a boronate ester or boronic acid in the presence of a palladium catalyst and base. Many boronates suitable for use in preparing compounds for use according to the invention are commercially available, for example from Boron Molecular Limited of Noble Park, Australia, or from Combi-Blocks Inc, of San Diego, USA. Where the boronates are not commercially available, they can be prepared by methods known in the art, for example as described in the review article by N. Miyaura and A. Suzuki, *Chem. Rev.* 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid.

Compounds of the formula (I) wherein E is a non-aromatic cyclic group and is linked to the bicyclic group by a nitrogen atom can be prepared by the reaction of a compound of the formula (XVI) where T is N, with a compound of the formula (XVII) or a protected derivative thereof, where R$^1$, Q$^1$, Q$^2$ and G are as defined herein and the ring E represents a cyclic group E containing a nucleophilic NH group as a ring member.

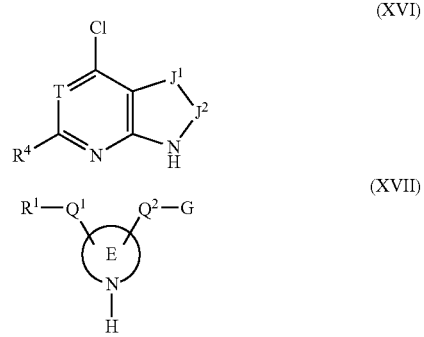

The reaction is typically carried out in a polar solvent such as an alcohol (e.g. ethanol, propanol or n-butanol) at an elevated temperature, for example a temperature in the region from 90° C. to 160° C., optionally in the presence of a non-interfering amine such as triethylamine. The reaction may be carried out in a sealed tube, particularly where the desired reaction temperature exceeds the boiling point of the solvent. When T is N, the reaction is typically carried out at a temperature in the range from about 100° C. to 130° C. but, when T is CH, higher temperatures may be required, for example up to about 160° C., and hence higher boiling solvents such as dimethylformamide may be used. In general, an excess of the nucleophilic amine will be used and/or an additional non-reacting base such as triethylamine will be included in the reaction mixture. Heating of the reaction mixture may be accomplished by normal means or by the use of a microwave heater.

In order to prepare compounds of the formula (I) wherein T is CH, the hydrogen atom of the group CH may be replaced by an activating group in order to facilitate nucleophilic displacement of the chlorine atom by the amine (XVII). The activating group is typically one which can be removed subsequent to the nucleophilic displacement reaction. One such activating group is an ester group such as ethoxycarbonyl or methoxycarbonyl which can be removed by hydrolysis and decarboxylation. Hydrolysis of the ethoxycarbonyl or methoxycarbonyl group to the carboxylic acid is typically carried out using an aqueous alkali such as sodium hydroxide, and the decarboxylation step is typically conducted by heating to an elevated temperature (e.g. 150° C. to 190° C.).

Compounds of the formula (XVI) are commercially available or can be prepared according to methods well known to the skilled person. For example, compounds of the formula (XVI) where T is N and $J^1$-$J^2$ is CH=N can be prepared from the corresponding hydroxy compound by reaction with a chlorinating agent such as $POCl_3$. Compounds of the formula (XVI) where $J^1$-$J^2$ is HN—C(O) can be prepared by the reaction of an ortho-diamino compound of the formula (XVIII) with carbonyl di-imidazole in the presence of a non-interfering base such as triethylamine.

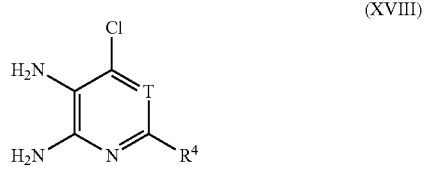

(XVIII)

Compounds of the formula (XVI) where T is $CR^5$ and $J^1$-$J^2$ is $(R^7)H$=$CH(R^6)$ can be prepared from the corresponding N-oxide of the formula (XIX) by reaction with phosphorus oxychloride at an elevated temperature, for example the reflux temperature of $POCl_3$.

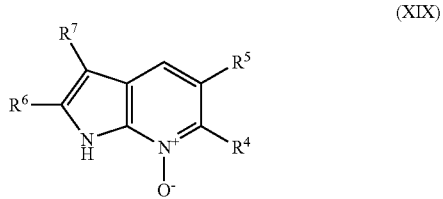

(XIX)

Intermediate compounds of the formula (XVII) wherein E is a piperidine group, $Q^1$ is a saturated hydrocarbon linking group and $Q^1$ and $Q^2$ are both linked to the 4-position of the piperidine group can be prepared by the sequence of reactions shown in Scheme 2.

Scheme 2

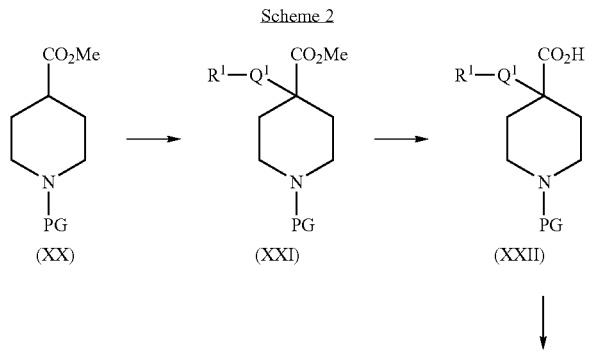

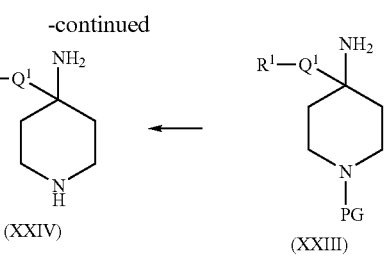

In Scheme 2,4-methoxycarbonyl-piperidine is first protected in standard fashion, for example by means of a t-butyloxycarbonyl(boc) group by reaction with di-tert-butylcarbonate in the presence of a non-interfering base to give the protected compound (XX). The protected piperidine carboxymethyl ester (XX) is then alkylated at the α-position relative to the carbonyl group of the ester by reacting with a strong base such as lithium diisopropylamide (LDA) and a compound of the formula $R^1Q^1$-Hal where Hal is a halogen, preferably bromine, and $Q^1$ is a saturated hydrocarbon group. The ester (XXI) is then hydrolysed to the corresponding carboxylic acid (XXII) using an alkali metal hydroxide such as sodium hydroxide. The carboxylic acid (XXII) can be used to prepare a range of different amine intermediates which can, in turn, be converted into compounds of the formula (II). For example, as shown in Scheme 2, the carboxylic acid can be converted to the acid chloride (e.g. by treatment with oxalyl chloride and optionally a catalytic quantity of DMF, or by treatment of a salt of the acid with oxalyl chloride) and then reacted with sodium azide to form the acid azide (not shown). The acid azide can then be heated to bring about rearrangement in a Curtius reaction (see Advanced Organic Chemistry, $4^{th}$ edition, by Jerry March, John Wiley & sons, 1992, pages 1091-1092) to give compound (XXIII) in which the amino group is attached directly to the piperidine ring. The amine (XXIII) is then deprotected according to standard methods (e.g. using hydrochloric acid in the case of a Boc protecting group) and reacted with a compound of the formula (XIV) to give a compound of the formula (I) as defined herein.

In an alternative sequence of reactions, the ester (XXI) can be reduced to the corresponding alcohol which, following deprotection of the piperidine ring nitrogen atom, can be reacted with a compound of the formula (XXI) to give a compound of the formula (I) in which $Q^2$ is $CH_2$ and G is OH. Alternatively, the alcohol can be oxidised to the aldehyde using Dess-Martin periodinane (see Dess, D. B.; Martin, J. C. J. Org. Soc., 1983, 48, 4155 and Organic Syntheses, Vol. 77, 141) or tetrapropylammonium perruthenate (TPAP). The resulting aldehyde can be used for a variety of synthetic interconversions such as reductive amination using sodium cyanoborohydride and an amine $HNR^2R^3$ to give a compound of the formula (XVII) in which Q2 is $CH_2$ and G is $HNR^2R^3$.

The carboxylic acid (XXII) can also be converted to an amide by reaction with an amine $HNR^2R^3$ under conditions suitable for forming an amide bond. The coupling reaction between the acid (XXII) and the amine $HNR^2R^3$ is preferably carried out in the presence of a reagent of the type commonly used in the formation of peptide linkages. Examples of such reagents include 1,3-dicyclohexylcarbodiimide (DCC) (Sheehan et al, J. Amer. Chem. Soc. 1955, 77, 1067), 1-ethyl-3-(3'-dimethylaminopropyl)-carbodiimide (referred to herein either as EDC or EDAC) (Sheehan et al., J. Org. Chem., 1961, 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al., *Tetrahedron Letters*, 1990, 31, 205). Carbodiimide-based coupling agents are advantageously used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber.*, 103, 708, 2024-2034). Preferred coupling reagents include EDC (EDAC) and DCC in combination with HOAt or HOBt.

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

Where the amine $HNR^2R^3$ is ammonia, the amide coupling reaction can be carried out using 1,1'-carbonyldiimidazole (CDI) to activate the carboxylic acid before addition of the ammonia.

As an alternative, a reactive derivative of the carboxylic acid, e.g. an anhydride or acid chloride, may be used. Reaction with a reactive derivative such an anhydride is typically accomplished by stirring the amine and anhydride at room temperature in the presence of a base such as pyridine.

The resulting amide (not shown) can be reduced using a hydride reducing agent such as lithium aluminium hydride in the presence of aluminium chloride to give the corresponding amine.

Compounds of the formula ((XVII) in which E is a piperidine group, $Q^1$ is a bond and $R^1$ is an aryl or heteroaryl group can be prepared using the sequence of steps shown in Scheme 3.

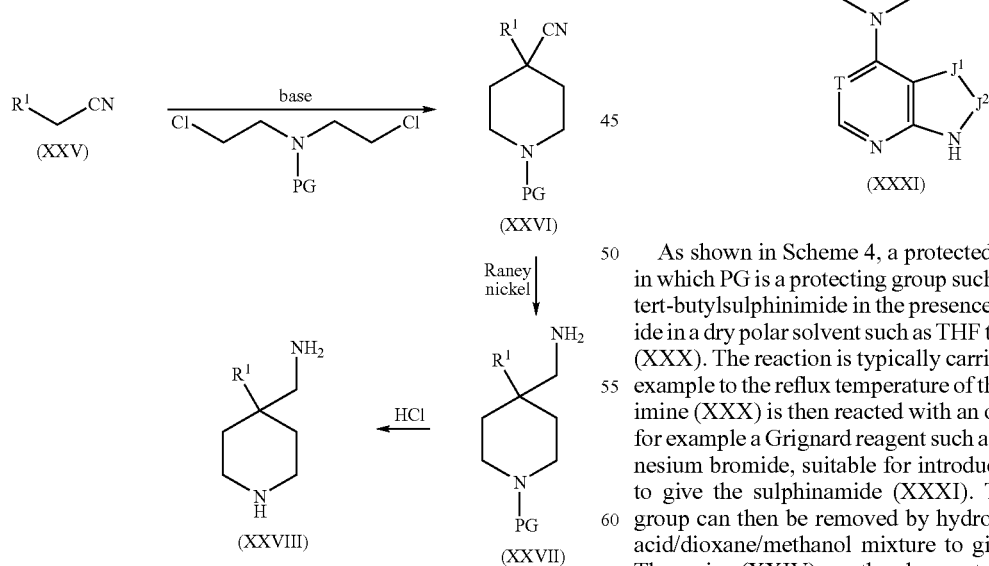

As shown in Scheme 3, the nitrile (XXV) in which $R^1$ is an aryl or heteroaryl group is reacted with a base and N-protected (PG=protecting group) bis-(2-chloroethyl)amine to give the piperidine nitrile (XXVI) which can then be reduced to give the amine (XXVII) using Raney nickel and then deprotected (e.g. using HCl when the protecting group is acid labile) to give amine (XXVIII). Alternatively, the nitrile (XXVI) can be reacted with a compound of the formula (XVI) to give a compound of the formula (I) in which $Q^2$ and G together form a nitrile group.

Compounds of the formula (I) in which E is a piperidine ring, $Q^2$ is a bond and G is an amino group can also be prepared by the reaction sequence shown in Scheme 4.

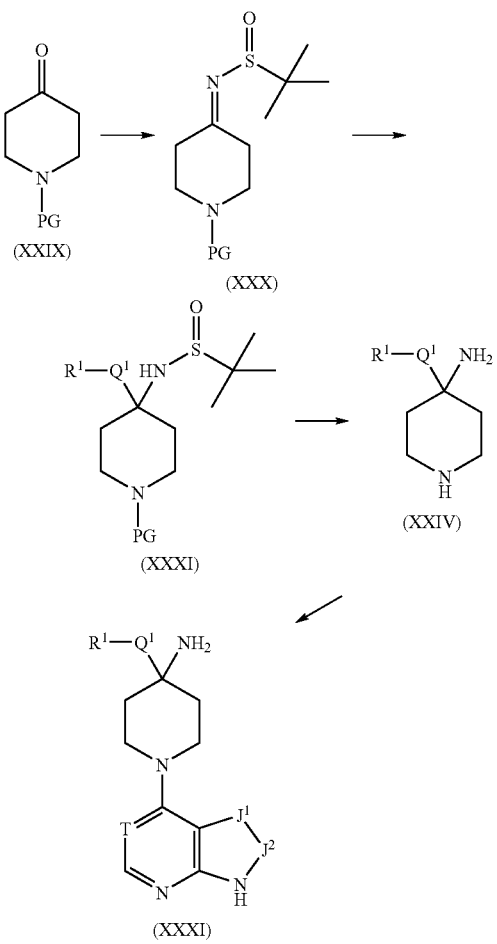

As shown in Scheme 4, a protected 4-piperidone (XXIX), in which PG is a protecting group such as Boc, is reacted with tert-butylsulphinimide in the presence of titanium tetraethoxide in a dry polar solvent such as THF to give the sulphinimine (XXX). The reaction is typically carried out with heating, for example to the reflux temperature of the solvent. The sulphinimine (XXX) is then reacted with an organometallic reagent, for example a Grignard reagent such as an aralkyl or arylmagnesium bromide, suitable for introducing the moiety $R^1$-$Q^1$, to give the sulphinamide (XXXI). The tert-butylsulphinyl group can then be removed by hydrolysis in a hydrochloric acid/dioxane/methanol mixture to give the amine (XXIV). The amine (XXIV) can then be reacted with a chloro-heterocycle (XVI) under the conditions described above to give the product (XXXI), i.e. a compound of the formula (I) in which E is piperidine, $Q^2$ is a bond and G is an amino group.

The corresponding compound wherein $Q^2$ is a bond and G is an alkylamino (e.g. methylamino) group can be prepared from the tert-butylsulphinyl intermediate compound (XXXI) by reaction of the intermediate (XXXI) with a strong base, e.g. a metal hydride such as sodium hydride, followed by the addition of an alkyl halide such as methyl iodide. The reaction is typically carried out in a polar aprotic solvent such as dimethylformamide at a reduced temperature, for example 0-5° C.

Compounds of the formula (I) where $Q^1$ contains an amide bond can be prepared from intermediates of the formulae (XXXII) and (XXXIII) by reaction with intermediate (XI) above using a Suzuki coupling procedure (when $X^L$ is bromine) or by reaction with intermediate (XVI) (when $X^L$ is hydrogen and the group E contains a nucleophilic nitrogen atom) using the methods and conditions described above.

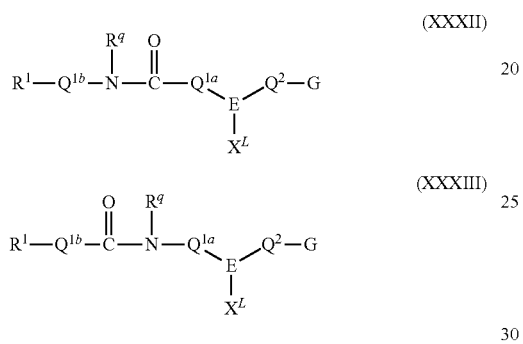

In formulae (XXXII) and (XXXIII), $Q^{1a}$ and $Q^{1b}$ are each a bond or a residue of the group $Q^1$, and $X^L$ is hydrogen or halogen such as bromine. For example, $Q^{1a}$ can be a bond and $Q^{1b}$ can be a group $CH_2$ and vice versa.

The compounds of formulae (XXXII) and (XXXIII) can be prepared by reacting together the appropriate carboxylic acid or activated derivative thereof (e.g. acid chloride) and the appropriate amine using the amide-forming conditions described above.

The formation of compounds of the formula (I) wherein the moiety $Q^1$ contains an amide group is illustrated by the sequence of reactions set out in Scheme 5.

Scheme 5

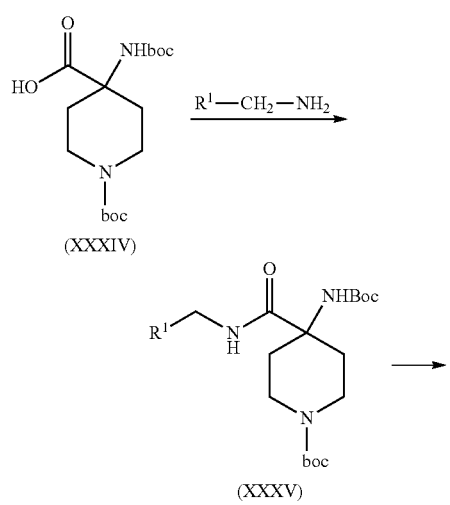

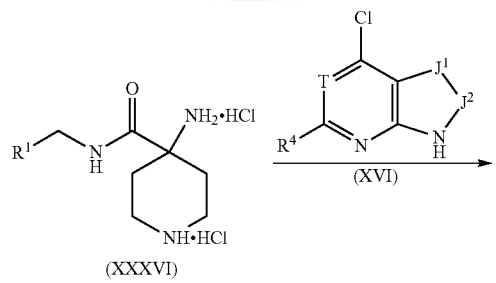

In Scheme 5, the boc-protected piperidine amino acid (XXXIV) is reacted with the arylamine or heteroarylamine $R^1$—$NH_2$ using the amide forming conditions set out above. Thus, for example, the amide-forming reaction can be carried out using HATU (see above) in the presence of a base such as N-ethyldiisopropylamine in a polar solvent such as DMF. The amide (XXXV) is then deprotected; in this case by treatment with acid to remove the boc group; and then reacted with the bicyclic chloro compound (XVI) at elevated temperature (e.g. approximately 100° C.) to give the product (XXXVII). The reaction with the chloro compound is typically carried out in a polar solvent such as a high boiling alcohol (e.g. n-butanol) in the presence of a non-interfering base such as triethylamine.

Compounds of the formula (I) in which $Q^1$ contains an ether linkage can be prepared in a manner analogous to the methods described above for the compounds in which $Q^1$ contains an amide bond. The preparation of compounds containing an ether linkage is illustrated by the sequence of reactions set out in Scheme 6.

Scheme 6

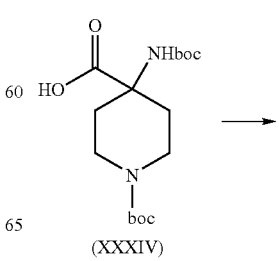

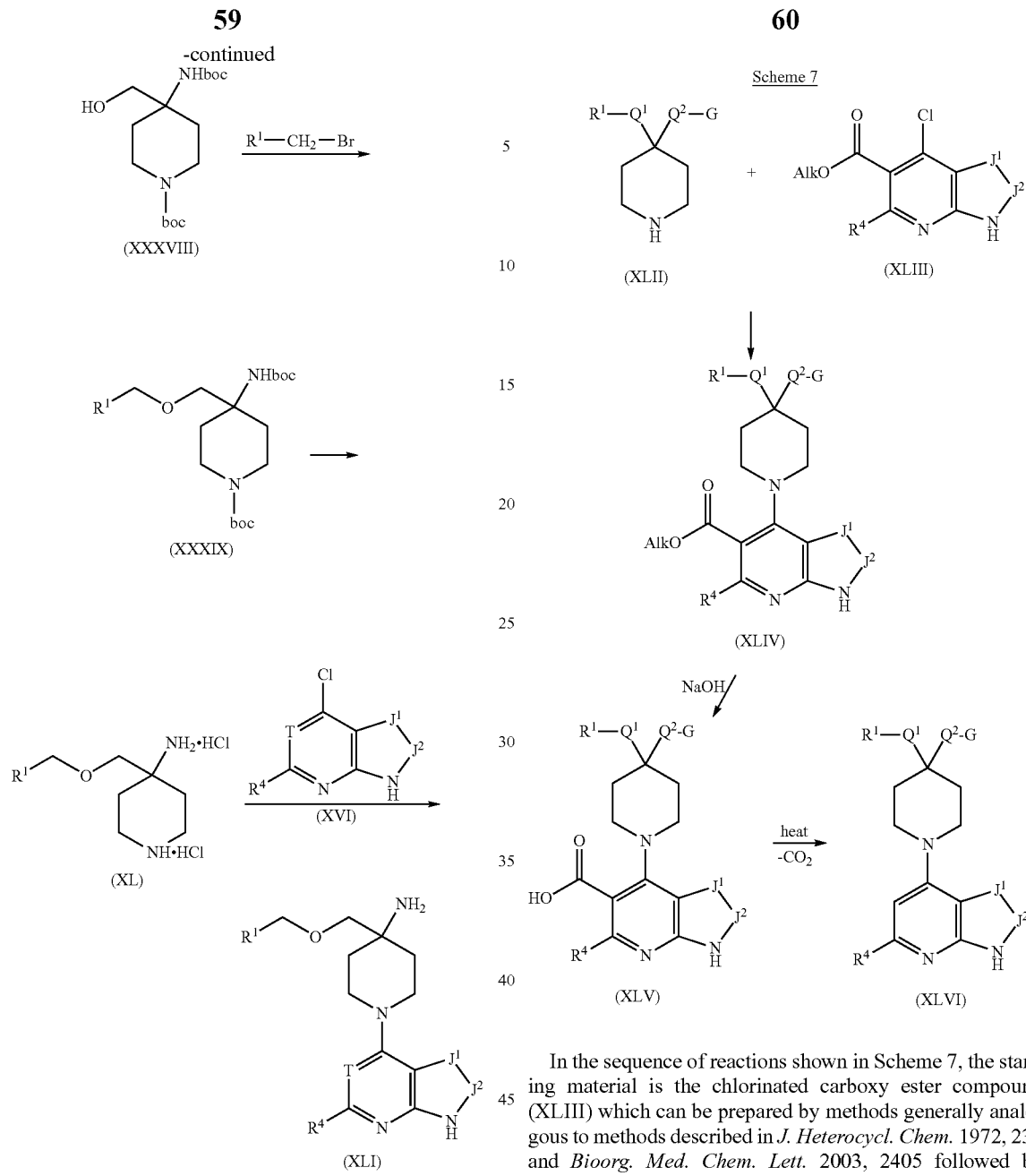

In Scheme 6, the N-protected piperidine amino acid (XXXIV) is reduced to the corresponding alcohol (XXXVIII) using a reducing agent such as lithium aluminium hydride in a polar aprotic solvent such as tetrahydrofuran, typically at around room temperature. The alcohol (XXXVIII) is then treated with a strong base, e.g. a metal hydride such as sodium hydride to form the alcholate which is then reacted with the arylmethyl- or heteroarylmethyl bromide R¹—CH₂—Br to form the ether (XXXIX). The ether-forming reaction is typically carried out at a reduced temperature (e.g. approximately 0° C. using an aprotic polar solvent such as DMF. The ether is then deprotected by standard methods and the deprotected ether (XL) is reacted with the chloro-compound (XVI) under the conditions described above to give the product (XLI).

Compounds of the formula (I) wherein T is CH, E is a piperidine group and J¹-J² is CH=N or CH=CH can be prepared according to the procedure illustrated in Scheme 7.

In the sequence of reactions shown in Scheme 7, the starting material is the chlorinated carboxy ester compound (XLIII) which can be prepared by methods generally analogous to methods described in *J. Heterocycl. Chem.* 1972, 235 and *Bioorg. Med. Chem. Lett.* 2003, 2405 followed by removal of any unwanted protecting groups where necessary. In formula (XLIII), AlkO is an alkoxy group, e.g. a $C_{1-3}$ alkoxy group such as methoxy or ethoxy (particularly ethoxy).

The substituted piperidine compound (XLII), suitably protected where necessary, is reacted with the chlorinated carboxy ester compound (XLIII), to give an ester intermediate of the formula (XLIV). The reaction may be carried out in a polar solvent such as a higher boiling alcohol (e.g. n-butanol) in the presence of a non-interfering base such as triethylamine at an elevated temperature (e.g. 90° C. to 130° C., more typically 100° C. to 120° C.). Heating can be effected by means of a microwave heater.

The carboxy ester group in the chlorinated carboxy ester compound (XLIII) functions as an activating group, rendering the chlorine atom more susceptible to nucleophilic displacement. Once the nucleophilic displacement reaction has taken place, the carboxy ester group has served its purpose and can be removed. Accordingly, hydrolysis of the ester intermediate (XLIV) to the carboxylic acid (XLV) is carried out using an aqueous alkali metal hydroxide such as potassium hydroxide or sodium hydroxide with heating where necessary. The carboxylic acid (XLV) is then decarboxylated to give the product (XLVI) by heating to an elevated temperature in excess of 100° C., for example a temperature in the range from about 120° C. to about 180° C.).

Once formed, many compounds of the formula (I) can be converted into other compounds of the formula (I) using standard functional group interconversions.

For example, compounds of the formula (I) or protected forms thereof wherein $J^1$-$J^2$ is CH=N can be converted into the corresponding compound where $J^1$-$J^2$ is N—C(CO) by bromination at the carbon atom in $J^1J^2$ with a brominating agent such as N-bromosuccinimide (NBS) followed by hydrolysis with a mineral acid such as hydrochloric acid.

Other examples of interconversions include the reduction of compounds of the formula (I) in which the $NR^2R^3$ forms part of a nitrile group to the corresponding amine. Compounds in which $NR^2R^3$ is an $NH_2$ group can be converted to the corresponding alkylamine by reductive alkylation, or by formation of the N-Boc derivative and reaction with an alkylating agent such as methyl iodide in the presence of a base. Alternatively, the amine can be converted to a cyclic group by methods well known to the skilled person.

Examples of functional group interconversions and reagents and conditions for carrying out such conversions can be found in, for example, *Advanced Organic Chemistry*, by Jerry March, 4$^{th}$ edition, 119, Wiley Interscience, New York, *Fiesers' Reagents for Organic Synthesis*, Volumes 1-17, John Wiley, edited by Mary Fieser (ISBN: 0-471-58283-2), and *Organic Syntheses*, Volumes 1-8, John Wiley, edited by Jeremiah P. Freeman (ISBN: 0-471-31192-8).

Protecting Groups

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a benzyl, benzhydryl(diphenylmethyl), or trityl (triphenylmethyl)ether; a trimethylsilyl or t-butyldimethylsilyl ether; or an acetyl ester (—OC(=O)CH$_3$, —OAc). An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2-(phenylsulphonyl)ethyloxy amide (—NH-Psec). Other protecting groups for amines, such as cyclic amines and heterocyclic N—H groups, include toluenesulphonyl(tosyl) and methanesulphonyl(mesyl) groups and benzyl groups such as a para-methoxybenzyl (PMB) group. A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O)CH$_3$).

Isolation and Purification of the Compounds for Use According to the Invention

The compounds for use according to the invention can be isolated and purified according to standard techniques well known to the person skilled in the art. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9.

Pharmaceutical Formulations

While it is possible for the compound for use according to the invention to be administered alone, it is preferable to present it as a pharmaceutical composition (e.g. formulation) comprising at least one active compound for use according to the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

Accordingly, in a further aspect, the invention provides compounds of the formula (I) and sub-groups thereof as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, interalia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of formula (I) as defined herein, or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Thus, tablet compositions can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastrointestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

The compounds for use according to the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules and chewable tablets. Known excipients can be blended with the solid solution to provide the desired dosage form. For example, a capsule can contain the solid solution blended with (a) a disintegrant and a lubricant, or (b) a disintegrant, a lubricant and a surfactant. A tablet can contain the solid solution blended with at least one disintegrant, a lubricant, a surfactant, and a glidant. The chewable tablet can contain the solid solution blended with a bulking agent, a lubricant, and if desired an additional sweetening agent (such as an artificial sweetener), and suitable flavours.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Therapeutic Uses

The compounds of formula (I) modulate (e.g. inhibit) the activity of ROCK kinase or protein kinase p70S6K. The compounds therefore find application in: (a) the treatment or prophylaxis of a disease or condition in which the modulation (e.g. inhibition) of ROCK kinase or protein kinase p70S6K is indicated; and/or (b) the treatment of a subject or patient population in which the modulation (e.g. inhibition) of ROCK kinase or protein kinase p70S6K is indicated; and/or (c) the treatment or prophylaxis of a disease or condition in which the modulation (e.g. inhibition) of the Rho signalling pathway is indicated; and/or (d) the treatment of a subject or patient population in which the modulation (e.g. inhibition) of the Rho signalling pathway is indicated.

Applicable Diseases and Conditions Related to ROCK Kinase Modulation

The invention therefore finds application in relation to diseases and conditions selected from: (a) tumour metastasis; (b) tumour invasion; (c) tumour progression; (d) tumour adhesion (e.g. tumour cell adhesion); (e) actinomycin contractility-dependent tumour metastasis, invasion or progression; (f) cell transformation; (g) ROCK-mediated tumour metastasis, invasion, progression or adhesion; (h) ROCK-mediated actinomycin contractility-dependent tumour metastasis, invasion or progression; (i) ROCK-mediated cell transformation.

The invention also finds application in relation to cancer (e.g. ROCK-mediated cancer), especially where the cancer (for example being a ROCK-mediated cancer) is selected from: (a) testicular germ cell tumours; (b) small breast carcinomas with metastatic ability; (c) bladder cancer; (d) ovarian cancer; (e) prostate cancer; and (f) hepatocellular carcinoma.

Other applicable diseases and conditions include the invasion, metastasis and tumour progression of any of the cancers defined herein.

The invention also finds application in relation to cardiovascular diseases or conditions, particularly those selected from: (a) hypertension; (b) heart dysfunction (e.g. chronic and congestive heart failure); (c) cardiac hypertrophy; (d) restenosis; (e) renal dysfunction (e.g. chronic renal failure); (f) atherosclerosis (arteriosclerosis); (g) cardioprotection; (h) allograft survival; (i) cerebral ischemia; (j) coronary vasospasm; and (k) vascular inflammation.

Other applicable diseases and conditions include muscle (e.g. smooth muscle) dysfunction, for example selected from: (a) asthma; (b) penile erectile dysfunction; (c) female sexual dysfunction; (d) over-active bladder I syndrome; and (e) abnormal smooth muscle (e.g. associated with hypertension).

Other applicable diseases and conditions include inflammation, wherein for example the inflammation comprises or is manifest by: (a) rheumatoid arthritis; (b) irritable bowel syndrome; (c) inflammatory bowel disease; (d) vascular inflammation, and (e) a neuroinflammatory disease or condition.

In embodiments relating to neuroinflammatory diseases or conditions, these may be selected from: (a) stroke; (b) multiple sclerosis; (c) Alzheimer's disease; (d) Parkinson's disease; (e) amyotrophic lateral sclerosis; and (f) inflammatory pain.

Other applicable diseases and conditions include CNS diseases or conditions, including those selected from: (a) spinal cord injury or trauma; (b) brain injury or trauma; (c) acute neuronal injury (e.g. stroke or traumatic brain injury); (d) Parkinson's disease; (e) Alzheimer's disease; (f) neurodegenerative conditions or diseases; (g) stroke (e.g. associated with hypertension); (h) cerebral vasospasm; (i) inhibition of neurite growth and sprouting; (O) inhibited neurite regeneration; (k) compromised post-trauma functional recovery; (l) demyelinating diseases or disorders; (m) inflammatory CNS diseases or disorders; (n) neuropathic pain; and (O) neurodegeneration.

Other applicable CNS diseases or conditions include those selected from: Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer Disease or dementia including dementia of mixed vascular and degenerative origin, pre-senile dementia, senile dementia and dementia associated with Parkinson's Disease, progressive supranuclear palsy or cortical basal degeneration, Parkinson's Disease, Frontotemporal dementia Parkinson's Type, Parkinson dementia complex of Guam, HIV dementia, diseases with associated neurofibrillar tangle pathologies, dementia pugilistica, amyotrophic lateral sclerosis, corticobasal degeneration, Down syndrome, Huntington's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, anxiety, schizophrenia, cognitive disorders, hair loss, contraceptive medication, predemented states, Age-Associated Memory Impairment, Age-Related Cognitive Decline, Cognitive Impairement No Dementia, mild cognitive decline, mild neurocognitive decline, Late-Life Forgetfulness, memory impairment and cognitive impairment, vascular dementia, dementia with Lewy bodies, Frontotemporal dementia and androgenetic alopecia.

Yet other applicable diseases and conditions include: (a) insulin resistance; (b) graft protection (e.g. cardiovascular or inflammatory graft protection); (c) diabetes; (d) asthma; (e) pulmonary vasoconstriction; (f) glaucoma; and (g) fibroses (e.g. liver fibrosis and kidney fibrosis).

Other applicable diseases and conditions include infectious diseases or conditions, including metazoan, protozoan, fungal, prion, viral or bacterial infestations, diseases or infections.

In such embodiments, the infectious disease or condition may comprise pathogen-mediated cytoskeletal rearrangement.

Proliferative Disorders (Including Cancers):

The invention also finds application as a means of preventing the growth of or inducing apoptosis of neoplasias. The invention will therefore prove useful in treating or preventing proliferative disorders such as cancers. Examples of such abnormalities include but are not limited to overexpression of one or more of the Rho signalling pathway members, or mutations in said members which lead to an increase in the basal activity of ROCK kinas(s) or the Rho signalling pathway (which may for example be associated with upregulation or overexpression or mutational activation of a growth factor receptor such as a growth factor selected from the epidermal growth factor receptor (EGFR), fibroblast growth factor receptor (FGFR), platelet derived growth factor receptor (PDGFR), insulin-like growth factor 1 receptor (IGF-1R) and vascular endothelial growth factor receptor (VEGFR) families).

The invention will be useful in treating other conditions which result from disorders in proliferation or survival such as viral infections, and neurodegenerative diseases for example.

The invention therefore finds broad application in the treatment of diseases in which there is a disorder of proliferation, apoptosis or differentiation.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoetic malignancy for example acute myeloid leukaemia, acute promyelocytic leukaemia, acute lymphoblastic leukaemia, chronic myeloid leukaemia, chronic lymphocytic leukaemia and other B-cell lymphoproliferative diseases, myelodysplastic syndrome, T-cell lymphoproliferative diseases including those derived from Natural Killer cells, Non-Hodgkin's lymphoma and Hodgkin's disease; Bortezomib sensitive and refractory multiple myeloma; hematopoetic diseases of abnormal cell proliferation whether pre malignant or stable such as myeloproliferative diseases including polycythemia vera, essential thrombocythemia and primary myelofibrosis; hairy cell lymphoma or Burkett's lymphoma; a hematopoietic tumour of myeloid lineage, for example acute and chronic myelogenous leukaemias, myelodysplastic syndrome, or promyelocytic leukaemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xenoderoma pigmentosum; keratoctanthoma; thyroid follicular cancer; or Kaposi's sarcoma.

Particular subsets of cancers include breast cancer, ovarian cancer, colon cancer, prostate cancer, oesophageal cancer, squamous cancer and non-small cell lung carcinomas. A further subset of cancers includes breast cancer, ovarian cancer, prostate cancer, endometrial cancer and glioma.

Immune Disorders:

Immune disorders for which the invention may be beneficial include but are not limited to autoimmune conditions and chronic inflammatory diseases, for example systemic lupus erythematosus, autoimmune mediated glomerulonephritis, rheumatoid arthritis, psoriasis, inflammatory bowel disease, and autoimmune diabetes mellitus, Eczema hypersensitivity reactions, asthma, COPD, rhinitis, and upper respiratory tract disease.

Other Therapeutic Uses:

ROCK-mediated physiological processes play a role in apoptosis, proliferation, differentiation and therefore the invention could also be useful in the treatment of the following diseases other than cancer and those associated with immune dysfunction; viral infections, for example herpes virus, pox virus, Epstein-Barr virus, Sindbis virus, adenovirus, HIV, HPV, HCV and HCMV; prevention of AIDS development in HIV-infected individuals; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, degenerative diseases of the musculoskeletal system, for example, osteoporosis and arthritis, aspirin-sensitive rhinosinusitis, cystic fibrosis, multiple sclerosis, kidney diseases.

The invention may also be useful in diseases resulting from insulin resistance and insensitivity, and the disruption of glucose, energy and fat storage such as metabolic disease and obesity.

Applicable Diseases and Conditions Related to Protein Kinase p70S6K Modulation

The invention therefore finds application in relation to conditions selected from: (a) cancer (e.g. p70S6K-mediated cancer); (b) tumour metastases; (c) immune dysfunction; (d) tissue damage (e.g. arising from inflammation); (e) chromosome 17q23 amplification (or conditions arising therefrom or associated therewith); (f) Peutz-Jeghers syndrome (or conditions arising therefrom or associated therewith); (g) LKB1 mutation(s) (or conditions arising therefrom or associated therewith); (h) BRCA1 mutation(s) (or conditions arising therefrom or associated therewith); (i) BRCA2 mutation(s) (or conditions arising therefrom or associated therewith); (j) dysfunctional apoptotic programmes; (k) growth factor receptor signal transduction, overexpression and activation in tumour tissue; (l) a metabolic disease or disorder; (m) those associated with abnormal cell proliferation and/or metabolism; and (n) neuronal disorders.

In such embodiments, the disease or condition arising from or associated with chromosome 17q23 amplification may be selected from: (a) primary breast tumours; (b) tumours (e.g. breast tumours) containing BRCA2 mutations; (c) tumours (e.g. breast tumours) containing BRCA1 mutations; (d) pancreatic tumours; (e) bladder tumours; and (f) neuroblastomas.

The disease or condition arising from or associated with LKB1 mutation(s) may be lung adenocarcinoma containing LKB1 mutation(s) (e.g. inactivating LKB1 mutation(s)).

The disease or condition arising from or associated with BRCA1/2 mutation(s) may be breast cancer.

The metabolic disease or disorder may be selected from: (a) obesity (for example age-induced obesity or diet-induced obesity); (b) diabetes; (c) metabolic syndrome; (d) insulin resistance; (e) hyperglycemia; (f) hyperaminoacidemia; and (g) hyperlipidmia.

Proliferative Disorders (Including Cancers):

The invention also finds application as a means of preventing the growth of or inducing apoptosis of neoplasias. The invention will therefore prove useful in treating or preventing proliferative disorders such as cancers. Examples of such abnormalities include but are not limited to overexpression of p70S6K (or the other syndromes described herein).

The invention will be useful in treating other conditions which result from disorders in proliferation or survival such as viral infections, and neurodegenerative diseases for example.

The invention therefore finds broad application in the treatment of diseases in which there is a disorder of proliferation, apoptosis or differentiation.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoetic malignancy for example acute myeloid leukaemia, acute promyelocytic leukaemia, acute lymphoblastic leukaemia, chronic myeloid leukaemia, chronic lymphocytic leukaemia and other B-cell lymphoproliferative diseases, myelodysplastic syndrome, T-cell lymphoproliferative diseases including those derived from Natural Killer cells, Non-Hodgkin's lymphoma and Hodgkin's disease. Bortezomib sensitive and refractory multiple myeloma; hematopoetic diseases of abnormal cell proliferation whether pre malignant or stable such as myeloproliferative diseases including polycythemia vera, essential thrombocythemia and primary myelofibrosis; hairy cell lymphoma, or Burkett's lymphoma; a hematopoietic tumour of myeloid lineage, for example acute and chronic myelogenous leukaemias, myelodysplastic syndrome, or promyelocytic leukaemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xenoderoma pigmentosum; keratoctanthoma; thyroid follicular cancer; or Kaposi's sarcoma.

Particular subsets of cancers include breast cancer, ovarian cancer, colon cancer, prostate cancer, oesophageal cancer, squamous cancer and non-small cell lung carcinomas. A further subset of cancers includes breast cancer, ovarian cancer, prostate cancer, endometrial cancer and glioma.

Immune Disorders:

Immune disorders for which the invention may be beneficial include but are not limited to autoimmune conditions and chronic inflammatory diseases, for example systemic lupus erythematosus, autoimmune mediated glomerulonephritis, rheumatoid arthritis, psoriasis, inflammatory bowel disease, and autoimmune diabetes mellitus, Eczema hypersensitivity reactions, asthma, COPD, rhinitis, and upper respiratory tract disease.

Other Therapeutic Uses:

p70S6K-mediated physiological processes play a role in apoptosis, proliferation, differentiation and therefore the invention could also be useful in the treatment of the following diseases other than cancer and those associated with immune dysfunction; viral infections, for example herpes virus, pox virus, Epstein-Barr virus, Sindbis virus, adenovirus, HIV, HPV, HCV and HCMV; prevention of AIDS development in HIV-infected individuals; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, degenerative diseases of the musculoskeletal system, for example, osteoporosis and arthritis, aspirin-sensitive rhinosinusitis, cystic fibrosis, multiple sclerosis, kidney diseases.

The invention may also be useful in diseases resulting from insulin resistance and insensitivity, and the disruption of glucose, energy and fat storage such as metabolic disease and obesity.

Applicable Interventions, Treatments and Prophylactic Methods Related to ROCK Kinase Modulation The invention contemplates ROCK-mediated intervention, treatment or prophylaxis of any kind. Thus, the invention finds application in relation to treatment or prophylaxis comprising: (a) the modulation (e.g. inhibition) of ROCK kinase; or (b) intervention at the level of the activity of ROCK kinase; or (c) intervention at the level of the Rho signalling pathway (e.g. at the level of RhoA and or RhoC).

Other applicable methods include interventions which effect: (a) muscle (e.g. smooth muscle) relaxation; (b) vascular muscle relaxation (e.g. to increase vascular blood flow); (c) nerve cell modulation; (d) reduction of cell proliferation; (e) reduction of cell migration; (f) suppression of cytoskeletal rearrangement upon pathogen invasion or infection; (g) acceleration of tissue regeneration; and (h) enhancement of post-traumatic functional recovery.

In such embodiments, the nerve cell modulation may comprise: (a) neuronal regeneration; (b) new axonal growth induction; (c) axonal rewiring across lesions within the CNS; (d) neurite outgrowth; (e) neurite differentiation; (f) axon pathfinding; (g) dendritic spine formation; (h) dendritic spine maintenance; (i) modulation of neurite growth cone collapse; and (j) modulation of neurite outgrowth inhibition.

Other applicable treatments include transplantation therapy (e.g. comprising graft protection).

Yet other applicable methods comprise a method of diagnosis and treatment of a disease state or condition, which method comprises: (i) screening a patient to determine whether a disease or condition from which the patient is or may be suffering is one which would be susceptible to treatment with a compound having activity against ROCK kinase; and (ii) where it is indicated that the disease or condition from which the patient is thus susceptible, thereafter administering to the patient a compound according to the invention.

Applicable Interventions, Treatments and Prophylactic Methods Related to p70S6K Modulation The invention contemplates protein kinase p70S6K-mediated intervention, treatment or prophylaxis of any kind. Thus, the invention finds application in relation to treatment or prophylaxis comprising: (a) the modulation (e.g. inhibition) of protein kinase p70S6K; (b) intervention at the level of the activity of protein kinase p70S6K; (b) inhibition of progression from G1 to S phase in the cell cycle in vivo; (c) inhibition of cell cycle proliferation at the G1 to S phase of the cell cycle; (d) use of a compound of formula (I) as a rapamycin surrogate; (e) use of a compound of formula (I) as a wortmannin surrogate; (f) the re-establishment of appropriate apoptotic programmes; (g) the inhibition of growth factor receptor signal transduction, overexpression and activation in tumour tissue; (h) modulation of neuronal cell differentiation; (i) modulation of cell motility; (O) modulation of cellular response(s); and (k) enhancing insulin sensitivity.

The treatment or prophylaxis may also comprise a method of diagnosis and treatment of a disease state or condition, which method comprises: (i) screening a patient to determine whether a disease or condition from which the patient is or may be suffering is one which would be susceptible to treatment with a compound having activity against protein kinase p70S6K; and (ii) where it is indicated that the disease or condition from which the patient is thus susceptible, thereafter administering to the patient a compound of formula (I) as herein defined.

Target Subjects or Patient Populations for ROCK Kinase Modulation

The subject or patient population may be selected from: (a) those in which ROCK kinase is dysfunctional (for example, hyperactive); and (b) those which have been subject to diagnostic tests for ROCK dysfunction (e.g. for ROCK hyperactivity); (c) those in which the Rho signalling pathway is dysfunctional; and (d) those which have been subject to diagnostic tests for Rho signalling pathway dysfunction.

Target Subjects or Patient Populations for p70S6K Modulation

The subject or patient population may be selected from: (a) those in which protein kinase p70S6K is dysfunctional (for example, hyperactive); (b) those which have been subject to diagnostic tests for p70S6K is dysfunction (e.g. for p70S6K hyperactivity); (c) those in which chromosome 17q23 is amplified; and (d) those which have been subject to diagnostic tests for amplification of chromosome 17q23; (e) those in which BRCA1 mutation(s) are present; (f) those which have been subject to diagnostic tests for BRCA1 mutation(s); (g) those in which BRCA2 mutation(s) are present; (h) those which have been subject to diagnostic tests for BRCA2 mutation(s); (i) those in which LKB1 mutation(s) are present; (j) those which have been subject to diagnostic tests for LKB1 mutation(s); and (k) those which have been screened as defined herein.

Methods of Treatment and Posology

The compounds of the formula (I) and sub-groups as defined herein will be useful in the prophylaxis or treatment of a range of disease states or conditions mediated by ROCK kinase or protein kinase p70S6K. Examples of such disease states and conditions are set out herein.

Compounds of the formula (I) are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds for use according to the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently, i.e. taken continuously for a given period such as a week, then discontinued for a period such as a week and then taken continuously for another period such as a week and so on throughout the duration of the treatment regimen. Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

The compounds as defined herein can be administered as the sole therapeutic agent or they can be administered in combination therapy with one of more other compounds for treatment of a particular disease state, for example a neoplastic disease such as a cancer as hereinbefore defined. Examples of other therapeutic agents or treatments that may be administered together (whether concurrently or at different time intervals) with the compounds of the formula (I) include but are not limited to:

Topoisomerase I inhibitors
Antimetabolites
Tubuiin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies
Radiotherapy, and,
Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self and agents such as megestrol acetate which can be used for the treatment of side-effects including oedema and thromoembolic episodes.

Each of the compounds present in the combinations may be given in individually varying dose schedules and via different routes.

Where the compound of the formula (I) is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds for use according to the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

Methods of Diagnosis

Prior to administration of a compound of the formula (I) as defined herein, a patient may be screened to determine whether a disease or condition from which the patient is or may be suffering is one which would be susceptible to treatment. For example, the patient may be screened for dysfunction in ROCK activity (e.g. elevated or up-regulated ROCK expression, mutations in ROCK genes or ROCK gene regulatory elements) or Rho signalling dysfunction (as described herein).

The term up-regulation includes elevated expression or over-expression, including gene amplification (i.e. multiple gene copies) and increased expression by a transcriptional effect, and hyperactivity and activation, including activation by mutations. The term diagnosis includes screening. By marker we include genetic markers including, for example, the measurement of DNA composition to identify mutations. The term marker also includes markers which are characteristic of up regulation including enzyme activity, enzyme levels, enzyme state (e.g. phosphorylated or not) and mRNA levels.

The above diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, or urine.

Identification of an individual carrying a mutation may mean that the patient would be particularly suitable for treatment according to the invention. Tumours may preferentially be screened for presence of a particular mutation/allele prior to treatment. The screening process will typically involve direct sequencing, oligonucleotide microarray analysis, or a mutant specific antibody.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, 3$^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques could be applicable in the present case.

Particular Considerations Arising in Respect of LKB1

DNA sequencing is a viable method of genetic testing for LKB1 mutation in the diagnostic laboratory (see for example J Med Genet (1999) 36: 365-368). This paper describes the screening of a set of 12 Peutz-Jeghers patients for germline mutations in LKB1 and report the results of this screening. Such protocols find application in the present invention.

Further details of appropriate protocols may be found for example in Shaw et al. (2004) Cancer Cell 6: 91-99 (which describes how the LKB1 tumor suppressor negatively regulates mTOR signaling) and in Jimenez et al. (2003) Cancer Res. 63: 1382-1388.

Amplification and Detection of ROCK Kinase

Detection of ROCK may be carried out at either the mRNA or protein level.

Specific examples of methods where levels of Rho and ROCK have been determined in clinical samples include:

American Journal of Pathology. 2002; 160:579-584. This paper describes immunohistochemistry performed on formalin-fixed tissues to characterize RhoC expression in human breast tissues.

Clinical Cancer Research Vol. 9, 2632-2641, July 2003. This paper describes the use of Western blotting to quantitate Rho and ROCK protein expression in paired tumour and nontumour surgical samples from 107 consecutive Japanese patients with bladder cancer.

Pancreas. 24(3):251-257, April 2002. This paper describes the expression of ROCK-1 in human pancreatic tissues by immunoblotting and immunohistochemistry.

World J Gastroenterol 2003 September; 9(9):1950-1953. This paper describes the examination of mRNA expression levels of RhoC gene by reverse transcription-polymerase chain reaction (RT-PCR) in hepatocellular carcinoma (HCC).

The relevant methodological disclosure relating to the quantitation of the levels of Rho and/or ROCK activity or expression contained in the above-mentioned publications are hereby incorporated herein by reference.

Amplification and Detection of Protein Kinase p70S6K

Detection of p70S6K may be carried out at either the mRNA or protein level.

Exemplary methods are described for example in J NaltI Cancer Inst (2000): 92, pp. 1252-9 (which describes detecting the activation of Ribosomal Protein S6 Kinase by complementary DNA and tissue microarray analysis uses comparative genomic hybridization (CGH) and cDNA and tissue microarray analyses to identify amplified and overexpressed genes).

The detection of overexpressed p70S6K is described in Int J Oncol (2004): 24 (4), pp. 893-900. This paper describes the pharmacolgenomic profiling of the PI3K/PTEN-Akt-mTOR pathway in common human tumours using immunohistoochemistry to compare high p70S6K, AKT expression to tumour sensitivity.

EXPERIMENTAL

The invention will now be illustrated, but not limited, by reference to the specific embodiments described in the following procedures and examples.

The starting materials for each of the procedures described below are commercially available unless otherwise specified.

Proton magnetic resonance ($^1$H NMR) spectra were recorded on a Bruker AV400 instrument operating at 400.13 MHz, in Me-d$_3$-OD at 27° C., unless otherwise stated and are reported as follows: chemical shift δ/ppm (number of protons, multiplicity where s=singlet, d=doublet, t=triplet, q=quartet, m=multiplet, br=broad). The residual protic solvent MeOH ($δ_H$=3.31 ppm) was used as the internal reference.

In the examples, the compounds prepared were characterised by liquid chromatography and mass spectroscopy using the systems and operating conditions set out below. Where chlorine is present, the mass quoted for the compound is for $^{35}$Cl. The operating conditions used are described below.

Platform System

| HPLC System: | Waters 2795 |
| --- | --- |
| Mass Spec Detector: | Micromass Platform LC |
| PDA Detector: | Waters 2996 PDA |
| | Polar Analytical conditions: |
| Eluent A: | H$_2$O (0.1% Formic Acid) |
| Eluent B: | CH$_3$CN (0.1% Formic Acid) |
| Gradient: | 00-50% eluent B over 3 minutes |
| Flow: | 1.5 ml/min |
| Column: | Phenomenex Synergi 4μ Hydro 80A, 50 × 4.6 mm |
| | MS conditions: |
| Capillary voltage: | 3.5 kV |
| Cone voltage: | 30 V |
| Source Temperature: | 120° C. |
| Scan Range: | 165-700 amu |
| Ionisation Mode: | ElectroSpray Negative, Positive or Positive & Negative |

FractionLynx System

| System: | Waters FractionLynx (dual analytical/prep) |
| --- | --- |
| HPLC Pump: | Waters 2525 |
| Injector-Autosampler: | Waters 2767 |
| Mass Spec Detector: | Waters-Micromass ZQ |
| PDA Detector: | Waters 2996 PDA |
| | Acidic Analytical conditions: |
| Eluent A: | H$_2$O (0.1% Formic Acid) |
| Eluent B: | CH$_3$CN (0.1% Formic Acid) |
| Gradient: | 5-95% eluent B over 5 minutes |
| Flow: | 2.0 ml/min |
| Column: | Phenomenex Synergi 4μ Max-RP 80A, 50 × 4.6 mm |
| | MS conditions: |
| Capillary voltage: | 3.5 kV |
| Cone voltage: | 25 V |
| Source Temperature: | 120° C. |
| Scan Range: | 125-800 amu |
| Ionisation Mode: | ElectroSpray Positive or ElectroSpray Positive & Negative |

LCT System

| HPLC System: | Waters Alliance 2795 Separations Module |
| --- | --- |
| Mass Spec Detector: | Waters/Micromass LCT |
| UV Detector: | Waters 2487 Dual λ Absorbance Detector |
| | Polar Analytical conditions: |
| Eluent A: | Methanol |
| Eluent B: | 0.1% Formic Acid in Water |
| Gradient: | Time (mins) A B |
| | 0 10 90 |
| | 0.5 10 90 |
| | 6.5 90 10 |
| | 10 90 10 |
| | 10.5 10 90 |
| | 15 10 90 |
| Flow: | 1.0 ml/min |
| Column: | Supelco DISCOVERY C$_{18}$ 5 cm × 4.6 mm i.d., 5 μm |
| | MS conditions: |
| Capillary voltage: | 3500 v (+ve ESI), 3000 v (−ve ESI) |
| Cone voltage: | 40 v (+ve ESI), 50 v (−ve ESI) |

| Source Temperature: | 100° C. |
| --- | --- |
| Scan Range: | 50-1000 amu |
| Ionisation Mode: | +ve/−ve electrospray ESI (Lockspray ™) |

LCT System 2

| HPLC System: | Waters Alliance 2795 Separations Module |
| --- | --- |
| Mass Spec Detector: | Waters/Micromass LCT |
| UV Detector: | Waters 2487 Dual λ Absorbance Detector |
| | Analytical conditions: |
| Eluent A: | Methanol |
| Eluent B: | 0.1% Formic Acid in Water |
| Gradient: | Time (mins) A B |
| | 0 10 90 |
| | 0.6 10 90 |
| | 1.0 20 80 |
| | 7.5 90 10 |
| | 9 90 10 |
| | 9.5 10 90 |
| | 10 10 90 |
| Flow: | 1 ml/min |
| Column: | Supelco DISCOVERY C$_{18}$ 5 cm × 4.6 mm i.d., 5 μm |
| | MS conditions: |
| Capillary voltage: | 3500 v (+ve ESI), 3000 v (−ve ESI) |
| Cone voltage: | 40 v (+ve ESI), 50 v (−ve ESI) |
| Source Temperature: | 100° C. |
| Scan Range: | 50-1000 amu |
| Ionisation Mode: | +ve/−ve electrospray ESI (Lockspray ™) |

In the examples below, the following key is used to identify the LCMS conditions used:

| PS-P | Platform System - polar analytical conditions |
| --- | --- |
| FL-A | FractionLynx System - acidic analytical conditions |
| LCT1 | LCT System 1 - polar analytical conditions |
| LCT2 | LCT System 2 - polar analytical conditions |

EXAMPLE 1

Methyl-[1-(9H-purin-6-yl)-piperidin-4-yl]-amine

1A. {1-[9-(Tetrahydro-pyran-2-yl)-9H-purin-6-yl]-piperidin-4-yl}-carbamic acid tert-butyl ester

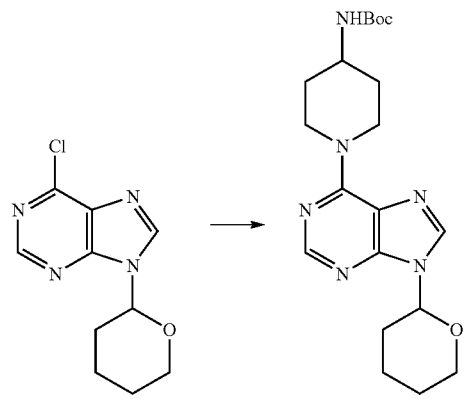 [SMILES: Clc1ncnc2c1ncn2C1CCCCO1 ; CC(C)(C)OC(=O)NC1CCN(c2ncnc3c2ncn3C2CCCCO2)CC1]

A mixture of 4-(N-Boc-amino)-piperidine (363.2 mg, 1.82 mmol), 9-(tetrahydropyran-2-yl)-6-chloropurine (219.2 mg, 0.92 mmol), n-butanol (9 ml) and triethylamine (0.68 ml, 4.55 mmol) was heated overnight at 100° C. After cooling to room temperature, the solvents were evaporated in vacuo. The crude product was purified by flash silica column chromatography eluting with 5% methanol in dichloromethane to afford the Boc protected compound as a white solid (352.7 mg, 0.88 mmol, 95%) LC-MS (LCT) $R_t$ 6.74 [M+H]$^+$ 403.

1B. Methyl-{1-[9-(tetrahydro-pyran-2-yl)-9H-purin-6-yl]-piperidin-4-yl}-carbamic acid tert-butyl ester nol in dichloromethane to afford the required compound as a white solid (83 mg, 0.2 mmol, 73%) LC-MS (LCT) $R_t$ 7.07 [M+H]$^+$417.

1C. Methyl-[1-(9H-purin-6-yl)-piperidin-4-yl]-amine

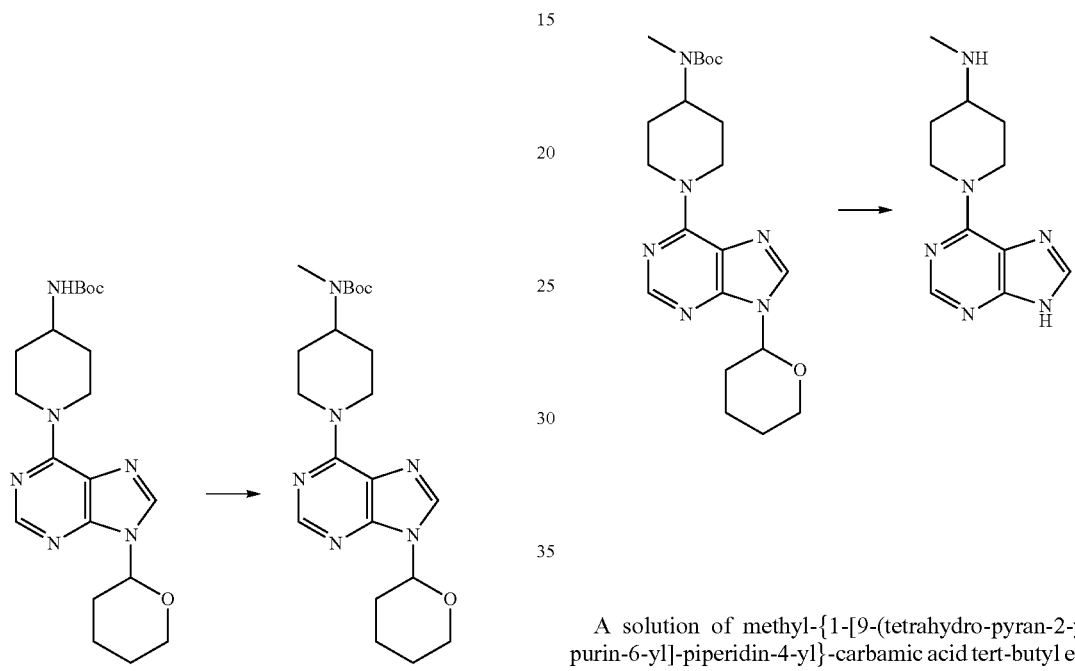

A solution of methyl-{1-[9-(tetrahydro-pyran-2-yl)-9H-purin-6-yl]-piperidin-4-yl}-carbamic acid tert-butyl ester (83 mg, 0.2 mmol), ethanol (4 ml) and 1M aqueous HCl solution (1 ml) was stirred overnight at room temperature. The solvents were then evaporated in vacuo and the crude product was purified with a flash NH$_2$ column (2 g, 15 ml) eluting with methanol to afford the required compound (18 mg, 0.08 mmol, 39%) LC-MS (LCT) $R_t$ 1.27 [M+H]$^+$] 233.

EXAMPLE 2

Benzyl-[1-(9H-purin-6-yl)-piperidin-4-yl]-amine

The {1-[9-(tetrahydro-pyran-2-yl)-9H-purin-6-yl]-piperidin-4-yl}-carbamic acid tert-butyl ester (107.7 mg, 0.27 mmol) of Example 1A was dissolved in anhydrous dimethylformamide (1 ml) and the solution was cooled to 0° C. in an ice bath. Sodium hydride (13 mg, 60% suspension in oil, 0.33 mmol) was added in small portions. The suspension was stirred vigorously for an additional 20 minutes at 0° C. and then the methyl iodide (0.020 ml, 0.32 mmol) was added drop wise. After stirring the reaction mixture for 30 minutes at 0° C. this was brought to room temperature and left stirring additionally overnight. Water (1.2 ml), followed by ethyl acetate (5 ml) was added to the reaction mixture. The organic layer was separated, washed with water, 0.1M HCl, a saturated aqueous NaHCO$_3$ solution, and brine before being dried and concentrated in vacuo. The crude product was purified by flash silica column chromatography eluting with 5% metha-

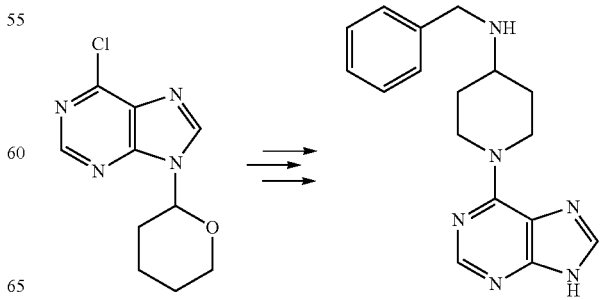

By following the method of Example 1, but using benzyl bromide in place of methyl iodide, the title compound was obtained. LC-MS (LCT) R$_t$ 3.17 [M+H]$^+$ 309

EXAMPLE 3

1-(9H-Purin-6-yl)piperidin-4-ylamine

3A. [1-(9H-Purin-6-yl)Piperidin-4-yl]carbamic acid tert-butyl ester

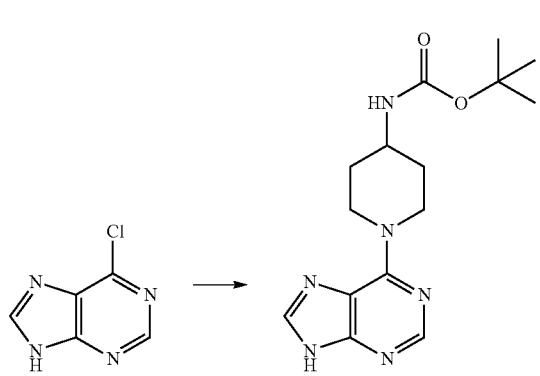 [SMILES: Clc1ncnc2[nH]cnc12 ; CC(C)(C)OC(=O)NC1CCN(c2ncnc3[nH]cnc23)CC1]

To a mixture of 6-chloropurine (0.050 g, 0.323 mmol) and piperidin-4-yl carbamic acid tert-butyl ester (0.129 g, 0.646 mmol) in n-butanol (3.2 ml) was added triethylamine (0.225 ml, 1.617 mmol). After heating at 100° C. for 20 hours, solvent was removed and the resulting solid triturated with a DCM/methanol mix (3 ml/5 ml). Filtration gave the desired product as a white solid (0.080 g, 78%). LC/MS: (LCT) R$_t$ 5.37 [M+H]$^+$ 319.

3B. 1-(9H-Purin-6-yl)piperidin-4-ylamine

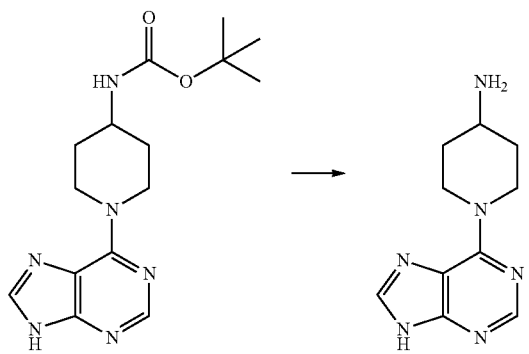 [SMILES: CC(C)(C)OC(=O)NC1CCN(c2ncnc3[nH]cnc23)CC1 ; NC1CCN(c2ncnc3[nH]cnc23)CC1]

A solution of the purine (0.052 g, 0.163 mmol) of Example 4A in 2M HCl (2 ml) was stirred at room temperature for 2 hours, and then evaporated to dryness. Solid phase extraction on SCX-II acidic resin, eluting with MeOH and then 1M NH$_3$ in MeOH, gave the deprotected amine as a white solid (0.034 g, 94%). LC/MS (LCT): R$_t$ 1.00 [M+H]$^+$ 219.

$^1$H NMR (MeOD) δ 1.33-1.58 (2H, m), 2.01 (2H, d, J=12.5 Hz), 2.97-3.15 (1H, m), 3.15-3.32 (2H, m), 5.38 (2H, d, J=13 Hz), 8.01 (1H, s), 8.21 (1H, s)

EXAMPLE 4

6-(4-Aminopiperidin-1-yl)-7,9-dihydropurin-8-one

4A. [1-(8-Oxo-8,9-dihydro-7H-purin-6-yl)piperidin-4-yl]carbamic acid tert-butyl ester

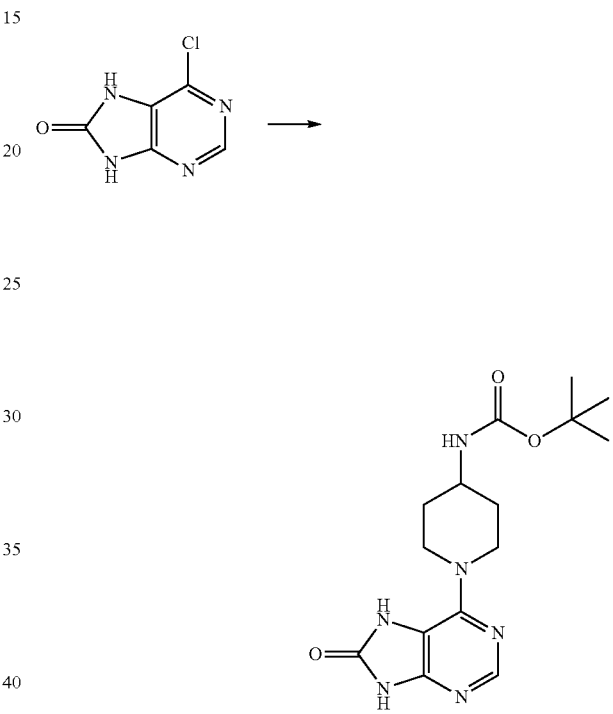

By reacting 6-chloro-7,9-dihydro-purin-8-one with piperidin-4-yl-carbamic acid tert-butyl ester according to the method of Example 4A, the title compound was obtained. LC/MS: (LCT) R$_t$ 5.68 [M+H]$^+$ 335.

4B.
6-(4-Aminopiperidin-1-yl)-7,9-dihydropurin-8-one

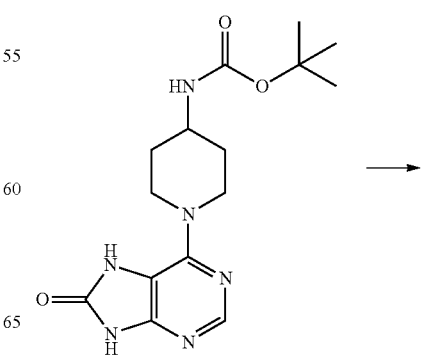

-continued

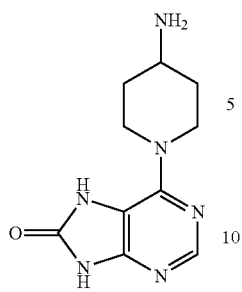

The product of Example 4A was deprotected according to the method of Example 4B to give the title compound. LC/MS (LCT): $R_t$ 1.27 [M+H]$^+$ 235.

$^1$H NMR (MeOD) δ 1.39-1.60 (2H, m), 1.92-2.07 (2H, m), 2.95-3.30 (3H, m), 4.30-4.45 (2H, m), 8.09 (1H, s)

EXAMPLE 5

6-(4-Benzyl-4-hydroxypiperidin-1-yl)-7,9-dihydro-purin-8-one 5A. 6-(4-Benzyl-4-hydroxypiperidin-1-yl)-7,9-dihydropurin-8-one

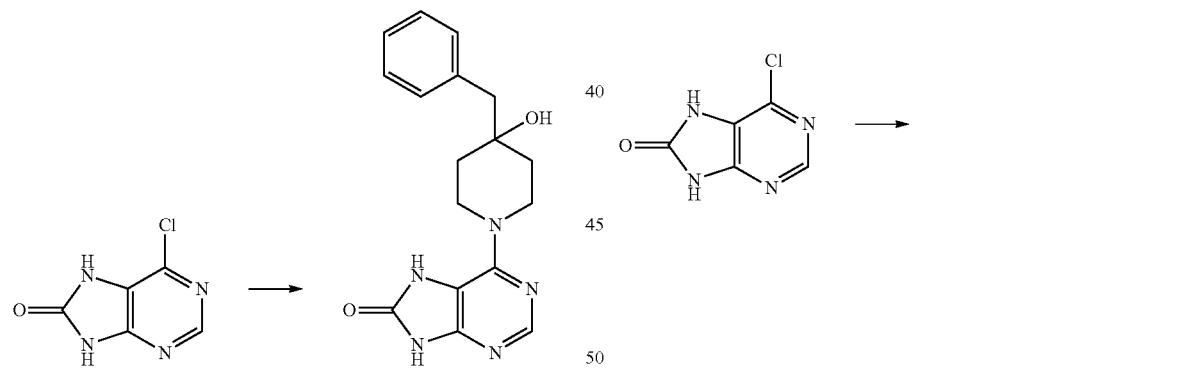

4-Benzyl-1-methyl-piperidin-4-ol was reacted with 6-chloro-7,9-dihydro-purin-8-one under conditions analogous to those set out in Example 3A to give the title compound LC/MS: (LCT) $R_t$ 5.68 [M+H]$^+$ 326.

By following the method of Example 3A or methods closely similar thereto, but using 6-chloro-7,9-dihydro-purin-8-one instead of 6-chloropurine, the following compounds were prepared.

$^1$H NMR (DMSO) δ 1.38-1.60 (4H, m), 2.70 (2H, s), 3.22-3.35 (2H, m), 3.94 (2H, d, J=13 Hz), 4.44 (1H, br s), 7.18-7.33 (5H, m), 8.05 (1H, s)

EXAMPLE 6

6-(piperazin-1-yl)-7,9-dihydropurin-8-one

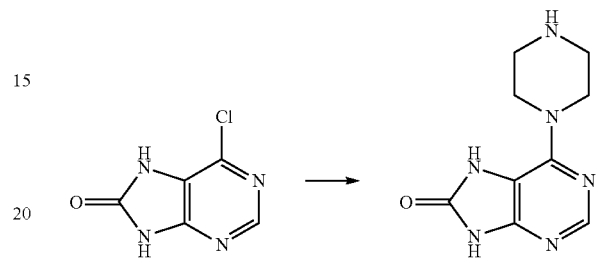

LC/MS: (LCT) $R_t$ 1.27 [M+H]$^+$ 221.

$^1$H NMR (d$_6$-DMSO) δ 2.75 (4H, br s), 3.41 (4H, br s), 8.02 (1H, s)

EXAMPLE 7

(3S)-6-(3-Benzyloxymethylpiperazin-1-yl)-7,9-dihydropurin-8-one

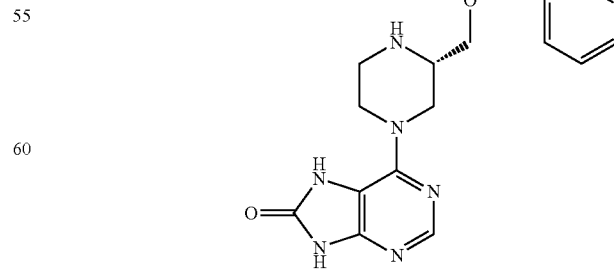

LC/MS: (LCT) $R_t$ 3.88 [M+H]$^+$ 341.

¹H NMR (MeOD) δ 2.59-3.08 (5H, m), 3.36-3.50 (2H, m), 3.94-4.11 (2H, m), 4.46 (2H, s), 7.13-7.34 (5H, m), 8.02 (1H, s)

¹H NMR (MeOD) δ 1.34-1.40 (2H, m), 1.92-1.97 (2H, m), 2.61-3.00 (7H, m), 4.20-4.25 (2H, m), 7.11-7.24 (5H, m), 8.01 (1H, s)

EXAMPLE 8

6-(4-Phenethylaminopipieridin-1-yl)-7,9-dihydro-purin-8-one

EXAMPLE 9

6-[4-(2-Chlorobenzylamino)-piperidin-1-yl]-7,9-dihydro-purin-8-one

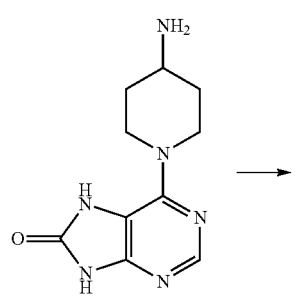

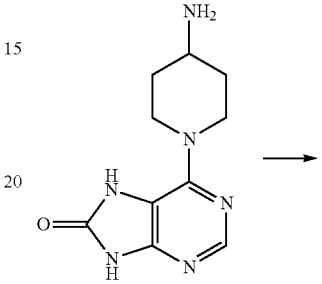

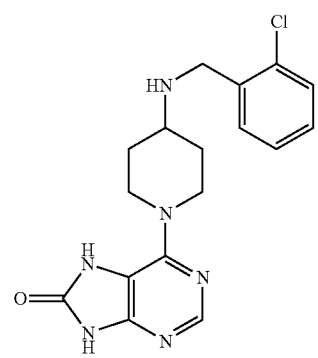

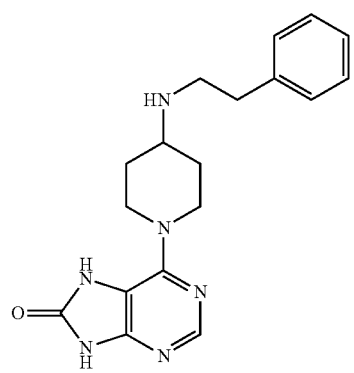

A mixture of 6-(4-aminopiperidin-1-yl)-7,9-dihydropurin-8-one (Example 4B, 0.045 g, 0.20 mmol), phenylacetaldehyde (0.025 ml, 0.20 mmol), NaBH(OAc)₃ (0.065 g, 0.30 mmol) and acetic acid (5 drops) in 1,2-dichloroethane (2 ml) and MeOH (0.5 ml) was stirred at room temperature for 2 hours. The solution was absorbed onto a 5 g SCX-II acidic resin cartridge and eluted with MeOH, then 1M NH₃-MeOH. The basic eluant was concentrated. Preparative thin layer chromatography (t.l.c.), eluting with 1% NH₃ (aq)/9% MeOH/90% CH₂Cl₂ gave the product as an off white solid (0.007 g, 10%). LC/MS: (LCT) R$_t$ 3.62 [M+H]⁺ 339.

Following the method of Example 8 but using 2-chlorobenzaldehyde instead of phenylacetaldehyde gave the title compound. LC/MS: (LCT) R$_t$ 3.65 [M+H]⁺ 359, 361.

¹H NMR (MeOD) δ 1.30-1.46 (2H, m), 1.95-2.00 (2H, m), 2.70-2.79 (1H, m), 2.92-3.01 (2H, m), 3.88 (2H, s), 4.18-4.23 (2H, m), 7.14-7.41 (4H, m), 8.00 (1H, s)

EXAMPLE 10

6-[4-(3-Chlorobenzylamino)-piperidin-1-yl]-7,9-dihydro-purin-8-one

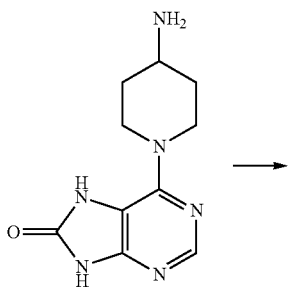

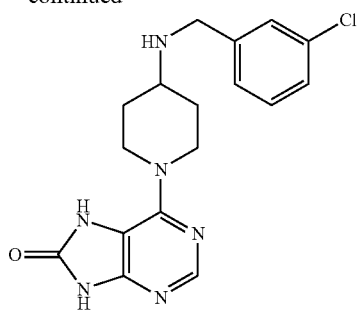

Following the method of Example 8 but using 3-chlorobenzaldehyde instead of phenylacetaldehyde gave the title compound LC/MS: (LCT) $R_t$ 3.77 [M+H]$^+$ 359, 361.

$^1$H NMR (MeOD) δ 1.19-1.44 (2H, m), 1.81-1.96 (2H, m), 2.61-2.76 (1H, m), 2.29-3.00 (2H, m), 4.74 (2H, s), 4.17-4.23 (2H, m), 7.15-7.27 (3H, m), 7.33 (1H, s), 8.00 (1H, s)

EXAMPLE 11

1-(1H-Pyrazolo[3,4-d]pyrimidin-4-yl)-piperidin-4-ylamine

11A. [1-(1H-Pyrazolo[3,4-d]pyrimidin-4-yl)-piperidin-4-yl]-carbamic acid tert-butyl ester

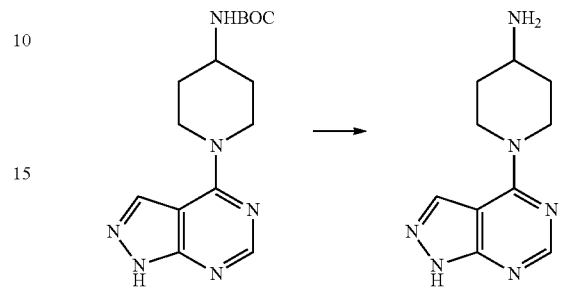

To a solution of 4-chloro-1H-pyrazolo[3,4-d]pyrimidine (*J. Amer. Chem. Soc.* 1957, 79, 6407-6413) (59 mg, 0.38 mmol) in ethanol (2 ml) was added triethylamine (100 μl, 0.72 mmol) and 4-(N-Boc-amino)piperidine (134 mg, 0.67 mmol). The solution was heated at 80° C. for 3 hours, and then cooled to room temperature. The solution was evaporated to dryness and the residue purified by recrystallisation (isopropanol) to yield the product (32 mg, 26% yield).

11B. 1-(1H-Pyrazolo[3,4-d]pyrimidin-4-yl)-piperidin-4-ylamine

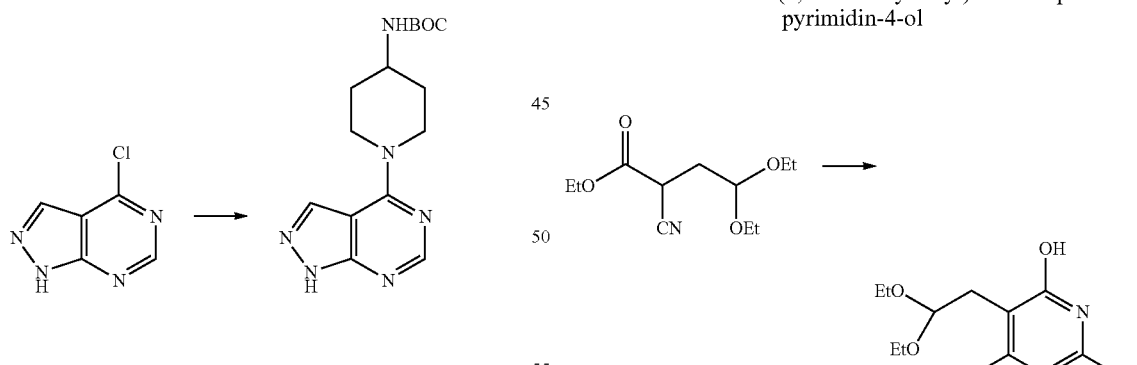

To [1-(1H-pyrazolo[3,4-d]pyrimidin-4-yl)-piperidin-4-yl]-carbamic acid tert-butyl ester (28 mg, 0.088 mmol) was added HCl (1 ml, 4M solution in dioxane, 4 mmol). The suspension was stirred at room temperature for 1 hour, and then diluted with diethyl ether (4 ml). The ethereal layer was discarded and the solid washed with a further portion of diethyl ether (2 ml). The ethereal layer was again discarded, and the resultant solid dried under high vacuum to yield the desired product (34 mg). The free base was liberated by dissolution of this material in methanol, loading onto an acidic resin SCX-2 cartridge, and elution from the cartridge with ammonia in methanol. LC/MS $R_t$ 0.86 [M+H]$^+$ 219

EXAMPLE 12

1-(7H-Pyrrolo[2,3-d]pyrimidin-4-yl)-piperidin-4-ylamine

12A. 6-Amino-5-(2,2-diethoxy-ethyl)-2-mercapto-pyrimidin-4-ol

To ethanol (200 ml) was added sodium (2.05 g, 89 mmol) in small portions. The solution was stirred until complete dissolution of the sodium metal. 2-Cyano-4,4-diethoxy-butyric acid ethyl ester (*J. Chem. Soc.,* 1960, 131-138) (9.292 g, 40.5 mmol) was then added as a solution in ethanol (50 ml), followed by addition of thiourea (3.08 g, 40.4 mmol). The solution was heated at 85° C. for 18 hours, and then cooled to room temperature. The solution was concentrated, and saturated aqueous ammonium chloride solution (150 ml) was added. The mixture was stirred at room temperature for 18 hours, after which time the solid was collected by filtration, and washed with water (20 ml) to yield the product (3.376 g, 36%).

12B. 6-Amino-5-(2,2-diethoxy-ethyl)-pyrimidin-4-ol

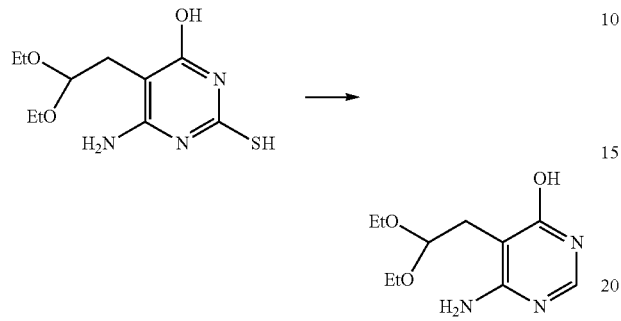

To a suspension of 6-amino-5-(2,2-diethoxy-ethyl)-2-mercapto-pyrimidin-4-ol (1.19 g, 4.6 mmol) in water (50 ml) was added Raney nickel (Aldrich Raney 2800 nickel, 4.8 ml). The mixture was heated at reflux for 1 hour, and then the hot solution was filtered through Celite®. The nickel residue was washed with further water (100 ml), and these washings were filtered through Celite. The aqueous filtrate was evaporated to dryness to yield the title product (0.747 g, 71%).

12C. 7H-Pyrrolo[2,3-d]pyrimidin-4-ol

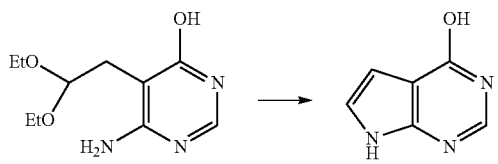 [SMILES: CCOC(Cc1c(N)ncnc1O)OCC ; Oc1ncnc2[nH]ccc12]

This compound was prepared as described in *J. Chem. Soc.*, 1960, pp. 131-138.

12D. 4-Chloro-7H-pyrrolo[2,3-d]pyrimidine

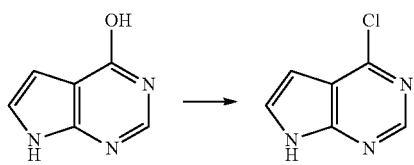 [SMILES: Oc1ncnc2[nH]ccc12 ; Clc1ncnc2[nH]ccc12]

To 7H-pyrrolo[2,3-d]pyrimidin-4-ol (0.425 g, 3.14 mmol) was added phosphorus oxychloride (4 ml). The mixture was heated at reflux for 90 minutes and then cooled to room temperature. The solution was poured onto cracked ice, and extracted with chloroform (3×50 ml) and ethyl acetate (100 ml). The extracts were then dried and concentrated, and the residue obtained triturated with hot ethyl acetate (200 ml) to yield the title compound (0.204 g, 42%).

12E. [1-(7H-Pyrrolo[2,3-d]pyrimidin-4-yl)-piperidin-4-yl]-carbamic acid tert-butyl ester

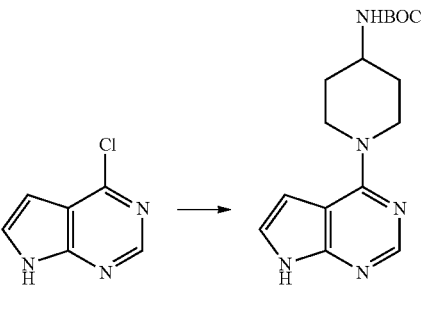

To a solution of 4-chloro-7H-pyrrolo[2,3-d]pyrimidine (74 mg, 0.48 mmol) in ethanol (1 ml) was added triethylamine (200 µl, 1.43 mmol) and 4-N-Boc-aminopiperidine (106 mg, 0.53 mmol). The solution was heated at 80° C. for 4 hours, and then cooled to room temperature. The precipitate was collected by filtration and washed with ethanol (2 ml), then dried under vacuum to yield the product (57 mg, 36%). LC/MS (LCT) $R_t$ 4.57 $[M+H]^+$ 318

12F. 1-(7H-Pyrrolo[2,3-d]pyrimidin-4-yl)-piperidin-4-ylamine

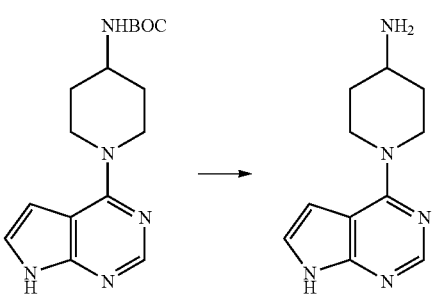

To [1-(7H-Pyrrolo[2,3-d]pyrimidin-4-yl)-piperidin-4-yl]-carbamic acid tert-butyl ester (57 mg, 0.18 mmol) was added HCl (1 ml, 4M solution in dioxane, 4 mmol). The solution was stirred at room temperature for 1 hour, and then diethyl ether was added (4 ml). The ethereal layer was discarded and the solid triturated with a further portion of ether (4 ml) and dried [product mass 27 mg]. A portion of the product was dissolved in methanol, absorbed onto an acidic resin SCX-2 cartridge, and the free base was eluted with 1M ammonia in methanol. LC/MS (LCT) $R_t$ 0.81 [M+H]$^+$ 218

EXAMPLE 13

1-(1H-Pyrrolo[2,3-b]pyridin-4-yl)-piperidin-4-ylamine

13A. 1H-Pyrrolo[2,3-b]pyridine 7-oxide

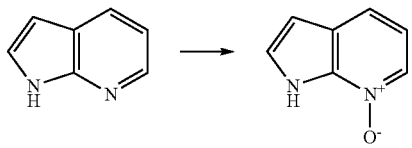 [SMILES: c1cnc2[nH]ccc2c1 ; [O-][n+]1cccc2cc[nH]c21]

To a solution of 7-azaindole (3.04 g, 25 mmol) in DME (60 ml) was added 77% m-chloroperoxybenzoic acid (6.8 g, 12 mmol). The resulting yellow solution was stirred at room temperature for 1.5 hours, during which time the product precipitated. The mixture was filtered and the solid washed with diethyl ether to give 7-hydroxy-1H-pyrrolo[2,3-b]pyridinium m-chlorobenzoate (3.9 g, 13.3 mmol, 53%). A suspension of 7-hydroxy-1H-pyrrolo[2,3-b]pyridinium m-chlorobenzoate (3.9 g, 13.3 mmol) in water (35 ml) was basified to pH 11 with a saturated aqueous solution of potassium carbonate. The 1H-pyrrolo[2,3-b]pyridine 7-oxide started to precipitate. The mixture was kept in the fridge overnight for further precipitation to occur. The solid was filtered, washed with hexane and diethyl ether to afford the required oxide as a white solid (1.35 g, 10 mmol, 40%). LC/MS (LCT) $R_t$ 2.60 [M+H]$^+$ 135.

13B. 4-Chloro-1H-pyrrolo[2,3-b]pyridine

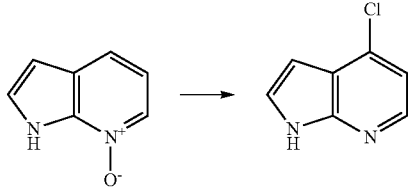 [SMILES: [O-][n+]1cccc2cc[nH]c21 ; Clc1ccnc2[nH]ccc12]

A mixture of 1H-pyrrolo[2,3-b]pyridine 7-oxide (1.35 g, 10 mmol) and phosphorous oxychloride (7.6 ml) was refluxed for 6 hours. After cooling down the reaction mixture to room temperature, ice (90 ml) was added and the mixture was basified to pH 9 with a saturated aqueous solution of potassium carbonate. The brownish solid was filtered, washed with water, hexane and diethyl ether (547 mg, 3.6 mmol, 36%). LC/MS (LCT) $R_t$ 5.74 [M+H]$^+$ 153, 155.

13C. [1-(1H-Pyrrolo[2,3-b]pyridin-4-yl)-piperidin-4-yl]-carbamic acid tert-butyl ester

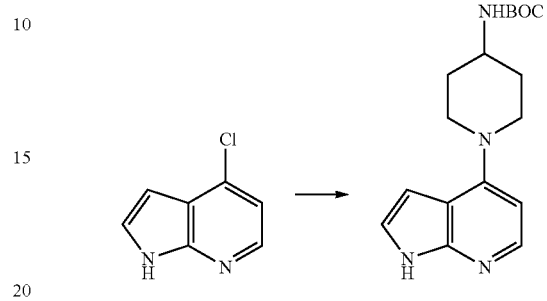

A mixture of 4-chloro-1H-pyrrolo[2,3-b]pyridine (100 mg, 0.64 mmol), 4-N-(Boc-amino)-piperidine (453 mg, 2.24 mmol) and N-methyl-pyrrolidinone (0.2 ml) was microwaved for 1 hour at 160° C. The solution was diluted with methanol and purified through an SCX acidic resin cartridge eluting initially with methanol and then with a 3M solution of ammonia in methanol. The crude product was further purified by flash silica column chromatography eluting with 8% methanol in dichloromethane to afford the required compound (56 mg, 0.18 mmol, 28%). LC/MS (LCT) $R_t$ 4.64 [M+H]$^+$ 317.

13D. 1-(1H-Pyrrolo[2,3-b]pyridin-4-yl)-piperidin-4-ylamine

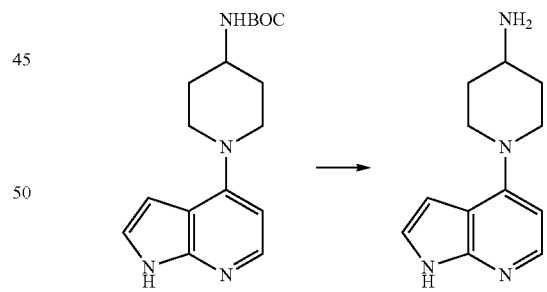

Trifluoroacetic acid (1 ml) was added dropwise to a solution of [1-(1H-Pyrrolo[2,3-b]pyridin-4-yl)-piperidin-4-yl]-carbamic acid tert-butyl ester (19 mg, 0.06 mmol) in dichloromethane (1 ml), with stirring and cooling on ice. After 2.5 hours, the solvents were concentrated in vacuo and the crude product was purified on a basic resin NH$_2$ cartridge (2 g, 15 ml) eluting with methanol to afford the required compound (12.5 mg, 0.058 mmol, 96%). LC-MS (LCT) R$_t$ 0.95 [M+H]$^+$ 217

EXAMPLE 14

C-[4-(4-Chloro-phenyl)-1-(7H-pyrrolo[2,3-d]pyrimidin-4-yl)-piperidin-4-yl]-methylamine

14A.
4-(4-Chlorophenyl)-4-cyanopiperidin-1-carboxylic acid tert-butyl ester

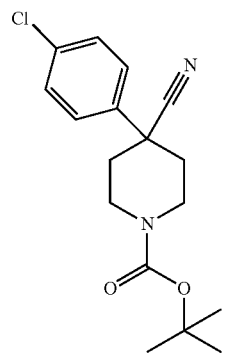 [SMILES: CC(C)(C)OC(=O)N1CCC(C#N)(c2ccc(Cl)cc2)CC1]

4-Chlorophenylacetonitrile was reacted with three equivalents of sodium hydride and one equivalent of N-tert-butyloxycarbonyl-bis-(2-chloroethyl)amine in DMF, initially at room temperature and then at 60° C. to give, after work up, the N-protected piperidine nitrile title compound.

14B. 4-Aminomethyl-4-(4-chlorophenyl)piperidine-1-carboxylic acid tert-butyl ester

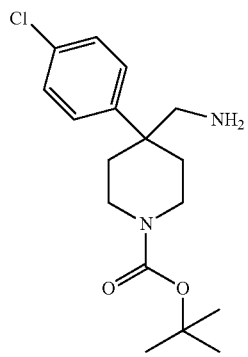 [SMILES: CC(C)(C)OC(=O)N1CCC(CN)(c2ccc(Cl)cc2)CC1]

To a solution of 4-(4-chlorophenyl)-4-cyanopiperidin-1-carboxylic acid tert-butyl ester (0.355 g, 1.107 mmol) in ethanol (20 ml) at room temperature was added Raney Nickel (Raney Nickel 2800, 1 ml) and the suspension stirred under 1 atmosphere of hydrogen for 20 hours. The suspension was filtered through celite and the filtrate concentrated to give the amine as an oil (0.258 g, 69%). LC/MS: (LCT) R$_t$ 5.02 [M-Bu$^t$-NH$_2$]$^+$324.

14C.
C-[4-(4-chlorophenyl)piperidin-4-yl]methylamine hydrochloride

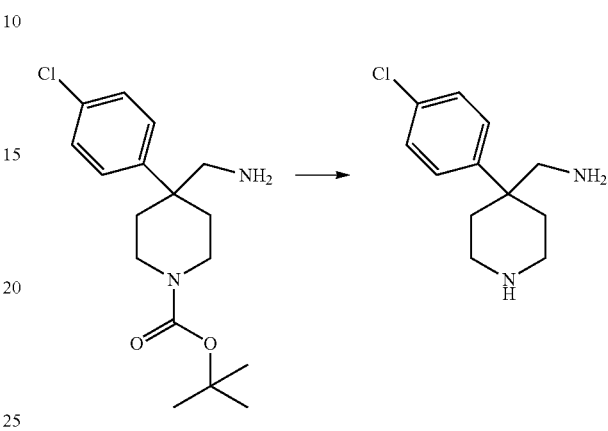

To a solution of 4-aminomethyl-4-(4-chlorophenyl)piperidine-1-carboxylic acid tert-butyl ester (0.258 g, 0.794 mmol) in methanol (10 ml) at room temperature was added 2M hydrochloric acid (10 ml). After 18 h the solution was concentrated to dryness to give the amine salt as a white foam (0.232 g, 98%). $^1$H NMR (MeOD) □ 2.10-2.22 (2H, m), 2.60-2.66 (2H, m), 2.92-3.02 (2H, m), 3.24 (2H, s), 3.37-3.46 (2H, m), 7.51-7.59 (4H, m).

14D. C-[4-(4-Chloro-Phenyl)-1-(7H-pyrrolo[2,3-d]pyrimidin-4-yl)-piperidin-4-yl]-methylamine

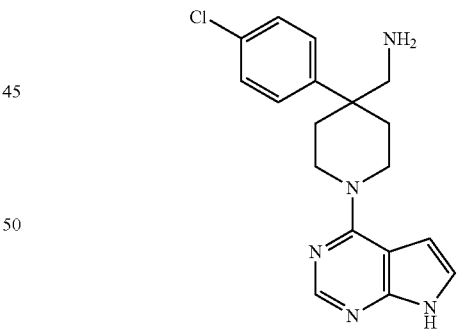

A solution of C-[4-(4-chlorophenyl)piperidin-4-yl]methylamine hydrochloride (0.060 g, 0.202 mmol), 4-chloro-7H-pyrrolo[2,3-d]pyrimidine (0.031 g, 0.202 mmol) and triethylamine (0.14 ml, 1.008 mmol) in n-butanol (2 ml) was heated at 100° C. for 2 days. The reaction mixture was evaporated to dryness and purified by Solid phase extraction on SCX-II acidic resin, eluting with MeOH then 1M NH$_3$ in MeOH, to give the crude amine. Purification by silica column chromatography (15%-20% methanol in DCM) gave an off white foam solid (0.018 g, 26%). LC/MS (LCT): R$_t$ 3.60 [M+H]$^+$ 341.

$^1$H NMR (MeOD) δ 1.87-1.98 (2H, m), 2.33-2.43 (2H, m), 2.82, (2H, s), 3.45-3.55 (2H, m), 4.43-4.46 (2H, m), 6.65 (1H, d, J=4 Hz), 7.13 (1H, d, J=4 Hz), 7.44-7.52 (4H, m), 8.13 (1H, s)

EXAMPLE 15

C-[4-(4-Chloro-phenyl)-1-(9H-purin-6-yl)-piperidin-4-yl]-methylamine

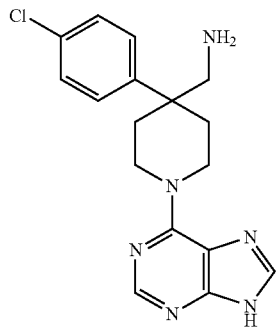 [SMILES: NCC1(c2ccc(Cl)cc2)CCN(c2ncnc3[nH]cnc23)CC1]

The product of Example 14C was reacted with 6-chloropurine following a method analogous to the method of Example 2 to give the title compound. LC/MS: (LCT) R$_t$ 3.91 [M+H]$^+$ 342.

$^1$H NMR (MeOD) δ 1.85-1.95 (2H, m), 3.31-2.46 (2H, m), 2.83 (2H, s), 3.57-3.70 (2H, m), 4.85-5.00 (2H, m), 7.45-7.57 (4H, m), 8.01 (1H, s), 8.20 (1H, s)

EXAMPLE 16

4-Benzyl-1-(9H-purin-6-yl)piperidin-4-ylamine 16A. 4-Benzylpiperidine-1,4-dicarboxylic acid, 1-tert-butyl ester 4-methyl ester

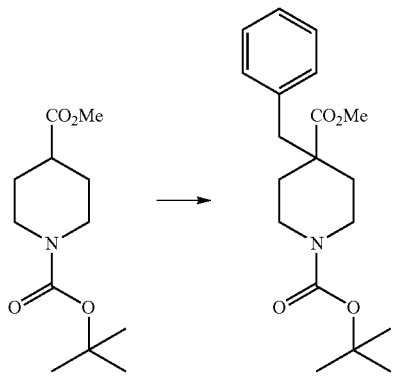 [SMILES: COC(=O)C1CCN(C(=O)OC(C)(C)C)CC1 ; COC(=O)C1(Cc2ccccc2)CCN(C(=O)OC(C)(C)C)CC1]

To a solution of isopropylamine (1.34 ml, 9.559 mmol) in THF (40 ml) at 0° C. was added n-butyllithium (3.65 ml of a 2.5M sol. In hexanes, 9.125 mmol). The resulting LDA solution was added via cannula to a solution of piperidine-1,4-dicarboxylic acid 1-tert-butyl ester 4 methyl ester (2.11 g, 8.690 mmol) in THF (40 ml) and HMPA (8 ml) at −78° C. and stirring continued for 1 hour. Benzyl bromide (1.19 ml, 9.994 mmol) in THF (5 ml) was then added and the solution warmed to room temperature over 2 hours. After stirring for 18 h, saturated aqueous ammonium chloride (200 ml) was added and the aqueous phase extracted with diethyl ether (2×100 ml). Organic phases were combined, dried over magnesium sulphate and concentrated to dryness. Purification by silica column chromatography (0.5% methanol in DCM) gave the ester as an oil (1.816 g, 63%). LC/MS: (LCT) R$_t$ 7.67 [M+H]$^+$ 333.

16B. 4-Benzylpiperidine-1,4-dicarboxylic acid mono-tert-butyl ester

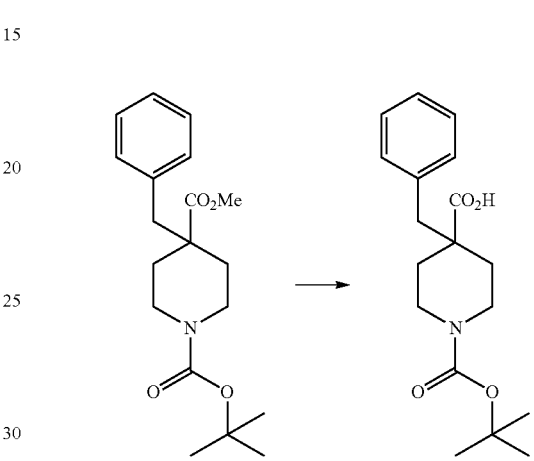

To a solution of 4-benzylpiperidine-1,4-dicarboxylic acid 1-tert-butyl ester 4-methyl ester (1.772 g, 5.315 mmol) in dioxane (24 ml), methanol (12 ml), and water (12 ml) at room temperature was added lithium hydroxide monohydrate (4.460 g, 106.292 mmol). After stirring at 50° C. for 2 days the solution was acidified to pH 6 using 2M HCl and the resulting white precipitate extracted with diethyl ether (2×100 ml). The organic phases were combined, dried over sodium sulphate and concentrated to dryness to give the acid as a white solid (1.477 g, 87%). LC/MS (LCT): R$_t$ 7.37 [M+H]$^+$ 319.

16C. 4-Benzyl-1-(9H-purin-6-yl)piperidin-4-ylamine

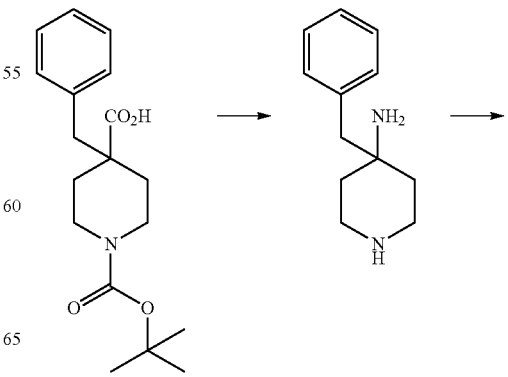

-continued

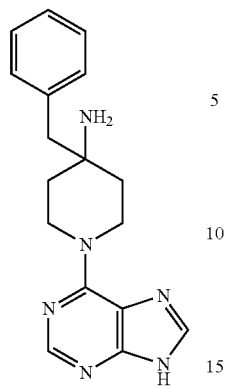

To a mixture of acid (1.467 g, 4.593 mmol) and triethylamine (1.28 ml, 9.186 mmol) in THF (46 ml) at −15° C. was added isobutyl chloroformate (0.901 ml, 6.890 mmol). After 1 h a solution of sodium azide (0.597 g, 9.186 mmol) in water (10 ml) was added and the solution warmed to room temperature overnight. Water (100 ml) was added and the aqueous phase extracted with diethyl ether (3×50 ml). Organic phases were combined, washed with saturated sodium bicarbonate (50 ml) and dried over sodium sulphate. Toluene (100 ml) was added and the overall volume reduced to approximately 90 ml. The resulting solution was warmed to 90° C. for 2 h, then cooled and added to 10% hydrochloric acid (70 ml). The biphasic mixture was warmed to 90° C. for 24 hours. The organic phase was separated and concentrated to dryness to give the crude amine salt (883 mg), which was used without further purification.

A portion of amine salt (0.044 g, 0.1680 mmol), 6-chloropurine (0.026 g, 0.1680 mmol) and triethylamine (0.117 ml, 0.8399 mmol) in n-butanol (1.7 ml) was heated to 100° C. for 24 hours. The mixture was concentrated to dryness then washed with methanol (5 ml), with the resulting solid dissolved in 2M $NH_3$ in methanol and passed through a —$NH_2$ isolute column (2 g). Concentration of the filtrate gave the amine as a solid (0.037 g, 71% from amine salt). LC/MS (LCT): $R_t$ 3.89 [M+H]$^+$ 308.

$^1$H NMR (DMSO) δ 1.51-1.78 (4H, m), 2.88 (2H, s), 3.97-4.21 (4H, m), 7.25-7.40 (5H, m), 8.12 (1H, s), 8.20 (1H, s)

EXAMPLE 17

4-(4-Chlorobenzyl)-1-(7H-pyrrolo[2,3-d]pyrimidin-4-yl)piperidin-4-ylamine

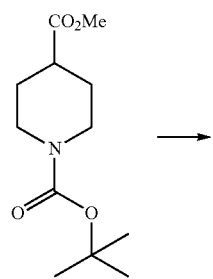

-continued

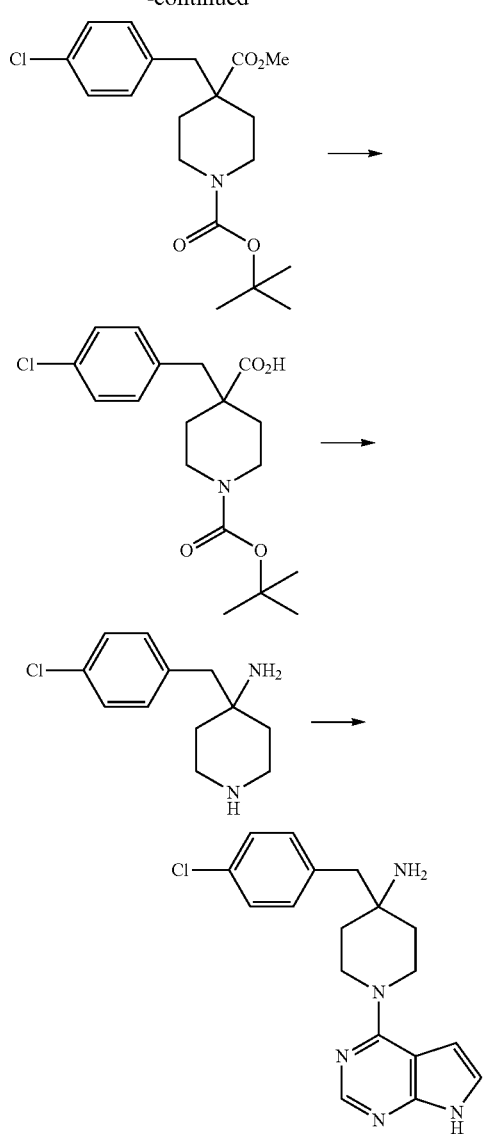

17A. 4-(4-Chlorobenzyl)piperidine-1,4-dicarboxylic acid 1-tert-butyl ester 4-methyl ester To a solution of isopropylamine (3.71 ml, 26.45 mmol) in THF (110 ml) at 0° C. was added n-butyllithium (10.1 ml of a 2.5M solution in hexanes, 25.25 mmol). The resulting LDA solution was added via cannula to a solution of piperidine-1,4-dicarboxylic acid 1-tert-butyl ester 4-methyl ester (5.85 g, 24.04 mmol) in THF (110 ml) and HMPA (20 ml) at −78° C. and stirring was continued for 1 hour. 4-Chlorobenzyl chloride (6.4 ml, 50.49 mmol) in THF (20 ml) was added and the solution was warmed to room temperature over 2 hours. After stirring for 18 hours, saturated aqueous ammonium chloride (500 ml) was added and the aqueous phase was extracted with diethyl ether (2×200 ml). The organic phases were combined, dried over magnesium sulphate and concentrated to dryness. Purification by silica column chromatography (0.5% methanol in DCM) gave the ester as an oil (3.03 g, 34%). LC-MS (LCT1) m/z 390 [M+Na$^+$], $R_t$ 8.02 min.

17B. 4-(4-Chlorobenzyl)piperidine-1,4-dicarboxylic acid mono-tert-butyl ester To a solution of 4-(4-chlorobenzyl)piperidine-1,4-dicarboxylic acid 1-tert-butyl ester 4-methyl ester (1.515 g, 4.117 mmol) in dioxane (20 ml), methanol (10 ml) and water (10 ml) at room temperature was added lithium hydroxide monohydrate (3.455 g, 82.341 mmol). After stirring at 50° C. for 2 days the solution was acidified to pH 6 with 2M HCl and the resulting white precipitate was extracted with diethyl ether (2×100 ml). The organic phases were combined, dried over sodium sulphate and concentrated to dryness, to give the acid as a white solid (1.460 g, 100%). LC-MS (LCT) m/z 376 [M+Na$^+$], R$_t$ 7.62 min.

17C. 4-(4-Chlorobenzyl)piperidin-4-yl amine

To a mixture of the acid (1.46 g, 4.126 mmol) and triethylamine (1.15 ml, 8.252 mmol) in THF (41 ml) at −15° C. was added isobutyl chloroformate (0.812 ml, 6.189 mmol). After 1 hour, a solution of sodium azide (0.536 g, 8.252 mmol) in water (10 ml) was added and the solution was warmed to room temperature overnight. Water (100 ml) was added and the aqueous phase was extracted with diethyl ether (3×50 ml). The organic phases were combined, washed with saturated sodium bicarbonate (50 ml) and dried over sodium sulphate. Toluene (100 ml) was added and the overall volume was reduced to approximately 90 ml. The resulting solution was warmed to 90° C. for 2 h, then cooled and added to 10% hydrochloric acid (70 ml). The biphasic mixture was warmed to 90° C. for 24 hours. The organic phase was separated and concentrated to dryness to give the crude amine salt (1.109 g).

The crude amine salt was dissolved in 2M NaOH (20 ml) and di-tert-butyl dicarbonate (1.61 g, 7.391 mmol) added. After 2 days the aqueous phase was extracted with diethyl ether (2×50 ml). The organic phases were combined, washed with 1M HCl (20 ml), saturated sodium bicarbonate (20 ml) and brine (20 ml), then dried over magnesium sulphate and concentrated. Purification by column chromatography (50% diethyl ether in hexanes) gave the doubly BOC-protected amine (0.685 g), which was subsequently deprotected by stirring with 4M HCl in dioxane (10 ml) and methanol (10 ml) at room temperature for 2 days. Concentration gave the desired amine as the bis-hydrochloride salt (0.492 g, 40% from acid).

$^1$H NMR (MeOD) δ 7.48-7.44 (m, 2H), 7.35-7.32 (m, 2H), 3.53-3.47 (4H, m), 3.21 (s, 2H), 2.18-2.13 (4H, m).

17D. 4-(4-Chlorobenzyl)-1-(7H-pyrrolo[2,3-d]pyrimidin-4-yl)piperidin-4-ylamine A solution of 4-(4-chlorobenzyl)piperidin-4-yl amine hydrochloride (0.060 g, 0.2016 mmol), 4-chloro-7H-pyrrolo[2,3-d]pyrimidine (0.031 g, 0.2016 mmol) and triethylamine (0.140 ml, 1.0079 mmol) in n-butanol (2.0 ml) was heated to 100° C. for 24 hours. Concentration and purification by preparative silica TLC gave a white solid (0.034 g, 49%). LC-MS (LCT) m/z 342 [M+H$^+$], R$_t$ 3.25 min.

$^1$H NMR (MeOD) δ 1.53-1.94 (4H, m), 2.81 (2H, s), 3.75-3.90 (2H, m), 4.21-4.41 (2H, m), 6.64 (1H, d, J=4 Hz), 7.13 (1H, J=4 Hz), 7.27-7.36 (4H, m), 8.14 (1H, s)

EXAMPLE 18

4-(4-Chlorobenzyl)-1-(9H-purin-6-yl)piperidin-4-yl amine

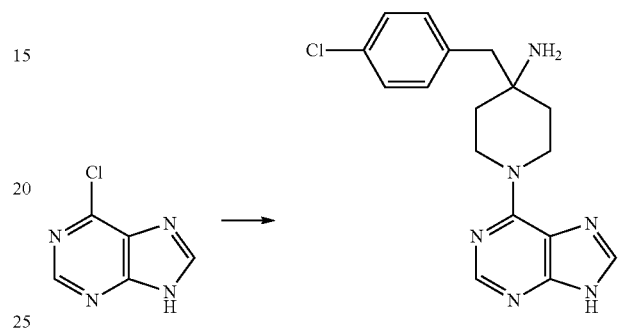

The title compound was prepared as described in Example 17 using 6-chloropurine in place of 4-chloro-7H-pyrrolo[2,3-d]pyrimidine. LC-MS (LCT) m/z 343 [M+H$^+$], R$_t$ 4.02 min.

$^1$H NMR (MeOD) δ 1.40-1.74 (4H, m), 2.68 (2H, s), 3.79-3.89 (2H, m), 4.59-4.77 (2H, m), 7.10-7.23 (4H, m), 7.89 (1H, s), 8.08 (1H, s)

EXAMPLE 19

C-[4-(4-Chlorobenzyl)-1-(7H-pyrrolo[2,3-d]pyrimidin-4-yl)piperidin-4-yl]methylamine

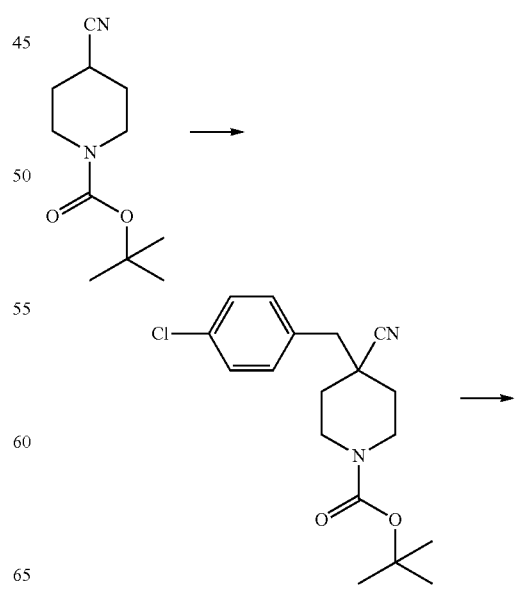

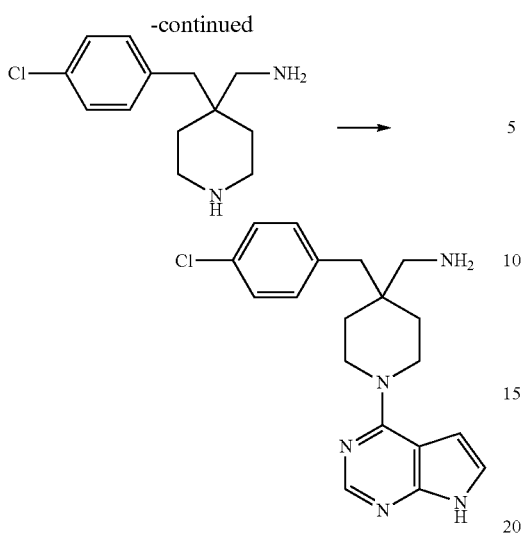

19A.
4-(4-Chlorobenzyl)-4-cyanopiperidine-1-carboxylic acid tert-butyl ester To a solution of isopropylamine (1.53 ml, 10.94 mmol) in THF (30 ml) at −78° C. was added n-butyllithium (4.38 ml of a 2.5M solution in hexanes, 10.938 mmol). After 10 minutes, a solution of 4-cyanopiperidine-1-carboxylic acid tert-butyl ester in THF (12 ml) was added. After a further 1 hour, a solution of 4-chlorobenzyl chloride (1.84 g, 11.4 mmol) in THF (5 ml) was added and the solution warmed to room temperature over 15 hours. Water (150 ml) was added and the aqueous phase extracted with diethyl ether (150 ml). The organic phase was dried over magnesium sulphate and concentrated to give a crude solid that was purified by recrystallisation from diethyl ether/hexane in two batches to give the product as a white solid (2.650 g, 83%). LC-MS (LCT2) m/z 357 [M+Na$^+$], 235 [M-Boc]$^+$, R$_t$ 8.02 min.

19B. C-[4-(4-Chlorobenzyl)piperidin-4-yl]methyl amine

To a solution of 4-(4-chlorobenzyl)-4-cyanopiperidine-1-carboxylic acid tert-butyl ester (0.500 g, 1.493 mmol) in methanol (3 ml) was added 4M HCl in dioxane (10 ml). After stirring for 19 hours, the solution was concentrated to give the deprotected amine as the hydrochloride salt (0.405 g).

The amine salt was dissolved in 1M BH$_3$.THF in THF (15 ml, 15 mmol) at room temperature and stirred for 2 days. The reaction was quenched with methanol (10 ml), concentrated, redissolved in methanol (10 ml) and 4M HCl in dioxane (20 ml) and the resulting solution refluxed for 6 hours. Concentration and purification by SCX-2 Isolute column (5 g), eluting with 1M NH$_3$/MeOH, gave the desired amine, which was converted to the bis-hydrochloride salt by dissolving in 2M aqueous HCl (6 ml) and methanol (6 ml) followed by concentration to give the product as a white solid (0.285 g, 61%). $^1$H NMR (MeOD)-free amine-δ 7.31-7.28 (m, 2H), 7.20-7.17 (m, 2H), 2.94-2.75 (m, 4H), 2.70 (s, 2H), 2.52 (s, 2H), 1.45-1.41 (m, 4H).

19C. C-[4-(4-Chlorobenzyl)-1-(7H-pyrrolo[2,3-d]pyrimidin-4-yl)piperidin-4-yl]methylamine A solution of C-[4-(4-chlorobenzyl)piperidin-4-yl]methyl amine hydrochloride (0.063 g, 0.2016 mmol), 4-chloro-7H-pyrrolo[2,3-d]pyrimidine (0.031 g, 0.2016 mmol) and triethylamine (0.140 ml, 1.0079 mmol) in n-butanol (2.0 ml) was heated to 100° C. for 24 hours. Concentration and purification by SCX-2 Isolute column (2 g), eluting with 1M NH$_3$/MeOH, followed by silica column chromatography (15% methanol in DCM) gave a white solid (0.040 g, 56%). LC-MS (LCT2) m/z 356 [M+H$^+$], R$_t$ 2.97 min.

$^1$H NMR (MeOD) δ 1.61 (4H, br s), 2.62 (2H, s), 2.79 (2H, s), 3.90-3.94 (2H, m), 4.05-4.08 (2H, m), 6.63 (1H, d, J=3 Hz), 7.12 (J=3 Hz), 7.22-7.32 (4H, m), 8.13 (1H, s)

EXAMPLE 20

6-[4-Aminomethyl-4-(4-chlorophenyl)piperidin-1-yl]-7,9-dihydropurin-8-one

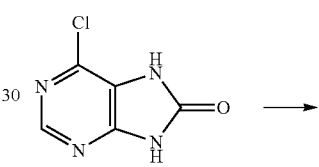

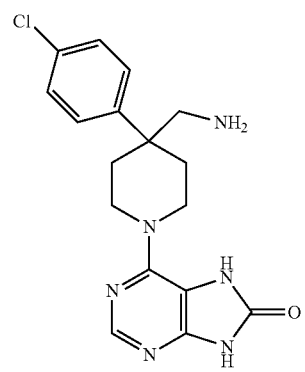

The title compound was prepared as described in Example 14 using 6-chloro-8-oxopurine in place of 4-chloro-7H-pyrrolo[2,3-d]pyrimidine. LC-MS (LCT) m/z 359 [M+H$^+$], R$_t$ 4.09 min.

$^1$H NMR (MeOD) δ 1.84-1.98 (2H, m), 2.30-2.42 (2H, m), 2.82 (2H, s), 3.24-3.40 (2H, m), 3.94-4.10 (2H, m), 7.42-7.49 (4H, m), 8.11 (1H, s)

EXAMPLE 21

C-[4-(4-Chlorophenyl)-1-(1H-pyrrolo[2,3-b]pyridin-4-yl)piperidin-4-yl]methylamine

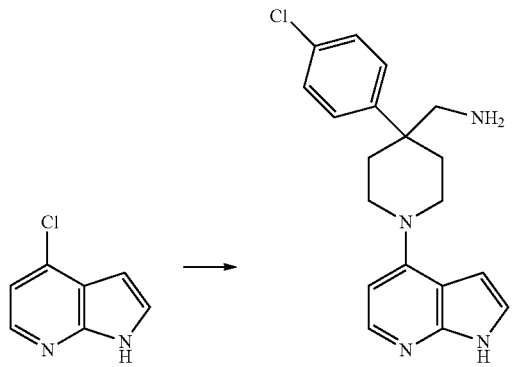 [SMILES: Clc1ccnc2[nH]ccc12 ; NCC1(c2ccc(Cl)cc2)CCN(c2ccnc3[nH]ccc23)CC1]

The title compound was prepared in a similar manner to Example 14, using 4-chloro-7-azaindole in place of 4-chloro-7H-pyrrolo[2,3-d]pyrimidine, with NMP as solvent and microwave heating at 155° C. LC-MS (LCT2) m/z 341 [M+H$^+$], R$_t$ 2.85 min.

$^1$H NMR (MeOD) δ 1.98-2.13 (2H, m), 2.37-2.49 (2H, m), 2.84 (2H, s), 3.18-3.28 (2H, m), 3.76-3.90 (2H, m), 6.46 (1H, d, J=6 Hz), 6.54 (1H, d, J=3.5 Hz), 7.18 (1H, d, J=3.5 Hz), 7.42-7.51 (4H, m), 7.91 (1H, d, J=6 Hz)

EXAMPLE 22

6-[4-Aminomethyl-4-(4-chlorophenyl)piperidin-1-yl]-7-ethyl-7,9-dihydro-purin-8-one

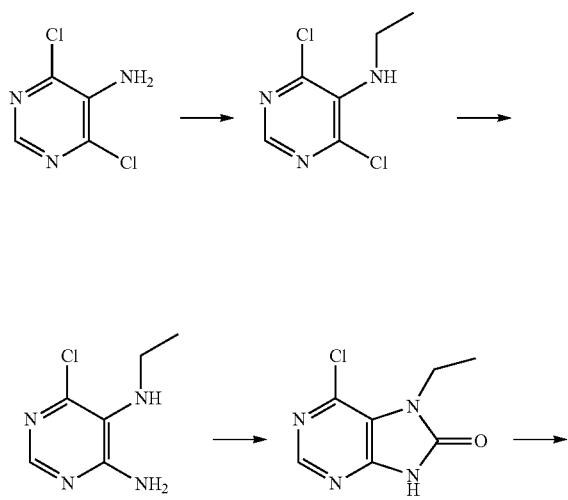

-continued

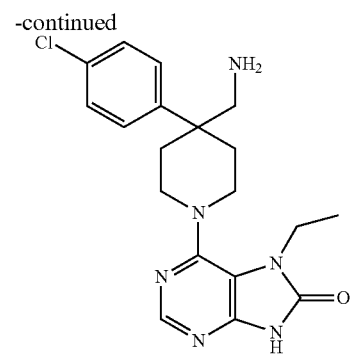

22A. Ethyl(4,6-dichloropyrimidin-5-yl)amine

Sodium hydride (55%, 0.17 g, 4.0 mmol) was added in a single portion to a solution of (4,6-dichloropyrimidin-5-yl)amine (0.61 g, 3.72 mmol) and ethyl iodide (0.30 mL, 3.8 mmol) in dry DMF (3 mL) at room temperature. The suspension was stirred for 18 hours, then diluted with saturated aqueous ammonium chloride (5 mL) and water (20 mL). The mixture was extracted with diethyl ether (30 mL), and the extract was dried, filtered and concentrated. Flash column chromatography on silica, eluting with 10% ethyl actetate—hexanes, gave ethyl(4,6-dichloropyrimidin-5-yl)amine (0.321 g, 1.67 mmol, 45%). LC-MS (LCT2) m/z 192, 194 [M+H$^+$], R$_t$ 6.07 min.

22B N$^5$-Ethyl-6-chloropyrimidine-4,5-diamine

A suspension of ethyl(4,6-dichloropyrimidin-5-yl)amine (0.31 g, 1.61 mmol) and concentrated aqueous ammonia (10 mL) in ethanol (3 mL) was heated to 100° C. in a sealed tube for 16 hours. The solution was cooled and evaporated to dryness. The residue was partitioned between ethyl acetate (20 mL) and dilute brine (10 mL). The organic layer was dried, filtered and concentrated to give N$^5$-ethyl-6-chloropyrimidine-4,5-diamine (0.214 g, 1.24 mmol, 77%) as a waxy solid. LC-MS (LCT2) m/z 173, 175 [M+H$^+$], R$_t$ 3.97.

22C. 7-Ethyl-6-chloro-7,9-dihydropurin-8-one

A solution of N$^5$-ethyl-6-chloropyrimidine-4,5-diamine (0.21 g, 1.22 mmol) and 1,1-carbonyldiimidazole (0.40 g, 2.44 mmol) in 1,4-dioxane (5 mL) was degassed, flushed with nitrogen and refluxed under nitrogen for 22 h. The solution was cooled and partitioned between ethyl acetate (15 mL), 1M hydrochloric acid (10 mL) and brine (5 mL). The organic layer was dried, filtered and concentrated to give 7-ethyl-6-chloro-7,9-dihydropurin-8-one (0.146 g, 0.735 mmol, 60%) as a yellow solid. LC-MS (LCT2) m/z 199, 201 [M+H$^+$], R$_t$ 4.62 min.

22D. 6-[4-Aminomethyl-4-(4-chlorophenyl)piperidin-1-yl]-7-ethyl-7,9-dihydro-purin-8-one A solution of 7-benzyl-6-chloro-7,9-dihydropurin-8-one (0.015 g, 0.075 mmol), C-[4-(4-chlorophenyl)piperidin-4-yl]methylamine bis hydrochloride (0.025 g, 0.085 mmol) and triethylamine (0.11 mL, 0.85 mmol) in n-butanol (0.5 mL) was heated at 150° C. in a microwave reactor for 3 h. The cooled mixture was partitioned between ethyl acetate (30 mL) and water (5 mL) and the organic layer was dried, filtered and concentrated. Purification on SCX-II acid resin, eluting with methanol then 1M ammonia/methanol, gave 6-[4-aminomethyl-4-(4-chlorophenyl)piperidin-1-yl]-7-ethyl-7,9-dihydropurin-8-one as a cream solid (0.016 g, 0.041 mmol, 56%). LC-MS (LCT2) m/z 387 [M+H⁺], $R_t$ 4.18 min.

EXAMPLE 23

C-[4-(4-Chlorobenzyl)-1-(9H-purin-6-yl)piperidin-4-yl]methylamine

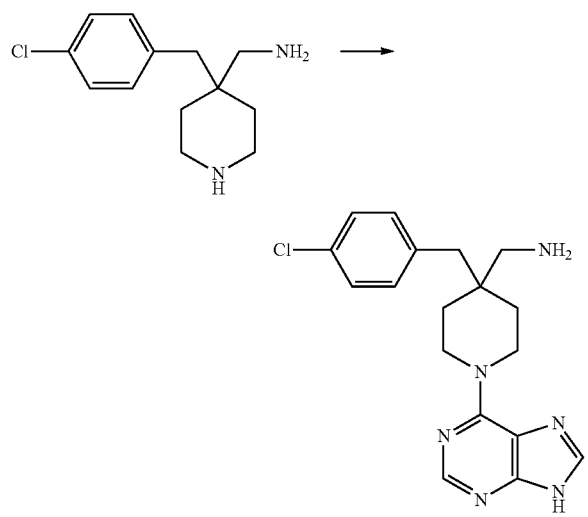

The title compound was prepared as described in Example 19 using 6-chloropurine in place of 4-chloro-7H-pyrrolo[2,3-d]pyrimidine. LC-MS (LCT2) m/z 357 [M+H⁺], $R_t$ 4.07 min.

¹H NMR (MeOD) δ 1.57-1.62 (4H, m), 2.64 (2H, s), 2.82 (2H, s), 4.20-4.28 (2H, m), 4.39-4.47 (2H, m), 7.21-7.33 (4H, m), 7.98 (1H, s), 8.18 (2H, s)

EXAMPLE 24

4-(4-Chlorophenyl)-1-(7H-pyrrolo[2,3-d]pyrimidin-4-yl)piperidine-4-carbonitrile

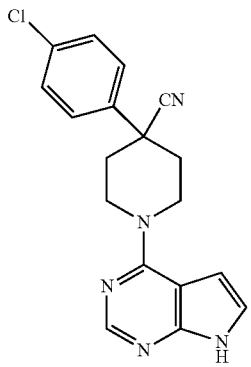

24A. 4-(4-Chlorophenyl)piperidine-4-carbonitrile

To absolution of 4-(4-chlorophenyl)-4-cyanopiperidine-1-carboxylic acid tert-butyl ester (1.000 g, 3.12 mmol) in methanol (5 ml) at rt was added 4M HCl in dioxane (15 ml). After stirring for 20 h the solution was concentrated to give the deprotected amine as the hydrochloride salt (0.785 g, 98%). LC-MS (LCT2) m/z 221 [M+H⁺], $R_t$ 2.84 min.

24B. 4-(4-Chlorophenyl)-1-(7H-pyrrolo[2,3-d]pyrimidin-4-yl)piperidine-4-carbonitrile A solution of 4-(4-chlorophenyl)piperidine-4-carbonitrile hydrochloride (0.055 g, 0.2155 mmol), 4-chloro-7H-pyrrolo[2,3-d]pyrimidine (0.033 g, 0.2155 mmol) and triethylamine (0.150 ml, 1.0775 mmol) in n-butanol (2.0 ml) was heated to 100° C. for 2 days. Concentration and trituration with methanol (3 ml) gave a white solid (0.058 g, 80%). LC-MS (LCT2) m/z 338 [M+H⁺], $R_t$ 6.17 min.

¹H NMR (DMSO) δ 2.03-2.15 (2H, m), 2.26-2.31 (2H, m), 3.36-3.41 (2H, m), 4.91 (2H, d, J=14 Hz), 6.66-6.68 (1H, m), 7.23-7.25 (11H, m), 7.50-7.63 (4H, m), 8.21 (1H, s)

EXAMPLE 25

4-(4-Chlorophenyl)-1-(7H-pyrrolo[2,3-d]pyrimidin-4-yl)piperidin-4-ylamine

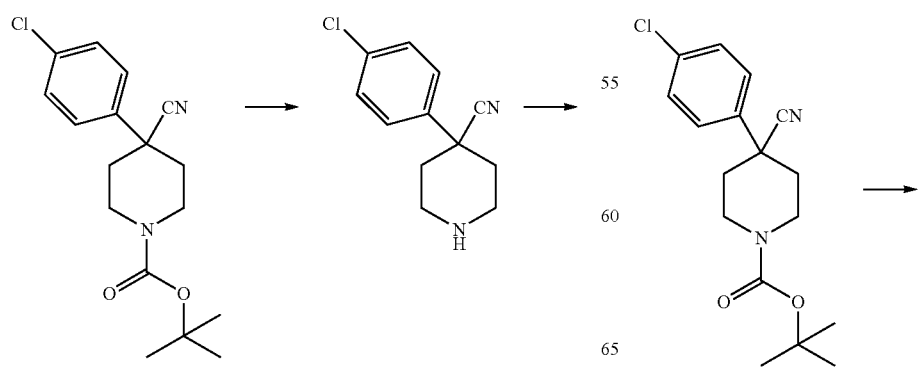

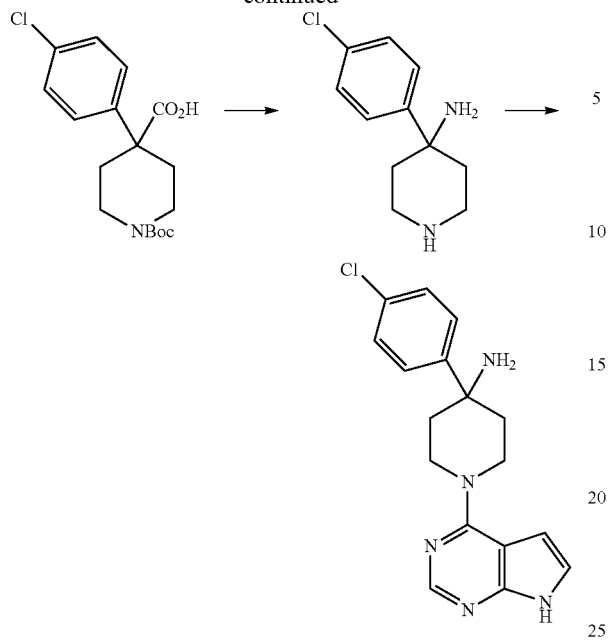

25A. 4-(4-Chlorophenyl)piperidine-1,4-dicarboxylic acid mono-tert-butyl ester A solution of 4-(4-chlorophenyl)-4-cyanopiperidine-1-carboxylic acid tert-butyl ester (0.683 g, 2.129 mmol) in 6M HCl (20 ml) was refluxed for 4 days. The solution was cooled, basified with NaOH and di-tert-butyl dicarbonate (0.558 g, 2.555 mmol) added. After stirring for 24 h the solution was extracted with diethyl ether (2×75 ml). The organic phases were combined, washed with brine (50 ml), dried over magnesium sulphate and concentrated. Purification by silica column chromatography (5% methanol in DCM) gave the acid as a white foam (0.339 g, 47%). LC-MS (LCT2) m/z 362 [M+Na$^+$], R$_t$ 8.17 min.

25B. 4-(4-Chlorophenyl)piperidin-4-yl amine

The title compound was prepared using the method described for Example 17C. $^1$H NMR (MeOD) δ 7.74-7.70 (m, 2H), 7.65-7.61 (m, 2H), 3.61-3.52 (m, 2H), 3.07-2.93 (m, 4H), 2.56-2.44 (m, 2H).

25C. 4-(4-Chlorophenyl)-1-(7H-pyrrolo[2,3-d]pyrimidin-4-yl)piperidin-4-ylamine A solution of 4-(4-chlorophenyl)piperidin-4-yl amine hydrochloride (0.030 g, 0.1058 mmol), 4-chloro-7H-pyrrolo[2,3-d]pyrimidine (0.016 g, 0.1058 mmol) and triethylamine (0.074 ml, 0.5289 mmol) in n-butanol (1.0 ml) was heated to 100° C. for 2 days. Concentration and purification by SCX-2 Isolute column (2 g), eluting with 1M NH$_3$/MeOH, followed by silica column chromatography (20% methanol in DCM) gave a white solid (0.026 g, 74%). LC-MS (LCT2) m/z 328 [M+H$^+$], R$_t$ 2.59 min.

$^1$H NMR (MeOD) δ 1.90-1.95 (2H, m), 2.18-2.34 (2H, m), 3.93-4.03 (2H, m), 4.20-4.29 (2H, m), 6.67 (1H, d, J=4 Hz), 7.15 (1H, d, J=4 Hz), 7.16-7.58 (4H, m), 8.16 (1H, s)

EXAMPLE 26

C-[4-(3-Chlorophenyl)-1-(7H-pyrrolo[2,3-d]pyrimidin-4-yl)piperidin-4-yl]methylamine

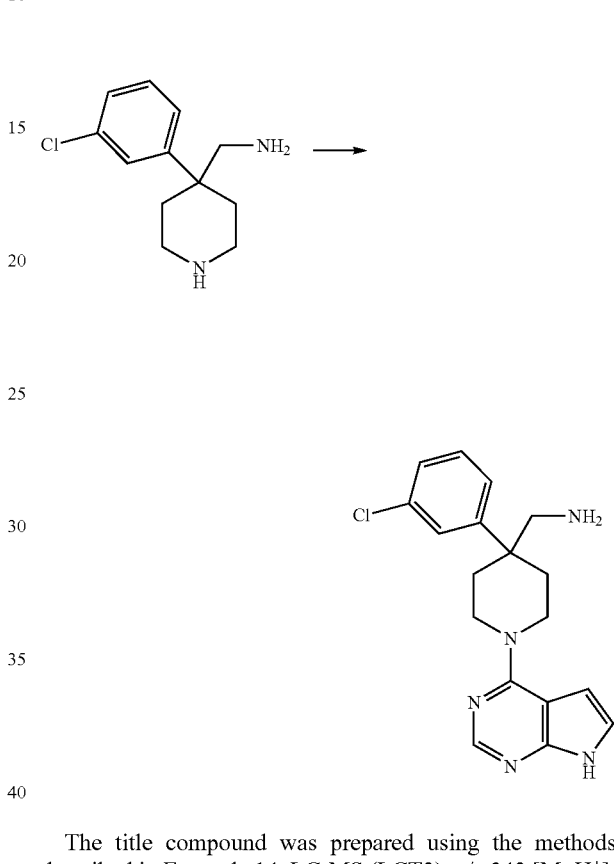

The title compound was prepared using the methods described in Example 14. LC-MS (LCT2) m/z 342 [M+H$^+$], R$_t$ 2.55 min.

$^1$H NMR (MeOD) δ 1.86-1.91 (2H, m), 2.30 (2H, d, J=14 Hz), 2.78 (2H, s), 3.43-3.50 (2H, m), 4.29-4.33 (2H, m), 6.59-6.60 (1H, m), 7.10-7.11 (1H, m), 7.27-7.29 (1H, m), 7.36-7.41 (2H, m), 7.47 (1H, s), 8.13 (1H, s)

EXAMPLE 27

C-[4-(3-Chlorophenyl)-1-(9H-purin-6-yl)piperidin-4-yl]methylamine

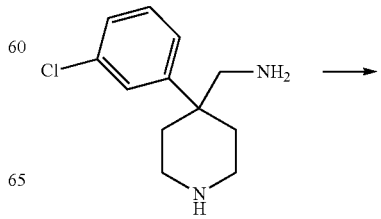

-continued

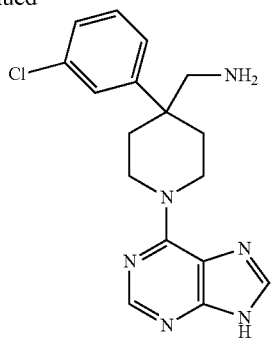

The title compound was prepared using the methods described in described in Examples 14 and 15. LC-MS (LCT2) m/z 343 [M+H$^+$], R$_t$ 3.60 min.

$^1$H NMR (DMSO) δ 1.81-1.90 (2H, m), 2.12-2.19 (2H, m), 2.70 (2H, s), 3.33 (2H, br s), 3.52 (2H, br s), 4.69 (2H, br s), 7.29-7.45 (4H, m), 8.10 (1H, s), 8.19 (1H, s)

EXAMPLE 28

C-[4-(3,4-Dichlorophenyl)-1-(7H-pyrrolo[2,3-d]pyrimidin-4-yl)piperidin-4-yl]methylamine

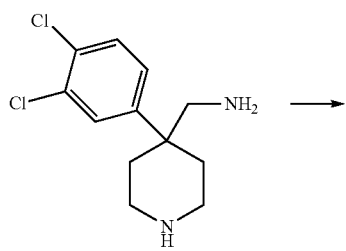

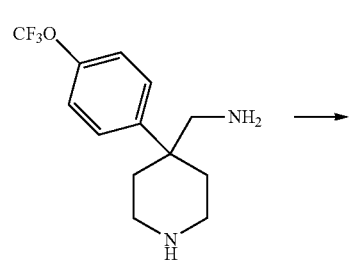

The title compound was prepared using the methods described in Example 14. LC-MS (LCT2) m/z 376 [M+H$^+$], R$_t$ 3.29 min.

$^1$H NMR (DMSO) δ 1.83-1.91 (2H, m), 2.16-2.25 (2H, m), 2.78 (2H, s), 3.39-3.47 (2H, m), 4.20-4.25 (2H, m), 6.58 (1H, d, J=3 Hz), 7.17 (1H, d, J=3 Hz), 7.41-7.45 (1H, m), 7.57-7.65 (2H, m), 8.13 (1H, s)

EXAMPLE 29

C-[4-(3,4-Dichlorophenyl)-1-(9H-purin-6-yl)piperidin-4-yl]methylamine

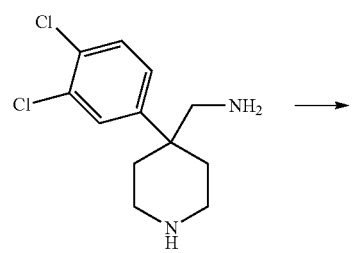

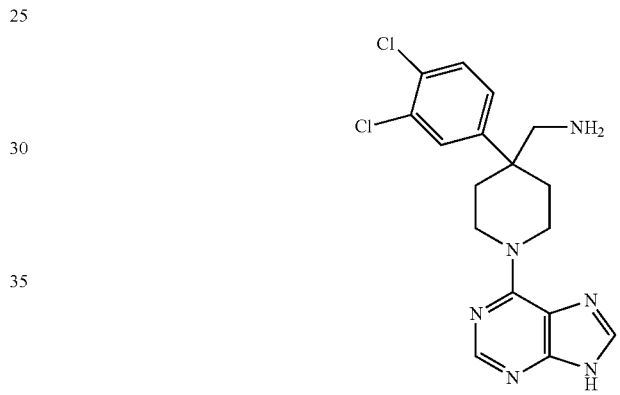

The title compound was prepared using the methods described in Examples 14 and 15. LC-MS (LCT2) m/z 377 [M+H$^+$], R$_t$ 4.37 min.

$^1$H NMR (DMSO) δ 1.88-1.97 (2H, m), 2.23-2.28 (2H, m), 3.00 (2H, s), 3.66 (2H, br s), 7.73 (2H, br s), 7.46-7.50 (1H, m), 7.58-7.73 (2H, m), 8.09 (1H, s), 8.21 (1H, s)

EXAMPLE 30

C-[1-(7H-pyrrolo[2,3-d]pyrimidin-4-yl)-4-trifluoromethoxyphenyl)piperidin-4-yl]methylamine

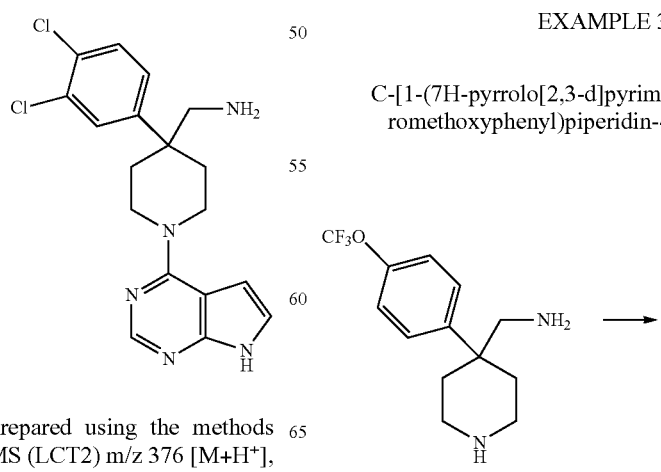

-continued

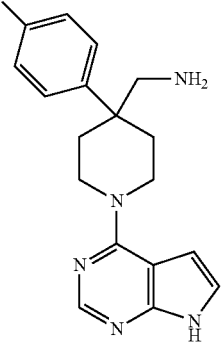

The title compound was prepared using the methods described in Example 14. LC-MS (LCT2) m/z 392 [M+H⁺], $R_t$ 3.25 min.

¹H NMR (MeOD) δ 1.17-1.21 (2H, m), 1.61-1.64 (2H, m), 2.08 (2H, s), 2.73-2.78 (2H, m), 3.59-3.63 (2H, m), 5.88 (1H, d, J=3.5 Hz), 6.38 (1H, d, J=3.5 Hz), 6.59-6.61 (2H, m), 6.83-6.84 (2H, m), 7.38 (1H, s)

EXAMPLE 31

C-[1-(9H-Purin-6-yl)-4-(4-trifluoromethoxyphenyl)piperidin-4-yl]methylamine

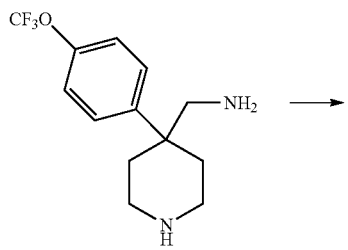

The title compound was prepared using the methods described in Examples 14 and 15. LC-MS (LCT2) m/z 393 [M+H⁺], $R_t$ 4.30 min.

¹H NMR (MeOD) δ 1.88-1.99 (2H, m), 2.35-2.41 (2H, m), 2.83 (2H, s), 3.62-3.71 (2H, m), 4.79-4.95 (2H, m), 7.34-7.57 (2H, m), 7.57-7.66 (2H, m), 7.99 (1H, s), 8.20 (1H, s)

EXAMPLE 32

C-[1-(7H-Pyrrolo[2,3-d]pyrimidin-4-yl)-4-(4-trifluoromethylphenyl)piperidin-4-yl]methylamine

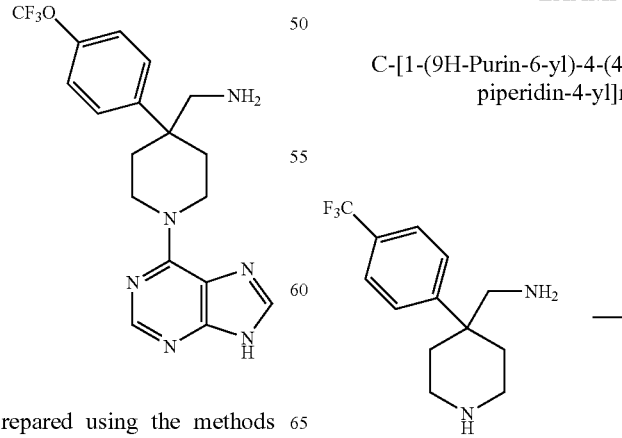

The title compound was prepared using the methods described in Example 14. LC-MS (LCT2) m/z 376 [M+H⁺], $R_t$ 3.07 min.

¹H NMR (MeOD) δ 1.93-2.04 (2H, m), 2.40-2.46 (2H, m), 2.87 (2H, s), 3.47-3.58 (2H, m), 4.36-4.43 (2H, m), 6.65 (1H, d, J=3.5 Hz), 7.13 (1H, d, J=3.5 Hz), 7.68-7.77 (4H, m), 8.13 (1H, s)

EXAMPLE 33

C-[1-(9H-Purin-6-yl)-4-(4-trifluoromethylphenyl)piperidin-4-yl]methylamine

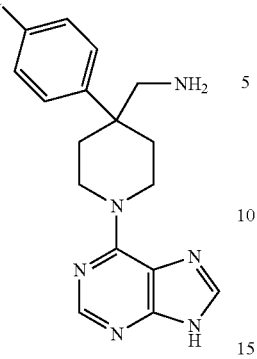

The title compound was prepared using the methods described in Examples 14 and 15. LC-MS (LCT2) m/z 377 [M+H⁺], $R_t$ 4.19 min.

$^1$H NMR (MeOD) δ 1.92-2.03 (2H, m), 2.41-2.46 (2H, m), 2.87 (2H, s), 3.62-3.71 (2H, m) 4.79-4.87 (2H, m), 7.69-7.78 (4H, m), 8.02 (1H, s), 8.21 (1H, s)

EXAMPLE 34

C[1-(7H-Pyrrolo[2,3-d]pyrimidin-4-yl)-4-(3-trifluoromethylphenyl)piperidin-4-yl]methylamine

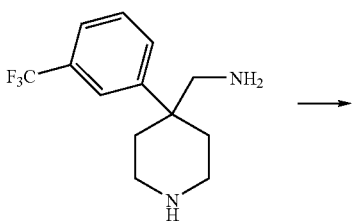

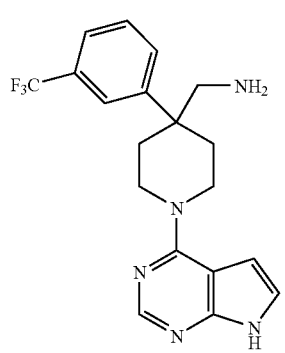

The title compound was prepared using the methods described in Example 14. LC-MS (LCT2) m/z 376 [M+H⁺], $R_t$ 2.90 min.

$^1$H NMR (MeOD) δ 1.96-2.07 (2H, m), 2.40-2.45 (2H, m), 2.89 (2H, s), 3.49-3.59 (2H, m), 4.33-4.42 (2H, m), 6.66 (1H, d, J=3.5 Hz), 7.14 (1H, d, J=3.5 Hz), 7.61-7.81 (4H, m), 8.14 (1H, s)

EXAMPLE 35

C-[1-(9H-Purin-6-yl)-4-(3-trifluoromethylphenyl)piperidin-4-yl]methylamine

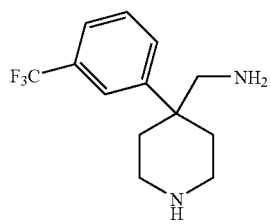

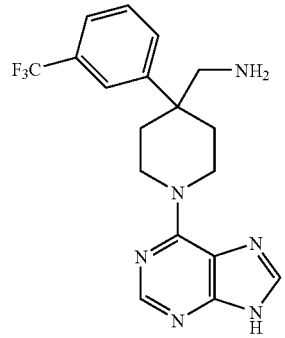

The title compound was prepared using the methods described in Examples 14 and 15. LC-MS (LCT2) m/z 377 [M+H⁺], $R_t$ 3.97 min.

$^1$H NMR (MeOD) δ 1.94-2.05 (2H, m), 2.39-2.44 (2H, m), 2.89 (2H, s), 3.65-3.73 (2H, m), 4.80-5.10 (2H, m), 7.51-7.81 (4H, m), 8.02 (1H, s), 8.21 (1H, s)

EXAMPLE 36

C-[4-(3,4-Difluorophenyl)-1-(7H-Pyrrolo[2,3-d]pyrimidin-4-yl)piperidin-4-yl]methylamine

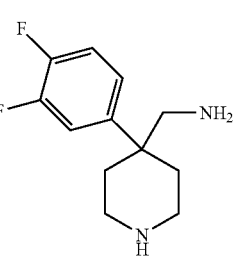

-continued

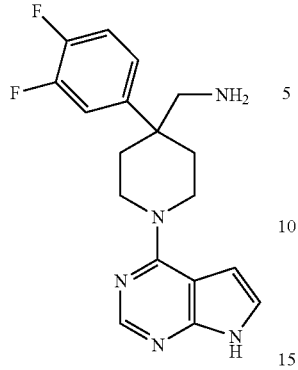

The title compound was prepared using the methods described in Example 14. LC-MS (LCT2) m/z 344 [M+H⁺], $R_t$ 2.42 min.
¹H NMR (MeOD) δ 1.88-1.99 (2H, m), 2.32-2.37 (2H, m), 2.84 (2H, s), 3.45-3.57 (2H, m), 4.34-4.41 (2H, m), 6.64 (1H, d, J=3.5 Hz), 7.13 (1H, d, J=3.5 Hz), 7.31-7.47 (3H, m), 8.14 (1H, s)

EXAMPLE 37

C-[4-(3,4-Difluorophenyl)-1-(9H-purin-6-yl)piperidin-4-yl]methylamine

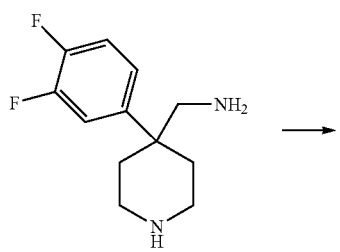
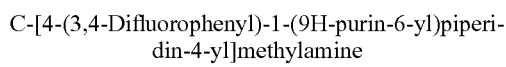

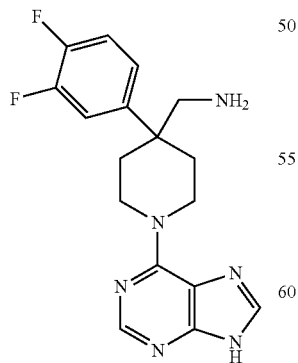

The title compound was prepared using the methods described in Examples 14 and 15. LC-MS (LCT2) m/z 345 [M+H⁺], $R_t$ 3.42 min.
¹H NMR (MeOD) δ 1.87-1.98 (2H, m), 2.31-2.36 (2H, m), 2.82 (2H, s), 3.64-3.72 (2H, m), 4.79-4.95 (2H, m), 7.29-7.48 (3H, m), 8.02 (1H, s), 8.21 (1H, s)

EXAMPLE 38

C-[4-(4-Methoxyphenyl)-1-(7H-pyrrolo[2,3-d]pyrimidin-4-yl)piperidin-4-yl]methylamine

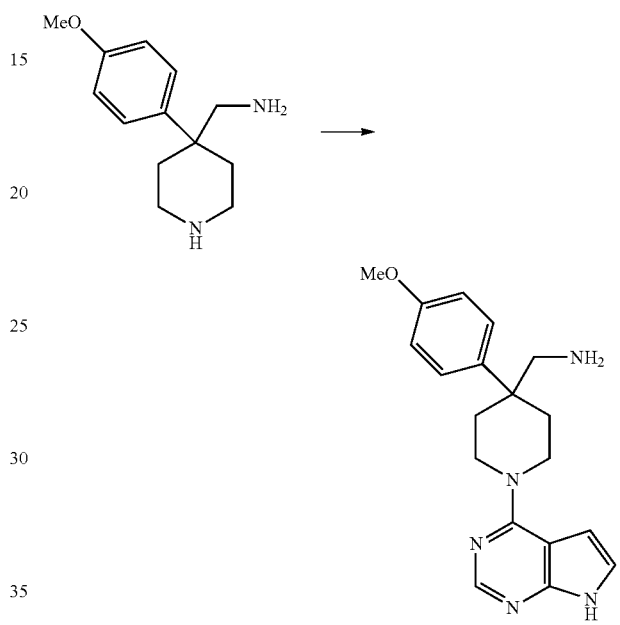
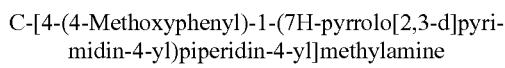

The title compound was prepared using the methods described in Example 14. LC-MS (LCT2) m/z 338 [M+H⁺], $R_t$ 2.37 min.
¹H NMR (MeOD) δ 1.82-1.93 (2H, m), 2.36-2.42 (2H, m), 2.81 (2H, s), 3.41-3.51 (2H, m), 3.83 (3H, s), 4.38-4.45 (2H, m), 6.63 (1H, d, J=3.5 Hz), 7.00-7.03 (2H, m), 7.12 (1H, d, J=3.5 Hz), 7.39-7.42 (2H, m), 8.13 (1H, s)

EXAMPLE 39

C-[4-(4-Methoxyphenyl)-1-(9H-purin-6-yl)piperidin-4-yl]methylamine

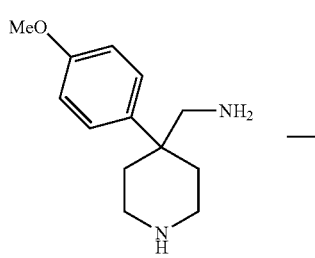
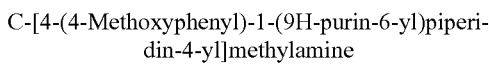

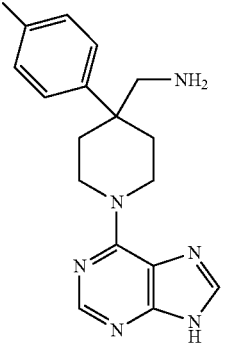

The title compound was prepared using the methods described in Examples 14 and 15. LC-MS (LCT2) m/z 339 [M+H⁺], R_t 3.20 min.

¹H NMR (MeOD) δ 1.81-1.91 (2H, m), 2.37-2.42 (2H, m), 2.77 (2H, s), 3.53-3.63 (2H, m), 3.84 (3H, s), 4.80-5.10 (2H, m), 7.02 (2H, d, J=9 Hz), 7.41 (2H, d, J=9 Hz), 8.01 (1H, s), 8.20 (1H, s)

EXAMPLE 40

C-[4-(4-Benzyloxyphenyl)-1-(7H-pyrrolo[2,3-d]pyrimidin-4-yl)piperidin-4-yl]methylamine

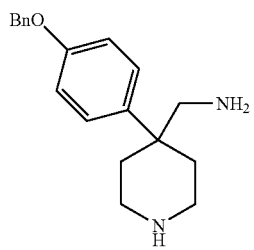 →

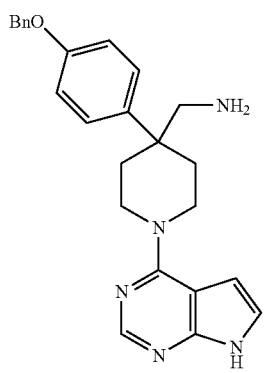

The title compound was prepared using the methods described in Example 14. LC-MS (LCT2) m/z 414 [M+H⁺], R_t 3.87 min.

¹H NMR (MeOD) δ 1.84-1.89 (2H, m), 2.36-2.38 (2H, m), 2.78 (2H, s), 3.44-3.49 (2H, m), 4.37-4.40 (2H, m), 5.11 (2H, s), 6.62-6.64 (1H, m), 7.07-7.13 (3H, m), 7.30-7.46 (7H, m), 8.12 (1H, s)

EXAMPLE 41

C-[4-(4-Benzyloxyphenyl)-1-(9H-purin-6-yl)piperidin-4-yl]methylamine

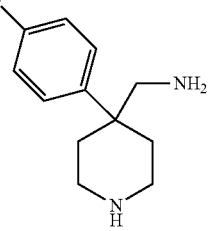 →

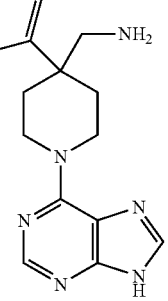

The title compound was prepared using the methods described in Examples 14 and 15. LC-MS (LCT2) m/z 415 [M+H⁺], R_t 4.85 min.

¹H NMR (MeOD) δ 1.81-1.91 (2H, m), 2.37-2.42 (2H, m), 2.73 (2H, s), 3.54-3.63 (2H, m), 4.80-5.10 (2H, m), 5.13 (2H, s), 7.09 (2H, d, J=9 Hz), 7.32-7.48 (7H, m), 8.01 (1H, s), 8.20 (1H, s)

EXAMPLE 42

[4-(4-Chloro-phenyl)-1-(7H-pyrrolo[2,3-d]pyrimidin-4-yl)-piperidin-4-ylmethyl]-methyl-amine

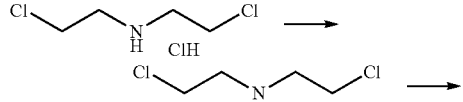

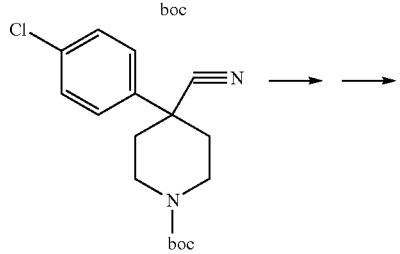

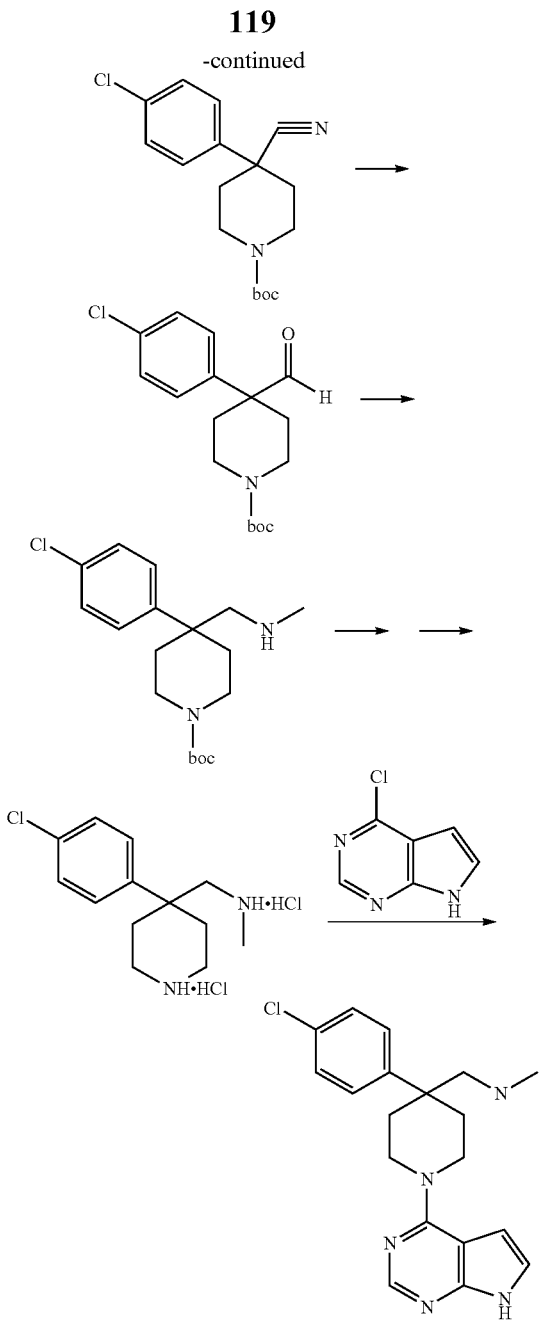

42A. Bis-(2-chloro-ethyl)-carbamic acid tert-butyl ester

A suspension of bis-(2-chloro-ethyl)-amine hydrochloride (5 g, 0.028 mol) in dichloromethane (42 ml) was rapidly stirred with 10% aqueous sodium hydroxide (28 ml) in an ice bath, to which di-tert-butyl dicarbonate (6.11 g, 0.028 mol) in dichloromethane (28 ml) was added. After stirring at room temperature for 18.5 hours, dichloromethane (30 ml) was added to the reaction mixture and the two phases were separated. The aqueous phase was further extracted with dichloromethane (30 ml). The combined organic layers were dried ($Mg_2SO_4$), filtered and concentrated to give bis-(2-chloro-ethyl)-carbamic acid tert-butyl ester (6.74 g, 0.028 mol, 100%). $^1$H NMR (250 MHz, $CDCl_3$): 1.48 (9H, s), 3.62-3.68 (8H, m).

42B. 4-(4-Chlorophenyl)-4-cyano-piperidine-1-carboxylic acid tert-butyl ester

Sodium hydride (60% dispersion in mineral oil, 2.9 g, 72.3 mmol) was added in small portions, over a period of 1 hour, to a solution of bis-(2-chloro-ethyl)-carbamic acid tert-butyl ester (6.74 g, 28 mmol) and 4-chlorobenzyl cyanide (3.8 g, 25 mmol) in anhydrous dimethylformamide (25 ml). The reaction mixture was heated at 65° C. for 1 hour and then stirred at room temperature for 89 hours. After this period, the reaction mixture was poured into ice/water (60 ml) and extracted with ethyl acetate (2×100 ml). The combined organic layers were washed with water and brine, dried, filtered and concentrated. Flash column chromatography on silica, eluting with hexane/dichloromethane/ethyl acetate (8:1:1), gave 4-(4-chlorophenyl)-4-cyano-piperidine-1-carboxylic acid tert-butyl ester (5.6 g, 17.5 mmol, 70%) as a white solid. LC-MS (LCT) m/z 320 [$M^+$], $R_t$ 7.71 min.

42C. 4-(4-Chlorophenyl)-4-formyl-piperidine-1-carboxylic acid tert-butyl ester

A solution of 4-(4-chlorophenyl)-4-cyano-piperidine-1-carboxylic acid tert-butyl ester (2.0 g, 6.2 mmol) in dry toluene (30 ml) at −78° C., under nitrogen, was treated with a solution of DIBAL-H (10 ml, 10 mmol, 1M solution in toluene). The reaction was maintained at −78° C. for 3 hours, at which time it was quenched by slow addition a saturated solution of ammonium chloride (7.3 ml) and allowed to warm to room temperature. The reaction mixture was poured into water (50 ml) and extracted with ethyl acetate (2×100 ml). The organic layer was separated, dried ($Mg_2SO_4$), filtered and concentrated. Flash column chromatography on silica, eluting with 20% ethyl acetate in hexane, gave 4-(4-chlorophenyl)-4-formyl-piperidine-1-carboxylic acid tert-butyl ester (453 mg, 1.4 mmol, 22%) as a white solid. LC-MS (LCT2) m/z 346 [$M+Na^+$], $R_t$ 8.49 min.

42D. 4-(4-Chloro-phenyl)-4-methylaminomethyl-piperidine-1-carboxylic acid tert-butyl ester A mixture of methylamine in ethanol (18 ml, 33% in ethanol) and 4-(4-chlorophenyl)-4-formyl-piperidine-1-carboxylic acid tert-butyl ester (206 mg, 0.62 mmol) was stirred at room temperature overnight. The solvents were concentrated. The crude material was redissolved in methanol (18 ml) followed by addition of sodium borohydride (49 mg, 1.29 mmol). After stirring for 40 minutes at room temperature, the mixture was partitioned between ethyl acetate (100 ml) and a saturated aqueous solution of sodium hydrogen carbonate (100 ml). After separation of the two phases the aqueous phase was re-extracted with ethyl acetate (100 ml). The combined organic layers were dried ($Na_2SO_4$), filtered and concentrated. Flash column chromatography on silica, eluting with 10% methanol in dichloromethane gave 4-(4-chlorophenyl)-4-methylaminomethyl-piperidine-1-carboxylic acid tert-butyl ester (142 mg, 0.42 mmol, 68%). GC-MS m/z 239 [$(M-Boc)^+$], $R_t$ 5.18 min. $^1$H NMR (250 MHz, $CDCl_3$): 1.43 (9H, s), 1.80-1.88 (2, m), 2.15-2.24 (2, m), 2.31 (3H, s), 2.81 (2H, s), 2.98-3.09 (2H, m), 3.72-3.78 (2H, m), 7.32 (2H, d, 9 Hz), 7.38 (2H, d, 9 Hz).

42E. [4-(4-Chlorophenyl)-piperidin-4-ylmethyl]-methylamine bishydrochloride

A 4M solution of hydrochloric acid in dioxane (10 ml) was added dropwise to a solution of 4-(4-chlorophenyl)-4-methylaminomethyl-piperidine-1-carboxylic acid tert-butyl ester (142 mg, 0.42 mmol) in methanol (10 ml). The reaction was stirred overnight at room temperature. After this period of time, the solvents were concentrated to give [4-(4-chlorophenyl)-piperidin-4-ylmethyl]-methylamine bis-hydrochloride (132 mg, 0.42 mmol, 100%). This compound was used in the subsequent step without further purification. LC-MS (LCT2) m/z 239 [M+H⁺], R$_t$ 0.53 min.

42F. [4-(4-Chlorophenyl)-1-(7H-pyrrolo[2,3-d]pyrimidin-4-yl)-piperidin-4-ylmethyl]-methylamine A solution of 4-chloro-7H-pyrrolo[2,3-d]pyrimidine (15.5 mg, 0.1 mmol), [4-(4-chlorophenyl)-piperidin-4-ylmethyl]-methylamine bis-hydrochloride (34 mg, 0.11 mmol) and triethylamine (150 μL, 0.7 mmol) in n-butanol (1 ml) was heated at 100° C. in a microwave reactor for 60 minutes. After cooling the reaction the solvents were concentrated. Purification on SCX-II acid resin, eluting with methanol then 2M ammonia/methanol, followed by further purification by flash column chromatography on silica, eluting with 15% methanol in dichloromethane, gave [4-(4-chlorophenyl)-1-(7H-pyrrolo[2,3-d]pyrimidin-4-yl)-piperidin-4-ylmethyl]-methylamine (12.3 mg, 0.034 mmol, 34%). LC-MS (LCT2) m/z 356 [M+H⁺], R$_t$ 2.64 min.

$^1$H NMR (MeOD) δ 1.94-2.05 (2H, m), 2.28 (3H, s), 2.36-2.41 (2H, m), 2.80 (2H, s), 3.50-3.61 (2H, m), 4.30-4.39 (2H, m), 6.65 (1H, d, J=4 Hz), 7.14 (1H, d, J=4 Hz), 7.42-7.52 (4H, m), 8.13 (1H, s)

EXAMPLE 43

[4-(4-Chlorophenyl)-1-(7H-pyrrolo[2,3-d]pyrimidin-4-yl)-piperidin-4-ylmethyl]-isopropylamine

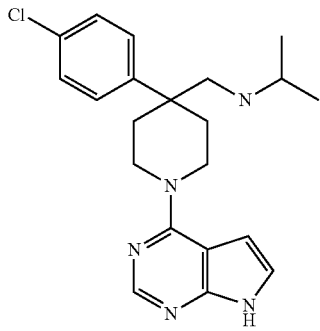 [SMILES: CC(C)NCC1(c2ccc(Cl)cc2)CCN(c2ncnc3[nH]ccc23)CC1]

The title compound was prepared by the method described in Example 42, but replacing methylamine with isopropylamine in step 44D. LC-MS (LCT2) m/z 384 [M+H⁺], R$_t$ 2.80 min.

$^1$H NMR (MeOD) δ 0.97 (6H, d, J=8 Hz), 1.96-2.07 (2H, m), 2.35-2.41 (2H, m), 2.61 (1H, septet, J=8 Hz), 2.83 (2H, s), 3.52-3.62 (2H, s), 4.31-4.37 (2H, m), 6.65 (1H, d, J=4 Hz), 7.14 (1H, d, J=4 Hz), 7.43 (2H, d, J=8 Hz), 7.52 (2H, d, J=8 Hz), 8.13 (1H, s)

EXAMPLE 44

[4-(4-Chlorobenzyl)-1-(7H-pyrrolo[2,3-d]pyrimidin-4-yl)-piperidin-4-yl]-dimethylamine

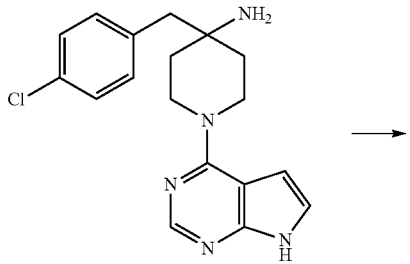

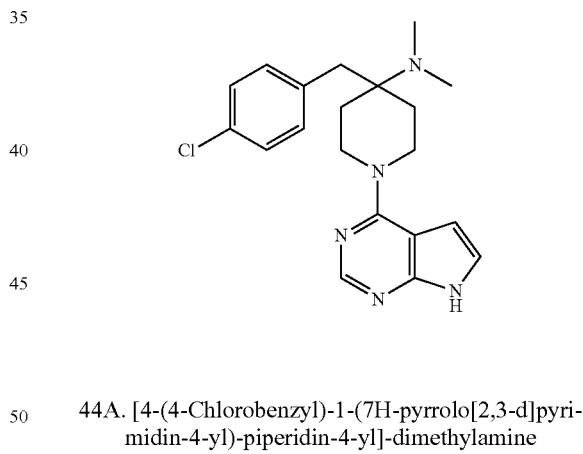

44A. [4-(4-Chlorobenzyl)-1-(7H-pyrrolo[2,3-d]pyrimidin-4-yl)-piperidin-4-yl]-dimethylamine A mixture of 4-(4-chlorobenzyl)-1-(7H-pyrrolo[2,3-d]pyrimidin-4-yl)-piperidin-4-ylamine from Example 17 (20 mg, 0.06 mmol), formic acid (0.16 ml, 96%) and formaldehyde (4 μl, 0.05 mmol, 37% in water) was heated at 100° C. for 48 hours. After cooling the reaction mixture to room temperature, the mixture was basified to pH 10 by addition of a 1M aqueous solution of sodium hydroxide, followed by extraction with ethyl acetate (20 ml). The organic layer was dried (Mg$_2$SO$_4$), filtered and concentrated. Flash column chromatography on silica, eluting with 15% methanol in dichloromethane gave [4-(4-chlorobenzyl)-1-(7H-pyrrolo[2,3-d]pyrimidin-4-yl)-piperidin-4-yl]-dimethylamine (3.8 mg, 0.01 mmol, 17%). LC-MS (LCT2) m/z 370 [M+H⁺], R$_t$ 2.62 min.

¹H NMR (MeOD) δ 1.42-1.53 (2H, m), 2.02-2.18 (2H, m), 2.43 (6H, s), 2.81 (2H, s), 3.51-3.61 (2H, m), 4.30-4.35 (2H, m), 6.60 (1H, d, J=4 Hz), 7.09 (1H, d, J=4 Hz), 7.17-7.28 (4H, m), 8.06 (1H, s)

EXAMPLE 45

C-[4-(3,4-Dichlorobenzyl)-1-(7H-pyrrolo[2,3-d]pyrimidin-4-yl)piperidin-4-yl]methylamine

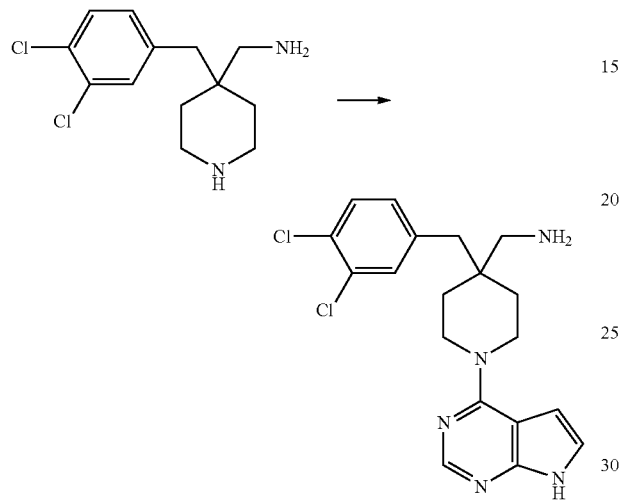

The title compound was prepared using the methods described in Example 19. LC-MS (LCT2) m/z 390 [M+H⁺], R$_t$ 3.37 min.

¹H NMR (MeOD) δ 1.48-1.64 (4H, m), 2.63 (2H, s), 2.81 (2H, s), 3.85-4.16 (4H, m), 6.64 (1H, d, J=3.5 Hz), 7.12-7.21 (2H, m), 7.44-7.47 (2H, m), 8.13 (1H, s)

EXAMPLE 46

C-[4-(3,4-Dichlorobenzyl)-1-(9H-purin-6-yl)piperidin-4-yl]methylamine

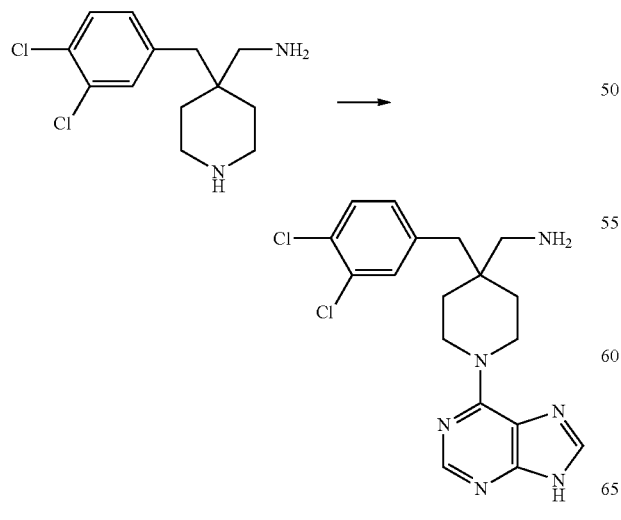

The title compound was prepared using the methods described in Examples 19 and 23. LC-MS (LCT2) m/z 391 [M+H⁺], R$_t$ 4.42 min.

¹H NMR (MeOD) δ 1.40-1.53 (4H, m), 2.51 (2H, s), 2.69 (2H, s), 4.00-4.11 (2H, m), 4.30-4.40 (2H, m), 7.03-7.08 (1H, m), 7.30-7.35 (2H, m), 7.88 (1H, s), 8.08 (1H, s)

EXAMPLE 47

C-[1-(7H-Pyrrolo[2,3-d]pyrimidin-4-yl)-4-(4-trifluoromethoxybenzyl)piperidin-4-yl]methylamine

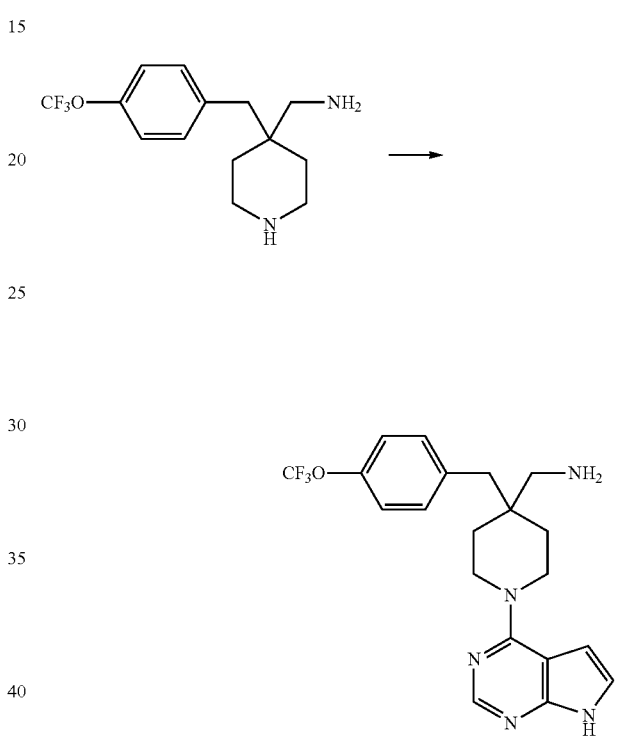

The title compound was prepared using the methods described in Example 19. LC-MS (LCT2) m/z 406 [M+H⁺], R$_t$ 3.39 min.

¹H NMR (MeOD) δ 1.61-1.65 (4H, m), 2.63 (2H, s), 2.86 (2H, s), 3.89-4.15 (4H, m), 6.64 (1H, d, J=4 Hz), 7.13 (1H, d, J=4 Hz), 7.21-7.37 (4H, m), 8.13 (1H, s)

EXAMPLE 48

C-[1-(9H-Purin-6-yl)-4-(4-trifluoromethoxybenzyl)piperidin-4-yl]methylamine

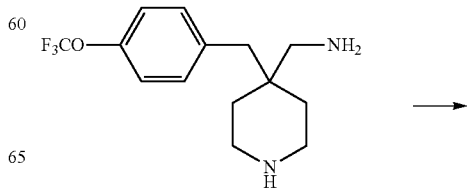

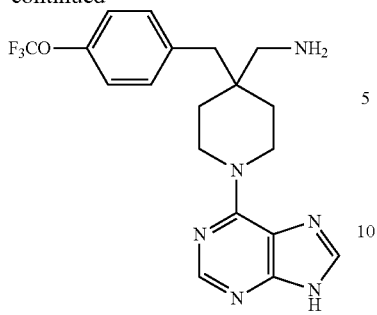

The title compound was prepared using the methods described in Examples 19 and 23. LC-MS (LCT2) m/z 407 [M+H⁺], R_t 4.42 min.

¹H NMR (MeOD) δ 1.54-1.63 (4H, m), 2.64 (2H, s), 2.86 (2H, s), 4.18-4.28 (2H, m), 4.40-4.50 (2H, m), 7.20-7.36 (4H, m), 8.01 (1H, s), 8.21 (1H, s)

EXAMPLE 49

4-(3,4-Dichlorobenzyl)-1-(7H-pyrrolo[2,3-d]pyrimidin-4-yl)piperidin-4-ylamine

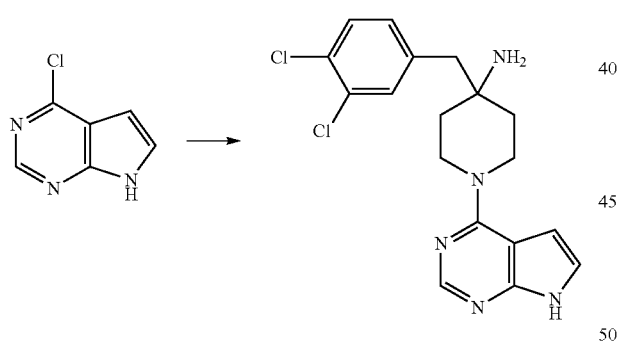

The title compound was prepared using the methods described in Example 17. LC-MS (LCT) m/z 376 [M+H⁺], R_t 3.30 min.

¹H NMR (MeOD) δ 1.54-1.61 (2H, m), 1.72-1.83 (2H, m), 2.79 (2H, s), 3.73-3.84 (2H, m), 4.28-4.37 (2H, m), 6.64 (1H, d, J=3.5 Hz), 7.13 (1H, d, J=3.5 Hz), 7.18-7.22 (1H, m), 7.46-7.54 (2H, m), 8.14 (1H, s)

EXAMPLE 50

4-(3,4-Dichlorobenzyl)-1-(9H-purin-6-yl)piperidin-4-yl amine

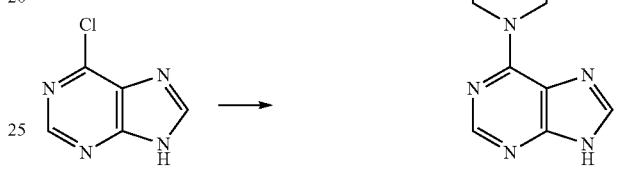

The title compound was prepared using the methods described in Examples 17 and 18. LC-MS (LCT) m/z 377 [M+H⁺], R_t 4.19 min.

¹H NMR (MeOD) δ 1.37-1.46 (2H, m), 1.58-1.69 (2H, m), 2.67 (2H, s), 3.76-3.85 (2H, m), 4.65-4.75 (2H, m), 7.05-7.09 (1H, m), 7.32-7.36 (2H, m), 7.88 (1H, s), 8.08 (1H, s)

EXAMPLE 51

1-(7H-pyrrolo[2,3-d]pyrimidin-4-yl)-4-(4-trifluoromethoxybenzyl)piperidin-4-ylamine

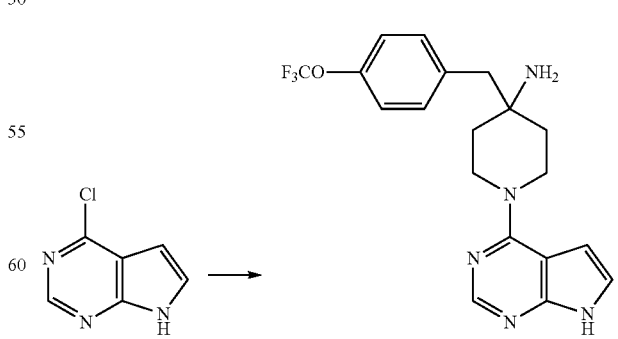

The title compound was prepared using the methods described in Example 17. LC-MS (LCT) m/z 392 [M+H⁺], R_t 3.34 min.

$^1$H NMR (MeOD) δ 1.56-1.61 (2H, m), 1.74-1.85 (2H, m), 2.85 (2H, s), 3.76-3.87 (2H, m), 4.26-4.35 (2H, m), 6.64 (1H, d, J=3.5 Hz), 7.13 (1H, d, J=3.5 Hz), 7.23-7.39 (4H, m), 8.14 (1H, s)

EXAMPLE 52

1-(9H-Purin-6-yl)-4-(4-trifluoromethoxybenzyl)piperidin-4-ylamine

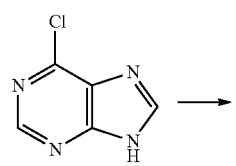
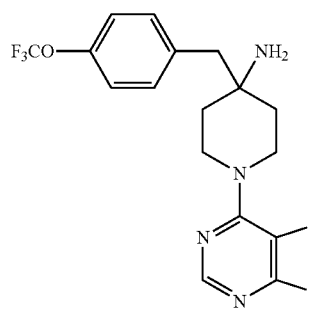

The title compound was prepared using the methods described in Examples 17 and 18. LC-MS (LCT) m/z 393 [M+H$^+$], R$_t$ 4.20 min.

$^1$H NMR (MeOD) δ 1.55-1.60 (2H, m), 1.72-1.92 (2H, m), 2.85 (2H, s), 3.92-4.02 (2H, m), 4.76-4.88 (2H, m), 7.23-7.38 (4H, m), 8.01 (1H, s), 8.21 (1H, s)

EXAMPLE 53

1-(7H-pyrrolo[2,3-d]pyrimidin-4-yl)-4-(3-chlorobenzyl)piperidin-4-ylamine

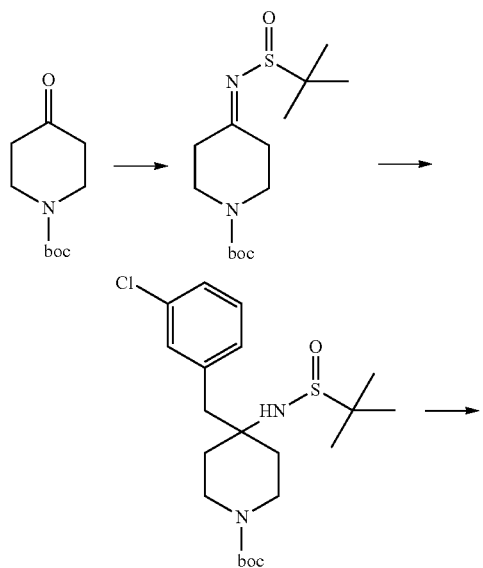
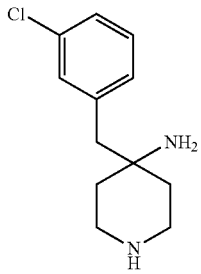
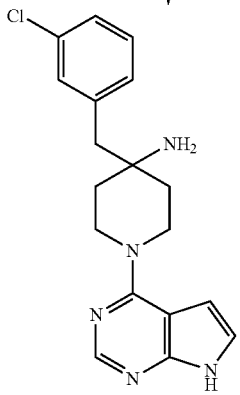

53A. 4-(3-chlorobenzyl)-4-(2-methylpropane-2-sulphinylamino)-piperidine-1-carboxylic acid tert-butyl ester A solution of N-BOC-piperidone (0.205 g, 1.03 mmol), t-butylsulphinamide (0.13 g, 1.07 mmol) and titanium tetraethoxide (0.42 ml, 2.0 mmol) in dry THF (5 ml) was refluxed under nitrogen for 5 h. The cooled solution was diluted with brine (10 ml) and ethyl acetate (10 ml). The suspension was shaken, the filtered through Celite, washing with ethyl acetate (10 ml). The two-phase filtrate was separated and the organic layer was dried (Na$_2$SO$_4$) filtered and concentrated to give the crude sulphinimine (0.293 g). The crude sulphinimine (0.293 g) was suspended in dry THF (2 ml) and stirred at room temperature under nitrogen. A solution of 3-chlorobenzyl magnesium bromide (ca. 4 mmol) (freshly prepared as a solution in diethyl ether from 3-chlorobenzylbromide and magnesium turnings) was added to give an orange solution. After 3 hours, the mixture was diluted with saturated aqueous ammonium chloride (20 ml) and extracted with ethyl acetate (20 ml). The extract was washed with water (20 ml), brine (10 ml), dried (Na$_2$SO$_4$), filtered and concentrated. Flash column chromatography, eluting with 50% ethyl acetate—hexanes, gave 4-(3-chlorobenzyl)-4-(2-methylpropane-2-sulphinylamino)-piperidine-1-carboxylic acid tert-butyl ester as a straw-coloured foam (0.139 g, 0.324 mmol, 31%). LC-MS (LCT) m/z 451, 453 [M+Na$^+$], R$_t$ 8.22 min.

53B. 1-(7H-pyrrolo[2,3-d]pyrimidin-4-yl)-4-(3-chlorobenzyl)piperidin-4-ylamine A solution of 4-(3-chlorobenzyl)-4-(2-methylpropane-2-sulpinylamino)-piperidine-1-carboxylic acid tert-butyl ester (0.134 g, 0.312 mmol) and 4M HCl in dioxane (2 ml, 8 mmol) in dry methanol (2 ml) was stirred at room temperature for 5 hours. The mixture was concentrated then applied to an acidic resin cartridge (SCX-II, 5 g) and eluted with methanol and 2M ammonia-methanol. The amine-containing fractions were further purified by application to a basic resin cartridge (NH$_2$, 2 g), eluting with methanol, to give the crude amine as a yellow oil (0.063 g). A solution of the crude amine (0.063 g), triethyl amine (0.3 ml, 2 mmol) and 4-4-chloro-7H-pyrrolo [2,3-d]pyrimidine (0.039 g, 0.25 mmol) in dry 1-butanol (1 ml) was refluxed under nitrogen for 16 hours. The solution was concentrated and applied to an acidic resin column (SCX, 2 g) then eluted with methanol and 1M ammonia-methanol. The basic fractions were combined and concentrated. Flash silica column chromatography, eluting with 10% methanol—dichloromethane, gave the product as a yellow oil. Trituration and washing with diethyl ether gave a cream solid (0.031 g, 0.0907 mmol, 29%). LC-MS (LCT) m/z 344, 342 [M+H$^+$], R$_t$ 2.90 min.

$^1$H NMR (MeOD) δ 1.45 (2H, d, J=13 Hz), 1.63-1.68 (2H, m), 2.69 (2H, s), 3.65-3.69 (2H, m), 4.19 (2H, d, J=14 Hz), 6.52 (1H, d, 4 Hz), 7.01 (1H, d, J=4 Hz), 7.08 (1H, d, J=7 Hz), 7.15-7.21 (3H, m), 8.01 (1H, s)

EXAMPLE 54

4-(4-Chlorobenzyl)-1-(1H-pyrrolo[2,3-b]pyridin-4-yl)-piperidin-4-ylamine

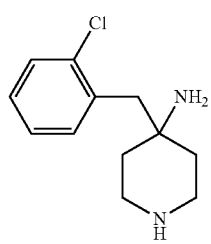

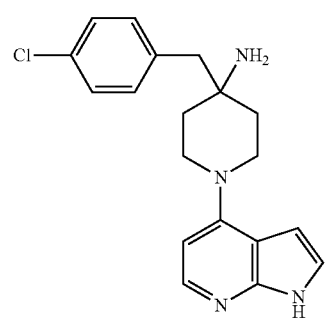

The title compound was prepared in a similar manner to Examples 14 and 17, using 4-fluoro-1-triisopropylsilanyl-1H-pyrrolo[2,3-b]pyridine (*Org Lett* 2003, 5, 5023-5026) in place of 4-chloro-7H-pyrrolo[2,3-d]pyrimidine, with NMP as solvent and microwave heating at 160° C. LC-MS (LCT2) m/z 341, 343 [M+H$^+$], R$_t$ 2.39 min.

$^1$H NMR (CDCl$_3$) δ 0.98-1.47 (2H, m), 1.76-1.80 (2H, m), 2.65 (2H, s), 3.43-3.48 (2H, m), 3.78-3.81 (2H, m), 6.37 (1H, d, J=6 Hz), 6.46 (1H, d, J=4 Hz), 7.05-7.07 (3H, m), 7.23-7.25 (2H, m), 7.86 (1H, d, J=6 Hz)

EXAMPLE 55

4-(2-Chlorobenzyl)-1-(7H-pyrrolo[2,3-d]pyrimidin-4-yl)piperidin-4-ylamine

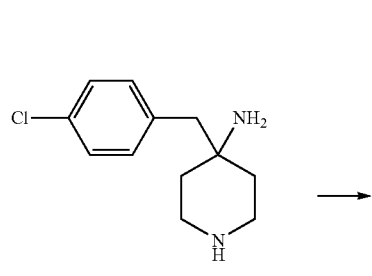

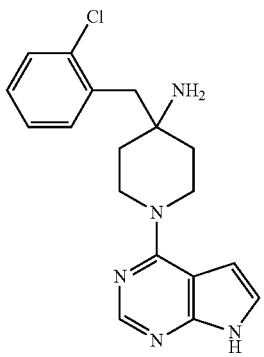

The title compound was prepared as described in Example 53. LC-MS (LCT2) m/z 342 [M+H$^+$], R$_t$ 2.86 min.

$^1$H NMR (MeOD) δ 1.61-1.63 (2H, m), 1.82-1.87 (2H, m), 3.01 (2H, s), 3.68-3.73 (2H, m), 4.37-4.40 (2H, m), 6.60-6.62 (1H, m), 7.11-7.12 (1H, m), 7.23-7.29 (2H, m), 7.37-7.43 (2H, m), 8.11 (1H, s)

EXAMPLE 56

4-(4-tert-Butylbenzyl)-1-(7H-pyrrolo[2,3-d]pyrimidin-4-yl)piperidin-4-ylamine

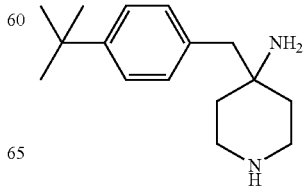

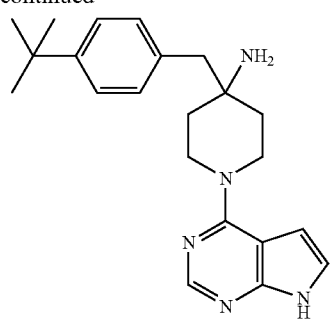

The title compound was prepared as described in Example 53. LC-MS (LCT2) m/z 364 [M+H⁺], R_t 4.24 min.

¹H NMR (MeOD) δ 1.32 (9H, s), 1.55-1.58 (2H, m), 1.75-1.81 (2H, m), 2.78 (2H, s), 3.79-3.85 (2H, m), 4.24-4.29 (2H, m), 6.63 (1H, d, J=4 Hz), 7.13 (1H, d, J=4 Hz), 7.37 (2H, d, J=8 Hz), 7.37 (2H, d, J=8 Hz), 8.12 (1H, s)

EXAMPLE 57

4-(3-Methoxybenzyl)-1-(7H-pyrrolo[2,3-d]pyrimidin-4-yl)piperidin-4-ylamine

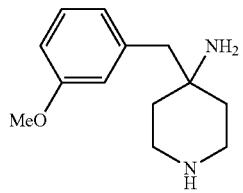

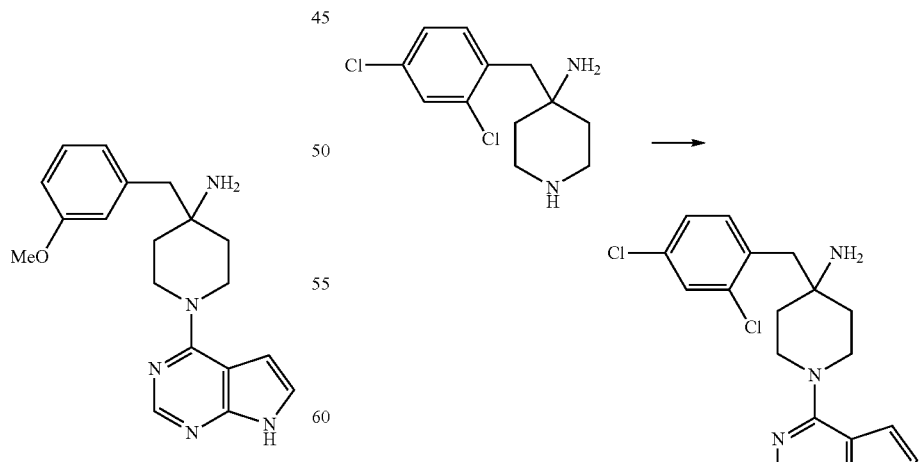

The title compound was prepared as described in Example 53. LC-MS (LCT2) m/z 338 [M+H⁺], R_t 2.61 min.

¹H NMR (MeOD) δ 1.53-1.55 (2H, m), 1.72-1.77 (2H, m), 2.73 (2H, s), 3.75-3.79 (2H, m), 3.78 (3H, s), 4.23-4.26 (2H, m), 6.58-6.59 (1H, m), 6.80-6.82 (3H, m), 7.09-7.10 (1H, m), 7.20-7.21 (1H, m), 8.12 (1H, s)

EXAMPLE 58

4-(3-Trifluoromethoxybenzyl)-1-(7H-pyrrolo[2,3-d]pyrimidin-4-yl)piperidin-4-ylamine

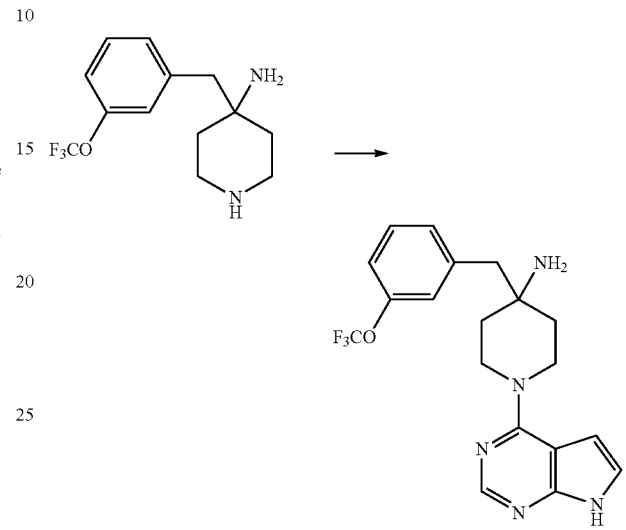

The title compound was prepared as described in Example 53. LC-MS (LCT2) m/z 392 [M+H⁺], R_t 3.47 min.

¹H NMR (MeOD) δ 1.40-1.43 (2H, m), 1.59-1.65 (2H, m), 2.68 (2H, s), 3.60-3.64 (2H, m), 4.16-4.18 (2H, m), 6.47 (1H, d, J=3.5 Hz), 6.98 (1H, d, J=3.5 Hz), 7.03-7.12 (2H, m), 7.26-7.29 (1H, m), 8.01 (1H, s)

EXAMPLE 59

4-(2,4-Dichlorobenzyl)-1-(7H-pyrrolo[2,3-d]pyrimidin-4-yl)piperidin-4-ylamine

The title compound was prepared as described in Example 53. LC-MS (LCT2) m/z 376 [M+H⁺], R_t 3.53 min.

¹H NMR (MeOD) δ 1.59-1.62 (2H, m), 1.79-1.84 (2H, m), 2.98 (2H, s), 3.67-3.72 (2H, m), 4.38-4.41 (2H, m), 6.62-6.63 (1H, m), 7.11-7.13 (1H, m), 7.30-7.48 (3H, m), 8.11 (1H, s)

EXAMPLE 60

4-(2-Chloro-4-fluorobenzyl)-1-(7H-Pyrrolo[2,3-d]pyrimidin-4-yl)piperidin-4-ylamine

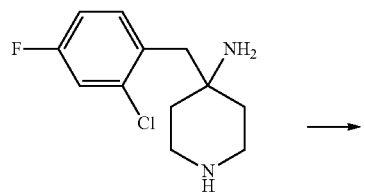

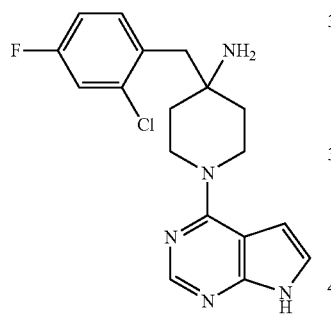

The title compound was prepared as described in Example 53. LC-MS (LCT2) m/z 360 [M+H⁺], R_t 2.98 min.

¹H NMR (MeOD) δ 1.56-1.59 (2H, m), 1.76-1.81 (2H, m), 2.92 (2H, s), 3.64-3.68 (2H, m), 4.36-4.38 (2H, m), 6.58-6.59 (1H, m), 7.01-7.05 (1H, m), 7.09-7.10 (1H, m), 7.19-7.21 (1H, m), 7.35-7.38 (1H, m), 8.11 (1H, s)

EXAMPLE 61

4-(2,6-Dichlorobenzyl)-1-(7H-pyrrolo[2,3-d]pyrimidin-4-yl)piperidin-4-ylamine

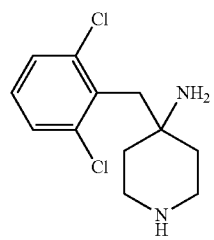

-continued

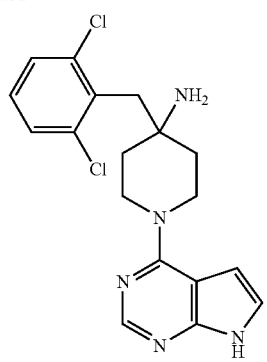

The title compound was prepared as described in Example 53. LC-MS (LCT2) m/z 376 [M+H⁺], R_t 3.11 min.

¹H NMR (MeOD) δ 1.70-1.73 (2H, m), 1.86-1.90 (2H, m), 3.24 (2H, s), 3.59-3.64 (2H, m), 4.41-4.44 (2H, m), 6.58-6.59 (1H, m), 7.08-7.09 (1H, m), 7.17-7.20 (1H, m), 7.38-7.40 (2H, m), 8.09 (1H, s)

EXAMPLE 62

[4-(4-Chlorobenzyl)-1-(7H-pyrrolo[2,3-d]pyrimidin-4-yl)piperidin-4-yl]methylamine

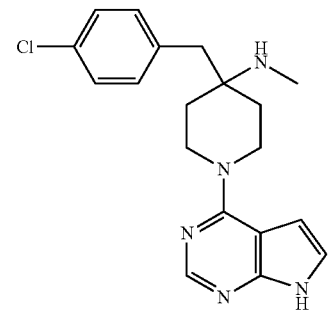

62A 4-(4-Chlorobenzyl)-4-(2-methylpropane-2-sulfinylamino)piperidine-1-carboxylic acid tert-butyl ester The title compound was prepared as described in Example 53. LC-MS (LCT2) m/z 451 [M+Na$^+$], R$_t$ 8.39 min.

62B 4-(4-Chlorobenzyl)-4-[methyl(2-methylpropane-2-sulfinyl)amino]piperidine-1-carboxylic acid tert-butyl ester To a solution of 4-(4-chlorobenzyl)-4-(2-methylpropane-2-sulfinylamino)-piperidine-1-carboxylic acid tert-butyl ester (205 mg, 0.478 mmol) in DMF (4.8 mL) at 0° C. was added sodium hydride (25 mg of a 60% dispersion in mineral oil, 0.621 mmol). After 15 min methyl iodide (33 □l, 0.526 mmol) was added, and the solution warmed to rt. After 12 h, sodium hydride (120 mg, 60% dispersion in mineral oil, 3.00 mmol) and methyl iodide (165 □l, 2.65 mmol) were added. After 30 min water (20 mL) was added and the solution extracted with ethyl acetate (3×20 mL). Organic extracts were combined, dried over magnesium sulphate and the resulting crude product was purified by silica column chromatography, eluting with 66% ethyl acetate—hexanes, to give the title product as an oil (163 mg, 77%). LC-MS (LCT2) m/z 465 [M+Na$^+$], R$_t$ 8.41 min.

62C [4-(4-Chlorobenzyl)piperidin-4-yl]methylamine

The title compound was prepared as described in Example 53 by treatment of the product of 62B with HCl. LC-MS (LCT2) m/z 239 [M+H$^+$], R$_t$ 0.59 min.

62D [4-(4-Chlorobenzyl)-1-(7H-pyrrolo[2,3-d]pyrimidin-4-yl)piperidin-4-yl]methylamine The title compound was prepared as described in Example 53. LQ-MS (LCT2) m/z 356 [M+H$^+$], R$_t$ 2.72 min.
$^1$H NMR (MeOD) δ 1.62-1.65 (4H, m), 2.44 (3H, s), 2.82 (2H, s), 3.74-3.78 (2H, m), 4.21-4.34 (2H, m), 6.61-6.62 (1H, m), 7.10-7.12 (1H, m), 7.17-7.19 (2H, m), 7.30-7.32 (2H, m), 8.12 (1H, s)

EXAMPLE 63

1-(7H-Pyrrolo[2,3-d]pyrimidin-4-yl)-4-(2-trifluoromethoxybenzyl)piperidin-4-ylamine

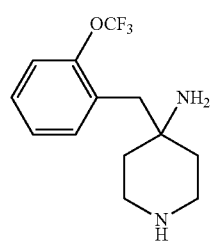

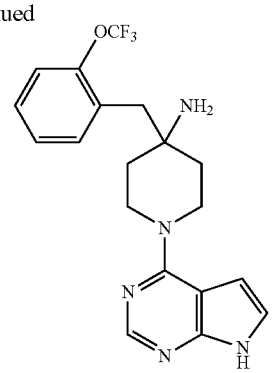

The title compound was prepared as described in Example 53. LC-MS (LCT2) m/z 392 [M+H$^+$], R$_t$ 3.31 min.
$^1$H NMR (MeOD) δ 1.57-1.59 (2H, m), 1.74-1.78 (2H, m), 2.90 (2H, s), 3.73-3.78 (2H, m), 4.30-4.34 (2H, m), 6.59-6.61 (1H, m), 7.11-7.13 (1H, m), 7.33-7.44 (4H, m), 8.12 (1H, s)

EXAMPLE 64

4-(2,5-Dichlorobenzyl)-1-(7H-pyrrolo[2,3-d]pyrimidin-4-yl)piperidin-4-ylamine

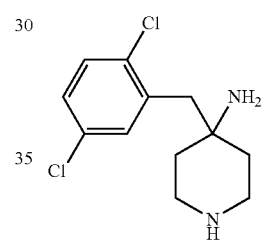

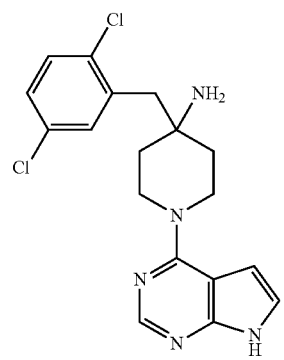

The title compound was prepared as described in Example 53. LC-MS (LCT2) m/z 376 [M+H$^+$], R$_t$ 3.34 min.
$^1$H NMR (MeOD) δ 1.59-1.61 (2H, m), 1.79-1.84 (2H, m), 3.64 (2H, s), 3.64-3.69 (2H, m), 4.38-4.41 (2H, m), 6.59-6.60

(1H, m), 7.10-7.12 (1H, m), 7.21-7.25 (1H, m), 7.30-7.32 (1H, m), 7.41-7.43 (1H, m), 8.12 (1H, s)

EXAMPLE 65

4-(2,3-Dichlorobenzyl)-1-(7H-pyrrolo[2,3-d]pyrimidin-4-yl)piperidin-4-ylamine

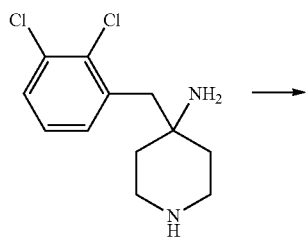

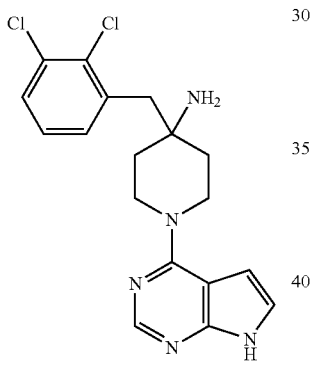

The title compound was prepared as described in Example 53. LC-MS (LCT2) m/z 376 [M+H$^+$], R$_t$ 3.16 min.

$^1$H NMR (MeOD) δ 1.58-1.61 (2H, m), 1.79-1.84 (2H, m), 2.95 (2H, s), 3.64-3.69 (2H, m), 4.38-4.41 (2H, m), 6.59-6.60 (1H, m), 7.10-7.11 (1H, m), 7.21-7.25 (1H, m), 7.36-7.43 (2H, m), 8.11 (1H, s)

EXAMPLE 66

4-(4-tert-Butylbenzyl)-1-(1H-pyrrolo[2,3-b]pyridin-4-yl)-piperidin-4-ylamine

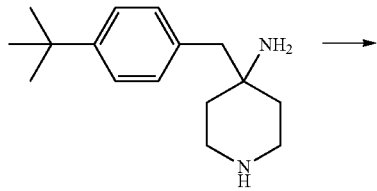

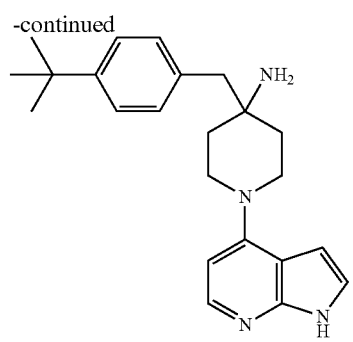

The title compound was prepared in a similar manner to Example 54. LC-MS (LCT2) m/z 363 [M+H$^+$], R$_t$ 3.19 min.

$^1$H NMR (MeOD) δ 1.33 (9H, s), 1.60-1.65 (2H, m), 1.85-1.92 (2H, m), 2.81 (2H, s), 3.48-3.52 (2H, m), 3.70-3.78 (2H, s), 6.52-6.52 (2H, m), 7.17-7.21 (3H, m), 7.38-7.40 (2H, m), 7.90-7.91 (1H, m)

EXAMPLE 67

4-(2,4-Dichlorobenzyl)-1-(1H-pyrrolo[2,3-b]pyridin-4-yl)-piperidin-4-ylamine

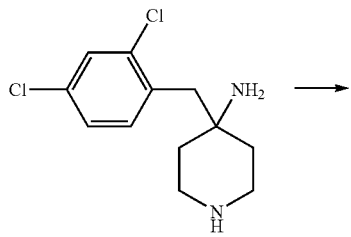

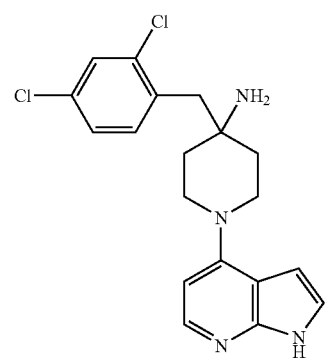

The title compound was prepared in a similar manner to Example 54. LC-MS (LCT2) m/z 375, 377, 379 [M+H$^+$], R$_t$ 2.80 min.

$^1$H NMR (MeOD) δ 1.52-1.55 (2H, m), 1.81-1.86 (2H, m), 2.90 (2H, s), 3.31-3.35 (2H, m), 3.68-3.70 (2H, m), 6.38-6.39

(2H, m), 7.06 (1H, d, J=4), 7.21 (1H, dd, J=8, 2 Hz), 7.29 (1H, d, J=8 Hz), 7.38 (1H, d, J=2), 7.80 (1H, d, J=6 Hz)

EXAMPLE 68

C-[4-(4-Chlorophenyl)-1-(1H-pyrrolo[2,3-b]pyridin-4-yl)-piperidin-4-yl]-methylamine

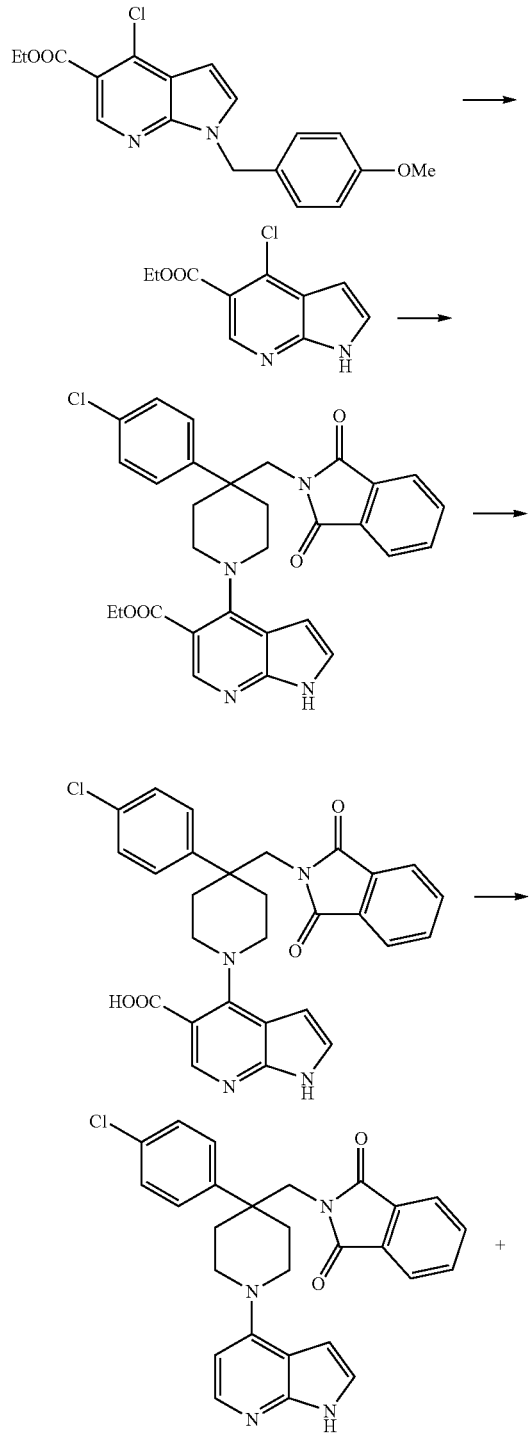

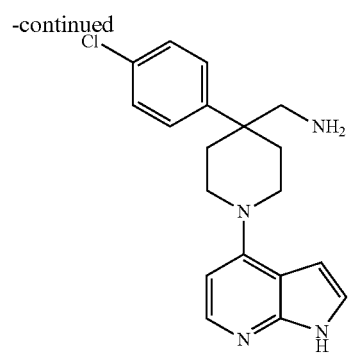

68A.
4-Chloro-1H-pyrrolo[2,3-b]pyridine-5-carboxylic acid ethyl ester

To a solution of 4-chloro-1-(4-methoxybenzyl)-1H-pyrrolo[2,3-b]pyridine-5-carboxylic acid ethyl ester (prepared as described in J. Heterocycl. Chem. 1972, 235 and Bioorg. Med. Chem. Lett. 2003, 2405) (3.48 g, 10 mmol) in TFA (20 mL), conc. $H_2SO_4$ (1.5 mL) and anisole (3 mL) were added at room temperature. The resulting solution was stirred at this temperature for 3 hours and then basified slowly by addition of ice-cold aqueous $NaHCO_3$. The aqueous solution was extracted with ethyl acetate and the combined organic layers were dried ($Na_2SO_4$) and concentrated. The residue was filtered and washed with n-hexanes to give a yellow solid (1.04 g, 46%). LC-MS (LCT2) m/z 226 [M+H$^+$], $R_t$ 6.22 min.

68B 4-[4-(4-Chlorophenyl)-4-(1,3-dioxo-1,3-dihydroisoindol-2-ylmethyl)-piperidin-1-yl]-1H-Pyrrolo[2,3-b]pyridine-5-carboxylic acid ethyl ester A mixture of 4-chloro-1H-pyrrolo[2,3-b]pyridine-5-carboxylic acid ethyl ester (34 mg, 0.15 mmol), and 2-[4-(4-chlorophenyl)-piperidin-4-ylmethyl]-isoindole-1,3-dione (prepared by treatment of C-[4-(4-chlorophenyl)piperidin-4-yl]methylamine hydrochloride, Example 14, Step C with phthalic anhydride in acetic acid at 120° C.) (54 mg, 0.15 mmol) and triethylamine (0.1 mL) in n-butanol (2 mL) was irradiated in a microwave reactor (300W) for 1 hr at 120° C. with simultaneous air-cooling. The resulting solids were broken up, washed with methanol, filtered and dried to give a cream-coloured solid (49 mg, 60%). LC-MS (LCT2) m/z 544 [M+H$^+$], $R_t$ 7.83 min.

68C. 4-[4-(4-Chlorophenyl)-4-(1,3-dioxo-1,3-dihydroisoindol-2-ylmethyl)-piperidin-1-yl]-1H-Pyrrolo[2,3-b]pyridine-5-carboxylic acid 4-[4-(4-Chlorophenyl)-4-(1,3-dioxo-1,3-dihydroisoindol-2-ylmethyl)-piperidin-1-yl]-1H-pyrrolo[2,3-b]pyridine-5-carboxylic acid ethyl ester (49 mg, 0.09 mmol) was hydrolysed in a mixture of 2M NaOH (1 mL) and 1,4-dioxane (1 mL) at 80° C. overnight. The solution was acidified by dropwise addition of conc. HCl. Solvents were evaporated and the resulting solid was filtered and washed with water, then dried. A white solid (45 mg) was obtained which was used in the next step without further purification.

68D. C-[4-(4-Chloro-phenyl)-1-(1H-pyrrolo[2,3-b]pyridin-4-yl)-piperidin-4-yl]-methylamine A mixture of crude 4-[4-(4-chlorophenyl)-4-(1,3-dioxo-1,3-dihydroisoindol-2-ylmethyl)-piperidin-1-yl]-1H-pyrrolo

[2,3-b]pyridine-5-carboxylic acid (12.8 mg, 0.025 mmol) and water (1 mL) was irradiated in a microwave reactor (250W) for 2 hrs at 180° C. The resulting suspension was filtered and the filtrate was concentrated. Preparative TLC gave the product (4 mg, 47%). LC-MS (LCT2) m/z 342 [M+H$^+$], R$_t$ 2.19 min.

$^1$H NMR (MeOD) δ 2.00 (2H, m), 2.42 (2H, m), 2.85 (2H, s), 3.40 (2H, m), 4.00 (2H, m), 6.45 (1H, d, J=5.8 Hz), 7.50 (4H, m), 8.06 (1H, d, J=5.8 Hz), 8.2 (1H, s)

EXAMPLE 69

4-Amino-1-(7H-pyrrolo[2,3-d]pyrimidin-4-yl)-piperidine-4-carboxylic acid 4-chloro-benzylamide

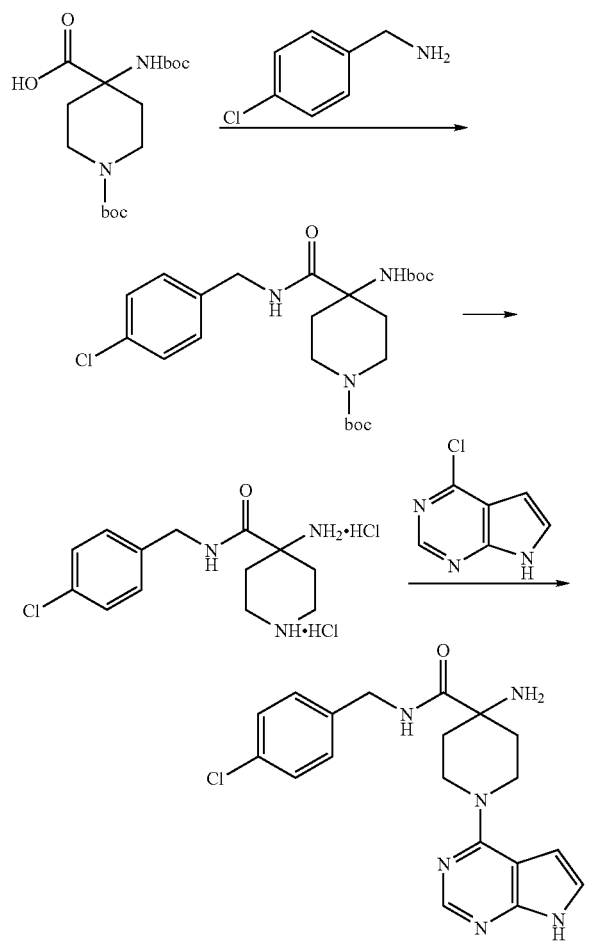

69A. 4-tert-Butoxycarbonylamino-4-(4-chloro-benzylcarbamoyl)-piperidine-1-carboxylic acid tert-butyl ester Dry DMF (1 mL) was added to a mixture of 4-tert-butoxycarbonylamino-piperidine-1,4-dicarboxylic acid mono tert-butyl ester (151 mg, 0.44 mmol) and HATU (220 mg, 0.58 mmol) under nitrogen. N-Ethyldiisopropylamine (0.38 mL, 2.1 mmol) was added to the solution and the reaction mixture was stirred for 15 min. 4-Chlorobenzylamine (70 uL, 0.57 mmol) was added and the solution was stirred for 23 h at rt and under nitrogen. The reaction mixture was partioned between dichloromethane (10 mL) and water (10 mL). The aqueous phase was further extracted with dichloromethane (20 mL). The combined organic layers were dried (Mg$_2$SO$_4$), filtered and concentrated. Flash column chromatography on silica, eluting with 4% methanol in dichloromethane, gave 4-tert-butoxycarbonylamino-4-(4-chloro-benzylcarbamoyl)-piperidine-1-carboxylic acid tert-butyl ester (177 mg, 0.38 mmol, 86%). LC-MS (LCT2) m/z 490 [M+Na$^+$], R$_t$ 8.09 min.

69B. 4-Amino-piperidine-4-carboxylic acid 4-chloro-benzylamide dihydrochloride A 4M solution of HCl in dioxane (7.7 ml, 31 mmol) was added dropwise to a solution of 4-tert-butoxycarbonylamino-4-(4-chloro-benzylcarbamoyl)-piperidine-1-carboxylic acid tert-butyl ester (96 mg, 0.20 mmol) in methanol (7.7 mL) and stirred at rt for 17 h. The solvents were concentrated to give 4-amino-piperidine-4-carboxylic acid 4-chloro-benzylamide dihydrochloride (71 mg, 0.20 mmol, 100%) that was used in the next step without further purification.

$^1$H NMR (500 MHz, CD$_3$OD): 2.18 (2H, m), 2.64 (2H, m), 3.44 (4H, m), 4.47 (2H, s), 7.36 (4H, m).

69C. 4-Amino-1-(7H-pyrrolo[2,3-d]pyrimidin-4-yl)-piperidine-4-carboxylic acid 4-chloro-benzylamide A degassed mixture of 4-amino-piperidine-4-carboxylic acid 4-chloro-benzylamide dihydrochloride (48 mg, 0.13 mmol), 4-chloro-7H-pyrrolo[2,3-d]pyrimidine (21 mg, 0.12 mmol), triethylamine (126 uL, 0.9 mmol) and n-butanol (1.2 mL) was stirred at 100° C. for 18 h. The solvents were removed by evaporation and the crude mixture was first purified on a SCX-II acid resin, eluting with methanol then 2M ammonia/methanol, and then by preparative TLC, eluting with 10% methanol in dichloromethane, to give 4-amino-1-(7H-pyrrolo[2,3-d]pyrimidin-4-yl)-piperidine-4-carboxylic acid 4-chloro-benzylamide (37 mg, 0.096 mmol, 80%). LC-MS (LCT2) m/z 385 [M+H$^+$], R$_t$ 2.84 min.

$^1$H NMR (MeOD) δ 1.60-1.62 (2H, m), 2.19-2.25 (2H, m), 3.65-3.71 (2H, m), 4.38 (2H, s), 4.47-4.50 (2H, m), 6.65 (1H, d, J=4 Hz), 7.14 (1H, d, J=4 Hz), 7.27-7.33 (4H, m), 8.14 (1H, s)

EXAMPLE 70

4-Amino-1-(7H-pyrrolo[2,3-d]pyrimidin-4-yl)-piperidine-4-carboxylic acid 3-chloro-benzylamide

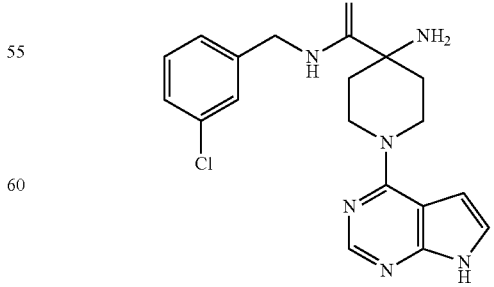

The title compound was prepared as described for Example 69. LC-MS (LCT2) m/z 385 [M+H$^+$], R$_t$ 2.94 min.

¹H NMR (MeOD) δ 1.60-1.63 (2H, m), 2.20-2.25 (2H, m), 3.65-3.71 (2H, m), 4.39 (2H, s), 4.48-4.51 (2H, m), 6.65 (1H, d, J=4 Hz), 7.14 (1H, d, J=4 Hz), 7.22-7.32 (4H, m), 8.14 (1H, s)

EXAMPLE 71

4-Amino-1-(7H-pyrrolo[2,3-d]pyrimidin-4-yl)-piperidine-4-carboxylic acid 4-trifluoromethyl-benzylamide

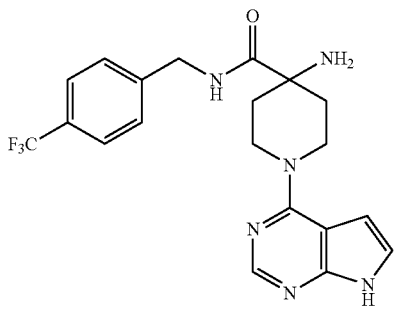 [SMILES: NC1(C(=O)NCc2ccc(C(F)(F)F)cc2)CCN(c2ncnc3[nH]ccc23)CC1]

The title compound was prepared as described for Example 69. LC-MS (LCT2) m/z 419 [M+H⁺], R$_t$ 3.26 min.

¹H NMR (MeOD) δ 1.62-1.64 (2H, m), 2.20-2.26 (2H, m), 3.65-3.71 (2H, m), 4.48-4.51 (4H, m), 6.65 (1H, d, J=4 Hz), 7.14 (1H, d, J=4 Hz), 7.49 (2H, d, J=8 Hz), 7.63 (2H, d, J=8 Hz), 8.14 (1H, s)

EXAMPLE 72

4-Amino-1-(7H-pyrrolo[2,3-d]pyrimidin-4-yl)-piperidine-4-carboxylic acid 4-fluoro-benzylamide

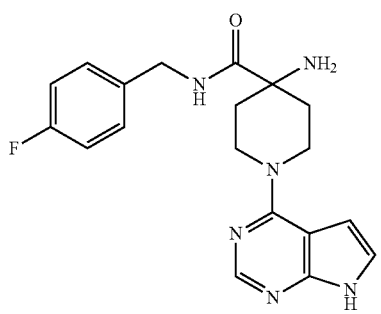 [SMILES: NC1(C(=O)NCc2ccc(F)cc2)CCN(c2ncnc3[nH]ccc23)CC1]

The title compound was prepared as described for Example 69. LC-MS (LCT2) m/z 369 [M+H⁺], R$_t$ 2.43 min.

¹H NMR (MeOD) δ 1.59-1.62 (2H, m), 2.19-2.25 (2H, m), 3.65-3.70 (2H, m), 4.38 (2H, s), 4.47-4.50 (2H, m), 6.65 (1H, d, J=4 Hz), 7.05 (2H, dd, J=8.5 Hz), 7.14 (1H, d, J=4 Hz), 7.30-7.33 (2H, m), 8.14 (1H, s)

EXAMPLE 73

4-Amino-1-(7H-pyrrolo[2,3-d]pyrimidin-4-yl)-piperidine-4-carboxylic acid 2-chloro-benzylamide

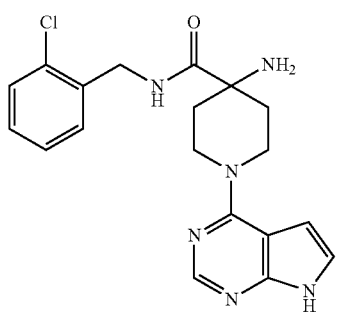 [SMILES: NC1(C(=O)NCc2ccccc2Cl)CCN(c2ncnc3[nH]ccc23)CC1]

The title compound was prepared as described for Example 69. LC-MS (LCT2) m/z 385 [M+H⁺], R$_t$ 2.77 min.

¹H NMR (MeOD) δ 1.61-1.64 (2H, m), 2.21-2.26 (2H, m), 3.66-3.71 (2H, m), 4.49-4.50 (4H, m), 6.65 (1H, d, J=4 Hz), 7.14 (1H, d, J=4 Hz), 7.27-7.41 (4H, m), 8.14 (1H, s)

EXAMPLE 74

4-Amino-1-(7H-pyrrolo[2,3-d]pyrimidin-4-yl)-piperidine-4-carboxylic acid 4-trifluoromethoxy-benzylamide

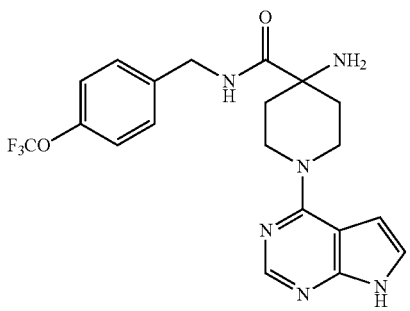 [SMILES: NC1(C(=O)NCc2ccc(OC(F)(F)F)cc2)CCN(c2ncnc3[nH]ccc23)CC1]

The title compound was prepared as described for Example 69. LC-MS (LCT2) m/z 435 [M+H⁺], R$_t$ 3.55 min.

$^1$H NMR (MeOD) δ 1.61-1.63 (2H, m), 2.20-2.25 (2H, m), 3.66-3.71 (2H, m), 4.42 (2H, s), 4.48-4.51 (2H, m), 6.65 (1H, d, J=4 Hz), 7.14 (1H, d, J=4 Hz), 7.24 (2H, d, J=7 Hz), 7.40 (2H, d, J=7 Hz), 8.14 (1H, s)

EXAMPLE 75

4-Amino-1-(7H-pyrrolo[2,3-d]pyrimidin-4-yl)-piperidine-4-carboxylic acid (4-chloro-benzyl)-methyl-amide

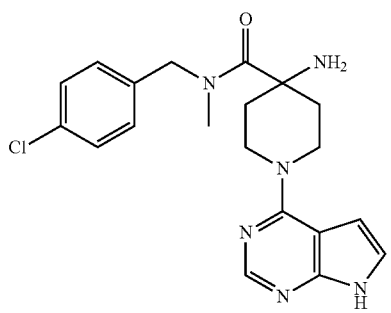 [SMILES: CN(Cc1ccc(Cl)cc1)C(=O)C1(N)CCN(c2ncnc3[nH]ccc23)CC1]

The title compound was prepared as described for Example 69. LC-MS (LCT2) m/z 399 [M+H$^+$], R$_t$ 3.13 min.

$^1$H NMR (MeOD) δ 1.76-1.78 (2H, m), 2.33-2.37 (2H, m), 3.18 (3H, brs), 4.02-4.11 (4H, m), 4.95 (2H, s), 6.62-6.64 (1H, m), 7.10-7.13 (1H, m), 7.22-7.26 (2H, m), 7.32-7.36 (2H, m), 8.13 (1H, s)

EXAMPLE 76

4-Amino-1-(7H-pyrrolo[2,3-d]pyrimidin-4-yl)-piperidine-4-carboxylic acid 4-tert-butyl-benzylamide

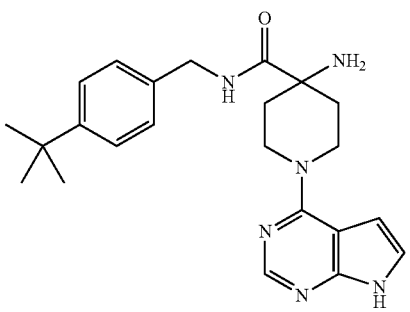 [SMILES: CC(C)(C)c1ccc(CNC(=O)C2(N)CCN(c3ncnc4[nH]ccc34)CC2)cc1]

The title compound was prepared as described for Example 69. LC-MS (LCT2) m/z 407 [M+H$^+$], R$_t$ 4.28 min.

$^1$H NMR (MeOD) δ 1.31 (9H, s), 1.56-1.63 (2H, m), 2.18-2.25 (2H, m), 3.60-3.70 (2H, m), 4.37 (2H, s), 4.40-4.50 (2H, m), 6.65 (1H, d, J=4 Hz), 7.14 (1H, d, J=4 Hz), 7.24 (2H, d, J=8 Hz), 7.36 (2H, d, J=8 Hz), 8.14 (1H, s)

EXAMPLE 77

4-Amino-1-(7H-pyrrolo[2,3-d]pyrimidin-4-yl)-piperidine-4-carboxylic acid 2,4-dichloro-benzylamide

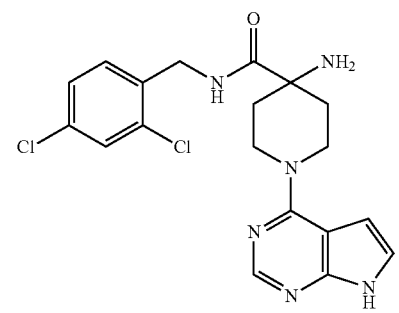 [SMILES: NC1(C(=O)NCc2ccc(Cl)cc2Cl)CCN(c2ncnc3[nH]ccc23)CC1]

The title compound was prepared as described for Example 69. LC-MS (LCT2) m/z 419 [M+H$^+$], R$_t$ 3.69 min.

$^1$H NMR (MeOD) δ 1.62-1.64 (2H, m), 2.17-2.25 (2H, m), 3.65-3.71 (2H, m), 4.47-4.51 (4H, m), 6.65 (1H, d, J=4 Hz), 7.14 (1H, d, J=4 Hz), 7.31-7.33 (2H, m), 7.47-7.47 (1H, d, J=1.5 Hz), 8.14 (1H, s)

EXAMPLE 78

4-Amino-1-(7H-pyrrolo[2,3-d]pyrimidin-4-yl)-piperidine-4-carboxylic acid 3,4-dichloro-benzylamide

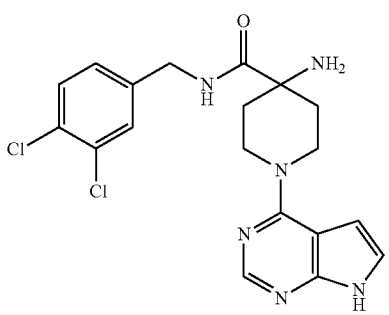 [SMILES: NC1(C(=O)NCc2ccc(Cl)c(Cl)c2)CCN(c2ncnc3[nH]ccc23)CC1]

The title compound was prepared as described for Example 69. LC-MS (LCT2) m/z 419 [M+H$^+$], R$_t$ 3.65 min.

¹H NMR (MeOD) δ 1.60-1.62 (2H, m), 2.18-2.24 (2H, m), 3.65-3.70 (2H, m), 4.37 (2H, s), 4.48-4.50 (2H, m), 6.64 (1H, d, J=4 Hz), 7.13 (1H, d, J=4 Hz), 7.22-7.24 (1H, m), 7.46-7.48 (2H, m), 8.14 (1H, s)

EXAMPLE 79

4-(4-Chloro-benzyloxymethyl)-1-(7H-pyrrolo[2,3-d]pyrimidin-4-yl)-piperidin-4-ylamine

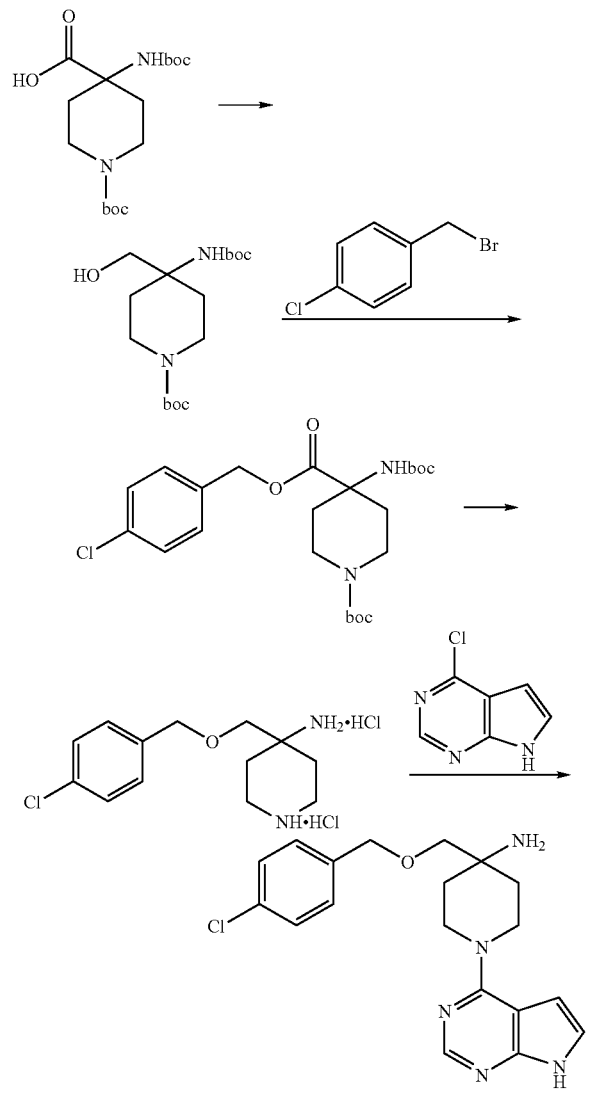

79A. 4-tert-Butoxycarbonylamino-4-hydroxymethyl-piperidine-1-carboxylic acid tert-butyl ester A 1M solution of lithium aluminum hydride in tetrahydrofuran (1.66 mL, 1.66 mmol) was added dropwise to a cooled (0° C.) solution of 4-tert-butoxycarbonylamino-piperidine-1,4-dicarboxylic acid mono-tert-butyl ester (400 mg, 1.1 mmol) in dry tetrahydrofuran (5 mL). The solution was stirred for 3 h at rt under nitrogen. Water (172 μL) and 10% sodium hydroxide aq (232 μL) were added and the mixture was stirred for 2 h. Further water (172 μL) was added and the mixture was filtered through a pad of celite and washed with diethyl ether. The crude product was purified by flash column chromatography on silica, eluting with 10% methanol in dichloromethane, to give 4-tert-butoxycarbonylamino-4-hydroxymethyl-piperidine-1-carboxylic acid tert-butyl ester (178 mg, 0.54 mmol, 49%). LC-MS (LCT2) m/z 353 [M+Na⁺], $R_t$ 6.67 min.

79B. 4-tert-Butoxycarbonylamino-4-(4-chloro-benzyloxymethyl)-piperidine-1-carboxylic acid tert-butyl ester Sodium hydride (60% suspension in oil, 4.9 mg, 0.11 mmol) was added in small portions to a cooled (0° C.) solution of 4-tert-butoxycarbonylamino-4-hydroxymethyl-piperidine-1-carboxylic acid tert-butyl ester (19 mg, 0.057 mmol) in dry DMF (0.2 mL). The suspension was stirred vigorously at 0° C. for 15 min followed by addition of 4-chlorobenzyl bromide (14 mg, 0.066 mmol). After stirring for 45 min at 0° C., the reaction mixture was warmed to rt. When TLC showed complete consumption of the starting material, the reaction mixture was partioned between ethyl acetate (5 mL) and water (2 mL). The aqueous phase was further extracted with ethyl acetate (5 mL). The combined organic layers were dried (Mg₂SO₄), filtered and concentrated. Flash column chromatography on silica, eluting with 1% methanol in dichloromethane, gave 4-tert-butoxycarbonylamino-4-(4-chloro-benzyloxymethyl)-piperidine-1-carboxylic acid tert-butyl ester (6 mg, 0.013 mmol, 22%). LC-MS (LCT2) m/z 477 [M+Na⁺], $R_t$ 8.74 min.

79C. 4-(4-Chloro-benzyloxymethyl)-piperidin-4-ylamine dihydrochloride

A 4M solution of HCl in dioxane (0.68 ml, 2.7 mmol) was added dropwise to a solution of 4-tert-butoxycarbonylamino-4-(4-chloro-benzyloxymethyl)-piperidine-1-carboxylic acid tert-butyl ester (12 mg, 0.028 mmol) in methanol (1 mL). The solution was stirred at rt for 17 h. The solvents were removed by evaporation to give 4-(4-chloro-benzyloxymethyl)-piperidin-4-ylamine dihydrochloride (9.2 mg, 0.028 mmol, 100%) that was used in the next step without further purification.

¹H NMR (500 MHz, CD₃OD): 2.12-2.24 (4H, m), 3.22-3.32 (2H, m), 3.42-3.45 (2H, m), 3.75 (2H, s), 4.66 (2H, s), 7.38-7.43 (4H, m).

79D. 4-(4-Chloro-benzyloxymethyl)-1-(7H-pyrrolo[2,3-d]pyrimidin-4-yl)-piperidin-4-ylamine A degassed mixture of 4-(4-chloro-benzyloxymethyl)-piperidin-4-ylamine dihydrochloride (9.2 mg, 0.028 mmol), 4-chloro-7H-pyrrolo[2,3-d]pyrimidine (5.9 mg, 0.035 mmol), triethylamine (36 uL, 0.2 mmol) and n-butanol (0.35 mL) was stirred at 100° C. for 17 h. The solvents were removed by evaporation. The crude mixture was purified on an SCX-II acid resin, eluting with methanol then 2M ammonia/methanol, and then by preparative TLC eluting with 10% methanol in dichloromethane, to give 4-(4-chloro-benzyloxymethyl)-1-(7H-pyrrolo[2,3-d]pyrimidin-4-yl)-piperidin-4-ylamine (8.2 mg, 0.022 mmol, 78%). LC-MS (LCT2) m/z 372 [M+H⁺], $R_t$ 3.19 min.

¹H NMR (MeOD) δ 1.66-1.70 (2H, m), 1.86-1.88 (2H, m), 3.47 (2H, s), 3.95-3.98 (2H, m), 4.03-4.06 (2H, m), 4.57 (2H, s), 6.62 (1H, d, J=4 Hz), 7.13 (1H, d, J=4 Hz), 7.34-7.37 (4H, m), 8.14 (1H, s)

EXAMPLE 80

4-Amino-1-(7H-pyrrolo[2,3-d]pyrimidin-4-yl)-piperidine-4-carboxylic acid 2,4-difluoro-benzylamide

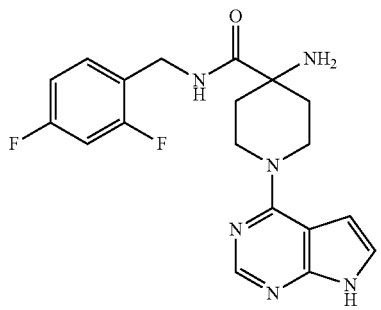 [SMILES: NC1(C(=O)NCc2ccc(F)cc2F)CCN(c2ncnc3[nH]ccc23)CC1]

The title compound was prepared as described for Example 69. LC-MS (LCT2) m/z 387 [M+H⁺], R_t 2.46 min.

¹H NMR (MeOD) δ 1.59-1.61 (2H, m), 2.18-2.24 (2H, m), 3.66-3.71 (2H, m), 4.43 (2H, s), 4.46-4.49 (2H, m), 6.63 (1H, d, J=4 Hz), 6.92-6.96 (2H, m), 7.13 (1H, d, J=4 Hz), 7.84-7.87 (1H, m), 8.14 (1H, s)

EXAMPLE 81

[4-Amino-1-(7H-pyrrolo[2,3-d]pyrimidin-4-yl)-piperidin-4-yl]-(3,4-dihydro-1H-isoquinolin-2-yl)-methanone

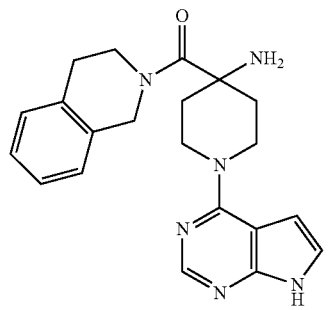 [SMILES: NC1(C(=O)N2CCc3ccccc3C2)CCN(c2ncnc3[nH]ccc23)CC1]

The title compound was prepared according to the method described in Example 69. LC-MS (LCT2) m/z 377 [M+H⁺], R_t 2.73 min.

¹H NMR (CD₃OD) δ 1.70-1.80 (2H, m), 2.25-2.35 (2H, m), 2.80-2.95 (2H, m), 4.04-4.08 (6H, m), 4.90-5.00 (2H, m), 6.63 (1H, s), 7.05-7.16 (5H, m), 8.14 (1H, s).

EXAMPLE 82

[4-Amino-1-(7H-pyrrolo[2,3-d]pyrimidin-4-yl)-piperidin-4-yl]-(2-phenyl-pyrrolidin-1-yl)-methanone

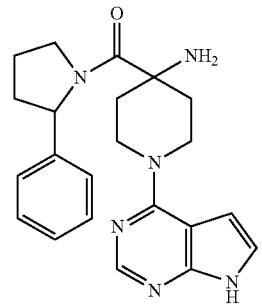 [SMILES: NC1(C(=O)N2CCCC2c2ccccc2)CCN(c2ncnc3[nH]ccc23)CC1]

The title compound was prepared according to the method described in Example 69. LC-MS (LCT2) m/z 391 [M+H⁺], R_t 2.68 min.

¹H NMR (CD₃OD) δ 1.50-2.31 (8H, m), 3.65-4.04 (5H, m), 4.20-4.40 (1H, m), 5.10-5.20 (1H, m), 6.63 (1H, s), 7.12-7.29 (6H, m), 8.11 (1H, s).

EXAMPLE 83

4-(4-Chlorobenzyl)-1-(1H-pyrazolo[3,4-b]pyridin-4-yl)-piperidin-4-ylamine

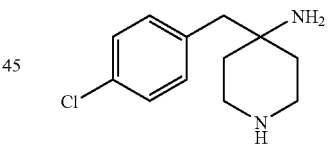

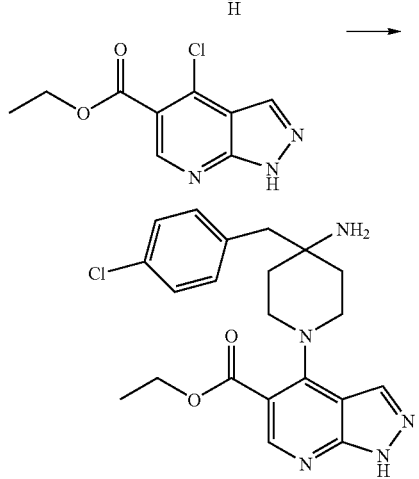

-continued

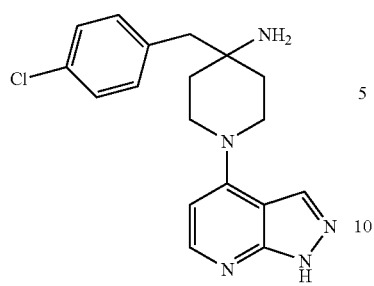

83A. 4-[4-Amino-4-(4-chlorobenzyl)-piperidin-1-yl]-1H-pyrazolo[3,4-b]Pyridine-5-carboxylic acid ethyl ester A mixture of 4-chloro-1H-pyrrolo[2,3-b]pyridine-5-carboxylic acid ethyl ester (Example 68A) (50 mg, 0.22 mmol), 4-(4-chlorobenzyl)-piperidin-4-ylamine hydrochloride (65 mg, 0.22 mmol) and triethylamine (150μ) in n-butanol (1.5 mL) was irradiated in a microwave reactor (200W) for 1 hr at 100° C. After cooling, the solvent was evaporated. The solids obtained were dissolved in ethyl acetate, the organic layer was washed with aqueous sodium hydrogen carbonate, brine and then dried ($Na_2SO_4$). Evaporation of the organic solution gave 4-[4-amino-4-(4-chlorobenzyl)-piperidin-1-yl]-1H-pyrazolo[3,4-b]pyridine-5-carboxylic acid ethyl ester as an off-white solid (80 mg, 87%). LC-MS (LCT2) m/z 415 [M+H$^+$], $R_t$ 3.99 min.

$^1$H NMR (d$_6$-DMSO) δ 1.30 (3H, t, J=7 Hz), 1.36 (2H, m), 1.68 (2H, m), 2.68 (2H, s), 3.50 (2H, m), 3.60 (2H, m), 4.25 (2H, q, J=7 Hz), 7.25 (2H, d, J=8.3 Hz), 7.35 (2H, d, J=8.3 Hz), 8.20 (1H, s), 8.40 (1H, s), 13.50 (1H, s)

83B. 4-(4-Chlorobenzyl)-1-(1H-pyrazolo[3,4-b]pyridin-4-yl)-piperidin-4-ylamine 4-[4-Amino-4-(4-chlorobenzyl)-piperidin-1-yl]-1H-pyrazolo[3,4-b]pyridine-5-carboxylic acid ethyl ester (55 mg, 0.13 mmol) was suspended in 2M potassium hydroxide (1.5 mL) and irradiated in a microwave reactor (250W) for 2 hours at 120° C. After cooling, water (2 mL) was added and the solids formed were collected by filtration. The filtrate was extracted with ethyl acetate (2×4 mL) and dried ($Na_2SO_4$). The extracts were evaporated and the resulting yellow solids were combined with the previous material and dissolved in acetone (10 mL) and n-hexanes (2 mL). The solvents were concentrated until precipitation occurred. The solids were collected by filtration and washed with n-hexanes to give 4-(4-chlorobenzyl)-1-(1H-pyrazolo[3,4-b]pyridin-4-yl)-piperidin-4-ylamine as a light yellow powder (26 mg, 57%). LC-MS (LCT2) m/z 342 [M+H$^+$], $R_t$ 2.07 min.

$^1$H NMR (d$_6$-DMSO) δ 1.38 (2H, m), 1.62 (2H, m), 2.65 (2H, s), 3.50 (2H, m), 3.85 (2H, m), 6.35 (1H, d, J=5 Hz), 7.27 (2H, d, J=8 Hz), 7.34 (2H, d, J=8 Hz), 8.02 (1H, d, J=5 Hz), 8.15 (1H, s), 13.13 (1H, s)

EXAMPLE 84

4-(4-tert-Butyl-benzyl)-1-(1H-pyrazolo[3,4-b]Pyridin-4-yl)-piperidin-4-ylamine

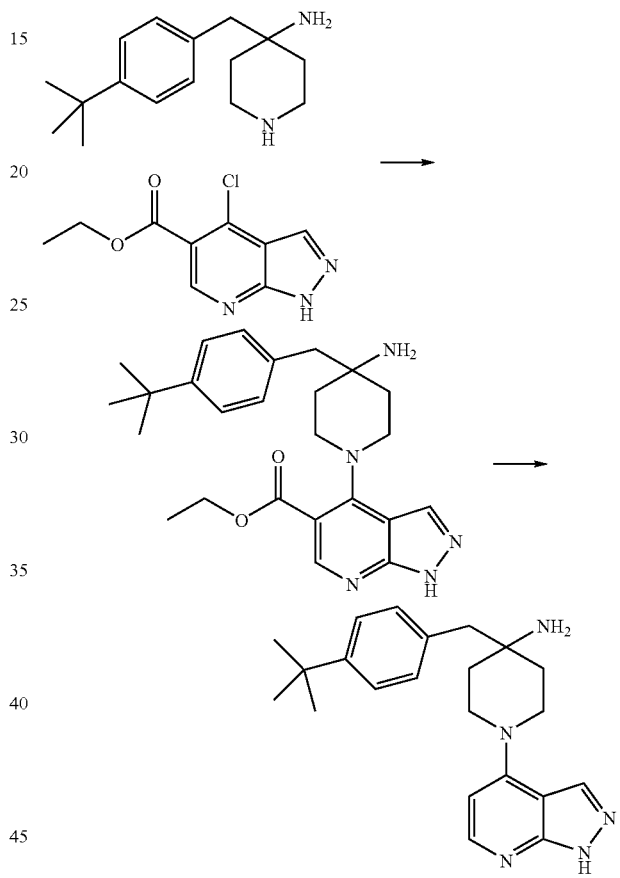

84A. 4-[4-Amino-4-(4-tert-butyl-benzyl)-piperidin-1-yl]-1H-pyrazolo[3,4-b]pyridine-5-carboxylic acid ethyl ester A mixture of 4-chloro-1H-pyrrolo[2,3-b]pyridine-5-carboxylic acid ethyl ester (Example 68A) (50 mg, 0.22 mmol), 4-(4-tert-butyl-benzyl)-piperidin-4-ylamine hydrochloride (70.8 mg, 0.22 mmol) and triethylamine (150 μL) in n-butanol (1.5 mL) was irradiated in a microwave reactor (200W) for 1 hour at 100° C. After cooling, the solvent was evaporated and the residue was purified by column chromatography (EtOAc-MeOH 4:1) to give an off-white solid (63 mg, 65%).

LC-MS (LCT2) m/z 436 [M+H$^+$], $R_t$ 5.01 min.

$^1$H NMR (d$_6$-DMSO) δ 1.38 (9H, s), 1.38 (3H, t, J=7 Hz), 1.85 (4H, m), 3.0 (2H, s), 3.62 (2H, m), 3.70 (2H, m), 4.25 (2H, q, J=7 Hz), 7.15 (2H, d, J=8.2 Hz), 7.30 (2H, d, J=8.2 Hz), 8.20 (1H, s), 8.40 (1H, s), 13.45 (1H, s)

84B. 4-(4-tert-Butyl-benzyl)-1-(1H-pyrazolo[3,4-b]pyridin-4-yl)-piperidin-4-ylamine 4-[4-Amino-4-(4-tert-butyl-benzyl)-piperidin-1-yl]-1H-pyrazolo[3,4-b]pyridine-5-carboxylic acid ethyl ester (23 mg, 0.053 mmol) was suspended in 2M potassium hydroxide (1 mL) and irradiated in a microwave reactor (250W) for 2 hours at 120° C. After cooling, water (2 mL) was added and the aqueous layer was extracted with ethyl acetate (2×4 mL). The organic layers were dried (Na$_2$SO$_4$) and concentrated to give a yellow solid (9 mg, 47%).

LC-MS (LCT2) m/z 364 [M+H$^+$], R$_t$ 2.80 min.

$^1$H NMR (CD$_3$OD) δ 1.32 (9H, s), 1.63 (2H, m), 1.86 (2H, m), 2.80 (2H, s), 3.70 (2H, m), 3.95 (2H, m), 6.46 (1H, d, J=5.8 Hz), 7.20 (2H, J=8 Hz), 7.40 (2H, J=8 Hz), 8.08 (1H, d, J=5.8 Hz), 8.20 (1H, s)

EXAMPLE 85

4-(4-tert-Butyl-benzyl)-1-(1H-pyrrolo[2,3-b]pyridin-4-yl)-piperidin-4-ylamine

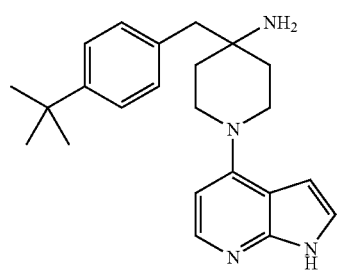 [SMILES: CC(C)(C)c1ccc(CC2(N)CCN(c3ccnc4[nH]ccc34)CC2)cc1]

The title compound was prepared as described for Example 54. LC-MS (LCT2) m/z 363 [M+H$^+$], R$_t$ 3.19 min.

$^1$H NMR (CD$_3$OD) δ 1.33 (9H, s), 1.60-1.65 (2H, m), 1.85-1.90 (2H, m), 2.81 (2H, s), 3.48-3.52 (2H, m), 3.72-3.78 (2H, m), 6.50-6.52 (2H, m), 7.17-7.21 (3H, m), 7.39 (2H, d, J=8 Hz), 7.92 (1H, d, J=5 Hz)

EXAMPLE 86

N-[4-Amino-1-(7H-pyrrolo[2,3-d]pyrimidin-4-yl)-piperidin-4-ylmethyl]-4-chloro-benzamide

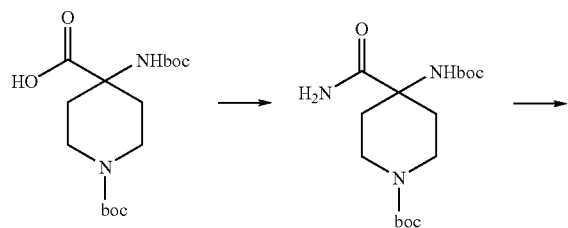

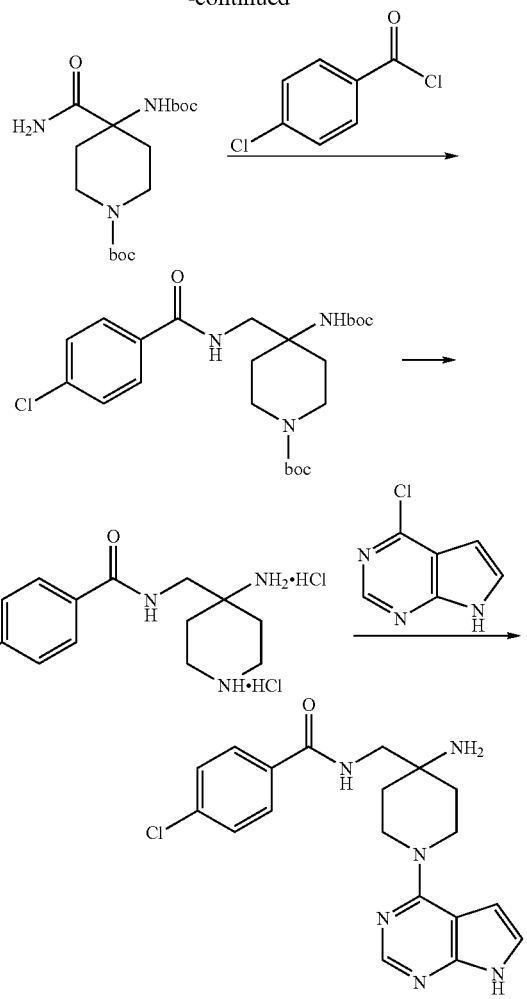

86A. 4-tert-Butoxycarbonylamino-4-carbamoyl-piperidine-1-carboxylic acid tert-butyl ester 1-Hydroxybenzotriazole hydrate (150 mg, 1.1 mmol) and 1-(3-dimethylaminopropyl)-3-ethyl-carbodiimide hydrochloride (214 mg, 1.1 mmol) were added to a stirred solution of 4-tert-butoxycarbonylamino-piperidine-1,4-dicarboxylic acid mono-tert-butyl ester (149 mg, 0.44 mmol) in DMF (9 mL). The reaction mixture was stirred for 80 minutes, and ammonium hydroxide (1.2 mL, ammonia sol. aq.) was added. After stirring for a further 20 hours at room temperature, brine (18 mL) and water (3 mL) were added to the reaction mixture. The aqueous phase was extracted with ethyl acetate (2×12 mL) and the combined organic phases were dried (Mg$_2$SO$_4$), filtered and concentrated to give 4-tert-butoxycarbonylamino-4-carbamoyl-piperidine-1-carboxylic acid tert-butyl ester (147 mg, 0.43 mmol, 97%). LC-MS (LCT2) m/z 366 [M+Na$^+$], R$_t$ 6.63 min.

86B. 4-Aminomethyl-4-tert-butoxycarbonylamino-piperidine-1-carboxylic acid tert-butyl ester A 1M solution of borane complex in THF (2.25mL, 2.25 mmol) was added to a cooled solution (0° C.) of 4-tert-butoxycarbonylamino-4-carbamoyl-piperidine-1-carboxylic acid tert-butyl ester (107 mg, 0.3 mmol) in THF (4.3 mL).

After stirring for 5 minutes at 0° C. the reaction mixture was allowed to warm to room temperature. The reaction mixture was further warmed to 60° C. and stirred overnight. The reaction mixture was cooled to room temperature and methanol (5.1 mL) was added. After stirring for 30 minutes, the solvents were removed by evaporation. The reaction mixture was partitioned between an aqueous saturated solution of ammonium chloride (10 mL) and dichloromethane (10 mL). After further extraction of the aqueous phase with dichloromethane (20 mL), the combined organic phases were dried ($Mg_2SO_4$), filtered and concentrated. Flash column chromatography on silica, eluting with 5% methanol in dichloromethane, gave 4-aminomethyl-4-tert-butoxycarbonylamino-piperidine-1-carboxylic acid tert-butyl ester (5.5 mg, 0.017 mmol, 6%). LC-MS (LCT2) m/z 352 [M+Na$^+$], $R_t$ 7.16 min.

86C. 4-tert-Butoxycarbonylamino-4-[(4-chloro-benzoylamino)-methyl]-piperidine-1-carboxylic acid tert-butyl ester To absolution of 4-aminomethyl-4-tert-butoxycarbonylamino-piperidine-1-carboxylic acid tert-butyl ester (12.2 mg, 0.037 mmol) and triethylamine (16 µL, 0.12 mmol) in dry dichloromethane (4 mL) was added 4-chlorobenzoyl chloride (5 µL, 0.037 mmol). After stirring for 18 hours at room temperature, the reaction mixture was partionated between dichloromethane (2 mL) and water (1 mL) with 10% aqueous sodium hydroxide (0.1 mL). The two layers were separated and the aqueous phase was further extracted with dichloromethane (2 mL). The combined organic layers were dried ($Mg_2SO_4$), filtered and concentrated. Preparative TLC, eluting with 10% methanol-dichloromethane, gave 4-tert-butoxycarbonylamino-4-[(4-chloro-benzoylamino)-methyl]-piperidine-1-carboxylic acid tert-butyl ester (6 mg, 0.013 mmol, 35%). LC-MS (LCT2) m/z 490 [M+Na$^+$], $R_t$ 8.20 min.

86D. N-(4-Amino-piperidin-4-ylmethyl)-4-chloro-benzamide dihydrochloride

A 4M solution of HCl in dioxane (0.3 ml, 1.2 mmol) was added dropwise to a solution of 4-tert-butoxycarbonylamino-4-[(4-chloro-benzoylamino)-methyl]-piperidine-1-carboxylic acid tert-butyl ester (5.8 mg, 0.012 mmol) in methanol (0.5 mL). The solution was stirred at room temperature for 17 hours. The solvents were concentrated to give N-(4-amino-piperidin-4-ylmethyl)-4-chloro-benzamide dihydrochloride (6.1 mg, quantitative) that was used in the next step without further purification. $^1$H NMR (CD$_3$OD) δ 2.23-2.30 (4H, m), 3.46-3.61 (4H, m), 3.89 (2H, s), 7.58 (2H, d, J=7 Hz), 8.03 (2H, d, J=7 Hz).

86E. N-[4-Amino-1-(7H-pyrrolo[2,3-d]pyrimidin-4-yl)-piperidin-4-ylmethyl]-4-chloro benzamide A degassed mixture of crude N-(4-amino-piperidin-4-ylmethyl)-4-chloro-benzamide dihydrochloride (6.1 mg), 4-chloro-7H-pyrrolo[2,3-d]pyrimidine (2.6 mg, 0.016 mmol), triethylamine (16 µL, 0.09 mmol) and n-butanol (0.3 mL) was stirred at 100° C. for 17 hours. The solvents were concentrated. The crude mixture was first purified on an SCX-II acidic resin, eluting with methanol then 2M ammonia-methanol, and then by preparative TLC, eluting with 15% methanol-dichloromethane, to give N-[4-amino-1-(7H-pyrrolo[2,3-d]pyrimidin-4-yl)-piperidin-4-ylmethyl]-4-chloro-benzamide (3.3 mg, 0.009 mmol, 69% over 2 steps). LC-MS (LCT2) m/z 385 [M+H$^+$], $R_t$ 2.58 min.

$^1$H NMR (CD$_3$OD) δ 1.79-1.81 (2H, m), 1.95-1.97 (2H, m), 3.67 (2H, s), 4.20-4.17 (4H, m), 6.72 (1H, d, J=5 Hz), 7.23 (1H, d, J=5 Hz), 7.58 (2H, d, J=7 Hz), 7.96 (2H, d, J=7 Hz), 8.24 (1H, s).

EXAMPLEs 87 to 90

By following the methods described above, or methods analogous thereto, the compounds of Examples 87 to 90 were prepared.

EXAMPLE 87

4-Biphenyl-4-ylmethyl-1-(7H-pyrrolo[2,3-d]pyrimidin-4-yl)-piperidin-4-ylamine

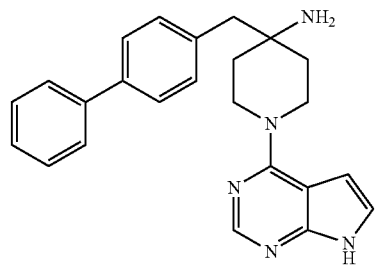 [SMILES: NC1(Cc2ccc(-c3ccccc3)cc2)CCN(c2ncnc3[nH]ccc23)CC1]

EXAMPLE 88

4-Biphenyl-2-ylmethyl-1-(7H-pyrrolo[2,3-d]pyrimidin-4-yl)-piperidin-4-ylamine

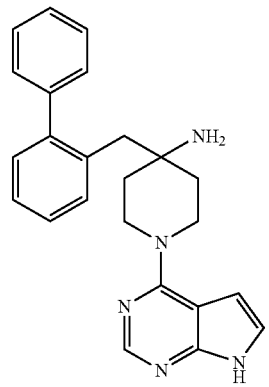 [SMILES: NC1(Cc2ccccc2-c2ccccc2)CCN(c2ncnc3[nH]ccc23)CC1]

EXAMPLE 89

4-(2-Methoxy-benzyl)-1-(7H-pyrrolo[2,3-d]pyrimidin-4-yl)-Piperidin-4-ylamine

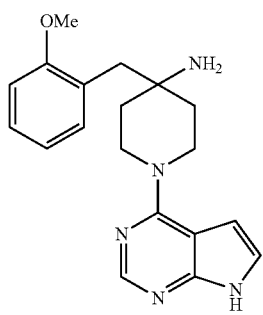 [SMILES: COc1ccccc1CC1(N)CCN(c2ncnc3[nH]ccc23)CC1]

EXAMPLE 90

4-Naphthalen-1-ylmethyl-1-(7H-pyrrolo[2,3-d]perimidin-4-yl)-piperidin-4-ylamine

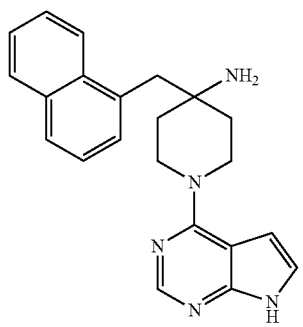 [SMILES: NC1(Cc2cccc3ccccc23)CCN(c2ncnc3[nH]ccc23)CC1]

EXAMPLEs 91 to 94

By following the methods described above, or methods analogous thereto, the compounds of Examples 91 to 94 are prepared.

EXAMPLE 91

4-Amino-1-(7H-pyrrolo[2,3-d]pyrimidin-4-yl)-piperidine-4-carboxylic acid 4-chloro-2-fluoro-benzylamide

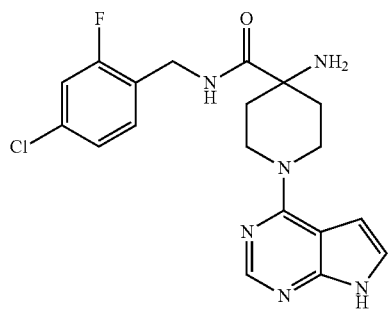 [SMILES: NC1(C(=O)NCc2ccc(Cl)cc2F)CCN(c2ncnc3[nH]ccc23)CC1]

EXAMPLE 92

4-Amino-1-(7H-pyrrolo[2,3-d]pyrimidin-4-yl)-piperidine-4-carboxylic acid (biphenyl-3-ylmethyl)-amide

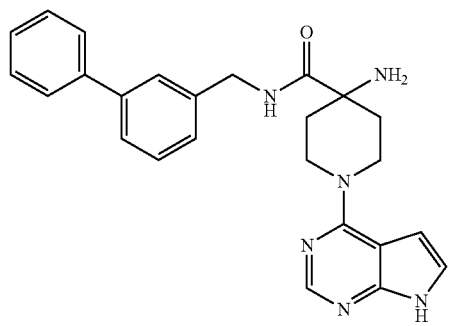 [SMILES: NC1(C(=O)NCc2cccc(-c3ccccc3)c2)CCN(c2ncnc3[nH]ccc23)CC1]

EXAMPLE 93

4-Biphenyl-3-ylmethyl-1-(7H-Pyrrolo[2,3-d]pyrimidin-4-yl)-piperidin-4-ylamine

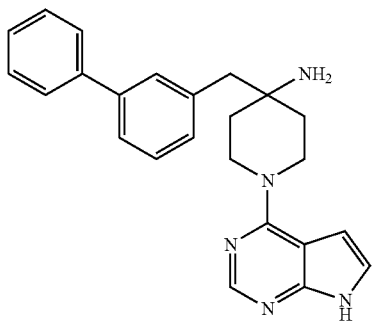 [SMILES: NC1(Cc2cccc(-c3ccccc3)c2)CCN(c2ncnc3[nH]ccc23)CC1]

EXAMPLE 94

4-(6-Chloro-biphenyl-3-ylmethyl)-1-(7H-pyrrolo[2,3-d]pyrimidin-4-yl)-piperidin-4-Y amine

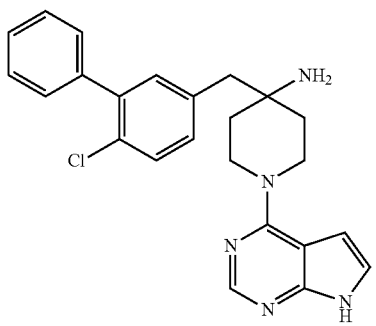 [SMILES: NC1(Cc2ccc(Cl)c(-c3ccccc3)c2)CCN(c2ncnc3[nH]ccc23)CC1]

Biological Activity

EXAMPLE 95

Anti-Proliferative Activity

The anti-proliferative activities of compounds for use according to the invention are determined by measuring the ability of the compounds to inhibition of cell growth in a number of cell lines. Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. All cell lines are obtained from ECACC (European Collection of cell Cultures) or ATCC.

In particular, compounds for use according to the invention were tested against the PC3 cell line (ATCC Reference: CRL-1435) derived from human prostate adenocarcinoma. Many compounds for use according to the invention were found to have $IC_{50}$ values of less than 25 µM in this assay and preferred compounds have $IC_{50}$ values of less than 15 µM.

Pharmaceutical Formulations

EXAMPLE 96

(i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

v) Injectable Formulation III

A formulation for i.v. delivery by injection or infusion can be prepared by dissolving the compound of formula (I) (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

viii) Lyophilised Formulation

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

EXAMPLE 97

ROCK-II (h) Assay Protocol

In a final reaction volume of 25 µl, ROCK-II (h) (5-10 mU) is incubated with 50 mM Tris pH 7.5, 0.1 mM EGTA, 30 µM KEAKEKRQEQIAKRRRLSSLRASTSKSGGSQK (SEQ ID NO:1), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

EXAMPLE 98

Anti-ROCK-II Activity

The compound of various examples described above were tested for anti-ROCK-II activity (assay as described above):

| Example No. | IC$_{50}$ (µM) |
|---|---|
| 4 | >1 |
| 14 | <0.1 |
| 17 | <1 |
| 30 | <0.03 |
| 54 | <0.01 |
| 69 | 0.143 |
| 55 | >1 |
| 56 | 2.7 |
| 59 | <0.03 |

Thus, the compounds tested exhibited inhibitory activity against ROCK-II.

EXAMPLE 99

P70s6 Radiometric Assay

Overview

P70S6 enzyme is bought from Upstate and used at 2 nM in the assay. The substrate S6 cocktail (AKRRRLSSLRA) (SEQ ID NO:2) is used at 25 µM (Km has not been determined). In the phosphoryl transfer reaction, the $^{33}$P-γ phosphate from ATP is transferred to the serine residue. The reaction mixture is transferred to a phosphocellulose filter plate where the peptide binds and the unused ATP is washed away. After washing, scintillant is added and the incorporated activity measured by scintillation counting.

Reagents
P70S6 kinase (T412E) active from Upstate (#14-486)
S6 kinase substrate cocktail from Upstate (#20-122)

| | |
|---|---|
| Assay Buffer | 10 mM MOPS pH 7.0 |
| | 0.1 mg/ml BSA |
| | 0.001% Brij-35 |
| | 0.5% glycerol |
| | 0.2 mM EDTA |
| | 10 mM MgCl$_2$ |
| | 0.01% β-mercaptoethanol |
| | Made as a 10X stock, stored at 20° C. in 2 ml aliquots |
| | 15 µM ATP |

ATP (10 mM stock) added fresh from concentrated stocks. ATP will break down over time, keep on ice as far as possible and use small aliquots to ensure the stock is fresh.
γ$^{33}$P-ATP APBiotech (BF1000)
12.5% orthophosphoric acid
0.5% orthophosphoric acid
Microscint 20 (Packard)
Assay Preparation
Enzyme mix (per 1 ml-100 assay points):
743.75 µl H20
250 µl 10× assay buffer
3.75 µl 10 mM ATP
2.5 µl enzyme
Substrate mix (per 1 ml-100 assay points):
250 µl S6 cocktail substrate
750 µl H20
3.5 µl $^{33}$P-ATP (BF1000 from APBiotech)
The amount of $^{33}$P-ATP added assumes it is on its reference date. The exact amount needs to be adjusted with time.
Compounds—prepare a dilution curve in DMSO in a polypropylene 96 well plate to 40× final assay concentration (final DMSO 2.5%).
Dilute 1:8 in water (adding 5 µl of compound to 35 µl water is sufficient).
Assay Setup
In a polypropylene 96 well plate add in order:
5 µl compound
10 µl substrate mix
10 µl enzyme mix
Final ATP concentration is approximately 15 µM. KM for ATP calculated to 47 uM radiometrically. Controls are "no compound" (DMSO only) and "no enzyme" (use 10 µl of the enzyme mix prior to adding enzyme). Cover with a plate seal (TopSeal A—Packard) or plastic lid from filter plate (moderate radiation barrier). Mix by gentle shaking. Incubate at room temperature for 50 minutes. Stop the reaction by adding 20 µl of 2% orthophosphoric acid.
Filtration Step
Pre-wet the wells of a Millipore MAPH NOB plate with 50 µl of 0.5% orthophosphoric acid wash buffer. Filter the liquid through on a Millipore vacuum filtration unit. Transfer the whole of the stopped reaction to the wells. Filter through. Wash twice with 200 µl of 0.5% orthophosphoric acid wash buffer. Vacuum to near dryness. Remove the plate support and allow to the filters to dry further on tissue paper. Snap the plate into an adapter for the Packard TopCount. Add 20 µl of Microscint 20 scintillant, seal with a sheet of Topseal A and count for 30s on the TopCount.

EXAMPLE 100

Anti-P70S6K Activity

The compounds of various examples were tested for anti-P70S6K activity (assay as described above):

| Example No. | IC$_{50}$ (μM) |
|---|---|
| 4 | 3 |
| 17 | 0.094 |
| 25 | 0.013 |
| 30 | 0.007 |
| 54 | 0.03 |
| 69 | 0.018 |
| 56 | 0.18 |
| 59 | 0.059 |

Thus, all compounds tested exhibited inhibitory activity against P70S6K.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method for inhibiting protein kinase P70S6K and/or ROCK kinase, which method comprises contacting the kinase with a compound of formula (Ic):

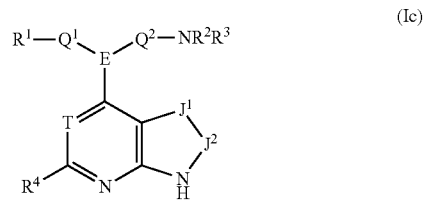

or salts, tautomers or N-oxides thereof, wherein
T is N or a group $CR^5$;
$J^1$-$J^2$ represents a group selected from $N\!=\!C(R^6)$, $(R^7)C\!=\!N$, $(R^8)N\!-\!C(O)$, $(R^8)_2C\!-\!C(O)$, $N\!=\!N$ and $(R^7)C\!=\!C(R^6)$;
E is piperidine substituted with 0-2 substituents $R^{11}$ selected from the group $R^{10}$;
$Q^1$ is a bond or a saturated hydrocarbon linker group containing from 1 to 3 carbon atoms, wherein one of the carbon atoms in the linker group may optionally be replaced by an oxygen or nitrogen atom, or an adjacent pair of carbon atoms may be replaced by $CONR^q$ or $NR^qCO$ where $R^q$ is hydrogen, $C_{1-4}$ alkyl or cyclopropyl, or $R^q$ is a $C_{1-4}$ alkylene chain that links to $R^1$ or to

---

SEQUENCE LISTING

<160> NUMBER OF SEQ ID NOS: 2

<210> SEQ ID NO 1
<211> LENGTH: 32
<212> TYPE: PRT
<213> ORGANISM: Artificial
<220> FEATURE:
<223> OTHER INFORMATION: Long S6 substrate kinase peptide

<400> SEQUENCE: 1

Lys Glu Ala Lys Glu Lys Arg Gln Glu Gln Ile Ala Lys Arg Arg
1               5                   10                  15

Leu Ser Ser Leu Arg Ala Ser Thr Ser Lys Ser Gly Gly Ser Gln Lys
            20                  25                  30

<210> SEQ ID NO 2
<211> LENGTH: 11
<212> TYPE: PRT
<213> ORGANISM: Artificial
<220> FEATURE:
<223> OTHER INFORMATION: S6 kinase substrate peptide

<400> SEQUENCE: 2

Ala Lys Arg Arg Arg Leu Ser Ser Leu Arg Ala
1               5                   10 another carbon atom of $Q^1$ to form a cyclic moiety; and wherein the carbon atoms of the linker group $Q^1$ may optionally bear one or more substituents selected from fluorine and hydroxy;

$Q^2$ is a bond or a saturated hydrocarbon linker group containing from 1 to 3 carbon atoms, wherein one of the carbon atoms in the linker group may optionally be replaced by an oxygen or nitrogen atom; and wherein the carbon atoms of the linker group may optionally bear one or more substituents selected from fluorine and hydroxy, provided that the hydroxy group when present is not located at a carbon atom α with respect to the $NR^2R^3$ group;

$R^1$ is hydrogen or phenyl which is unsubstituted or substituted by one or more substituents $R^{10}$ selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$—$R^b$ wherein $R^a$ is a bond, O, CO, $X^1C(X^2)$, $C(X^2)X^1$, $X^1C(X^2)X^1$, S, SO, $SO_2$, NRC, $SO_2NR^c$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)X^1$; with the proviso that when $R^1$ is hydrogen, $Q^2$ is a bond;

$R^c$ is selected from hydrogen and $C_{1-4}$ hydrocarbyl; and $X^1$ is O, S or $NR^c$ and $X^2$ is =O, =S or =$NR^c$;

provided that where the substituent group $R^{10}$ comprises a carbocyclic or heterocyclic group, the said carbocyclic or heterocyclic group may be unsubstituted or may itself be substituted with one or more further substituent groups $R^{10}$;

$R^2$ and $R^3$ are independently selected from hydrogen; $C_{1-4}$ hydrocarbyl and $C_{1-4}$ acyl wherein the hydrocarbyl and acyl groups are optionally substituted by one or more substituents selected from fluorine, hydroxy, cyano, amino, methylamino, dimethylamino, methoxy and a monocyclic or bicyclic aryl or heteroaryl group;

or $R^2$ and $R^3$ together with the nitrogen atom to which they are attached form a saturated monocyclic heterocyclic group having 4-7 ring members and optionally containing a second heteroatom ring member selected from O and N;

or one of $R^2$ and $R^3$ together with the nitrogen atom to which they are attached and one or more atoms from the group $Q^2$ form a saturated monocyclic heterocyclic group having 4-7 ring members and optionally containing a second heteroatom ring member selected from O and N;

or $NR^2R^3$ and a carbon atom of linker group $Q^2$ to which it is attached together form a cyano group; and $R^4$ is hydrogen;

$R^6$ is selected from hydrogen, chlorine, fluorine and methyl;

$R^8$ is selected from hydrogen, chlorine, fluorine and methyl;

$R^5$ is selected from hydrogen, halogen, $C_{1-5}$ saturated hydrocarbyl, cyano and $CF_3$; and $R^7$ is selected from hydrogen, chlorine, fluorine and methyl.

2. A method according to claim 1 wherein T is N or CH.

3. A method according to claim 1 wherein $J^1$-$J^2$ is selected from N=CH, HC=N, HC=CH and HN—C(O).

4. A method according to claim 1 wherein an adjacent pair of carbon atoms of $Q^1$ is replaced by $CONR^q$ or $NR^qCO$ where $R^q$ is hydrogen or $C_{1-4}$ alkyl.

5. A method according to claim 1 wherein $R^2$ and $R^3$ are independently selected from hydrogen, $C_{1-4}$ hydrocarbyl and $C_{1-4}$ acyl.

6. A method according to claim 5 wherein $R^2$ and $R^3$ are independently selected from hydrogen and methyl.

7. A method according to claim 1 wherein $R^1$ is substituted by one or more substituents $R^{10a}$ selected from halogen, hydroxy, trifluoromethyl, cyano, nitro, carboxy, amino, mono- or di-$C_{1-4}$ hydrocarbylamino, carbocyclic and heterocyclic groups having from 3 to 7 ring members; a group $R^a$—$R^b$ wherein $R^a$ is a bond, O, CO, OC(O), $NR^cC(O)$, $OC(NR^c)$, $C(O)O$, $C(O)NR^c$, $OC(O)O$, $NR^cC(O)O$, $OC(O)NR^c$, $NR^cC(O)NR^c$, S, SO, $SO_2$, $NR^c$, $SO_2NR^c$ or $NR^cSO_2$; and $R^b$ is selected from hydrogen, carbocyclic and heterocyclic groups having from 3 to 7 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 7 ring members and wherein one or more carbon atoms of the $C_{1-8}$ hydrocarbyl group may optionally be replaced by O, S, SO, $SO_2$, $NR^c$, OC(O), $NR^cC(O)$, $OC(NR^c)$, $C(O)O$, $C(O)NR^c$, $OC(O)O$, $NR^cC(O)O$, $OC(O)NR^c$ or $NR^cC(O)NR^c$; and $R^c$ is selected from hydrogen and $C_{1-4}$ hydrocarbyl.

8. A method according to claim 7 wherein $R^1$ is substituted by one or more substituents $R^{10c}$ selected from:
halogen,
hydroxy,
trifluoromethyl,
cyano,
amino, mono- or di-$C_{1-4}$ alkylamino,
cyclopropylamino,
monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy;
a group $R^a$-$R^b$;
$R^a$ is a bond, O, CO, OC(O), $NR^cC(O)$, $OC(NR^c)$, $C(O)O$, $C(O)NR^c$, S, SO, $SO_2$, $NR^c$, $SO_2NR^c$ or $NR^cSO_2$;
$R^b$ is selected from hydrogen, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy;
and $R^b$ is further selected from a $C_{1-8}$ hydrocarbyl group optionally substituted by one or more substituents selected from hydroxy, oxo, halogen, cyano, amino, mono- or di-$C_{1-4}$ alkylamino, monocyclic carbocyclic and heterocyclic groups having from 3 to 7 ring members of which 0, 1 or 2 are selected from O, N and S and the remainder are carbon atoms, wherein the monocyclic carbocyclic and heterocyclic groups are optionally substituted by one or more substituents selected from halogen, hydroxy, trifluoromethyl, cyano and methoxy, and wherein one or two carbon atoms of the $C_{1-8}$ hydrocarbyl group may optionally be replaced by O, S or $NR^c$; provided that $R^a$ is not a bond when $R^b$ is hydrogen; and $R^c$ is selected from hydrogen and $C_{1-4}$ alkyl.

9. A method according to claim 8 wherein $R^1$ is substituted by one or more substituents selected from hydroxy; $C_{1-4}$ acyloxy; fluorine; chlorine; bromine; trifluoromethyl; cyano; $C_{1-4}$ hydrocarbyloxy and $C_{1-4}$ hydrocarbyl each optionally substituted by one or more $C_{1-2}$ alkoxy, halogen, hydroxy or optionally substituted phenyl or pyridyl groups; $C_{1-4}$ acylamino; benzoylamino; pyrrolidinocarbonyl; piperidinocarbonyl; morpholinocarbonyl; piperazinocarbonyl; five and six membered heteroaryl groups containing one or two heteroatoms selected from N, O and S, the heteroaryl groups being optionally substituted by one or more $C_{1-4}$ alkyl substituents; optionally substituted phenyl; optionally substituted pyridyl; and optionally substituted phenoxy; wherein the optional substituent for the phenyl, pyridyl and phenoxy groups are 1, 2 or 3 substituents selected from $C_{1-2}$ acyloxy, fluorine, chlorine, bromine, trifluoromethyl, cyano, $C_{1-2}$ hydrocarbyloxy and $C_{1-2}$ hydrocarbyl each optionally substituted by methoxy or hydroxy.

10. A method according to claim 1 wherein $Q^1$ and $Q^2$ are attached to the same carbon atom in the group E.

11. A method according to claim 10 wherein E is a group B9

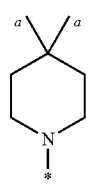

B9 wherein the points of attachment to the groups $Q^1$ and $Q^2$ are designated by the symbol $^a$ and the point of attachment to the bicyclic group is designated by the symbol *.

12. A method according to claim 1 wherein the compound has the formula (IV):

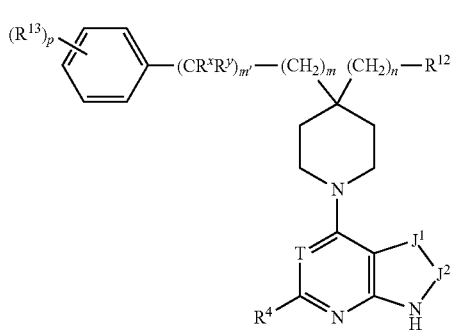

(IV)

or salts, tautomers or N-oxides thereof,
wherein m is 0, 1 or 2; m' is 0 or 1 provided that the sum of m and m' is in the range 0 to 2; n is 0 or 1; p is 0, 1, 2 or 3; $R^x$ and $R^y$ are the same or different and each is selected from hydrogen, methyl and fluorine; $R^{12}$ is CN or $NR^2R^3$ and each $R^{13}$ is independently selected from $R^{10}$.

13. A method according to claim 8 wherein the compound has the formula (VI):

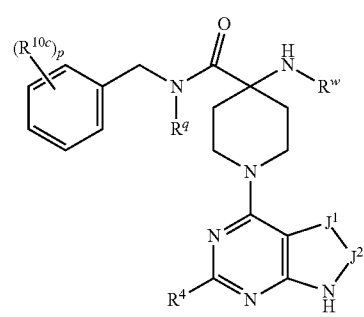

(VI)

or salts, tautomers or N-oxides thereof,
wherein $R^w$ is hydrogen or methyl, $R^q$ is hydrogen or methyl and p is 0, 1 or 2.

14. A method according to claim 1 wherein the compound has the formula (VII):

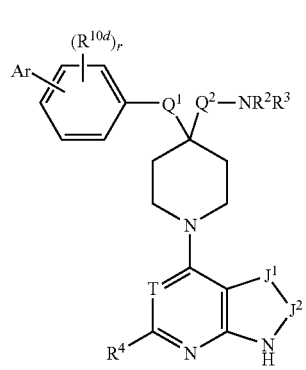

(VII)

or salts, tautomers or N-oxides thereof,
wherein Ar is a 5- or 6-membered monocyclic aryl or heteroaryl group having up to 2 heteroatom ring members selected from O, N and S and being optionally substituted by one or two substituents selected from fluorine, chlorine, methyl and methoxy; $R^{10d}$ is a substituent selected from fluorine, chlorine, methyl, trifluoromethyl, trifluoromethoxy and methoxy; and r is 0, 1 or 2.

15. A method according to claim 1 wherein T is N, $J^1$-$J^2$ is HC=CH, $Q^1$ is a bond, and $R^1$, $R^2$ and $R^3$ are hydrogen.

16. A method according to claim 15, wherein E is piperidine substituted with 1 substituent $R^{11}$ selected from the group $R^{10}$.

17. A method according to claim 16, wherein the group $R^{11}$ is selected from the group $R^a$—$R^b$.

* * * * *

UNITED STATES PATENT AND TRADEMARK OFFICE
CERTIFICATE OF CORRECTION

PATENT NO. : 8,796,293 B2  Page 1 of 1
APPLICATION NO. : 12/298462
DATED : August 5, 2014
INVENTOR(S) : Davies et al.

It is certified that error appears in the above-identified patent and that said Letters Patent is hereby corrected as shown below:

In the Claims

Column 165, Line 21: Claim 1, Delete "NRC," and insert, -- $NR^c$, --

Signed and Sealed this
Twenty-first Day of October, 2014

Michelle K. Lee
*Deputy Director of the United States Patent and Trademark Office*